US010730950B2

(12) United States Patent
Holland et al.

(10) Patent No.: US 10,730,950 B2
(45) Date of Patent: Aug. 4, 2020

(54) GITR ANTIBODIES, METHODS, AND USES

(71) Applicant: Janssen Biotech, Inc., Horsham, PA (US)

(72) Inventors: Cam Holland, Spring House, PA (US); John Kehoe, Spring House, PA (US); Linda Snyder, Spring House, PA (US); Alejandro Sepulveda, Spring House, PA (US); Daniel Villarreal, Spring House, PA (US)

(73) Assignee: Janssen Biotech, Inc., Horsham, PA (US)

( * ) Notice: Subject to any disclaimer, the term of this patent is extended or adjusted under 35 U.S.C. 154(b) by 0 days.

(21) Appl. No.: 15/453,451

(22) Filed: Mar. 8, 2017

(65) Prior Publication Data
US 2017/0260282 A1 Sep. 14, 2017

Related U.S. Application Data

(60) Provisional application No. 62/305,279, filed on Mar. 8, 2016, provisional application No. 62/407,106, filed on Oct. 12, 2016.

(51) Int. Cl.
| C07K 16/28 | (2006.01) |
| A61K 39/00 | (2006.01) |
| A61K 39/395 | (2006.01) |
| A61K 45/06 | (2006.01) |
| A61P 31/20 | (2006.01) |
| A61P 31/04 | (2006.01) |
| A61K 39/08 | (2006.01) |
| A61K 39/12 | (2006.01) |
| A61K 39/39 | (2006.01) |

(52) U.S. Cl.
CPC ...... C07K 16/2878 (2013.01); A61K 39/0011 (2013.01); A61K 39/3955 (2013.01); A61K 45/06 (2013.01); C07K 16/2818 (2013.01); A61K 2039/505 (2013.01); A61K 2039/507 (2013.01); C07K 2317/33 (2013.01); C07K 2317/34 (2013.01); C07K 2317/732 (2013.01); C07K 2317/92 (2013.01)

(58) Field of Classification Search
CPC .......... A61K 39/3955; A61K 2039/505; C07K 16/2878; C07K 2317/92
See application file for complete search history.

(56) References Cited

U.S. PATENT DOCUMENTS

| 5,747,498 A | 5/1998 | Schnur et al. |
| 5,969,110 A | 10/1999 | Beckmann et al. |
| 5,981,245 A | 11/1999 | Fox et al. |
| 6,057,124 A | 5/2000 | Bartley et al. |
| 6,232,447 B1 | 5/2001 | Cerretti |
| 6,413,932 B1 | 7/2002 | Cerretti |
| 6,479,635 B1 | 11/2002 | Anderson et al. |
| 6,521,424 B2 | 2/2003 | Cerretti |
| 6,596,852 B2 | 7/2003 | Cerretti et al. |
| 6,727,225 B2 | 4/2004 | Wiley |
| 6,737,056 B1 | 5/2004 | Presta |
| 6,740,511 B1 | 5/2004 | Van Raaij et al. |
| 9,255,151 B2 * | 2/2016 | Kwon ................ C07K 16/2878 |
| 9,255,152 B2 * | 2/2016 | Kwon ................ C07K 16/2878 |
| 2002/0042368 A1 | 4/2002 | Fanslow, III et al. |
| 2003/0162712 A1 | 8/2003 | Cerretti |
| 2006/0121580 A1 | 6/2006 | Ter Meulen et al. |
| 2006/0257397 A1 | 11/2006 | Throsby et al. |
| 2010/0021477 A1 | 1/2010 | Tsui et al. |
| 2011/0038867 A1 | 2/2011 | Pincelli et al. |
| 2012/0189639 A1 | 7/2012 | Schebye et al. |
| 2014/0286936 A1 | 9/2014 | Chambers et al. |
| 2015/0190506 A1 | 7/2015 | Cheung et al. |
| 2015/0337037 A1 | 11/2015 | Kim et al. |

FOREIGN PATENT DOCUMENTS

| WO | WO 89/11540 A1 | 11/1898 |
| WO | WO 95/19970 A1 | 7/1995 |
| WO | WO 98/01555 A2 | 1/1998 |
| WO | WO 98/02434 A1 | 1/1998 |
| WO | WO 98/14451 A1 | 4/1998 |
| WO | WO 03/002713 A2 | 6/2001 |
| WO | WO 03/086289 A2 | 10/2003 |
| WO | WO 2006/105021 A2 | 10/2006 |
| WO | WO 2007/059782 A1 | 5/2007 |
| WO | WO 2009/085462 A1 | 7/2009 |

(Continued)

OTHER PUBLICATIONS

Avogadri, et al., "Combination of Alphavirus replicon particle-based vaccination with immunomodulatory antibodies: therapeutic activity in the B16 melanoma mouse model and immune correlates," Cancer Immunol. Res. 2(5): 448-458 (2014).
Bianchini, et al., "CD4+ CD25$^{low}$GITR+ cells: A novel human CD4+ T-cell population with regulatory activity," European Journal of Immunology, 41: 2269-2278 (2011).
Blohm, et al., "Solid tumors "melt" from the inside after successful CD8 T cell attack," European Journal of Immunology, 36: 468-477 (2006).
Boissonnas, et al., "In vivo imaging of cytotoxic T cell infiltration and elimination of a solid tumor," The Journal of Experimental Medicine, 204(2): 345-356 (2007).
Brunner, et al., "Tumor-Infiltrating, Interleukin-33-Producing Effector-Memory CD8+ T Cells in Resected Hepatocellular Carcinoma Prolong Patient Survival," Hepatology, 61: 1957-1967 (2015).
Cartron, et al., "Therapeutic activity of humanized anti-CD20 monoclonal antibody and polymorphism in IgG Fc receptor FCλIIIa gene," Blood, 99: 754-758 (2002).

(Continued)

Primary Examiner — Ruixiang Li
(74) Attorney, Agent, or Firm — Kirk Baumeister

(57) ABSTRACT

Provided herein are antibodies that specifically bind to GITR. Also described are related polynucleotides capable of encoding the provided GITR-specific antibodies or antigen-binding fragments, cells expressing the provided antibodies or antigen-binding fragments, as well as associated vectors and detectably labeled antibodies or antigen-binding fragments. In addition, methods of using the provided antibodies are described. For example, the provided antibodies may be used to enhance an immune response in a subject against cancer.

12 Claims, 66 Drawing Sheets

Specification includes a Sequence Listing.

(56) References Cited

FOREIGN PATENT DOCUMENTS

| WO | WO 2011/028683 A1 | 3/2011 |
|---|---|---|
| WO | WO 2015/026684 A1 | 2/2015 |
| WO | WO 2015/031667 A2 | 3/2015 |
| WO | WO 2015/095186 | 6/2015 |
| WO | WO 2015/184099 A1 | 12/2015 |
| WO | WO 2015/187835 A2 | 12/2015 |

OTHER PUBLICATIONS

Chothia, et al., "Canonical Structures for the Hypervariable Regions of Immunoglobulins," Journal of Molecular Biology, 196: 901-917 (1987).
Chothia, et al., "Conformations of immunoglobulin hypervariable regions," Nature, 342: 877883 (1989).
Cline, et al., "Perspectives for Gene Therapy: Inserting New Genetic Information into Mammalian Cells by Physical Techniques and Viral Vectors," Pharma. Ther. 29: 69-92.
Cohen, et al., "Agonist Anti-GITR Monoclonal Antibody Induces Melanoma Tumor Immunity in Mice by Altering Regulatory T Cell Stability and Intra-Tumor Accumulation," PLoS One, 5(5): 1-12 (2010).
Cush, et al., "KLRG1$^+$NKG2A$^+$ CD8 T Cells Mediate Protection and Participate in Memory Responses during λ-Herpesvirus Infection," The Journal of Immunology, 186: 4051-4058 (2011).
Cuzzocrea, et al., "Genetic and pharmacological inhibition of GITR-GITRL interaction reduces chronic lung injury induced by bleomycin instillation," The FASEB Journal, 21: 117-129 (2007).
Cuzzocrea, et al., "Glucocorticoid-induced TNF receptor family gene (GITR) knockout mice exhibit a resistance t splanchnic artery occlusion (SAO) shock," Journal of Leukocyte Biology, 76: 933-940 (2004).
Cuzzocrea, et al., "Proinflammatory Role of Glucocorticoid-Induced TNF Receptor-Related Gene in Acute Lung Inflammation," The Journal of Immunology, 177: 631-641 (2006).
Emsley, et al., "Features and development of *Coot*," Acta Crystallographica, D66: 486-501 (2010).
Ferrara, et al., "Modulation of Therapeutic Antibody Effector Functions by Glycosylation Engineering: Influence of Golgi Enzyme Localization Domain and Co-Expression of Heterologous β1, 4-N-acetylglucosaminylatransferase III and Golgi α-mannosidase II," GLYCART biotechnology AG (2006).
Ferrara, et al., "The Carbohydraft at FCγRIIIa ASN-162," The Journal of Biological Chemistry, 281(8): 5032-5036 (2006).
Fridman, et al., "The immune contexture in human tumours: impact on clinical outcome,"Nature Reviews, 12: 298-306 (2012).
Fujiwara, et al., "Intratumoral CD4$^+$ T Lymphodepletion Sensitizes Poorly Immunogenic Melanomas to Immunotherapy with an OX40 Agonist," Journal of Investigative Dermatology, 134: 1884-1892 (2014).
Gadi, et al., "In vivo sensitization of ovarian tumors to chemotherapy by expression of *E. coli*purine nucleoside phosphorylase in a small fraction of cells," Gene Therapy, 7: 1738-1743 (2000).
Gurney, et al., "Identification of a new member of the tumor necrosis factor family and its receptor, a human ortholog of mouse GITR," Current Biology, 9: 215-218 (1999).
Hanaguchi, et al., "Human plasmacytosis predendritic cells activate NK cells through glucocorticoid-induced tumor necrosis factor receptor-ligand (GITRL)," Blood, 107: 3617-3623 (2006).
Holt, et al., "Domain antibodies: proteins for therapy," TRENDS in Biotechnology, 21(11): 484-490 (2003).
Wolfgang Kabsch, "XDS," Acta Crystallographica, D66: 125-132 (2010).
Ko, et al., "Treatment of advanced tumors with agonistic anti0GITR mAb and its effects on tumor-infiltrating Foxp3$^+$CD25$^+$CD4$^+$ regulatory T Cells," Journal of Experimental Medicine, 202 (7): 885-891 (2005).
Kober, et al., "The capacity of the TNF family members 4-1BBL, OX40L, CD70, GITRL, CD30L and LIGHT to costimulate human T Cells," European Journal of Immunology, 38 (10): 2678-2688 (2008).
Konno, et al., "Fucose content of monoclonal antibodies can be controlled by culture medium osmolality for high antibody-dependent cellular cytotoxicity," Cytotechnology, 64: 249-265 (2012).
Kwon, et al., "Identification of a Novel Activation-inducible Protein of the Tumor Necrosis Factor Receptor Superfamily and Its Ligand," The Journal of Biological Chemistry, 274 (10): 6056-6061 (1999).
Li, et al., "Expression of Glucocorticoid Induced TNF Receptor Family Related Protein (GITR) on peripheral T Cells from normal human donors and patients with non-infectious uveitis," Journal of Autoimmunity, 21: 83-92 (2003).
MacCallum, et al., "Antibody-antigen Interactions: Contact Analysis and Binding Site Topography," Journal of Molecular Biology, 262: 732-745 (1996).
Martin, et al., "Structural Families in Loops of Homologous Proteins: Automatic Classification, Modelling and Application to Antibodies," Journal of Molecular Biology, 263: 800-815 (1996).
McCoy, et al., "*Phaser* crystallographic software," Journal of Applied Crystallography, 40: 658-674 (2007).
McHugh, et al., "CD4$^+$CD25$^-$ Immunoregulatory T Cells: Gene Expression Analysis Reveals a Functional Role for the Glucocorticoid-Induced TNF Receptor," Immunity, 16: 311-323.
Mori, et al., Engineering Chinese Hamster Ovary Cells to Maximize Effector Function of Produced Antibodies Using FUT8 siRNA, Tokyo Research Laboratories (2004).
Myers, et al., "Optimal alignments in linear space," CABIOS, 4 (1): 11-17 (1988).
Needleman, et al., "A General Method Applicable to the Search for Similarities in the Amino Acid Sequence of Two Proteins," Journal of Molecular Biology, 48: 443-453 (1970).
Nocentini, et al., "A new member of the tumor necrosis factor/nerve growth factor receptor family inhibits T cell receptor-induced apoptosis," Proceedings of the National Academy of Science USA, 94: 6216-6221 (1997).
Nocentini, et al., "Pharmacological modulation of GITRL/GITR system: therapeutic perspectives," British Journal of Pharmacology, 165: 2089-2099 (2012).
Nocentini, et al., "GITR: a multifaceted regulator of Immunity belonging to the tumor necrosis factor receptor superfamily," European Journal of Immunology, 35: 1016-1022 (2005).
Nocentini, et al., "GITR/GITRL: More than an effector T cell co-stimulatory system," European Journal of Immunology, 37: 1165-1169 (2007).
Okayama et al., "A cDNA Cloning Vector That Permits Expression of cDNA Inserts in Mammalian Cells," Molecular and Cellular Biology, 3 (2): 280-289 (1983).
Oliver, et al., "EB66 cell line, a duck embryonic stem cell-derived substrate for the industrial production of therapeutic monoclonal antibodies with enhanced ADCC activity," mAbs, 2(4): 405-415 (2010).
Olson, et al., "Effector-like CD8$^+$ T cells in the memory population mediate potent protective immunity," Immunity, 38 (6): 1250-1260 (2013).
Pascal, et al., "HDX Workbench: Software for the Analysis of H/D Exchange MS Data," Journal of Am. Soc. Mass Spectrom., 23 (9): 1-16 (2012).
Pedersen, et al., "Comparison of Vaccine-Induced Effector CD8 T cell Responses Directed against Self- and Non-Self-Tumor Antigens: Implications for Cancer Immunotherapy," The Journal of Immunology, 191: 3955-3967 (2013).
Quezada, et al., "CTLA4 blockade and GM-CSF combination immunotherapy alters the intratumor balance of effector and regulatory T cells," The Journal of Clinical Investigations, 116 (7): 1935-1945 (2006).
Revets, et al., "Nanobodies as a novel agents for cancer therapy," Expert Opinion on Biological Therapy, 5 (1): 111-124 (2005).
Ronchetti, et al., "Role of GITR in activation response of T lymphocytes," Blood, 100: 350352 (2002).
Ronchetti, et al., "GITF, a member of the TNF receptor superfamily, is costimulatory to mouse T lymphocyte subpopulations," European Journal of Immunology, 34: 613-622 (2004).
Schaer, et al., "Modulation of GITF for cancer immunotherapy," Current Opinion in Immunology, 24: 217-224 (2012).

(56) References Cited

OTHER PUBLICATIONS

Schaer, et al., "Targeting tumor-necrosis factor receptor pathways for tumor immunotherapy," Journal for Immunotherapy of Cancer, 2 (7): 1-9 (2014).
Schoenborn, et al., "regulation of Interferon-γ During Innate and Adaptive Immune Response," Advances in Immunology, vol. 96, Chapter 2: 41-61 (2007).
Shevach, et al., "The GITR-GITRL interaction: co-stimulation or contrasuppression of regulatory activity," Nature Reviews, 6: 613-618 (2006).
Shi, et al., "De Novo Selection of High-Affinity Antibodies from Synthetic Fab Libraries Displayed on Phage as pIX Fusion Proteins," Journal of Molecular Biology, 397: 385-396 (2010).
Shields, et al., "Lack of Fucose on Human IgG1 N-Linked Ologosaccharide Improves Binding to Human FCγRIII and Antibody-dependent Cellular Toxicity," The Journal of BiologicalChemistry, 277 (30): 26733-26740 (2002).
Shimizu, et al., "Stimulation of $CD25^+CD4^+$ regulatory T cells through GITR breaks immunological self-tolerance," Nature Immunology, 3 (2): 136-142 (2002).
Shinkawa, et al., "The Absence of Fucose but Not the Presents of Galactose of Bisection N-Acetylglucosamine of Human IgG1 Complex-type Oligosaccharides Shows the Critical Role of Enhancing Antibody-dependent Cellular Cytotoxicity," The Journal of Biological Chemistry, 278(5): 3466-3473 (2003).
Slaney, et al., "Trafficking of T Cells into Tumors," Cancer Research, 74 (24): 7168-7174 (2014).
Steer, et al, "harnessing the immune response to treat cancer," Oncogene, 29: 6301-6313 (2010).
Tatsumi, et al., "Disease-associated Bias in T Helper Type 1 (Th1)/Th2 $CD4^+$ T Cell Responses Against MAGE-6 in HLA-$DRB1*0401^+$ Patients with Renal Cell Carcinoma or Melanoma," Journal of Experimental Medicine, 196 (5): 619-628 (2002).
Tone, et al., "Mouse glucocorticoid-induced tumor necrosis factor receptor ligand is costimulatory for T cells," Proceedings of the National Academy of Science, 100 (25): 15059-15064 (2003).
van Duikeren, et al, "Vaccine-Induced Effector-Memory $CD8^+$ T Cell Responses Predict Therapeutic Efficacy against Tumors," The Journal of Immunology, 189: 3397-3403 (2012).
Villarreal, et al., "Alarmin IL-33 Acts as an Immunoadjuvant to Enhance Antigen-Specific Tumor Immunity," Cancer Research, 74 (6): 1789-1800 (2014)
Villarreal, et al., "Ubiquitin-like Molecule ISG15 Acts as an Immune Adjuvant to Enhance Antigen-specific CD8 T-cell Tumor Immunity," Molecular Therapy, 23 (10): 1653-1662 (2015).
Ward, et al., "Binding activities of a repertoire of single immunoglobulin variable domains secreted from *Escherichia coli*," Letters to Nature, 341: 544-546 (1989).
Wu, et al., "A Novel Polymorphism of FCγRIIIa (CD16) Alters Receptor Function and Predisposes to Autoimmune Disease," Journal of Clinical Investigations, 100 (5): 1059-1070.
Ye, et al., "Contribution of Pulmonary $KLRG1^{high}$ and $KLRG1^{low}$ CD8 T cells to Effector and Memory Responses during Influenza Virus Infection," The Journal of Immunology, 189: 5206-5211 (2012).
Zhou, et al., "Development of a Simple and Rapid method for Producing Non-Fucosylated Oligomannose Containing Antibodies with Increased Effector Function," Biotechnology and Bioengineering, 99: 652-665 (2008).
UniProt Accession No. U2SSB6 (Dec. 9, 2009).
UniProt Accession No. A0A067JGQ0 (Nov. 11, 2015).
UniProt Accession No. A0A067KH38 (Nov. 11, 2015).

* cited by examiner

X-axis Legend

| B# | pDR |
|---|---|
| TRGB153 | pDR000021547 |
| TRGB160 | pDR000021516 |
| TRGB123 | pDR000021515 |
| TRGB121 | pDR000021496 |
| TRGB144 | pDR000021476 |
| TRGB159 | pDR000021469 |
| TRGB134 | pDR000021457 |
| TRGB162 | pDR000021448 |
| TRGB127 | pDR000021448 |
| TRGB119 | pDR000021434 |
| TRGB124 | pDR000021433 |

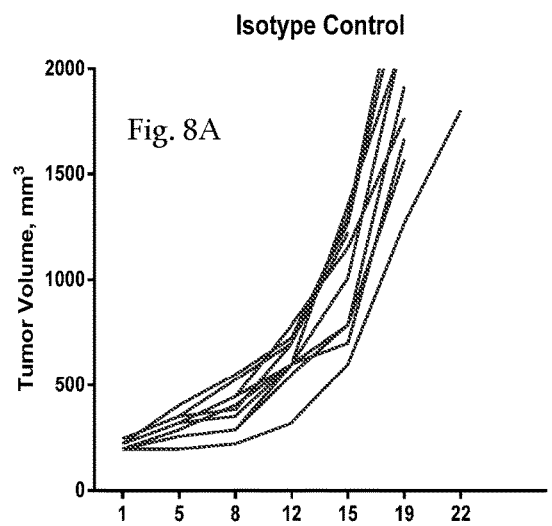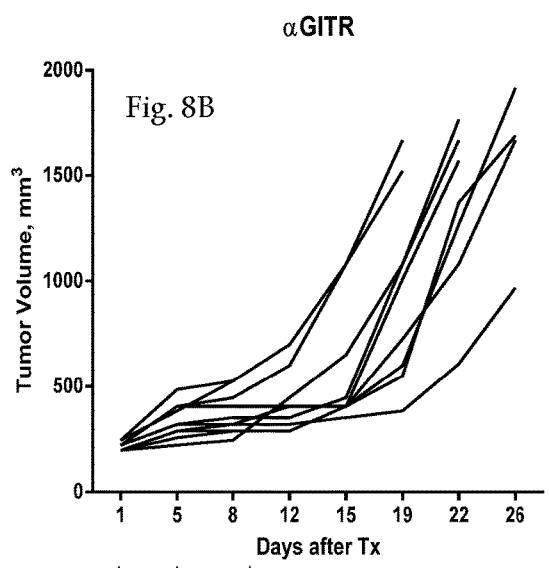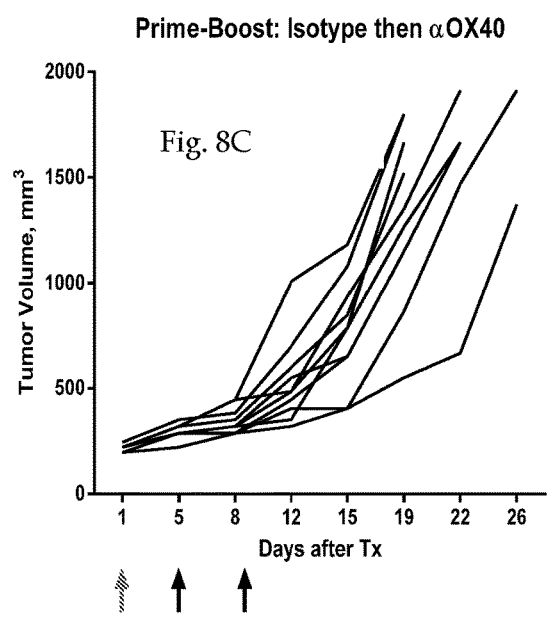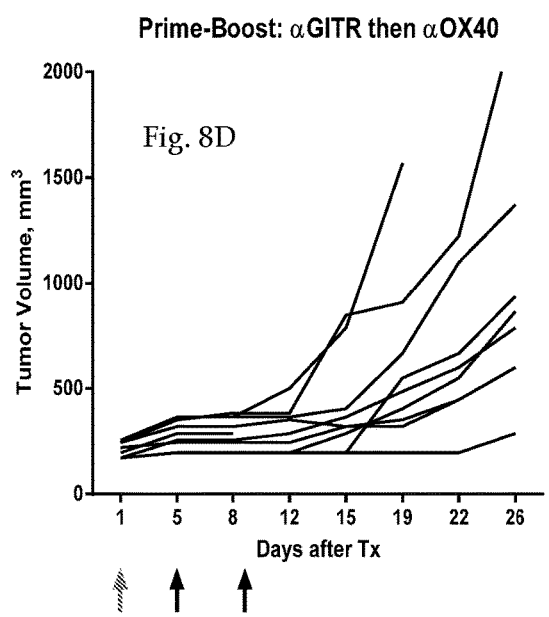

Fig. 9E
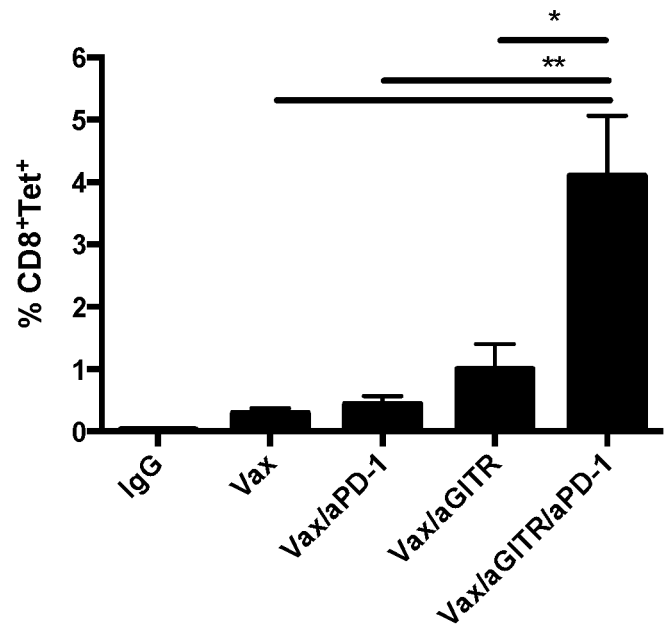
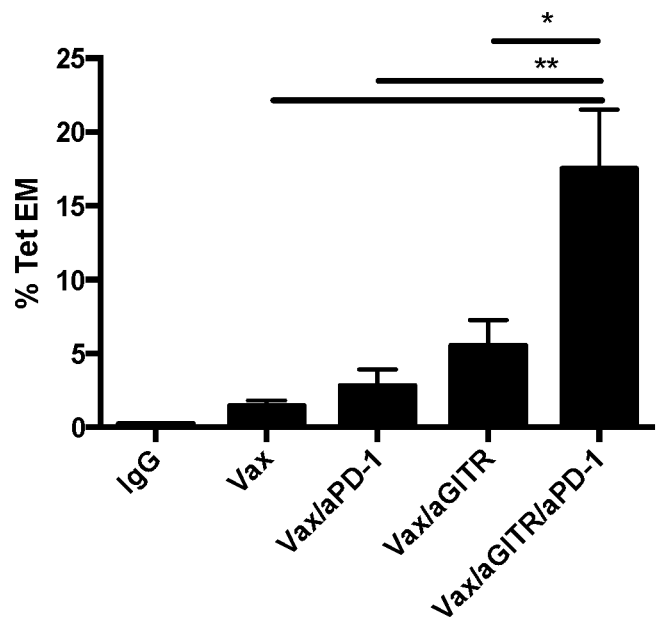

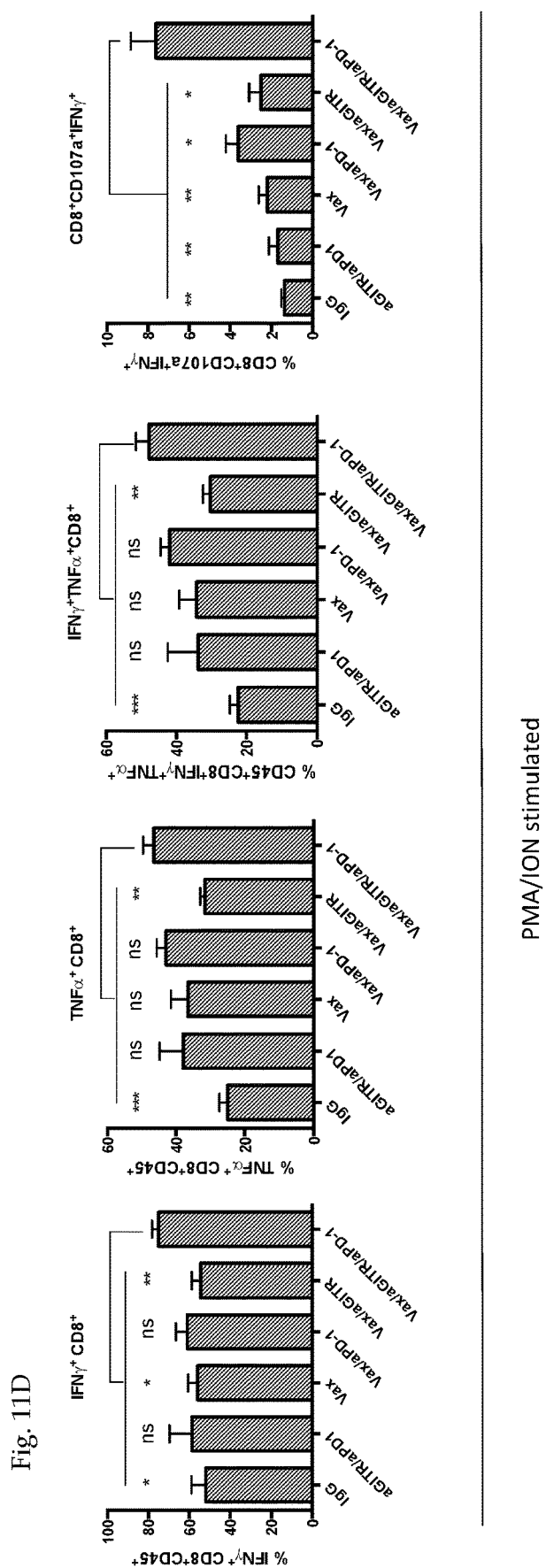

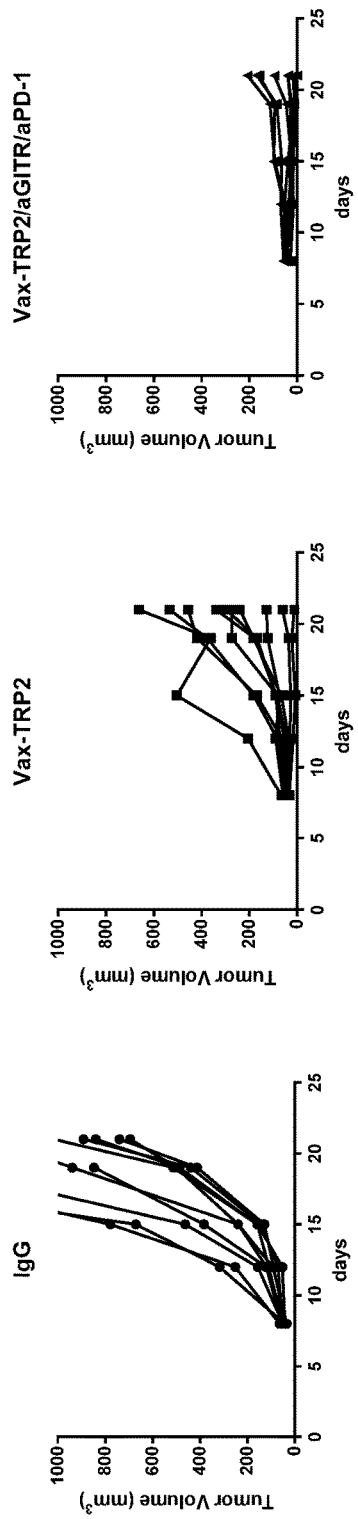

GITR ANTIBODIES, METHODS, AND USES

CROSS-REFERENCE TO RELATED APPLICATIONS

This application claims the benefit of U.S. Provisional Application Ser. No. 62/305,270, filed 8 Mar. 2016 and U.S. Provisional Application Ser. No. 62/407,106, filed 12 Oct. 2016. The entire content of the aforementioned applications is incorporated herein by reference in its entirety.

SEQUENCE LISTING

The instant application contains a Sequence Listing which has been submitted electronically in ASCII format and is hereby incorporated by reference in its entirety. Said ASCII copy, created on Feb. 21, 2017, is named JBI5082USNP_SL.txt and is 92,231 bytes in size.

TECHNICAL FIELD

The disclosure provided herein relates to monoclonal antibodies that specifically bind glucocorticoid-induced tumor necrosis factor receptor (GITR) and methods of producing and using the described antibodies.

BACKGROUND

Glucocorticoid-induced TNFR-related protein (GITR; also AITR, TNFRSF18, or CD357), a member of the TNFR superfamily, is expressed in many components of the innate and adaptive immune system and stimulates both acquired and innate immunity (Nocentini G et al., (1994) PNAS 94: 6216-6221; Hanabuchi S et al., (2006) Blood 107:3617-3623; Nocentini G & Riccardi C (2005) Eur J Immunol 35: 1016-1022; Nocentini G et al., (2007) Eur J Immunol 37: 1165-1169). It is expressed in several cells and tissues, including T, B, dendritic (DC) and Natural Killer (NK) cells and is activated by its ligand, GITR-L, mainly expressed on Antigen Presenting Cells (APCs), on endothelial cells, and also in tumor cells.

The GITR-GITRL system participates in the development of autoimmune/inflammatory responses and potentiates response to infection and tumors. For example, treating animals with GITR-Fc fusion protein ameliorates autoimmune/inflammatory diseases while GITR triggering is effective in treating viral, bacterial, and parasitic infections, as well in boosting immune response against tumors (Nocentini G et al., (2012) Br J Pharmacol 165: 2089-99). These effects are due to several concurrent mechanisms including: coactivation of effector T-cells, inhibition of regulatory T (Treg) cells, modulation of NK and dendritic cell function, activation of macrophages, and regulation of the extravasation process. The membrane expression of GITR is increased following T cell activation (Hanabuchi S et al, (2006) supra; Nocentini G & Riccardi C supra). Its triggering coactivates effector T lymphocytes (McHugh R S et al, (2002) Immunity 16: 311-323; Shimizu J et al, (2002) Nat Immunol 3: 135-142; Roncheti S et al, (2004) Eur J Immunol 34: 613-622; Tone M et al, (2003) PNAS 100: 15059-15064). GITR activation increases resistance to tumors and viral infections, is involved in autoimmune/inflammatory processes and regulates leukocyte extravasation (Nocentini G & Riccardi C (2005) supra; Cuzzocrea S et al, (2004) J Leukoc Biol 76: 933-940; Shevach E M & Stephens G L (2006) Nat Rev Immunol 6: 613-618; Cuzzocrea S et al, (2006) J Immunol 177: 631-641; Cuzzocrea S et al, (2007) FASEB J 21: 117-129).

Human GITR is expressed at very low levels in peripheral (non-activated) T cells. After T cell activation, GITR is strongly up-regulated for several days in both $CD4^+$ and $CD8^+$ cells (Kwon B et al, (1999) J Biol Chem 274: 6056-6061; Gurney A L et al, (1999) Curr Biol 9: 215-218; Ronchetti S et al, (2004) supra; Shimizu J et al, (2002) supra; Ji H B et al, (2004) supra; Ronchetti S et al, (2002) Blood 100: 350-352; Li Z et al, (2003) J Autoimmun 21: 83-92), with $CD4^+$ cells having a higher GITR expression than $CD8^+$ cells (Kober J et al, (2008) Eur J Immunol 38(10): 2678-88; Bianchini R et al, (2011) Eur J Immunol 41(8): 2269-78).

The role of human GITR in modulating immune responses indicates that it may be a suitable target for antibody-based therapy against diseases such as cancer. Antibodies against GITR are described (e.g. in WO200610502, WO2011028683, WO2015031667, WO20150353637, WO2015187835, WO2015184099, U.S. Pat. Nos. 9,255,151 and 9,255,152), but there is an ongoing need for novel agents and methods for modulating GITR activity against diseases, such as cancer.

SUMMARY

Provided herein are antibodies that specifically bind to GITR and antigen-binding fragments thereof. Also described are related polynucleotides capable of encoding the provided GITR-specific antibodies and antigen-binding fragments, cells expressing the provided antibodies and antigen-binding fragments, as well as associated vectors and detectably labeled antibodies and antigen-binding fragments. In addition, methods of using the provided antibodies and antigen-binding fragments are described. For example, given the role GITR plays in modulating an immune response, the GITR-specific antibodies have utility in treating a variety of GITR-related diseases or disorders in which it is desirable to modulate an immune response. For example, the GITR specific antibodies can be used in a variety of immunotherapy applications, such as the treatment of a variety of cancers.

GITR-Specific Antibodies

Described herein are isolated antibodies and antigen-binding fragments specific for GITR. In some embodiments, the GITR-specific antibodies and antigen-binding fragments bind human GITR. In some embodiments, the GITR-specific antibodies and antigen-binding fragments bind human GITR and cynomolgus monkey GITR. In some embodiments, the GITR-specific antibodies and antigen-binding fragments bind to an epitope including one or more residues from the GITR extracellular domain (ECD) as defined in SEQ ID NO:59. This GITR-specific antibody or antigen-binding fragment may bind to GITR with a binding affinity of 30 nM or less, may induce an increase in luciferase expression in an NF-κB luciferase gene assay and may induce ADCC in vitro with an $EC_{50}$ of 67 ng/mL or less.

Table 1 provides a summary of examples of some GITR-specific antibodies described herein:

TABLE 1

CDR sequences of mAbs generated against human GITR
(SEQ ID NO:)

| ID | HC-CDR1 | HC-CDR2 | HC-CDR3 | LC-CDR1 | LC-CDR2 | LC-CDR3 |
|---|---|---|---|---|---|---|
| TRGB5 | GFTFSGYW (1) | ISGSGGST (5) | AKDFYWDAFDY (12) | QSVSSY (28) | DAS (32) | QQRSNWPLT (35) |
| TRGB14 | GFTFSSYA (2) | ISGSGGST (5) | AKPIRGLDY (13) | QSVNNF (29) | DAS (32) | QQGFNAPLT (36) |
| TRGB20 | GFTFSGYW (1) | ISSDGGSK (6) | AKEVVYDHYAALDY (14) | QSVNSF (30) | YAS (33) | QQYIRWPLT (37) |
| TRGB23 | GGTFSSYA (3) | IIPIFGTA (7) | ARHGNWLHFNLDY (15) | QSVSSY (28) | DAS (32) | QQRSNWPLT (35) |
| TRGB25 TRGB190 | GGTFSSYA (3) | IIPIFGTA (7) | ARHRRFWLDY (16) | QSVSSY (28) | DAS (32) | QQRSNWPLT (35) |
| TRGB31 | GYSFTSYW (4) | IDPSDSDT (8) | ARVFPYYGLVLDY (17) | QSVSSY (28) | DAS (32) | QQRSNWPLT (35) |
| TRGB34 | GYSFTSYW (4) | IYPGDSDT (9) | ARDYGWHDFDY (18) | QSVSSY (28) | DAS (32) | QQRSNWPLT (35) |
| TRGB35 | GYSFTSYW (4) | IDPGDSDT (10) | ARHRWSTSLLLDY (19) | QSVSSY (28) | DAS (32) | QQRSNWPLT (35) |
| TRGB120 | GGTFSSYA (3) | IIPIFGTA (7) | ARPRRNTNELDY (20) | QSISSY (31) | AAS (34) | QQSYSTPLT (38) |
| TRGB127 | GGTFSSYA (3) | IIPIFGNA (11) | ARHVYKRGVLNY (21) | QSISSY (31) | AAS (34) | QQSYSTPLT (38) |
| TRGB134 | GGTFSSYA (3) | IIPIFGTA (7) | ARHRWGSGNLDY (22) | QSVSSY (28) | DAS (32) | QQRSNWPLT (35) |
| TRGB144 | GGTFSSYA (3) | IIPIFGTA (7) | ARHGFQRGYLDY (23) | QSVSSY (28) | DAS (32) | QQRSNWPLT (35) |
| TRGB153 | GGTFSSYA (3) | IIPIFGTA (7) | ARHAWLGHLDY (24) | QSVSSY (28) | DAS (32) | QQRSNWPLT (35) |
| TRGB159 | GGTFSSYA (3) | IIPIFGTA (7) | ARHGRNSGRLDY (25) | QSVSSY (28) | DAS (32) | QQRSNWPLT (35) |
| TRGB160 TRGB191 TRGB191.CLF | GFTFSNYW (27) | ISGSGGST (5) | AKDFYWDSFDY (26) | QSVSSY (28) | DAS (32) | QQRSNWPLT (35) |
| TRGB162 | GGTFSSYA (3) | IIPIFGNA (11) | ARHVYKRGVLNY (21) | QSVSSY (28) | DAS (32) | QQRSNWPLT (35) |

In some embodiments are provided a GITR-specific antibody, or an antigen-binding fragment thereof, comprising a heavy chain comprising a CDR1, a CDR2, and a CDR3 of any one of the antibodies described in Table 1 and a light chain comprising a CDR1, a CDR2, and a CDR3 of any one of the antibodies described in Table 1.

The IgG class is divided in four isotypes: IgG1, IgG2, IgG3 and IgG4 in humans. They share more than 95% homology in the amino acid sequences of the Fc regions but show major differences in the amino acid composition and structure of the hinge region. The Fc region mediates effector functions, such as antibody-dependent cellular cytotoxicity (ADCC) and complement-dependent cytotoxicity (CDC). In ADCC and ADCP, the Fc region of an antibody binds to Fc receptors (FcgRs) on the surface of immune effector cells such as natural killers and macrophages, leading to the lysis or phagocytosis of the targeted cells. In CDC, the antibodies kill the targeted cells by triggering the complement cascade at the cell surface. The antibodies described herein include antibodies with the described features of the variable domains in combination with any of the IgG isotypes, including modified versions in which the Fc sequence has been modified to effect different effector functions.

In some embodiments, the antibodies comprise the CDRs of the antibodies presented in Table 1 above. In some embodiments the described antibodies are capable of binding to GITR with a dissociation constant of 30 nM or less as measured by surface plasmon resonance (SPR). In some embodiments the described antibodies are capable of inducing an increase in luciferase expression in an NF-κB luciferase gene assay. In some embodiments the described antibodies are capable of inducing ADCC in vitro with an $EC_{50}$ of 67 ng/mL or less.

In addition to the described GITR-specific antibodies and antigen-binding fragments, also provided are polynucleotide sequences capable of encoding the described antibodies and antigen-binding fragments. Vectors comprising the described polynucleotides are also provided, as are cells expressing the GITR-specific antibodies or antigen-binding fragments provided herein. Also described are cells capable of expressing the disclosed vectors. These cells may be mammalian cells (such as 293F cells, CHO cells), insect cells (such as Sf7 cells), yeast cells, plant cells, or bacteria cells (such as E. coli). A process for the production of the described antibodies or antigen-binding fragments is also provided.

Methods of Using GITR-Specific Antibodies

Methods of using the described GITR-specific antibodies or antigen-binding fragments are also disclosed. Particular antibodies for use in the methods discussed in this section include those with the set of CDRs described for antibodies in Table 1. For example, the key role that GITR plays in an immune response makes it an attractive target for immunotherapy, including inducing or enhancing an immune response against desired tumor antigens or pathogenic antigens (e.g., viruses and other pathogenic organisms). As such, the GITR-specific antibodies have utility in the treatment of various cancers and infectious disease.

As noted above, GITR activation sends a co-activating signal to CD4+ and CD8+ T cells and prevents suppression of an immune response by regulatory T cells. Thus, in one embodiment, a GITR-specific antibody is administered to inhibit the suppression of effector T cell activity by regulatory T cells. Such inhibition can be assayed by a variety of methods known in the art, including, for example, by monitoring T cell proliferation, expression of known markers of activation, or cytokine secretion. In another embodiment, a GITR-specific antibody is administered to a subject to decrease the level of regulatory T cells, for instance the level of tumor regulatory T cells. In yet another embodiment, the activity of effector T cells is induced or enhanced by administering a GITR-specific antibody as provided herein. Specific assays for each of these methods are provided in the EXAMPLES.

GITR-Specific Antibody Kits

Described herein are kits including the disclosed GITR-specific antibodies or antigen-binding fragments thereof. The described kits may be used to carry out the methods of using the GITR-specific antibodies or antigen-binding fragments provided herein, or other methods known to those skilled in the art. In some embodiments the described kits may include the antibodies or antigen-binding fragments described herein and reagents for use in detecting the presence of GITR in a biological sample. Accordingly, the described kits may include one or more of the antibodies, or an antigen-binding fragment(s) thereof, described herein and a vessel for containing the antibody or fragment when not in use, instructions for use of the antibody or fragment, the antibody or fragment affixed to a solid support, and/or detectably labeled forms of the antibody or fragment, as described herein.

BRIEF DESCRIPTION OF THE DRAWINGS

FIG. 1A shows signals from Plate 1. FIG. 1C shows signals from Plate 3 FIG. 2A-2F. Agonist activity exhibited by the anti-GITR mAbs from the next-generation sequencing panel. Data shown are the Cell-Titer Glo signal from cells that were treated with the indicated reagent after being transfected with either the NF-kB luciferase reporter gene only or with both the GITR expression vector and the NF-kB luciferase reporter gene. FIG. 2A shows signals from Plate 1.

FIG. 8A-8D. Combination of surrogate anti-GITR antibody (DTA-1) and anti-OX-40 antibody (OX-86) is better than OX-86 alone in the syngeneic MC38 colon carcinoma model. Three injections of isotype rat IgG2b (FIG. 8A), or DTA-1 (FIG. 8B) was administered at 100 ug/antibody/ mouse to animals on days indicated by black arrowheads (n=10 per group) starting when tumor volumes reached 200 mm3. Sequencing of DTA-1 (d1) followed by OX-86 (d5, d9, FIG. 7D) was better than isotype Ab followed by OX-86 (FIG. 7C).

FIG. 9A, ELISpot analysis of IFNγ-secreting T cells from spleens of mice stimulated with $OVA_{257-264}$-specific peptide (d7). FIG. 9B, column graphs show polyfunctional subpopulations of single-, double- and triple-positive $CD8^+$ T cells releasing effector cytokines IFNγ, TNFα, and IL-2 to $OVA_{257-264}$ stimulation in the spleen (d7). FIG. 9C, profile of the cytolytic phenotype (d7). FIG. 9D, OVA-specific $CD8^+$ T cells in peripheral blood d7. Dot plots, representative of 5 mice shown in D. E, OVA-specific $CD8^+$ T cells in peripheral blood at d14. FIG. 9E and FIG. 9F, differentiation of OVA tetramer-specific $CD8^+$ memory T cells in the blood from treated mice at d14 after immunization. Each of the above experiments was repeated at least two times with similar results. *P<0.05; P<0.01; *P<0.001. Error bars indicate SEM. EM: effector memory; CM: central memory.

FIG. 10A, B16-OVA established tumors (~30-40 $mm^3$) were treated with the indicated treatments. FIG. 10B, Individual tumor responses, group tumor measurements (mean+/−SEM, C) and survival (FIG. 10D) were monitored over time. Graph represents mean tumor volume per group of animals studied and chart indicates number of tumor-free/total (FIG. 10C). Graphs are representative results of 1 of 3 independent experiments. *P<0.05; P<0.01; *P<0.001.

FIG. 11A-11D. Combination Vax/anti-GITR/anti-PD-1 therapy synergized to enhance the frequency and function of vaccine-induced antigen-specific responses of $CD8^+$ TILs. Shown are summary data of the intracellular cytokine staining for IFNγ, TNFα, INFγ/TNF and CD107a/IFNγ in $CD8^+$ TILS following $OVA_{257-264}$ restricted (CD8) peptide stimulation (FIG. 11A and FIG. 11B) or with PMA/ION stimulation (FIG. 11D) 12 to 15 days after tumor implantation. FIG. 11C, Bar graph shows the percentages of $H2-K^b$-SIINFEKL-restricted OVA tetramer-specific $CD8^+$ TILs of total $CD45^+$ cells in the tumor. Experiments were repeated at least two times with similar results. *P<0.05; P<0.01; *P<0.001. Error bars indicate SEM of n=4-5/group.

FIG. 12A, Percentages of Tregs assessed from the spleens of non-tumor bearing mice from FIG. 9B-9D, cohorts of B16-OVA tumor-bearing mice were treated with Vax, anti-GITR, and/or PD-1 combinations (as in FIG. 10). FIG. 12B, $CD8^+$ TILs as percentage of total $CD45^+$ cells 15 days after tumor implantation. FIG. 12C and FIG. 12D. Representative flow dot plots and summary data show the percentage of Tregs of $CD45^+$ TILs and the ratio of $CD8^+$ effector T cells to Tregs in the tumors of treated mice 15 days after tumor implantation. Statistical analyses are compared with Vax/anti-GITR/anti-PD-1. Results are representative of 2 to 3 independent experiments with 4 to 5 mice per group. *P<0.05; P<0.01; *P<0.001. Error bars indicate SEM.

FIG. 13A. Dosing schedule for the therapeutic depletion study. B6 mice (n=10/group) were injected s.c. with $4 \times 10^5$ B16-OVA tumor cells and when tumor diameters reached ~40 $mm^3$ they were depleted of CD8 cells, CD4 cells, or NK cells by administration of 200 μg each/mouse mAb at days 7, 8, 9, 11, 14, 17; day 8 is the day when treatment with Vax/anti-GITR/anti-PD-1 or IgG started. Vaccine was dosed on day 8; anti-GITR on day 8 and 14; anti-PD-1 on day 10, 13, 16, and 19 post-tumor implantation. FIG. 13B, Tumor volume was monitored twice a week (mean+/−SEM). FIG. 13C and FIG. 13D, Tumor-free mice (n=6-9 per group) after combination treatments were re-challenged with B16-OVA ($2 \times 10^5$; FIG. 13C) or B16.F10 ($1.5 \times 10^5$; FIG. 13D) cells on the same flank six months after primary tumor rejection. Age-matched mice were used for re-challenge controls. Results are representative of 2-3 independent experiments.

FIG. 14A, representative scatter plot graphs show the percentages of $H2-K^b$-SIINFEKL-restricted OVA-specific $CD8^+$ T-cells, (FIG. 14B) percentages of $KLRG1^+$ $CD8^+$ TILs, and (FIG. 14C) the percentages of tetramer-binding $KLRG1^+CD8^+$ TILs 15 days after tumor inoculation (4-5 mice/group). FIG. 14D, B6 mice (10 per group) were injected s.c. with $4 \times 10^5$ B16-OVA tumor cells and at day 8 when tumor diameters reached ~50 $mm^3$, therapy was initiated as in FIG. 13. 200 μg of aKLRG1 mAb was administered on days 7, 8, 9, 11, 14, 17, 20; day 8 being the day when treatment started. Tumor volume and survival were monitored twice a week. Overall graphs depict the mean+/−SEM of at least two independent experiments. *P<0.05; P<0.01; *P<0.001.

FIG. 15A, Schematic illustration of the schedule of TRP2 peptide vaccination alone or in combination with anti-GITR/anti-PD-1 therapy (or matched isotype IgGs) in B16-OVA tumor-bearing mice. FIG. 15B, Tumor growth was monitored over time, in groups (mean+/−SEM) and as individuals. Experiments were conducted at least two times with similar results. **P<0.01

FIG. 17A, the percentage of CD8+ T cells in the spleen after treatment with anti-KLRG-1 antibody. FIG. 17B, Representative flow plots showing percentages of $KLRG1^+CD8^+$ in the blood and spleen and (FIG. 17C) compiled data of the frequency and/or total cell numbers of $KLRG1^+CD8^+CD44^+$ and $KLRG1^+CD8^+Tet^+$ cells (left and right panels, respectively) in the blood and spleen. Results are representative of 2 independent experiments with 5 mice per group. *P<0.05; P<0.01; *P<0.001. Error bars indicate SEM.

FIG. 19A-19D. Illustrates the frequency of TILs harvested at day 16 post B16-OVA implantation (400,000 cells), and percentage of tumor infiltrating G-MDSCs (CD11b$^+$Ly6G$^+$Ly6C$^-$) (FIG. 19A), tumor-infiltrating IFNγ$^+$ TNFα$^+$ cytokine secreting CD8$^+$ T cells upon ex-vivo stimulation with OVA$_{257-264}$ peptide (FIG. 19B), H2-K$^b$-SIINFEKL OVA-specific CD8$^+$ TILs (FIG. 19C), and tumor-infiltrating Tregs (CD4$^+$CD44$^+$FOXP3$^+$CD25$^+$) (FIG. 19D). aCD122: anti-CD122 monoclonal antibody. *P<0.05; P<0.01; *P<0.001; ****P<0.0001.

Figure 20A:
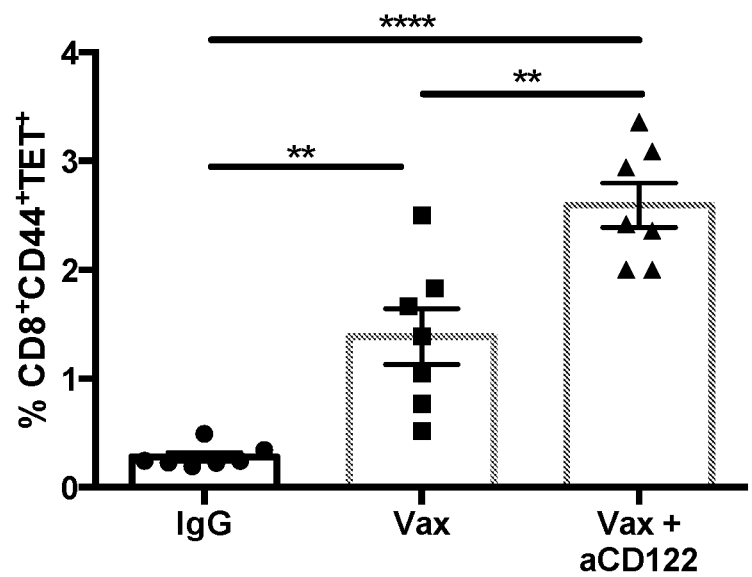
Figure 20B:
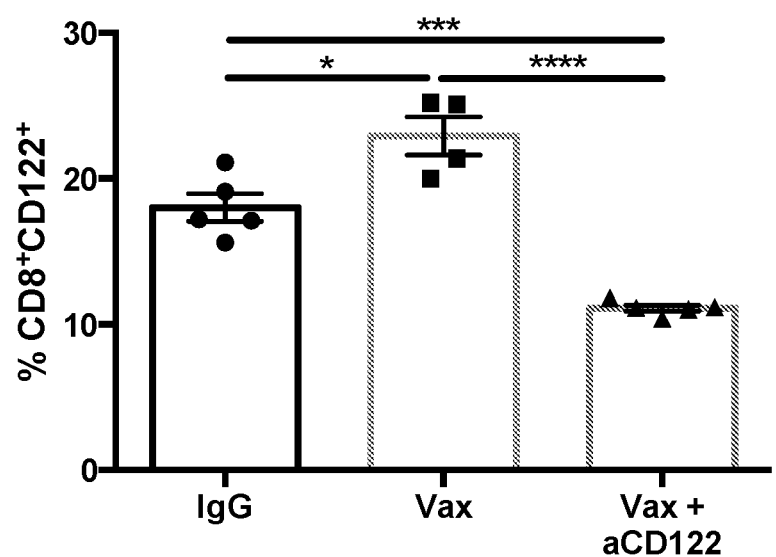
Figure 20C:
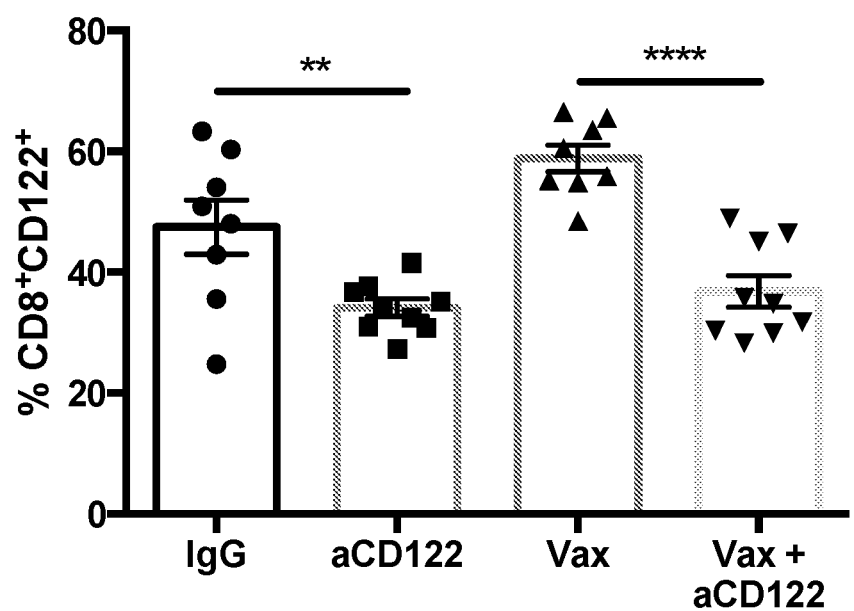

FIG. 20A-20C. Illustrates that anti-CD122 therapy enhances vaccine-induced antigen-specific CD8$^+$ T cell responses in the periphery of non-tumor bearing mice: percentage of H2-K$^b$-SIINFEKL-restricted OVA-specific CD8$^+$ T-cells (FIG. 20A); percentage of CD8$^+$CD122$^+$ T cell population after anti-CD122 treatment in blood in non-tumor bearing mice (FIG. 20B), percentage of CD8+ CD122+ T cell population after therapy treatment in the tumors of tumor-bearing mice (FIG. 20C). aCD122: anti-CD122 monoclonal antibody; Vax: vaccine. *P<0.05; P<0.01; *P<0.001; ****P<0.0001. Errors bars indicate SEM.

Figure 21A:
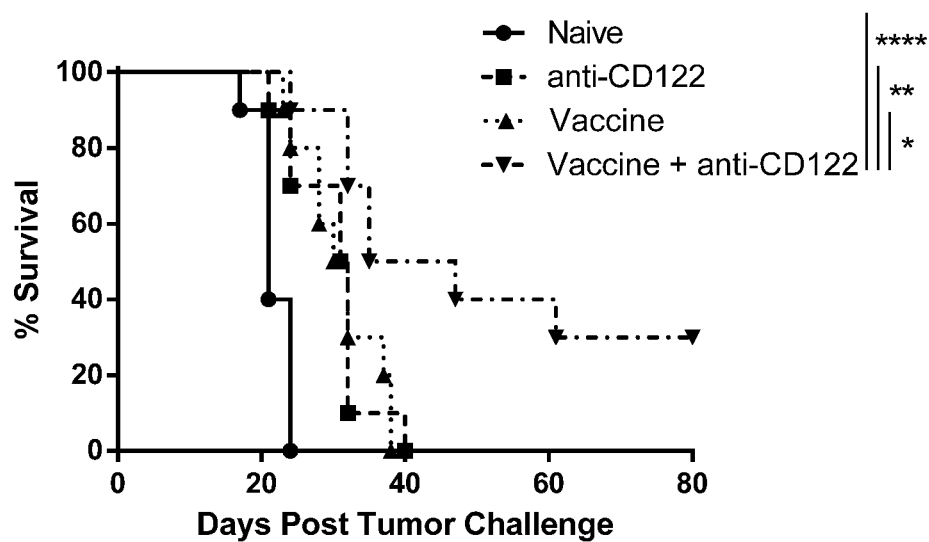
Figure 21B:
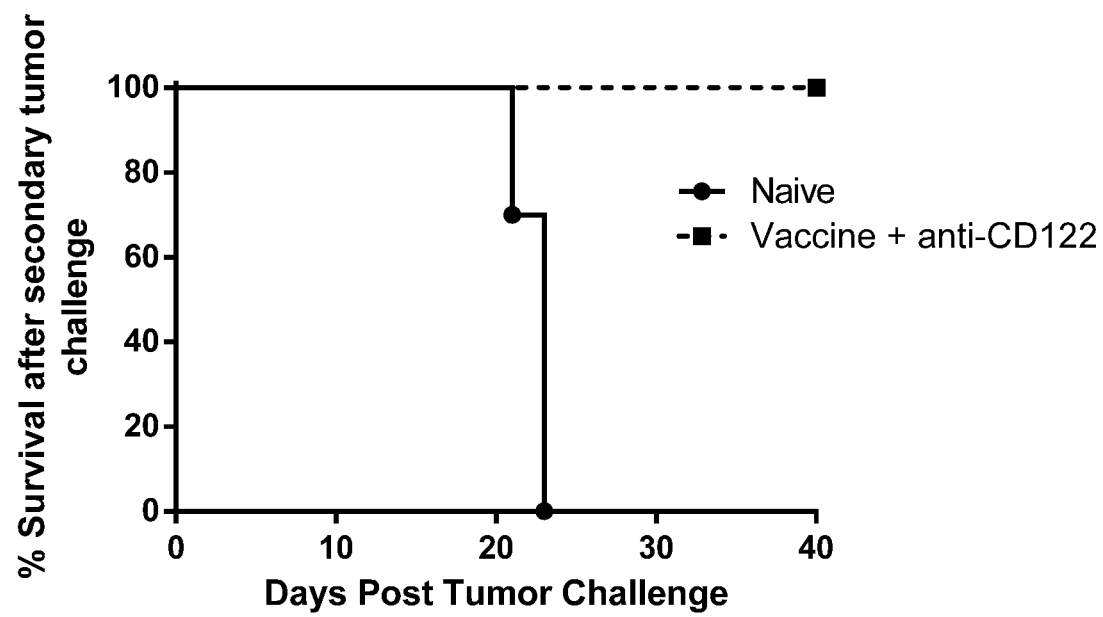

FIGS. 21A and 21B. Illustrates the survival of mice implanted with B16-OVA cells (400,000), followed by the treatment with anti-CD122 in combination with peptide vaccination (3 doses) (FIG. 21A). Mice treated with Vaccine/anti-CD122 in FIG. 32A that survived tumor free, were rechallenged with B16-ova cells; graph shows the percentage of mice rejecting a second tumor challenge (FIG. 21B).

Figure 22A:
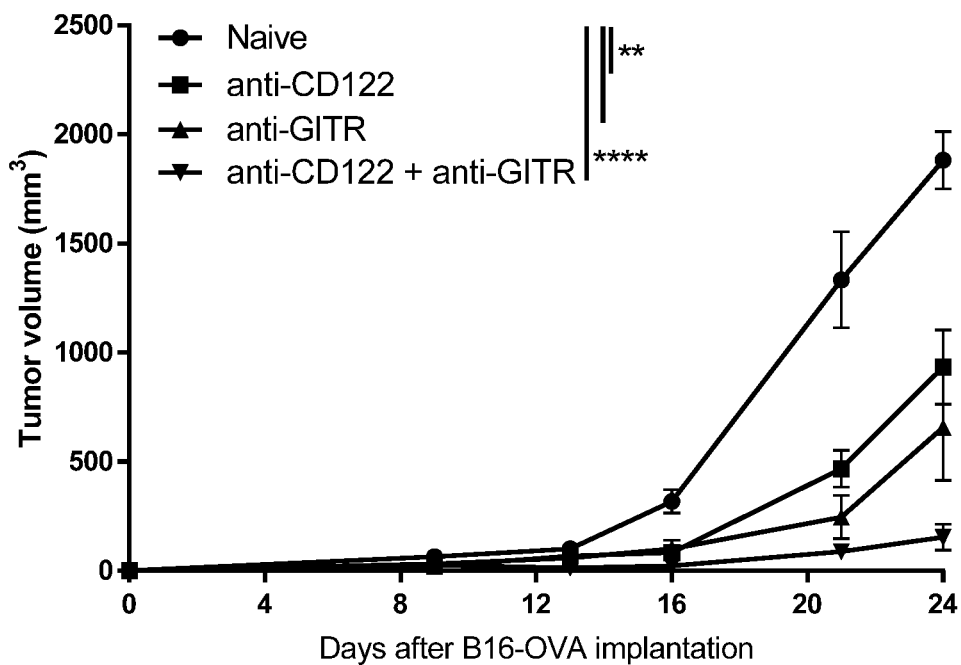
Figure 22B:
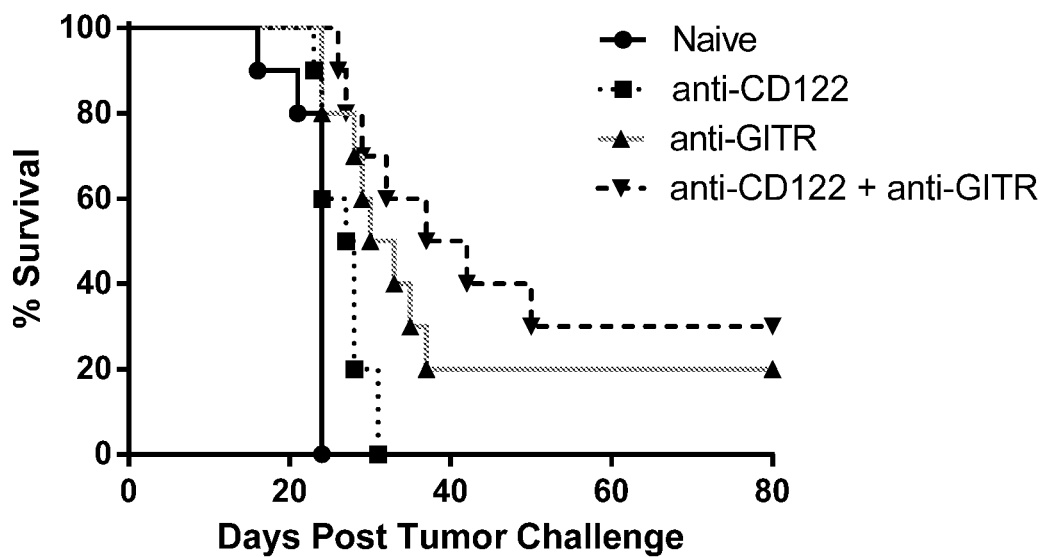

FIGS. 22A and 22B. Illustrates tumor growth (FIG. 22A) and survival of naïve mice (FIG. 22B) (n=10 per group) which received B16-OVA cells (400,000) implant, followed by a treatment with either anti-CD122, or anti-GITR, or a combination of anti-CD122 and anti-GITR, as indicated, on day 4 post implantation. *P<0.05; P<0.01; *P<0.001; ****P<0.0001.

Figure 23:
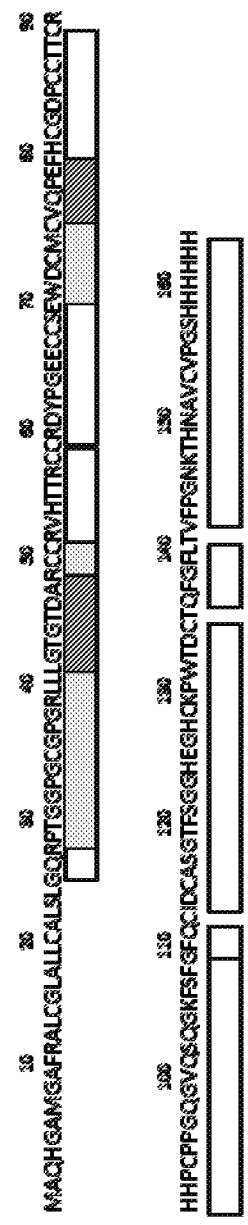

FIG. 23. Difference in deuteration levels for each segment of GITR-CED in the presence or absence of TRGB191.CLF. Each block represents the peptides that could be mapped and the extent of exchange relative to control at 60, 600, 3,600 and 14,400 sec. Grey: no deuterium protection; Dark grey: strong protection upon mAb binding; light grey: moderate protection upon mAb binding.

Figure 24:
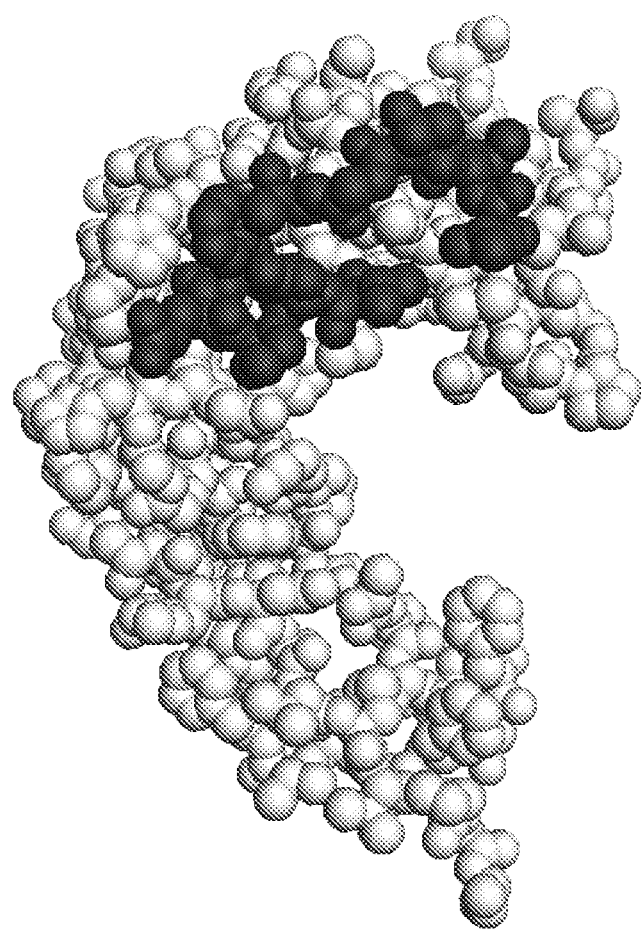

FIG. 24. Space-filling model of GITR ECD monomer with the TRGB191 epitope highlighted in black.

Figure 25A:
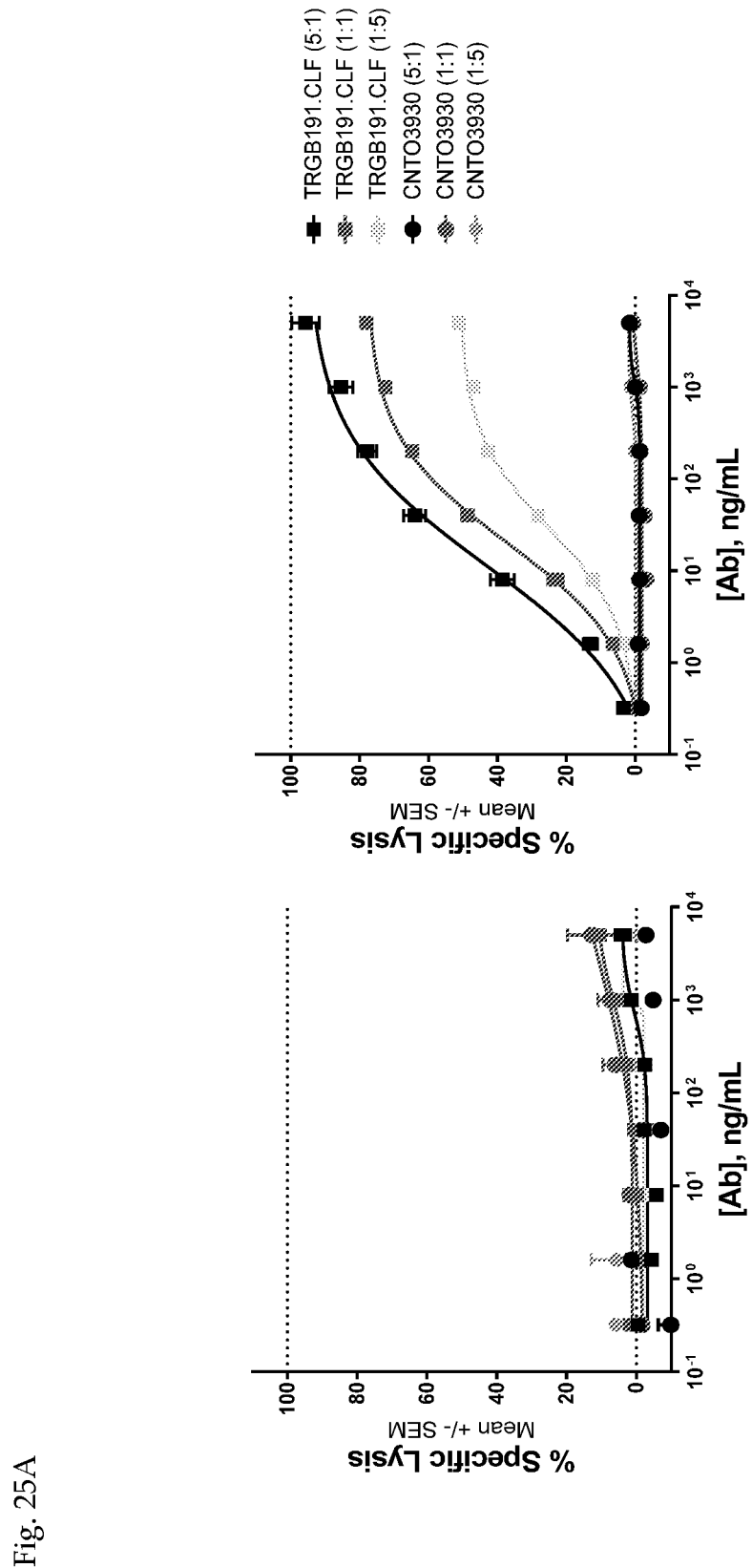
Figure 25B:
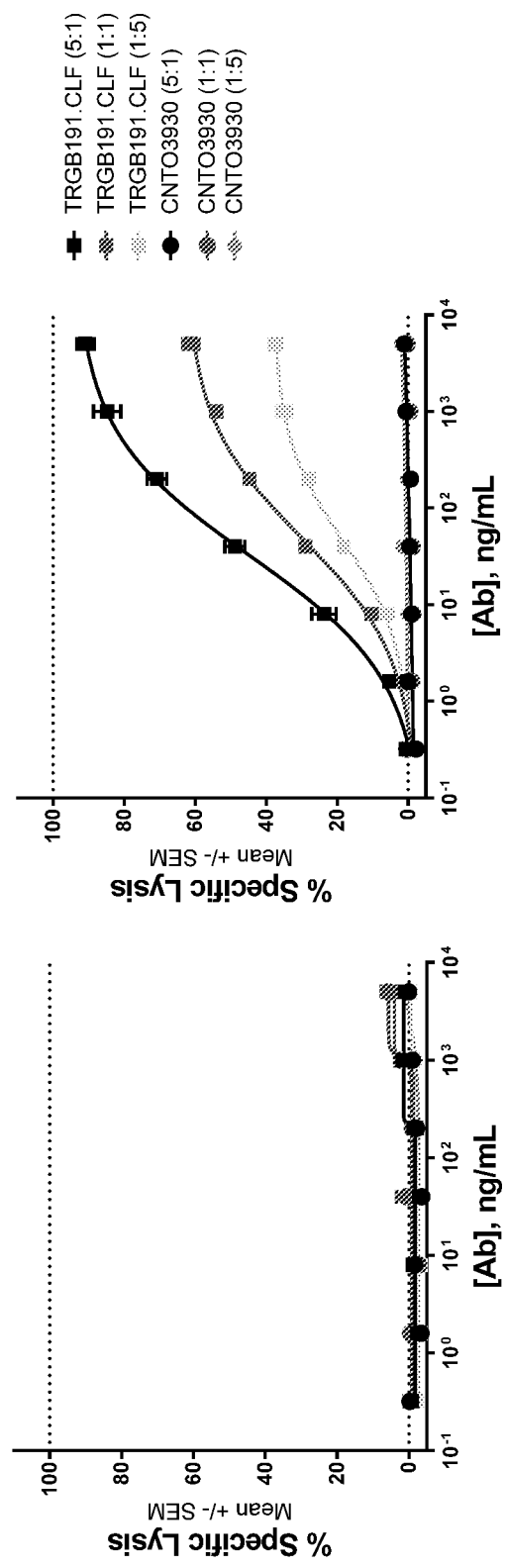

FIGS. 25A and 25B. ADCC activity of TRGB191.CLF on primary resting and activated CD4$^+$ and CD8$^+$ T cells. TRGB191.CLF and CNTO3930 (isotype control antibody) were evaluated for ADCC activity on resting CD4$^+$ (FIG. 25A, left panel) and resting CD8$^+$ T cells (FIG. 25B, left panel) or activated CD4$^+$ (FIG. 25A, right panel) and CD8$^+$ T cells (FIG. 25B, right panel). Percentage specific lysis is shown as the mean±standard error of the mean (SEM). E:T ratios are indicated in the legend. N=3 experimental replicates, n=12 per data point. [Ab]=antibody concentration.

Figure 26:
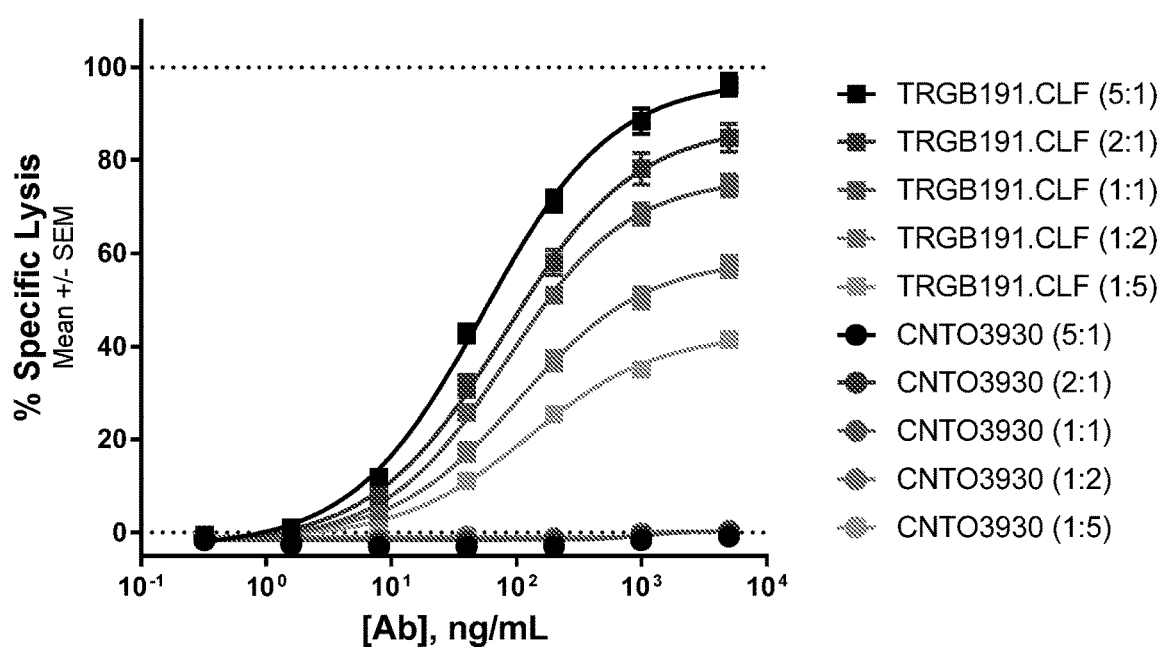

FIG. 26. ADCC activity of TRGB191.CLF on the JJN-3 cell line. TRGB191.CLF and CNTO3930 (isotype control antibody) were evaluated for ADCC activity using JJN-3 target cells and NK-92 158 V/V effector cells. Percentage specific lysis is shown as the mean±standard error of the mean (SEM). N=6 experimental replicates, n=12 to 24 per data point. [Ab]=antibody concentration.

Figure 27:
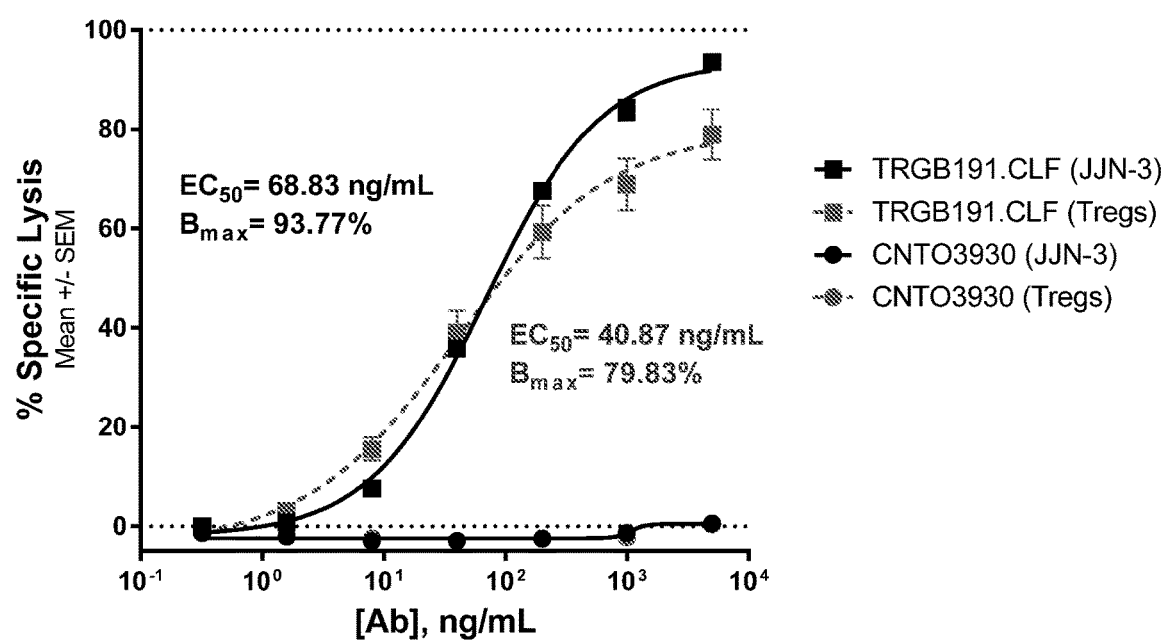

FIG. 27. TRGB191.CLF and CNTO3930 isotype control antibody were tested for ADCC activity on JJN-3 target cells and in vitro differentiated T$_{regs}$ as target cells, using NK-92 158 V/V effector cells. Percentage specific lysis is shown as the mean±standard error of the mean (SEM). N=3 experimental replicates, n=12 per data point. [Ab]=antibody concentration, EC$_{50}$=half maximal effective concentration, B$_{max}$=maximal lysis.

Figure 28A:
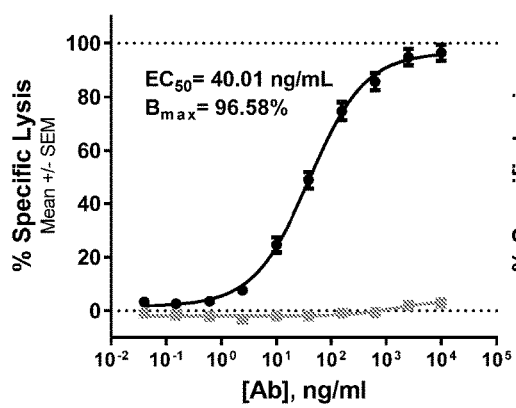
Figure 28B:
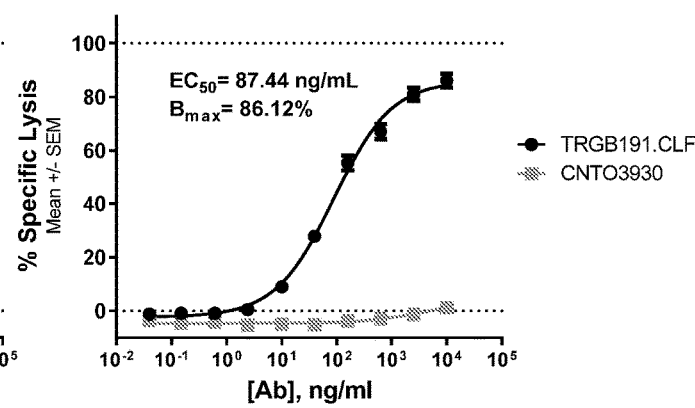

FIGS. 28A and 28B. ADCC activity of TRGB191.CLF using effector cells with high and low affinity FcγRIIIA polymorphisms. TRGB191.CLF and CNTO3930 were tested for ADCC activity on JJN-3 target cells, using NK-92 effector cells expressing (FIG. 28A) the 158V/V high affinity variant or (FIG. 28B) the 158F/F low affinity variant. Percentage specific lysis is shown as the mean±standard error of the mean (SEM). N=3 experimental replicates, n=12 per data point. [Ab]=antibody concentration, EC$_{50}$=half maximal effective concentration, B$_{max}$=maximal lysis.

Figure 29:
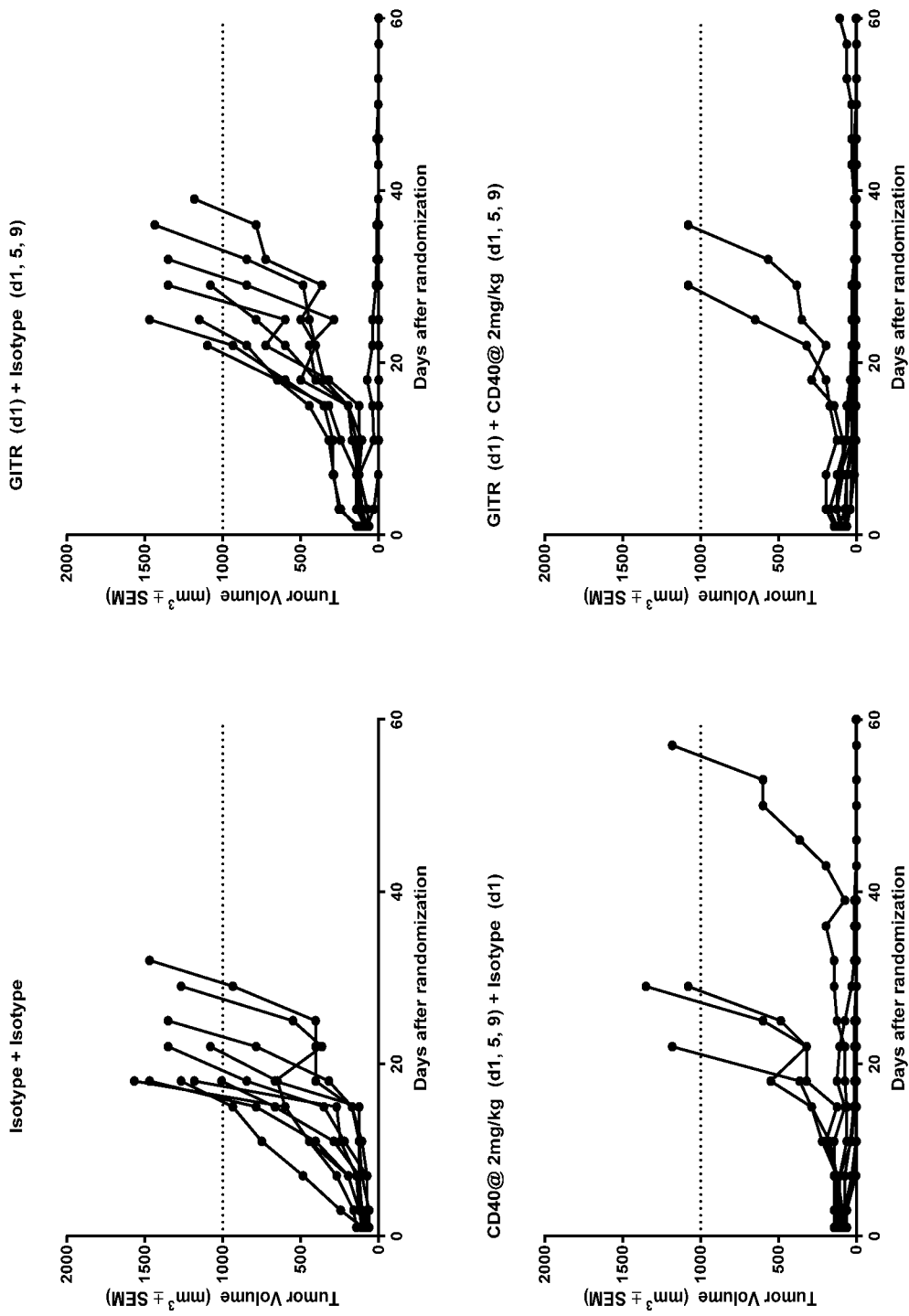

FIG. 29. DTA-1+FGK4.5 Treatment Leads to More Complete Tumor Regressions in MC38 Model Starting with 100 mm$^3$ Tumor Volumes.

Figure 30:
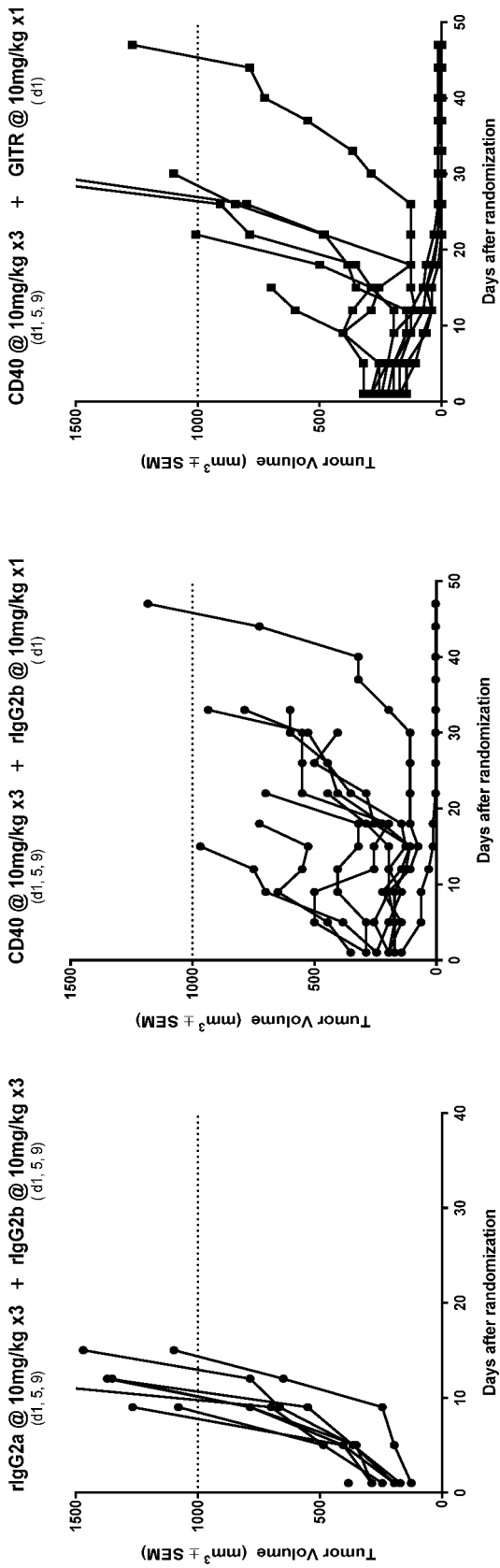

FIG. 30. DTA-1+FGK4.5 Treatment Leads to More Complete Tumor Regressions in MC38 Model Starting with 230 mm$^3$ Tumor Volumes.

Figure 31:
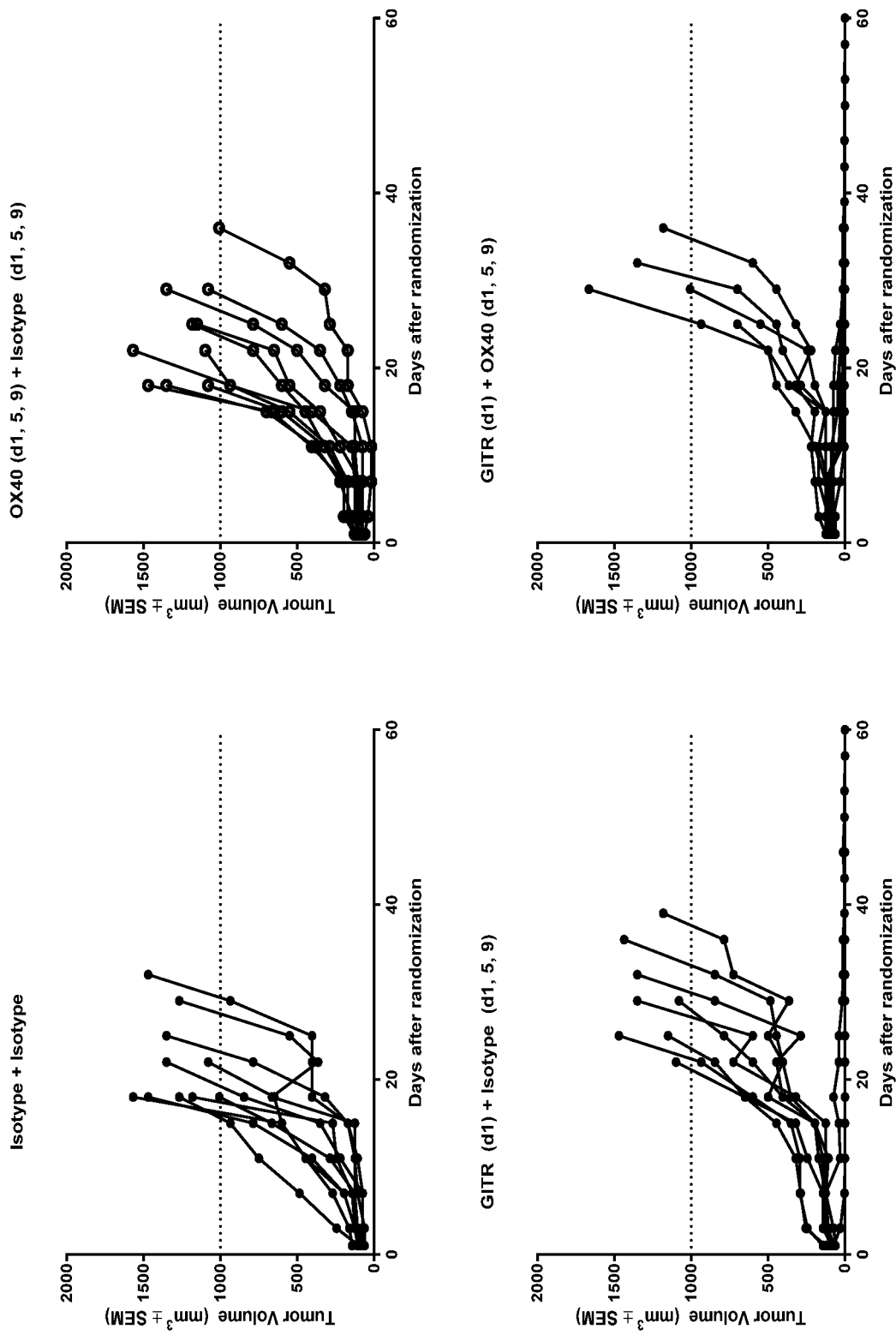

FIG. 31. DTA-1+OX86 Treatment Leads to More Complete Tumor Regressions in MC38 Model Starting with 100 mm$^3$ Tumor Volumes.

Figure 32:
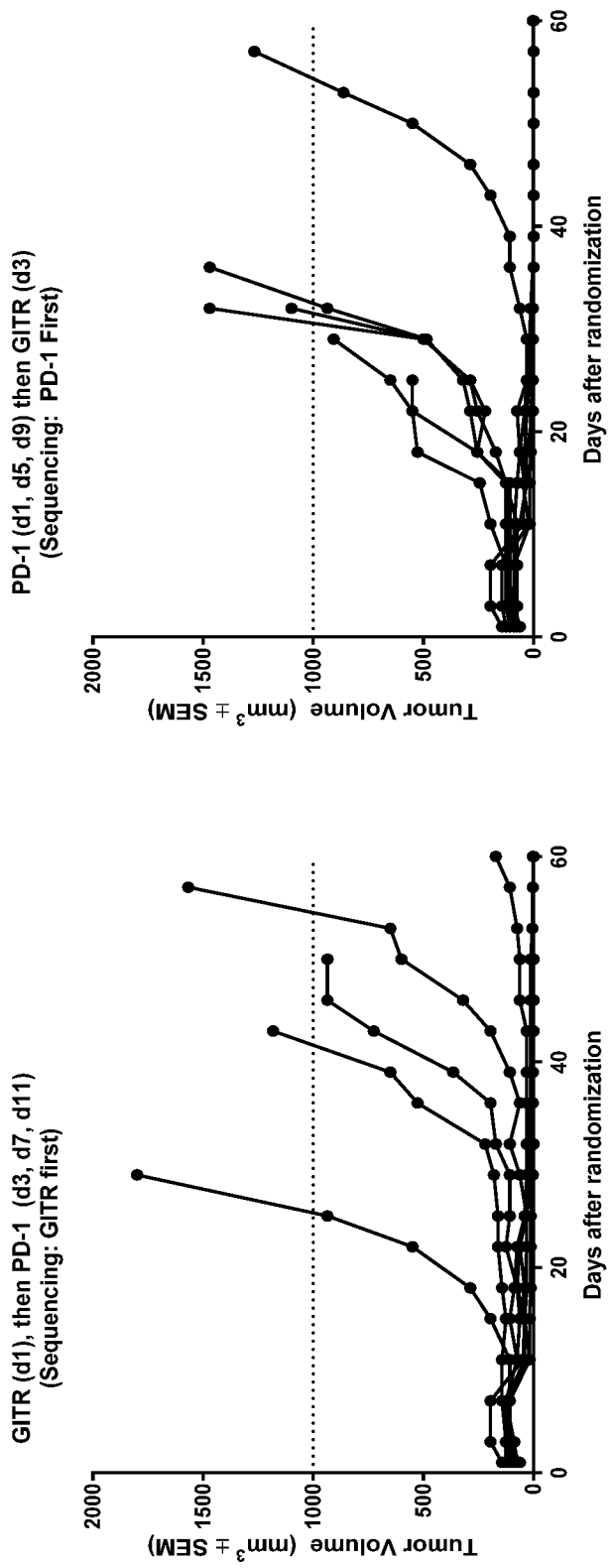

FIG. 32. DTA-1+RMPT-14 Treatment Leads to More Complete Tumor Regressions in MC38 Model Starting with 100 mm$^3$ Tumor Volumes.

DETAILED DESCRIPTION OF ILLUSTRATIVE EMBODIMENTS

Definitions

Various terms relating to aspects of the description are used throughout the specification and claims. Such terms are to be given their ordinary meaning in the art unless otherwise indicated. Other specifically defined terms are to be construed in a manner consistent with the definitions provided herein.

As used in this specification and the appended claims, the singular forms "a," "an," and "the" include plural referents unless the content clearly dictates otherwise. Thus, for example, reference to "a cell" includes a combination of two or more cells, and the like.

The term "about" as used herein when referring to a measurable value such as an amount, a temporal duration, and the like, is meant to encompass variations of up to ±10% from the specified value, as such variations are appropriate to perform the disclosed methods. Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

"Isolated" means a biological component (such as a nucleic acid, peptide or protein) has been substantially separated, produced apart from, or purified away from other biological components of the organism in which the component naturally occurs, i.e., other chromosomal and extrachromosomal DNA and RNA, and proteins. Nucleic acids, peptides and proteins that have been "isolated" thus include nucleic acids and proteins purified by standard purification methods. "Isolated" nucleic acids, peptides and proteins can be part of a composition and still be isolated if such composition is not part of the native environment of the nucleic acid, peptide, or protein. The term also embraces nucleic acids, peptides and proteins prepared by recombinant expression in a host cell as well as chemically synthesized nucleic acids. An "isolated" antibody or antigen-binding fragment, as used herein, is intended to refer to an antibody or antigen-binding fragment which is substantially free of other antibodies or antigen-binding fragments having different antigenic specificities (for instance, an isolated antibody that specifically binds to GITR is substantially free of antibodies that specifically bind antigens other than GITR). An isolated antibody that specifically binds to an epitope, isoform or variant of GITR may, however, have cross-reactivity to other related antigens, for instance from other species (such as GITR species homologs).

As used herein, the terms "glucocorticoid-induced TNFR-related protein" and "GITR" specifically include the human GITR protein, for example as described in GenBank Accession No. AF241229, NCBI Reference Sequence: NP_004186.1 and UniProtKB/Swiss-Prot Accession No. Q9Y5U5 (see also Kwon et al. 1999, J. Biol. Chem. 274, 6056-6061). GITR is also known in the scientific literature as AITR, CD357, TNFRSF18, and GITR-D.

As used herein, the terms "GITR ligand", "GITRL", and "GITR-L" refer to glucocorticoid-induced TNFR-related protein ligand. GITRL is otherwise known as activation-induced TNF-related ligand (AITRL) and tumor necrosis factor ligand superfamily member 18 (TNFSF18). GenBank accession number AF125303 provides an exemplary human GITRL nucleic acid sequence. GenBank™ accession number NP 005083 and Swiss-Prot accession number Q9UNG2 provide exemplary human GITRL amino acid sequences. In a particular embodiment, the GITRL is a human GITRL of SEQ ID NO: 65.

"Antibody" refers to all isotypes of immunoglobulins (IgG, IgA, IgE, IgM, IgD, and IgY) including various monomeric, polymeric and chimeric forms, unless otherwise specified. Specifically encompassed by the term "antibody" are polyclonal antibodies, monoclonal antibodies (mAbs), and antibody-like polypeptides, such as chimeric antibodies and humanized antibodies.

"Antigen-binding fragments" are any proteinaceous structure that may exhibit binding affinity for a particular antigen. Antigen-binding fragments include those provided by any known technique, such as enzymatic cleavage, peptide synthesis, and recombinant techniques. Some antigen-binding fragments are composed of portions of intact antibodies that retain antigen-binding specificity of the parent antibody molecule. For example, antigen-binding fragments may comprise at least one variable region (either a heavy chain or light chain variable region) or one or more CDRs of an antibody known to bind a particular antigen. Examples of suitable antigen-binding fragments include, without limitation diabodies and single-chain molecules as well as Fab, F(ab')2, Fc, Fabc, and Fv molecules, single chain (Sc) antibodies, individual antibody light chains, individual antibody heavy chains, chimeric fusions between antibody chains or CDRs and other proteins, protein scaffolds, heavy chain monomers or dimers, light chain monomers or dimers, dimers consisting of one heavy and one light chain, a monovalent fragment consisting of the VL, VH, CL and CH1 domains, or a monovalent antibody as described in WO2007059782, bivalent fragments comprising two Fab fragments linked by a disulfide bridge at the hinge region, a Fd fragment consisting essentially of the V.sub.H and C.sub.H1 domains; a Fv fragment consisting essentially of the VL and VH domains of a single arm of an antibody, a dAb fragment (Ward et al., Nature 341, 544-546 (1989)), which consists essentially of a VH domain and also called domain antibodies (Holt et al; Trends Biotechnol. 2003 November; 21(11):484-90); camelid or nanobodies (Revets et al; Expert Opin Biol Ther. 2005 January; 5(1): 111-24); an isolated complementarity determining region (CDR), and the like. All antibody isotypes may be used to produce antigen-binding fragments. Additionally, antigen-binding fragments may include non-antibody proteinaceous frameworks that may successfully incorporate polypeptide segments in an orientation that confers affinity for a given antigen of interest, such as protein scaffolds. Antigen-binding fragments may be recombinantly produced or produced by enzymatic or chemical cleavage of intact antibodies. The phrase "an antibody or antigen-binding fragment thereof" may be used to denote that a given antigen-binding fragment incorporates one or more amino acid segments of the antibody referred to in the phrase.

The terms "CDR", and its plural "CDRs", refer to a complementarity determining region (CDR) of which three make up the binding character of a light chain variable region (CDRL1, CDRL2 and CDRL3) and three make up the binding character of a heavy chain variable region (CDRH1, CDRH2 and CDRH3). CDRs contribute to the functional activity of an antibody molecule and are separated by amino acid sequences that comprise scaffolding or framework regions. The exact definitional CDR boundaries and lengths are subject to different classification and numbering systems. CDRs may therefore be referred to by Kabat, Chothia, contact or any other boundary definitions. Despite differing boundaries, each of these systems has some degree of overlap in what constitutes the so called "hypervariable regions" within the variable sequences. CDR definitions according to these systems may therefore differ in length and boundary areas with respect to the adjacent framework region. See for example Kabat et al., Sequences of Proteins of Immunological Interest, 5th ed. NIH Publication No. 91-3242 (1991); Chothia et al., "Canonical Structures For the Hypervariable Regions of Immunoglobulins," J. Mol. Biol. 196:901 (1987); and MacCallum et al., "Antibody-Antigen Interactions: Contact Analysis and Binding Site Topography," J. Mol. Biol. 262:732 (1996)), each of which is hereby incorporated by reference in its entirety.

Typically, CDRs form a loop structure that can be classified as a canonical structure. The term "canonical structure" refers to the main chain conformation that is adopted by the antigen binding (CDR) loops. From comparative structural studies, it has been found that five of the six antigen binding loops have only a limited repertoire of available conformations. Each canonical structure can be characterized by the torsion angles of the polypeptide backbone. Correspondent loops between antibodies may, therefore, have very similar three dimensional structures, despite high amino acid sequence variability in most parts of the loops (Chothia et al., "Canonical Structures For the Hypervariable Regions of Immunoglobulins," J. Mol. Biol. 196: 901 (1987); Chothia et al., "Conformations of Immunoglobulin Hypervariable Regions," I 342:877 (1989); Martin and Thornton, "Structural Families in Loops of Homologous Proteins: Automatic Classification, Modelling and Application to Antibodies," J. Mol. Biol. 263:800 (1996), each of which is incorporated by reference in its entirety). Furthermore, there is a relationship between the adopted loop structure and the amino acid sequences surrounding it. The conformation of a particular canonical class is determined by the length of the loop and the amino acid residues residing at key positions within the loop, as well as within the conserved framework (i.e., outside of the loop). Assignment to a particular canonical class can therefore be made based on the presence of these key amino acid residues.

The term "polypeptide" is used interchangeably with the term "protein" and in its broadest sense refers to a compound of two or more subunit amino acids, amino acid analogs or peptidomimetics. The subunits may be linked by peptide bonds. In another embodiment, the subunit may be linked by other bonds, e.g., ester, ether, etc. As used herein the term "amino acid" refers to either natural and/or unnatural or synthetic amino acids, including glycine and both the D and L optical isomers, amino acid analogs and peptidomimetics. A peptide of three or more amino acids is commonly called an oligopeptide if the peptide chain is short. If the peptide chain is long, the peptide is commonly called a polypeptide or a protein. "Specifically binds" or "binds specifically" or derivatives thereof when used in the context of antibodies, or antibody fragments, represents binding via domains encoded by immunoglobulin genes or fragments of immunoglobulin genes to one or more epitopes of a protein of interest, without preferentially binding other molecules in a sample containing a mixed population of molecules. Typically, an antibody binds to a cognate antigen with a $K_d$ of less than about $1 \times 10^{-8}$ M, as measured by a surface plasmon resonance assay or a cell-binding assay. Phrases such as "[antigen]-specific" antibody (e.g., GITR-specific antibody) are meant to convey that the recited antibody specifically binds the recited antigen.

"Polynucleotide," synonymously referred to as "nucleic acid molecule," "nucleotides" or "nucleic acids," refers to any polyribonucleotide or polydeoxyribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications may be made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short nucleic acid chains, often referred to as oligonucleotides.

A "vector" is a replicon, such as plasmid, phage, cosmid, or virus in which another nucleic acid segment may be operably inserted so as to bring about the replication or expression of the segment.

As used herein, the term "host cell" can be any type of cell, e.g., a primary cell, a cell in culture, or a cell from a cell line. In specific embodiments, the term "host cell" refers to a cell transfected with a nucleic acid molecule and the progeny or potential progeny of such a cell. Progeny of such a cell may not be identical to the parent cell transfected with the nucleic acid molecule, e.g., due to mutations or environmental influences that may occur in succeeding generations or integration of the nucleic acid molecule into the host cell genome. The terms "expression" and "production" are used synonymously herein, and refer to the biosynthesis of a gene product. These terms encompass the transcription of a gene into RNA. These terms also encompass translation of RNA into one or more polypeptides, and further encompass all naturally occurring post-transcriptional and post-translational modifications. The expression or production of an antibody or antigen-binding fragment thereof may be within the cytoplasm of the cell, or into the extracellular milieu such as the growth medium of a cell culture. The meaning of "substantially the same" can differ depending on the context in which the term is used. Because of the natural sequence variation likely to exist among heavy and light chains and the genes encoding them, one would expect to find some level of variation within the amino acid sequences or the genes encoding the antibodies or antigen-binding fragments described herein, with little or no impact on their unique binding properties (e.g., specificity and affinity). Such an expectation is due in part to the degeneracy of the genetic code, as well as to the evolutionary success of conservative amino acid sequence variations, which do not appreciably alter the nature of the encoded protein. Accordingly, in the context of nucleic acid sequences, "substantially the same" means at least 65% identity between two or more sequences. Preferably, the term refers to at least 70% identity between two or more sequences, more preferably at least 75% identity, more preferably at least 80% identity, more preferably at least 85% identity, more preferably at least 90% identity, more preferably at least 91% identity, more preferably at least 92% identity, more preferably at least 93% identity, more preferably at least 94% identity, more preferably at least 95% identity, more preferably at least 96% identity, more preferably at least 97% identity, more preferably at least 98% identity, and more preferably at least 99% or greater identity. The percent identity between two sequences is a function of the number of identical positions shared by the sequences (i.e., % homology=# of identical positions/total # of positions×100), taking into account the number of gaps, and the length of each gap, which need to be introduced for optimal alignment of the two sequences. The percent identity between two nucleotide or amino acid sequences may e.g. be determined using the algorithm of E. Meyers and W. Miller, Comput. Appl. Biosci 4, 11-17 (1988) which has been incorporated into the ALIGN program (version 2.0), using a PAM120 weight residue table, a gap length penalty of 12 and a gap penalty of 4. In addition, the percent identity between two amino acid sequences may be determined using the Needleman and Wunsch, J. Mol. Biol. 48, 444-453 (1970) algorithm.

The degree of variation that may occur within the amino acid sequence of a protein without having a substantial effect on protein function is much lower than that of a nucleic acid sequence, since the same degeneracy principles do not apply to amino acid sequences. Accordingly, in the context of an antibody or antigen-binding fragment, "substantially the same" means antibodies or antigen-binding fragments having 90%, 91%, 92%, 93%, 94%, 95%, 96%, 97%, 98%, or 99% identity to the antibodies or antigen-binding fragments described. Other embodiments include GITR-specific antibodies, or antigen-binding fragments, that have framework, scaffold, or other non-binding regions that do not share significant identity with the antibodies and antigen-binding fragments described herein, but do incorporate one or more CDRs or other sequences needed to confer binding that are 90%, 91%, 92%, 93%, 94%, 95%, 96%, 97%, 98%, or 99% identical to such sequences described herein.

"Binding affinity" generally refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($K_D$). Affinity can be measured and/or expressed in a number of ways known in the art, including, but not limited to, equilibrium dissociation constant ($K_D$), and equilibrium association constant ($K_A$). The $K_D$ is calculated from the quotient of $k_{off}/k_{on}$, whereas $K_A$ is calculated from the quotient of $k_{on}/k_{off}$. $k_{on}$ refers to the association rate constant of, e.g., an antibody to an antigen, and $k_{off}$ refers to the dissociation of, e.g., an antibody to an antigen. The $k_{on}$ and $k_{off}$ can be determined by techniques known to one of ordinary skill in the art, such as surface plasmon resonance.

The term "subject" refers to human and non-human animals, including all vertebrates, e.g., mammals and non-mammals, such as non-human primates, mice, rabbits, sheep, dogs, cats, horses, cows, chickens, amphibians, and reptiles. In many embodiments of the described methods, the subject is a human.

GITR-Specific Antibodies and Antigen-Binding Fragments

Described herein are isolated monoclonal antibodies or antigen-binding fragments that specifically bind GITR. The general structure of an antibody molecule comprises an antigen binding domain, which includes heavy and light chains, and the Fc domain, which serves a variety of functions, including complement fixation and binding antibody receptors.

The described GITR-specific antibodies or antigen-binding fragments include all isotypes, IgA, IgD, IgE, IgG and IgM, and synthetic multimers of the four-chain immunoglobulin structure. The described antibodies or antigen-binding fragments also include the IgY isotype generally found in hen or turkey serum and hen or turkey egg yolk.

The GITR-specific antibodies and antigen-binding fragments may be derived from any species by recombinant means. For example, the antibodies or antigen-binding fragments may be mouse, rat, goat, horse, swine, bovine, chicken, rabbit, camelid, donkey, human, or chimeric versions thereof. For use in administration to humans, non-human derived antibodies or antigen-binding fragments may be genetically or structurally altered to be less antigenic upon administration to a human patient.

In some embodiments, the antibodies or antigen-binding fragments are chimeric. As used herein, the term "chimeric" refers to an antibody, or antigen-binding fragment thereof, having at least some portion of at least one variable domain derived from the antibody amino acid sequence of a non-human mammal, a rodent, or a reptile, while the remaining portions of the antibody, or antigen-binding fragment thereof, are derived from a human.

In some embodiments, the antibodies are humanized antibodies. Humanized antibodies may be chimeric immunoglobulins, immunoglobulin chains or fragments thereof (such as Fv, Fab, Fab', F(ab')2 or other antigen-binding subsequences of antibodies) that contain minimal sequence derived from non-human immunoglobulin. For the most part, humanized antibodies are human immunoglobulins (recipient antibody) in which residues from a complementary-determining region (CDR) of the recipient are replaced by residues from a CDR of a non-human species (donor antibody) such as mouse, rat or rabbit having the desired specificity, affinity, and capacity. In general, the humanized antibody will comprise substantially all of at least one, and typically two, variable domains, in which all or substantially all of the CDR regions correspond to those of a non-human immunoglobulin and all or substantially all of the framework regions are those of a human immunoglobulin sequence. The humanized antibody may include at least a portion of an immunoglobulin constant region (Fc), typically that of a human immunoglobulin.

The antibodies or antigen-binding fragments described herein can occur in a variety of forms, but will include one or more of the antibody CDRs shown in Table 1. Described herein are isolated antibodies and antigen-binding fragments that specifically bind to GITR. In some embodiments, the GITR-specific antibodies or antigen-binding fragments are human IgG, or derivatives thereof. While the GITR-specific antibodies or antigen-binding fragments exemplified herein are human, the antibodies or antigen-binding fragments exemplified may be chimerized.

In some embodiments are provided a GITR-specific antibody, or an antigen-binding fragment thereof, comprising a heavy chain comprising a CDR1, a CDR2, and a CDR3 of any one of the antibodies described in Table 1 and a light chain comprising a CDR1, a CDR2, and a CDR3 of any one of the antibodies described in Table 1.

In some embodiments, the GITR-specific antibodies and antigen-binding fragments comprise a heavy chain CDR1 comprising SEQ ID NO: 1, a heavy chain CDR2 comprising SEQ ID NO: 5, a heavy chain CDR3 comprising SEQ ID NO: 12, a light chain CDR1 comprising SEQ ID NO: 28, a light chain CDR2 comprising SEQ ID NO: 32, and a light chain CDR3 comprising SEQ ID NO: 35. This GITR-specific antibody or antigen-binding fragment may comprise human framework sequences. This GITR-specific antibody or antigen-binding fragment may bind to GITR with an affinity of 30 nM or less, may induce an increase in luciferase expression in an NF-κB luciferase gene assay and may induce ADCC in vitro with an $EC_{50}$ of 67 ng/mL or less. In some embodiments, the GITR-specific antibodies and antigen-binding fragments comprise a heavy chain substantially the same as, or identical to, SEQ ID NO: 39 and a light chain substantially the same as, or identical to, SEQ ID NO: 55. The heavy chain and light chain of antibodies discussed in this paragraph are suitable for inclusion in bispecific constructs in which one arm is an anti-GITR arm.

In some embodiments, the GITR-specific antibodies and antigen-binding fragments comprise a heavy chain CDR1 comprising SEQ ID NO: 2, a heavy chain CDR2 comprising SEQ ID NO: 5, a heavy chain CDR3 comprising SEQ ID NO: 13, a light chain CDR1 comprising SEQ ID NO: 29, a light chain CDR2 comprising SEQ ID NO: 32, and a light chain CDR3 comprising SEQ ID NO: 36. This GITR-specific antibody or antigen-binding fragment may comprise human framework sequences. This GITR-specific antibody or antigen-binding fragment may bind to GITR with an affinity of 30 nM or less, may induce an increase in luciferase expression in an NF-κB luciferase gene assay and may induce ADCC in vitro with an $EC_{50}$ of 67 ng/mL or less. In some embodiments, the GITR-specific antibodies and antigen-binding fragments comprise a heavy chain substantially the same as, or identical to, SEQ ID NO: 40 and a light chain substantially the same as, or identical to, SEQ ID NO: 56 The heavy chain and light chain of antibodies discussed in this paragraph are suitable for inclusion in bispecific constructs in which one arm is an anti-GITR arm.

In some embodiments, the GITR-specific antibodies and antigen-binding fragments comprise a heavy chain CDR1 comprising SEQ ID NO: 1, a heavy chain CDR2 comprising SEQ ID NO: 6, a heavy chain CDR3 comprising SEQ ID NO: 14, a light chain CDR1 comprising SEQ ID NO: 30, a light chain CDR2 comprising SEQ ID NO: 33, and a light chain CDR3 comprising SEQ ID NO: 37. This GITR-specific antibody or antigen-binding fragment may comprise human framework sequences. This GITR-specific antibody or antigen-binding fragment may bind to GITR with an affinity of 30 nM or less, may induce an increase in luciferase expression in an NF-κB luciferase gene assay and may induce ADCC in vitro with an $EC_{50}$ of 67 ng/mL or less. In some embodiments, the GITR-specific antibodies and antigen-binding fragments comprise a heavy chain substantially the same as, or identical to, SEQ ID NO: 41 and a light chain substantially the same as, or identical to, SEQ ID NO: 57. The heavy chain and light chain of antibodies discussed in this paragraph are suitable for inclusion in bispecific constructs in which one arm is an anti-GITR arm.

In some embodiments, the GITR-specific antibodies and antigen-binding fragments comprise a heavy chain CDR1 comprising SEQ ID NO: 3, a heavy chain CDR2 comprising SEQ ID NO: 7, a heavy chain CDR3 comprising SEQ ID NO: 15, a light chain CDR1 comprising SEQ ID NO: 28, a light chain CDR2 comprising SEQ ID NO: 32, and a light chain CDR3 comprising SEQ ID NO: 35. This GITR-specific antibody or antigen-binding fragment may comprise human framework sequences. This GITR-specific antibody or antigen-binding fragment may bind to GITR with an affinity of 30 nM or less, may induce an increase in luciferase expression in an NF-κB luciferase gene assay and may induce ADCC in vitro with an $EC_{50}$ of 67 ng/mL or less. In some embodiments, the GITR-specific antibodies and antigen-binding fragments comprise a heavy chain substantially the same as, or identical to, SEQ ID NO: 42 and a light chain substantially the same as, or identical to, SEQ ID NO: 55. The heavy chain and light chain of antibodies discussed in this paragraph are suitable for inclusion in bispecific constructs in which one arm is an anti-GITR arm.

In some embodiments, the GITR-specific antibodies and antigen-binding fragments comprise a heavy chain CDR1 comprising SEQ ID NO: 3, a heavy chain CDR2 comprising SEQ ID NO: 7, a heavy chain CDR3 comprising SEQ ID NO: 16, a light chain CDR1 comprising SEQ ID NO: 28, a light chain CDR2 comprising SEQ ID NO: 32, and a light chain CDR3 comprising SEQ ID NO: 35. This GITR-specific antibody or antigen-binding fragment may comprise human framework sequences. This GITR-specific antibody or antigen-binding fragment may bind to GITR with an affinity of 30 nM or less, may induce an increase in luciferase expression in an NF-κB luciferase gene assay and may induce ADCC in vitro with an $EC_{50}$ of 67 ng/mL or less. In some embodiments, the GITR-specific antibodies and antigen-binding fragments comprise a heavy chain substantially the same as, or identical to, SEQ ID NO: 43 and a light chain substantially the same as, or identical to, SEQ ID NO: 55. The heavy chain and light chain of antibodies discussed in this paragraph are suitable for inclusion in bispecific constructs in which one arm is an anti-GITR arm.

In some embodiments, the GITR-specific antibodies and antigen-binding fragments comprise a heavy chain CDR1 comprising SEQ ID NO: 4, a heavy chain CDR2 comprising SEQ ID NO: 8, a heavy chain CDR3 comprising SEQ ID NO: 17, a light chain CDR1 comprising SEQ ID NO: 28, a light chain CDR2 comprising SEQ ID NO: 32, and a light chain CDR3 comprising SEQ ID NO: 35. This GITR-specific antibody or antigen-binding fragment may comprise human framework sequences. This GITR-specific antibody or antigen-binding fragment may bind to GITR with an affinity of 30 nM or less, may induce an increase in luciferase expression in an NF-κB luciferase gene assay and may induce ADCC in vitro with an $EC_{50}$ of 67 ng/mL or less. In some embodiments, the GITR-specific antibodies and antigen-binding fragments comprise a heavy chain substantially the same as, or identical to, SEQ ID NO: 44 and a light chain substantially the same as, or identical to, SEQ ID NO: 55. The heavy chain and light chain of antibodies discussed in this paragraph are suitable for inclusion in bispecific constructs in which one arm is an anti-GITR arm.

In some embodiments, the GITR-specific antibodies and antigen-binding fragments comprise a heavy chain CDR1 comprising SEQ ID NO: 4, a heavy chain CDR2 comprising SEQ ID NO: 9, a heavy chain CDR3 comprising SEQ ID NO: 18, a light chain CDR1 comprising SEQ ID NO: 28, a light chain CDR2 comprising SEQ ID NO: 32, and a light chain CDR3 comprising SEQ ID NO: 35. This GITR-specific antibody or antigen-binding fragment may comprise human framework sequences. This GITR-specific antibody or antigen-binding fragment may bind to GITR with an affinity of 30 nM or less, may induce an increase in luciferase expression in an NF-κB luciferase gene assay and may induce ADCC in vitro with an $EC_{50}$ of 67 ng/mL or less. In some embodiments, the GITR-specific antibodies and antigen-binding fragments comprise a heavy chain substantially the same as, or identical to, SEQ ID NO: 45 and a light chain substantially the same as, or identical to, SEQ ID NO: 55. The heavy chain and light chain of antibodies discussed in this paragraph are suitable for inclusion in bispecific constructs in which one arm is an anti-GITR arm.

In some embodiments, the GITR-specific antibodies and antigen-binding fragments comprise a heavy chain CDR1 comprising SEQ ID NO: 4, a heavy chain CDR2 comprising SEQ ID NO: 10, a heavy chain CDR3 comprising SEQ ID NO: 19, a light chain CDR1 comprising SEQ ID NO: 28, a light chain CDR2 comprising SEQ ID NO: 32, and a light chain CDR3 comprising SEQ ID NO: 35. This GITR-specific antibody or antigen-binding fragment may comprise human framework sequences. This GITR-specific antibody or antigen-binding fragment may bind to GITR with an affinity of 30 nM or less, may induce an increase in luciferase expression in an NF-κB luciferase gene assay and may induce ADCC in vitro with an $EC_{50}$ of 67 ng/mL or less. In some embodiments, the GITR-specific antibodies and antigen-binding fragments comprise a heavy chain substantially the same as, or identical to, SEQ ID NO: 46 and a light chain substantially the same as, or identical to, SEQ ID NO: 55. The heavy chain and light chain of antibodies discussed in this paragraph are suitable for inclusion in bispecific constructs in which one arm is an anti-GITR arm.

In some embodiments, the GITR-specific antibodies and antigen-binding fragments comprise a heavy chain CDR1 comprising SEQ ID NO: 3, a heavy chain CDR2 comprising SEQ ID NO: 7, a heavy chain CDR3 comprising SEQ ID NO: 20, a light chain CDR1 comprising SEQ ID NO: 31, a light chain CDR2 comprising SEQ ID NO: 34, and a light chain CDR3 comprising SEQ ID NO: 38. This GITR-specific antibody or antigen-binding fragment may comprise human framework sequences. This GITR-specific antibody or antigen-binding fragment may bind to GITR with an affinity of 30 nM or less, may induce an increase in luciferase expression in an NF-κB luciferase gene assay and may induce ADCC in vitro with an $EC_{50}$ of 67 ng/mL or less. In some embodiments, the GITR-specific antibodies and antigen-binding fragments comprise a heavy chain substantially the same as, or identical to, SEQ ID NO: 47 and a light chain substantially the same as, or identical to, SEQ ID NO: 58. The heavy chain and light chain of antibodies discussed in this paragraph are suitable for inclusion in bispecific constructs in which one arm is an anti-GITR arm.

In some embodiments, the GITR-specific antibodies and antigen-binding fragments comprise a heavy chain CDR1 comprising SEQ ID NO: 3, a heavy chain CDR2 comprising SEQ ID NO: 11, a heavy chain CDR3 comprising SEQ ID NO: 21, a light chain CDR1 comprising SEQ ID NO: 31, a light chain CDR2 comprising SEQ ID NO: 34, and a light chain CDR3 comprising SEQ ID NO: 38. This GITR-specific antibody or antigen-binding fragment may comprise human framework sequences. This GITR-specific antibody or antigen-binding fragment may bind to GITR with an affinity of 30 nM or less, may induce an increase in luciferase expression in an NF-κB luciferase gene assay and may induce ADCC in vitro with an $EC_{50}$ of 67 ng/mL or less. In some embodiments, the GITR-specific antibodies and antigen-binding fragments comprise a heavy chain substantially the same as, or identical to, SEQ ID NO: 48 and a light chain substantially the same as, or identical to, SEQ ID NO: 58. The heavy chain and light chain of antibodies discussed in this paragraph are suitable for inclusion in bispecific constructs in which one arm is an anti-GITR arm.

In some embodiments, the GITR-specific antibodies and antigen-binding fragments comprise a heavy chain CDR1 comprising SEQ ID NO: 3, a heavy chain CDR2 comprising SEQ ID NO: 7, a heavy chain CDR3 comprising SEQ ID NO: 22, a light chain CDR1 comprising SEQ ID NO: 28, a light chain CDR2 comprising SEQ ID NO: 32, and a light chain CDR3 comprising SEQ ID NO: 35. This GITR-specific antibody or antigen-binding fragment may comprise human framework sequences. This GITR-specific antibody or antigen-binding fragment may bind to GITR with an affinity of 30 nM or less, may induce an increase in luciferase expression in an NF-κB luciferase gene assay and may induce ADCC in vitro with an $EC_{50}$ of 67 ng/mL or less. In some embodiments, the GITR-specific antibodies and antigen-binding fragments comprise a heavy chain substantially the same as, or identical to, SEQ ID NO: 49 and a light chain substantially the same as, or identical to, SEQ ID NO: 55. The heavy chain and light chain of antibodies discussed in this paragraph are suitable for inclusion in bispecific constructs in which one arm is an anti-GITR arm.

In some embodiments, the GITR-specific antibodies and antigen-binding fragments comprise a heavy chain CDR1 comprising SEQ ID NO: 3, a heavy chain CDR2 comprising SEQ ID NO: 7, a heavy chain CDR3 comprising SEQ ID NO: 23, a light chain CDR1 comprising SEQ ID NO: 28, a light chain CDR2 comprising SEQ ID NO: 32, and a light chain CDR3 comprising SEQ ID NO: 35. This GITR-specific antibody or antigen-binding fragment may comprise human framework sequences. This GITR-specific antibody or antigen-binding fragment may bind to GITR with an affinity of 30 nM or less, may induce an increase in luciferase expression in an NF-κB luciferase gene assay and may induce ADCC in vitro with an $EC_{50}$ of 67 ng/mL or less. In some embodiments, the GITR-specific antibodies and antigen-binding fragments comprise a heavy chain substantially the same as, or identical to, SEQ ID NO: 50 and a light chain substantially the same as, or identical to, SEQ ID NO: 55. The heavy chain and light chain of antibodies discussed in this paragraph are suitable for inclusion in bispecific constructs in which one arm is an anti-GITR arm.

In some embodiments, the GITR-specific antibodies and antigen-binding fragments comprise a heavy chain CDR1 comprising SEQ ID NO: 3, a heavy chain CDR2 comprising SEQ ID NO: 7, a heavy chain CDR3 comprising SEQ ID NO: 24, a light chain CDR1 comprising SEQ ID NO: 28, a light chain CDR2 comprising SEQ ID NO: 32, and a light chain CDR3 comprising SEQ ID NO: 35. This GITR-specific antibody or antigen-binding fragment may comprise human framework sequences. This GITR-specific antibody or antigen-binding fragment may bind to GITR with an affinity of 30 nM or less, may induce an increase in luciferase expression in an NF-κB luciferase gene assay and may induce ADCC in vitro with an $EC_{50}$ of 67 ng/mL or less. In some embodiments, the GITR-specific antibodies and antigen-binding fragments comprise a heavy chain substantially the same as, or identical to, SEQ ID NO: 51 and a light chain substantially the same as, or identical to, SEQ ID NO: 55. The heavy chain and light chain of antibodies discussed in this paragraph are suitable for inclusion in bispecific constructs in which one arm is an anti-GITR arm.

In some embodiments, the GITR-specific antibodies and antigen-binding fragments comprise a heavy chain CDR1 comprising SEQ ID NO: 3, a heavy chain CDR2 comprising SEQ ID NO: 7, a heavy chain CDR3 comprising SEQ ID NO: 25, a light chain CDR1 comprising SEQ ID NO: 28, a light chain CDR2 comprising SEQ ID NO: 32, and a light chain CDR3 comprising SEQ ID NO: 35. This GITR-specific antibody or antigen-binding fragment may comprise human framework sequences. This GITR-specific antibody or antigen-binding fragment may bind to GITR with an affinity of 30 nM or less, may induce an increase in luciferase expression in an NF-κB luciferase gene assay and may induce ADCC in vitro with an $EC_{50}$ of 67 ng/mL or less.

In some embodiments, the GITR-specific antibodies and antigen-binding fragments comprise a heavy chain substantially the same as, or identical to, SEQ ID NO: 52 and a light chain substantially the same as, or identical to, SEQ ID NO: 55. The heavy chain and light chain of antibodies discussed in this paragraph are suitable for inclusion in bispecific constructs in which one arm is an anti-GITR arm.

In some embodiments, the GITR-specific antibodies and antigen-binding fragments comprise a heavy chain CDR1 comprising SEQ ID NO: 27, a heavy chain CDR2 comprising SEQ ID NO: 5, a heavy chain CDR3 comprising SEQ ID NO: 26, a light chain CDR1 comprising SEQ ID NO: 28, a light chain CDR2 comprising SEQ ID NO: 32, and a light chain CDR3 comprising SEQ ID NO: 35. This GITR-specific antibody or antigen-binding fragment may comprise human framework sequences. This GITR-specific antibody or antigen-binding fragment may bind to GITR with an affinity of 30 nM or less, may induce an increase in luciferase expression in an NF-κB luciferase gene assay and may induce ADCC in vitro with an $EC_{50}$ of 67 ng/mL or less. In some embodiments, the GITR-specific antibodies and antigen-binding fragments comprise a heavy chain substantially the same as, or identical to, SEQ ID NO: 53 and a light chain substantially the same as, or identical to, SEQ ID NO:

55. The heavy chain and light chain of antibodies discussed in this paragraph are suitable for inclusion in bispecific constructs in which one arm is an anti-GITR arm.

In some embodiments, the GITR-specific antibodies and antigen-binding fragments comprise a heavy chain CDR1 comprising SEQ ID NO: 3, a heavy chain CDR2 comprising SEQ ID NO: 11, a heavy chain CDR3 comprising SEQ ID NO: 21, a light chain CDR1 comprising SEQ ID NO: 28, a light chain CDR2 comprising SEQ ID NO: 32, and a light chain CDR3 comprising SEQ ID NO: 35. This GITR-specific antibody or antigen-binding fragment may comprise human framework sequences. This GITR-specific antibody or antigen-binding fragment may bind to GITR with an affinity of 30 nM or less, may induce an increase in luciferase expression in an NF-κB luciferase gene assay and may induce ADCC in vitro with an $EC_{50}$ of 67 ng/mL or less. In some embodiments, the GITR-specific antibodies and antigen-binding fragments comprise a heavy chain substantially the same as, or identical to, SEQ ID NO: 54 and a light chain substantially the same as, or identical to, SEQ ID NO: 55. The heavy chain and light chain of antibodies discussed in this paragraph are suitable for inclusion in bispecific constructs in which one arm is an anti-GITR arm.

In some embodiments, the GITR-specific antibodies and antigen-binding fragments comprise a heavy chain CDR1 comprising SEQ ID NO: 3, a heavy chain CDR2 comprising SEQ ID NO: 7, a heavy chain CDR3 comprising SEQ ID NO: 16, a light chain CDR1 comprising SEQ ID NO: 28, a light chain CDR2 comprising SEQ ID NO: 32, and a light chain CDR3 comprising SEQ ID NO: 35. This GITR-specific antibody or antigen-binding fragment may comprise human framework sequences. This GITR-specific antibody or antigen-binding fragment may bind to GITR with an affinity of 30 nM or less, may induce an increase in luciferase expression in an NF-κB luciferase gene assay and may induce ADCC in vitro with an $EC_{50}$ of 67 ng/mL or less. In some embodiments, the GITR-specific antibodies and antigen-binding fragments comprise a heavy chain substantially the same as, or identical to, SEQ ID NO: 63 and a light chain substantially the same as, or identical to, SEQ ID NO: 55. The heavy chain and light chain of antibodies discussed in this paragraph are suitable for inclusion in bispecific constructs in which one arm is an anti-GITR arm.

In some embodiments, the GITR-specific antibodies and antigen-binding fragments comprise a heavy chain CDR1 comprising SEQ ID NO: 27, a heavy chain CDR2 comprising SEQ ID NO: 5, a heavy chain CDR3 comprising SEQ ID NO: 26, a light chain CDR1 comprising SEQ ID NO: 28, a light chain CDR2 comprising SEQ ID NO: 32, and a light chain CDR3 comprising SEQ ID NO: 35. This GITR-specific antibody or antigen-binding fragment may comprise human framework sequences. This GITR-specific antibody or antigen-binding fragment may bind to GITR with an affinity of 30 nM or less, may induce an increase in luciferase expression in an NF-κB luciferase gene assay and may induce ADCC in vitro with an $EC_{50}$ of 67 ng/mL or less. In some embodiments, the GITR-specific antibodies and antigen-binding fragments comprise a heavy chain substantially the same as, or identical to, SEQ ID NO: 64 and a light chain substantially the same as, or identical to, SEQ ID NO: 55. The heavy chain and light chain of antibodies discussed in this paragraph are suitable for inclusion in bispecific constructs in which one arm is an anti-GITR arm.

Also disclosed are isolated polynucleotides that encode the antibodies or antigen-binding fragments that specifically bind to GITR. The isolated polynucleotides capable of encoding the variable domain segments provided herein may be included on the same, or different, vectors to produce antibodies or antigen-binding fragments. Polynucleotides encoding recombinant antigen-binding proteins also are within the scope of the disclosure. In some embodiments, the polynucleotides described (and the peptides they encode) include a leader sequence. Any leader sequence known in the art may be employed. The leader sequence may include, but is not limited to, a restriction site or a translation start site.

The GITR-specific antibodies or antigen-binding fragments described herein include variants having single or multiple amino acid substitutions, deletions, or additions that retain the biological properties (e.g., binding affinity or immune effector activity) of the described GITR-specific antibodies or antigen-binding fragments. These variants may include: (a) variants in which one or more amino acid residues are substituted with conservative or nonconservative amino acids, (b) variants in which one or more amino acids are added to or deleted from the polypeptide, (c) variants in which one or more amino acids include a substituent group, and (d) variants in which the polypeptide is fused with another peptide or polypeptide such as a fusion partner, a protein tag or other chemical moiety, that may confer useful properties to the polypeptide, such as, for example, an epitope for an antibody, a polyhistidine sequence, a biotin moiety and the like. Antibodies or antigen-binding fragments described herein may include variants in which amino acid residues from one species are substituted for the corresponding residue in another species, either at the conserved or nonconserved positions. In other embodiments, amino acid residues at nonconserved positions are substituted with conservative or nonconservative residues. The techniques for obtaining these variants, including genetic (deletions, mutations, etc.), chemical, and enzymatic techniques, are known to persons having ordinary skill in the art.

The GITR-specific antibodies or antigen-binding fragments described herein may embody several antibody isotypes, such as IgM, IgD, IgG, IgA and IgE. In some embodiments the antibody isotype is IgG1, IgG2, IgG3, or IgG4 isotype, preferably IgG1 isotype. Antibody or antigen-binding fragment thereof specificity is largely determined by the amino acid sequence, and arrangement, of the CDRs. Therefore, the CDRs of one isotype may be transferred to another isotype without altering antigen specificity. Alternatively, techniques have been established to cause hybridomas to switch from producing one antibody isotype to another (isotype switching) without altering antigen specificity. Accordingly, such antibody isotypes are within the scope of the described antibodies or antigen-binding fragments.

The GITR-specific antibodies or antigen-binding fragments described herein have binding affinities for GITR that include a dissociation constant ($K_D$) of less than about 30 nM. The affinity of the described GITR-specific antibodies, or antigen-binding fragments, may be determined by a variety of methods known in the art, such as surface plasmon resonance or ELISA-based methods. Assays for measuring affinity by SPR include assays performed using a BIAcore 3000 machine, where the assay is performed at room temperature (e.g. at or near 25° C.), wherein the antibody capable of binding to GITR is captured on the BIAcore sensor chip by an anti-Fc antibody (e.g. goat anti-human IgG Fc specific antibody Jackson ImmunoResearch laboratories Prod #109-005-098) to a level around 75 RUs, followed by the collection of association and dissociation data at a flow rate of 40 μl/min.

Also provided are vectors comprising the polynucleotides described herein. The vectors can be expression vectors. Recombinant expression vectors containing a sequence encoding a polypeptide of interest are thus contemplated as within the scope of this disclosure. The expression vector may contain one or more additional sequences such as but not limited to regulatory sequences (e.g., promoter, enhancer), a selection marker, and a polyadenylation signal. Vectors for transforming a wide variety of host cells are well known and include, but are not limited to, plasmids, phagemids, cosmids, baculoviruses, bacmids, bacterial artificial chromosomes (BACs), yeast artificial chromosomes (YACs), as well as other bacterial, yeast and viral vectors.

Recombinant expression vectors within the scope of the description include synthetic, genomic, or cDNA-derived nucleic acid fragments that encode at least one recombinant protein which may be operably linked to suitable regulatory elements. Such regulatory elements may include a transcriptional promoter, sequences encoding suitable mRNA ribosomal binding sites, and sequences that control the termination of transcription and translation. Expression vectors, especially mammalian expression vectors, may also include one or more nontranscribed elements such as an origin of replication, a suitable promoter and enhancer linked to the gene to be expressed, other 5' or 3' flanking nontranscribed sequences, 5' or 3' nontranslated sequences (such as necessary ribosome binding sites), a polyadenylation site, splice donor and acceptor sites, or transcriptional termination sequences. An origin of replication that confers the ability to replicate in a host may also be incorporated.

The transcriptional and translational control sequences in expression vectors to be used in transforming vertebrate cells may be provided by viral sources. Exemplary vectors may be constructed as described by Okayama and Berg, 3 *Mol. Cell. Biol.* 280 (1983).

In some embodiments, the antibody- or antigen-binding fragment-coding sequence is placed under control of a powerful constitutive promoter, such as the promoters for the following genes: hypoxanthine phosphoribosyl transferase (HPRT), adenosine deaminase, pyruvate kinase, beta-actin, human myosin, human hemoglobin, human muscle creatine, and others. In addition, many viral promoters function constitutively in eukaryotic cells and are suitable for use with the described embodiments. Such viral promoters include without limitation, Cytomegalovirus (CMV) immediate early promoter, the early and late promoters of SV40, the Mouse Mammary Tumor Virus (MMTV) promoter, the long terminal repeats (LTRs) of Maloney leukemia virus, Human Immunodeficiency Virus (HIV), Epstein Barr Virus (EBV), Rous Sarcoma Virus (RSV), and other retroviruses, and the thymidine kinase promoter of Herpes Simplex Virus. In one embodiment, the GITR-specific antibody or antigen-binding fragment thereof coding sequence is placed under control of an inducible promoter such as the metallothionein promoter, tetracycline-inducible promoter, doxycycline-inducible promoter, promoters that contain one or more interferon-stimulated response elements (ISRE) such as protein kinase R 2',5'-oligoadenylate synthetases, Mx genes, ADAR1, and the like.

Vectors described herein may contain one or more Internal Ribosome Entry Site(s) (IRES). Inclusion of an IRES sequence into fusion vectors may be beneficial for enhancing expression of some proteins. In some embodiments the vector system will include one or more polyadenylation sites (e.g., SV40), which may be upstream or downstream of any of the aforementioned nucleic acid sequences. Vector components may be contiguously linked, or arranged in a manner that provides optimal spacing for expressing the gene products (i.e., by the introduction of "spacer" nucleotides between the ORFs), or positioned in another way. Regulatory elements, such as the IRES motif, may also be arranged to provide optimal spacing for expression.

The vectors may comprise selection markers, which are well known in the art. Selection markers include positive and negative selection markers, for example, antibiotic resistance genes (e.g., neomycin resistance gene, a hygromycin resistance gene, a kanamycin resistance gene, a tetracycline resistance gene, a penicillin resistance gene), glutamate synthase genes, HSV-TK, HSV-TK derivatives for ganciclovir selection, or bacterial purine nucleoside phosphorylase gene for 6-methylpurine selection (Gadi et al., 7 *Gene Ther.* 1738-1743 (2000)). A nucleic acid sequence encoding a selection marker or the cloning site may be upstream or downstream of a nucleic acid sequence encoding a polypeptide of interest or cloning site.

The vectors described herein may be used to transform various cells with the genes encoding the described antibodies or antigen-binding fragments. For example, the vectors may be used to generate GITR-specific antibody or antigen-binding fragment-producing cells. Thus, another aspect features host cells transformed with vectors comprising a nucleic acid sequence encoding an antibody or antigen-binding fragment thereof that specifically binds GITR, such as the antibodies or antigen-binding fragments described and exemplified herein.

Numerous techniques are known in the art for the introduction of foreign genes into cells and may be used to construct the recombinant cells for purposes of carrying out the described methods, in accordance with the various embodiments described and exemplified herein. The technique used should provide for the stable transfer of the heterologous gene sequence to the host cell, such that the heterologous gene sequence is heritable and expressible by the cell progeny, and so that the necessary development and physiological functions of the recipient cells are not disrupted. Techniques which may be used include but are not limited to chromosome transfer (e.g., cell fusion, chromosome mediated gene transfer, micro cell mediated gene transfer), physical methods (e.g., transfection, spheroplast fusion, microinjection, electroporation, liposome carrier), viral vector transfer (e.g., recombinant DNA viruses, recombinant RNA viruses) and the like (described in Cline, 29 *Pharmac. Ther.* 69-92 (1985)). Calcium phosphate precipitation and polyethylene glycol (PEG)-induced fusion of bacterial protoplasts with mammalian cells may also be used to transform cells. Cells suitable for use in the expression of the GITR-specific antibodies or antigen-binding fragments described herein are preferably eukaryotic cells, more preferably cells of plant, rodent, or human origin, for example but not limited to NSO, CHO, CHOK1, perC.6, Tk-ts13, BHK, HEK293 cells, COS-7, T98G, CV-1/EBNA, L cells, C127, 3T3, HeLa, NS1, Sp2/0 myeloma cells, and BHK cell lines, among others. In addition, expression of antibodies may be accomplished using hybridoma cells. Methods for producing hybridomas are well established in the art.

Cells transformed with expression vectors described herein may be selected or screened for recombinant expression of the antibodies or antigen-binding fragments described herein. Recombinant-positive cells are expanded and screened for subclones exhibiting a desired phenotype, such as high level expression, enhanced growth properties, or the ability to yield proteins with desired biochemical characteristics, for example, due to protein modification or altered post-translational modifications. These phenotypes may be due to inherent properties of a given subclone or to mutation. Mutations may be effected through the use of chemicals, UV-wavelength light, radiation, viruses, insertional mutagens, inhibition of DNA mismatch repair, or a combination of such methods.

Methods of Using GITR-Specific Antibodies for Treatment

Provided herein are GITR-specific antibodies or antigen-binding fragments thereof for use in therapy. In particular, these antibodies or antigen-binding fragments may be useful in treating cancer. Accordingly, the invention provides a method of treating cancer comprising administering an antibody as described herein, such as GITR-specific antibodies or antigen-binding fragments. A couple aspects of GITR biology make it a potential target for the treatment of a variety of cancers. The first is that GITR activation, as described at length above, activates the immune system. Additionally, GITR-expressing effector T cells and regulatory T cells infiltrate multiple tumor types, yet there is little or no expression of GITR on non-hematopoetic cells. This distribution profile means that GITR-expressing cells can become concentrated at tumors. This combination of activities and distribution collectively makes GITR targeting an attractive approach for treating a variety of cancers. The antigen binding proteins can be used to treat both solid tumors, as well as hematological cancers, including leukemia.

The antibodies for use in these methods include those described herein above, for example a GITR-specific antibody or antigen-binding fragment with the features set out in Table 1, for example the CDRs or variable domain sequences, and in the further discussion of these antibodies.

In some embodiments described herein, immune effector properties of the GITR-specific antibodies may be modulated through Fc modifications by techniques known to those skilled in the art. For example, Fc effector functions such as Clq binding, complement dependent cytotoxicity (CDC), antibody-dependent cell-mediated cytotoxicity (ADCC), antibody-dependent cell-mediated phagocytosis (ADCP), down regulation of cell surface receptors (e.g., B cell receptor; BCR), etc. may be provided and/or controlled by modifying residues in the Fc responsible for these activities. "Antibody-dependent cell-mediated cytotoxicity" or "ADCC" refers to a cell-mediated reaction in which non-specific cytotoxic cells that express Fc receptors (FcRs) (e.g. Natural Killer (NK) cells, neutrophils, and macrophages) recognize bound antibody on a target cell and subsequently cause lysis of the target cell.

The ability of monoclonal antibodies to induce ADCC can be enhanced by engineering their oligosaccharide component. Human IgG1 or IgG3 are N-glycosylated at Asn297 with the majority of the glycans in the well-known biantennary G0, G0F, G1, G1F, G2 or G2F forms. Antibodies produced by non-engineered CHO cells typically have a glycan fucose content of about at least 85%. The removal of the core fucose from the biantennary complex-type oligosaccharides attached to the Fc regions enhances the ADCC of antibodies via improved Fc.gamma.RIIIa binding without altering antigen binding or CDC activity. Such mAbs can be achieved using different methods reported to lead to the successful expression of relatively high defucosylated antibodies bearing the biantennary complex-type of Fc oligosaccharides such as control of culture osmolality (Konno et al., Cytotechnology 64:249-65, 2012), application of a variant CHO line Lec13 as the host cell line (Shields et al., J Biol Chem 277:26733-26740, 2002), application of a variant CHO line EB66 as the host cell line (Olivier et al., MAbs; 2(4), 2010; Epub ahead of print; PMID:20562582), application of a rat hybridoma cell line YB2/0 as the host cell line (Shinkawa et al., J Biol Chem 278:3466-3473, 2003), introduction of small interfering RNA specifically against the .alpha. 1,6-fucosyltrasferase (FUT8) gene (Mori et al., Biotechnol Bioeng 88:901-908, 2004), or coexpression of .beta.-1,4-N-acetylglucosaminyltransferase III and Golgi .alpha.-mannosidase II or a potent alpha-mannosidase I inhibitor, kifunensine (Ferrara et al., J Biol Chem 281:5032-5036, 2006, Ferrara et al., Biotechnol Bioeng 93:851-861, 2006; Xhou et al., Biotechnol Bioeng 99:652-65, 2008).

In some embodiments described herein, ADCC elicited by the GITR antibodies may also be enhanced by certain substitutions in the antibody Fc. Exemplary substitutions are for example substitutions at amino acid positions 256, 290, 298, 312, 356, 330, 333, 334, 360, 378 or 430 (residue numbering according to the EU index) as described in U.S. Pat. No. 6,737,056.

Pharmaceutical Compositions and Administration

The pharmaceutical compositions provided herein comprise: a) an effective amount of a GITR-specific antibody or antibody fragment of the present invention, and b) a pharmaceutically acceptable carrier, which may be inert or physiologically active. In preferred embodiments, the GITR-specific antibody is a GITR-specific antibody as described herein, or an antigen-binding fragment thereof. As used herein, the term "pharmaceutically acceptable carriers" includes any and all solvents, dispersion media, coatings, antibacterial and antifungal agents, and the like that are physiologically compatible. Examples of suitable carriers, diluents and/or excipients include one or more of water, saline, phosphate buffered saline, dextrose, glycerol, ethanol, and the like, as well as any combination thereof. In many cases, it will be preferable to include isotonic agents, such as sugars, polyalcohols, or sodium chloride in the composition. In particular, relevant examples of suitable carrier include: (1) Dulbecco's phosphate buffered saline, pH.about.7.4, containing or not containing about 1 mg/mL to 25 mg/mL human serum albumin, (2) 0.9% saline (0.9% w/v sodium chloride (NaCl)), and (3) 5% (w/v) dextrose; and may also contain an antioxidant such as tryptamine and a stabilizing agent such as Tween 20®.

The compositions herein may also contain a further therapeutic agent, as necessary for the particular disorder being treated. Preferably, the GITR-specific antibody or antibody fragment and the supplementary active compound will have complementary activities that do not adversely affect each other. In a preferred embodiment, the further therapeutic agent is cytarabine, an anthracycline, histamine dihydrochloride, or interleukin 2. In a preferred embodiment, the further therapeutic agent is a chemotherapeutic agent.

The compositions of the invention may be in a variety of forms. These include for example liquid, semi-solid, and solid dosage forms, but the preferred form depends on the intended mode of administration and therapeutic application. Typical preferred compositions are in the form of injectable or infusible solutions. The preferred mode of administration is parenteral (e.g. intravenous, intramuscular, intraperitoneal, subcutaneous). In a preferred embodiment, the compositions of the invention are administered intravenously as a bolus or by continuous infusion over a period of time. In another preferred embodiment, they are injected by intramuscular, subcutaneous, intra-articular, intrasynovial, intratumoral, peritumoral, intralesional, or perilesional routes, to exert local as well as systemic therapeutic effects. Sterile compositions for parenteral administration can be prepared by incorporating the antibody, antibody fragment or antibody conjugate of the present invention in the required amount in the appropriate solvent, followed by sterilization by microfiltration. As solvent or vehicle, there may be used water, saline, phosphate buffered saline, dextrose, glycerol, ethanol, and the like, as well as combination thereof. In many cases, it will be preferable to include isotonic agents, such as sugars, polyalcohols, or sodium chloride in the composition. These compositions may also contain adjuvants, in particular wetting, isotonizing, emulsifying, dispersing and stabilizing agents. Sterile compositions for parenteral administration may also be prepared in the form of sterile solid compositions which may be dissolved at the time of use in sterile water or any other injectable sterile medium.

The GITR-specific antibody or antibody fragment may also be orally administered. As solid compositions for oral administration, tablets, pills, powders (gelatine capsules, sachets) or granules may be used. In these compositions, the active ingredient according to the invention is mixed with one or more inert diluents, such as starch, cellulose, sucrose, lactose or silica, under an argon stream. These compositions may also comprise substances other than diluents, for example one or more lubricants such as magnesium stearate or talc, a coloring, a coating (sugar-coated tablet) or a glaze.

As liquid compositions for oral administration, there may be used pharmaceutically acceptable solutions, suspensions, emulsions, syrups and elixirs containing inert diluents such as water, ethanol, glycerol, vegetable oils or paraffin oil. These compositions may comprise substances other than diluents, for example wetting, sweetening, thickening, flavoring or stabilizing products.

The doses depend on the desired effect, the duration of the treatment and the route of administration used; they are generally between 5 mg and 1000 mg per day orally for an adult with unit doses ranging from 1 mg to 250 mg of active substance. In general, the doctor will determine the appropriate dosage depending on the age, weight and any other factors specific to the subject to be treated.

Also provided herein are methods for killing a Treg cell by administering to a patient in need thereof a GITR specific antibody with ADCC activity and is able to recruit immune cells to kill the GITR-expressing Treg cell. Any of the GITR-specific antibodies or antibody fragments of the invention may be used therapeutically. In preferred embodiments, the GITR-specific antibody is a GITR-specific antibody as described herein or an antigen-binding fragment thereof.

In a preferred embodiment, GITR-specific antibodies or antibody fragments of the invention are used for the treatment of a hyperproliferative disorder in a mammal. In a more preferred embodiment, one of the pharmaceutical compositions disclosed above, and which contains a GITR-specific antibody or antibody fragment of the invention, is used for the treatment of a hyperproliferative disorder in a mammal. In one embodiment, the disorder is a cancer. A variety of different cancerous tumors have been demonstrated to contain GITR positive immune cells. Accordingly, these tumors are particularly attractive targets. Such tumors include, for instance, melanoma (including Stage III and Stage IV malignant melanoma), lung cancer (e.g., non-small cell lung cancer—NSCLC), head and neck cancer, prostate cancer, renal cell carcinoma and colorectal cancer. In preferred embodiments, the GITR-specific antibody is a GITR-specific antibody as described herein, or an antigen-binding fragment thereof.

Other cancers that can be treated with the antigen binding proteins include, but are not limited to, breast, prostate, endometrial, bladder, kidney, esophageal, testicular, ovarian, bladder, squamous cell carcinoma (e.g., squamous cell carcinoma of the head and neck-SCCHN), uveal melanoma, follicular lymphoma, cervical, brain, pancreatic, liver, lymphoma, Hodgkin's disease, multiple myeloma, gastric cancer, and astrocyctic cancer.

In treating any of the foregoing cancers, the treatment methods that are provided can be utilized to inhibit further tumor growth, induce tumor regression, increase progression-free survival and/or extend overall survival in an individual that has a tumor. In some embodiments, the GITR-specific antibody can also delay or prevent the onset of metastasis. Progress in treatment can be monitored using various methods. For instance, inhibition can result in reduced tumor size and/or a decrease in metabolic activity within the tumor. Both of these parameters can be measured by MRI or PET scans for example. Inhibition can also be monitored by biopsy to ascertain the level of necrosis, tumor cell death and the level of vascularity within the tumor. The extent of metastasis can be monitored using known methods. Accordingly, the pharmaceutical compositions of the invention are useful in the treatment or prevention of metastasis of a variety of cancers, including (but not limited to) the following: melanoma, lung, head and neck, renal cell, colorectal, breast, prostate, endometrial, bladder, kidney, esophageal, testicular, ovarian, squamous cell carcinoma (e.g., squamous cell carcinoma of the head and neck-SCCHN), uveal melanoma, follicular lymphoma, cervical, brain, pancreatic, liver, lymphoma, Hodgkin's disease, multiple myeloma, gastric, and astrocyctic.

Similarly, further provided herein is a method for inhibiting the growth of selected cell populations comprising contacting GITR-expressing immune cells with an effective amount of a GITR-specific antibody or antibody fragment of the present invention, either alone or in combination with other therapeutic agents. In preferred embodiments, the GITR-specific antibody is a GITR-specific antibody as described herein, or an antigen-binding fragment thereof. In a preferred embodiment, the further therapeutic agent is an immunotherapy i.e., an immunostimulatory agent that induces or enhances an immune response. Such agents can include, for example: 1) activators of dendritic cells, 2) vaccine adjuvants, 3) T cell stimulators, 4) inhibitors of immune checkpoints, and 5) inhibitors of suppressive cells, cytokines and/or enzymes.

In one embodiment, the immunostimulatory agent is a cancer vaccine. In addition to cancer vaccines comprised of cancer-associated antigens, vaccines useful in combination with the GITR-specific antibody include, without limitation, GM-CSF DNA and cell-based vaccines, dendritic cell vaccines, recombinant viral (e.g. vaccinia virus) vaccines, and heat shock protein (HSP) vaccines. Useful vaccines also include tumor vaccines, such as those formed of melanoma cells; and may be autologous or allogeneic. The vaccines may be, e.g., peptide, DNA or cell based. In one embodiment, the GITR-specific antibody is administered in combination with a CD8/CD4 Ag-specific peptide vaccine.

For clinical use, a therapeutically effective amount of the GITR-specific antibody or antigen-binding fragment is administered to a subject in need thereof. For example, the GITR-specific antibodies and antigen-binding fragments thereof may be useful in the treatment of cancerous tumors that contain GITR positive immune cells. In preferred embodiments, the GITR specific antibody is a GITR-specific antibody as described herein, or an antigen-binding fragment thereof. In some embodiments, the subject is a mammal, preferably a human. In some embodiments, the GITR-specific antibody or antigen-binding fragment will be administered as a solution that has been tested for sterility.

Dosage regimens in the above methods of treatment and uses are adjusted to provide the optimum desired response (e.g., a therapeutic response). For example, a single bolus may be administered, several divided doses may be administered over time or the dose may be proportionally reduced or increased as indicated by the exigencies of the therapeutic situation. Parenteral compositions may be formulated in dosage unit form for ease of administration and uniformity of dosage.

The efficient dosages and the dosage regimens for the GITR-specific antibodies and fragments depend on the disease or condition to be treated and may be determined by one skilled in the art. An exemplary, non-limiting range for a therapeutically effective amount of a compound of the present invention is about 0.001-10 mg/kg, such as about 0.001-5 mg/kg, for example about 0.001-2 mg/kg, such as about 0.001-1 mg/kg, for instance about 0.001, about 0.01, about 0.1, about 1 or about 10 mg/kg.

A physician or veterinarian having ordinary skill in the art may readily determine and prescribe the effective amount of the pharmaceutical composition required. For example, the physician or veterinarian could start doses of the GITR-specific antibody or fragment employed in the pharmaceutical composition at levels lower than that required in order to achieve the desired therapeutic effect and gradually increase the dosage until the desired effect is achieved. In general, a suitable daily dose of a GITR-specific antibody of the present invention will be that amount of the compound which is the lowest dose effective to produce a therapeutic effect. Administration may e.g. be parenteral, such as intravenous, intramuscular or subcutaneous. In one embodiment, the GITR-specific antibody or fragment may be administered by infusion in a weekly dosage of calculated by $mg/m^2$. Such dosages can, for example, be based on the mg/kg dosages provided above according to the following: dose (mg/kg)×70. Such administration may be repeated, e.g., 1 to 8 times, such as 3 to 5 times. The administration may be performed by continuous infusion over a period of from 2 to 24 hr, such as of from 2 to 12 hr. In one embodiment, the GITR-specific antibody or fragment may be administered by slow continuous infusion over a long period, such as more than 24 hours, in order to reduce toxic side effects.

In one embodiment, the GITR-specific antibody or fragment may be administered in a weekly dosage calculated as a fixed dose for up to eight times, such as from four to six times when given once a week. Such regimen may be repeated one or more times as necessary, for example, after six months or twelve months. Such fixed dosages can, for example, be based on the mg/kg dosages provided above, with a body weight estimate of 70 kg. The dosage may be determined or adjusted by measuring the amount of GITR-specific antibody of the present invention in the blood upon administration by for instance taking out a biological sample and using anti-idiotypic antibodies which target the GITR antigen binding region of the GITR-specific antibodies of the present invention.

In one embodiment, the GITR-specific antibody or fragment may be administered by maintenance therapy, such as, e.g., once a week for a period of six months or more.

A GITR-specific antibody or fragment may also be administered prophylactically in order to reduce the risk of developing cancer, delay the onset of the occurrence of an event in cancer progression, and/or reduce the risk of recurrence when a cancer is in remission.

The GITR-specific antibodies and fragments thereof as described herein may also be administered in combination therapy, i.e., combined with other therapeutic agents relevant for the disease or condition to be treated. Accordingly, in one embodiment, the antibody-containing medicament is for combination with one or more further therapeutic agent, such as a chemotherapeutic agent. In some embodiments, the other therapeutic agents include, but are not limited to, anti-neoplastic agents including alkylating agents including: nitrogen mustards, such as mechlorethamine, cyclophosphamide, ifosfamide, melphalan and chlorambucil; nitrosoureas, such as carmustine (BCNU), lomustine (CCNU), and semustine (methyl-CCNU); Temodal™ (temozolamide), ethylenimines/methylmelamine such as thriethylenemelamine (TEM), triethylene, thiophosphoramide (thiotepa), hexamethylmelamine (HMM, altretamine); alkyl sulfonates such as busulfan; triazines such as dacarbazine (DTIC); antimetabolites including folic acid analogs such as methotrexate and trimetrexate, pyrimidine analogs such as 5-fluorouracil (5FU), fluorodeoxyuridine, gemcitabine, cytosine arabinoside (AraC, cytarabine), 5-azacytidine, 2,2'-difluorodeoxycytidine, purine analogs such as 6-mercaptopurine, 6-thioguanine, azathioprine, 2'-deoxycoformycin (pentostatin), erythrohydroxynonyladenine (EHNA), fludarabine phosphate, and 2-chlorodeoxyadenosine (cladribine, 2-CdA); natural products including antimitotic drugs such as paclitaxel, vinca alkaloids including vinblastine (VLB), vincristine, and vinorelbine, taxotere, estramustine, and estramustine phosphate; pipodophylotoxins such as etoposide and teniposide; antibiotics such as actimomycin D, daunomycin (rubidomycin), doxorubicin, mitoxantrone, idarubicin, bleomycins, plicamycin (mithramycin), mitomycinC, and actinomycin; enzymes such as L-asparaginase; biological response modifiers such as interferon-alpha, IL-2, G-CSF and GM-CSF; miscellaneous agents including platinum coordination complexes such as cisplatin and carboplatin, anthracenediones such as mitoxantrone, substituted urea such as hydroxyurea, methylhydrazine derivatives including N-methylhydrazine (MIH) and procarbazine, adrenocortical suppressants such as mitotane (o,p-DDD) and aminoglutethimide; hormones and antagonists including adrenocorticosteroid antagonists such as prednisone and equivalents, dexamethasone and aminoglutethimide; Gemzar™ (gemcitabine), progestin such as hydroxyprogesterone caproate, medroxyprogesterone acetate and megestrol acetate; estrogen such as diethylstilbestrol and ethinyl estradiol equivalents; antiestrogen such as tamoxifen; androgens including testosterone propionate and fluoxymesterone/equivalents; antiandrogens such as flutamide, gonadotropin-releasing hormone analogs and leuprolide; and nonsteroidal antiandrogens such as flutamide. Therapies targeting epigenetic mechanism including, but not limited to, histone deacetylase inhibitors, demethylating agents (e.g., Vidaza) and release of transcriptional repression (ATRA) therapies can also be combined with the GITR antibodies.

Additional specific examples of chemotherapeutic agents include, taxol, taxenes (e.g., docetaxel and Taxotere), modified paclitaxel (e.g., Abraxane and Opaxio) doxorubicin, Avastin®, Sutent, Nexavar, and other multikinase inhibitors, cisplatin and carboplatin, etoposide, gemcitabine, and vinblastine. Specific inhibitors of other kinases can also be used in combination with the GITR antibodies, including but not limited to, MAPK pathway inhibitors (e.g., inhibitors of ERK, JNK and p38), PI3kinase/AKT inhibitors and Pim inhibitors. Other inhibitors include Hsp90 inhibitors, proteasome inhibitors (e.g., Velcade) and multiple mechanism of action inhibitors such as Trisenox.

Such combined administration may be simultaneous, separate or sequential, in any order. For simultaneous administration the agents may be administered as one composition or as separate compositions, as appropriate.

In one embodiment, a GITR-specific antibody or fragment thereof is administered in combination with another immunomodulatory agent, the immunomodulatory agent can be selected for example from the group consisting of a dendritic cell activator such as CD40 ligand and anti-CD40 agonist antibodies, as well as enhancers of antigen presentation, enhancers of T-cell tropism, inhibitors of tumor-related immunosuppressive factors, such as TGF-β (transforming growth factor beta), and IL-10.

Some methods involve administering a GITR-specific antibody or fragment thereof with a vaccine adjuvant. Such adjuvants include, for instance, IL-12, and various Toll Like Receptor (TLR) agonists, including CpG (a TLR 9 agonist), monophosphoryl lipid A (MPL—a TLR4 agonist), PolyI:C or PolyICLC (TLR3 agonist), and resiquimod and 852A (TLR 7/8 agonists).

In other therapeutic approaches, a GITR-specific antibody is administered in combination with T cell growth factors such as IL-15 and/or IL-17, or activators of these molecules. In related methods, a T cell stimulator is combined with a GITR antibody. Such stimulators include agonists of 4-1BB, such as agonist anti-4-1BB antibodies and 4-1BBL.

In one embodiment, a GITR-specific antibody or fragment thereof is administered with a T cell checkpoint inhibitor, e.g., molecules that send an inhibitory signal to the immune system. Examples of such agents include inhibitors of PD-1 or PD-L1 (B7-H1), such as anti-PD-1 antibodies, including nivolumab (Bristol-Myers Squibb) and pembrolizumab, also known as MK-3475 (Merck), pidilizumab (Curetech), AMP-224 (Amplimmune), and anti-PD-L1 antibodies, including MPDL3280A (Roche), MDX-1105 (Bristol Myer Squibb), MEDI-4736 (AstraZeneca) and MSB-0010718C (Merck). Other checkpoint inhibitors include antagonists of CTLA-4, such as anti-CTLA-4 antibodies. An exemplary anti-CTLA4 antibody is Yervoy® (ipilimumab) marketed by Bristol-Myers Squibb. Other exemplary CTLA-4 antibodies include tremelimumab (Pfizer), Ticilimumab (AstraZeneca) and AMGP-224 (Glaxo Smith Kline).

In yet other methods, a GITR specific antibody or fragment thereof is administered in combination with an inhibitor of an enzyme that has an immunosuppressive effect. An example is 1-methyl tryptophan (1MT), which is a small molecule inhibitor of indoleamine 2,3-dioxygenase.

The GITR specific antibody or fragment thereof can also be used in combination with T-VEC (talimogene laherparepvec) by Amgen.

In certain embodiments, the GITR specific antibody or fragment thereof is administered in combination with a bispecific antibody. The bispecific antibody can direct the immune system of a host, in particular the cytotoxic activity of T-cells, against cancer cells.

A GITR specific antibody or fragment thereof can also be administered in combination with a variety of targeted therapies. Examples of targeted therapies include, but are not limited to, use of therapeutic antibodies. Exemplary antibodies include, but are not limited to, those which bind to cell surface proteins Her2, CDC20, CDC33, mucin-like glycoprotein, and epidermal growth factor receptor (EGFR) present on tumor cells, OX40, PD-1, CD122, CD40, CTLA-4, and optionally induce a cytostatic and/or cytotoxic effect on tumor cells displaying these proteins. Exemplary antibodies also include HERCEPTIN® (trastuzumab), which may be used to treat breast cancer and other forms of cancer, and RITUXAN® (rituximab), ZEVALIN™ (ibritumomab tiuxetan), and LYMPHOCIDE™ (epratuzumab), which may be used to treat non-Hodgkin's lymphoma and other forms of cancer. Certain exemplary antibodies also include panitumumab (VECTIBIX®), ERBITUX® (IMC-C225); BEXXAR™ (iodine 131 tositumomab); KDR (kinase domain receptor) inhibitors; anti VEGF antibodies and antagonists (e.g., Avastin® and VEGAF-TRAP); anti VEGF receptor antibodies and antigen binding regions; anti-Ang-1 and Ang-2 antibodies and antigen binding regions; antibodies to Tie-2 and other Ang-1 and Ang-2 receptors; Tie-2 ligands; antibodies against Tie-2 kinase inhibitors; inhibitors of Hif-1a, and Campath™ (Alemtuzumab). In certain embodiments, cancer therapy agents are polypeptides which selectively induce apoptosis in tumor cells, including, but not limited to, the TNF-related polypeptide TRAIL.

In one embodiment, a GITR-specific antibody or fragment thereof, as provided herein is used in combination with one or more anti-angiogenic agents that decrease angiogenesis. Certain such agents include, but are not limited to, IL-8 antagonists; Campath, B-FGF; FGF antagonists; Tek antagonists (Cerretti et al., U.S. Publication No. 2003/0162712; Cerretti et al., U.S. Pat. No. 6,413,932, and Cerretti et al., U.S. Pat. No. 6,521,424); anti-TWEAK agents (which include, but are not limited to, antibodies and antigen binding regions); soluble TWEAK receptor antagonists (Wiley, U.S. Pat. No. 6,727,225); an ADAM distintegrin domain to antagonize the binding of integrin to its ligands (Fanslow et al., U.S. Publication No. 2002/0042368); anti-eph receptor and anti-ephrin antibodies; antigen binding regions, or antagonists (U.S. Pat. Nos. 5,981,245; 5,728,813; 5,969,110; 6,596,852; 6,232,447; 6,057,124); anti-VEGF agents (e.g., antibodies or antigen binding regions that specifically bind VEGF, or soluble VEGF receptors or a ligand binding regions thereof) such as Avastin® or VEGF-TRAP™, and anti-VEGF receptor agents (e.g., antibodies or antigen binding regions that specifically bind thereto), EGFR inhibitory agents (e.g., antibodies or antigen binding regions that specifically bind thereto) such as panitumumab, IRESSA™ (gefitinib), TARCEVA™ (erlotinib), anti-Ang-1 and anti-Ang-2 agents (e.g., antibodies or antigen binding regions specifically binding thereto or to their receptors, e.g., Tie-2/TEK), and anti-Tie-2 kinase inhibitory agents (e.g., antibodies or antigen binding regions that specifically bind and inhibit the activity of growth factors, such as antagonists of hepatocyte growth factor (HGF, also known as Scatter Factor), and antibodies or antigen binding regions that specifically bind its receptor "c-met" (e.g., rilotumumab and AMG 337, Amgen); anti-PDGF-BB antagonists; antibodies and antigen binding regions to PDGF-BB ligands; and PDGFR kinase inhibitors.

Other anti-angiogenic agents that can be used in combination with a GITR-specific antibody or fragment thereof include agents such as MMP-2 (matrix-metalloproteinase 2) inhibitors, MMP-9 (matrix-metalloproteinase 9) inhibitors, and COX-II (cyclooxygenase II) inhibitors. Examples of useful COX-II inhibitors include CELEBREX™ (celecoxib), valdecoxib, and rofecoxib.

A GITR-specific antibody or fragment thereof as provided herein can also be used in combination with a growth factor inhibitor. Examples of such agents, include, but are not limited to, agents that can inhibit EGF-R (epidermal growth factor receptor) responses, such as EGF-R antibodies (e.g., panitumumab (VECTIBIX®)), EGF antibodies, and molecules that are EGF-R inhibitors; VEGF (vascular endothelial growth factor) inhibitors, such as VEGF receptors and molecules that can inhibit VEGF; and erbB2 receptor inhibitors, such as organic molecules or antibodies that bind to the erbB2 receptor, for example, HERCEPTIN® (Genentech, Inc.). EGF-R inhibitors are described in, for example in U.S. Pat. No. 5,747,498, WO 98/14451, WO 95/19970, and WO 98/02434.

In some treatment applications, particularly when the cancer has metastasized to the bone such that the bone is negatively impacted, it can be useful to administer a GITR-specific antibody or fragment thereof with a therapeutic agent that inhibits further bone loss or aids in restoring bone that has been lost. Accordingly, the GITR-specific antibody or fragment thereof can be administered with a therapeutically effective amount of a bone growth promoting (anabolic) agent or a bone anti-resorptive agent including but not limited to: bone morphogenic factors designated BMP-1 to BMP-12; transforming growth factor-β and TGF-β family members; fibroblast growth factors FGF-1 to FGF-10; interleukin-1 inhibitors (including IL-1ra, antibodies to IL-1 and antibodies to IL-1 receptors); TNFα inhibitors (including etanercept, adalibumab and infliximab); RANK ligand inhibitors (including soluble RANK, osteoprotegerin and antagonistic antibodies that specifically bind RANK or RANK ligand, such as denosumab (XGEVA®)), Dkk-1 inhibitors (e.g., anti-Dkk-1 antibodies), parathyroid hormone, E series prostaglandins, bisphosphonates and bone-enhancing minerals such as fluoride and calcium. Anabolic agents that can be used in combination with the GITR antibodies and functional fragments thereof include parathyroid hormone and insulin-like growth factor (IGF), wherein the latter agent is preferably complexed with an IGF binding protein. An IL-1 receptor antagonist suitable for such combination treatment is described in WO89/11540 and a suitable soluble TNF receptor-1 is described in WO98/01555. Exemplary RANK ligand antagonists are disclosed, for example, in WO 03/086289, WO 03/002713, U.S. Pat. Nos. 6,740,511 and 6,479,635. In one embodiment, a method for treating a cancer includes administration of a therapeutically effective amount of a GITR-specific antibody as described herein, along with radiotherapy to a subject in need thereof. Radiotherapy may comprise radiation or associated administration of radiopharmaceuticals to a patient. The source of radiation may be either external or internal to the patient being treated (radiation treatment may, for example, be in the form of external beam radiation therapy (EBRT) or brachytherapy (BT)). Radioactive elements that may be used in practicing such methods include, e.g., radium, cesium-137, iridium-192, americium-241, gold-198, cobalt-57, copper-67, technetium-99, iodide-123, iodide-131, and indium-111.

Methods of Detecting GITR

Provided herein are methods for detecting GITR in a biological sample by contacting the sample with an antibody, or antigen-binding fragment thereof, described herein. As described herein, the sample may be derived from urine, blood, serum, plasma, saliva, ascites, circulating cells, circulating tumor cells, cells that are not tissue associated (i.e., free cells), tissues (e.g., surgically resected tumor tissue, biopsies, including fine needle aspiration), histological preparations, and the like. In some embodiments the described methods include detecting GITR in a biological sample by contacting the sample with any of the GITR-specific antibodies or antigen-binding fragments thereof described herein.

In some embodiments the sample may be contacted with more than one of the GITR-specific antibodies or antigen-binding fragments described herein. For example, a sample may be contacted with a first GITR-specific antibody, or antigen-binding fragment thereof, and then contacted with a second GITR-specific antibody, or antigen-binding fragment thereof, wherein the first antibody or antigen-binding fragment and the second antibody or antigen-binding fragment are not the same antibody or antigen-binding fragment. In some embodiments, the first antibody, or antigen-binding fragment thereof, may be affixed to a surface, such as a multiwell plate, chip, or similar substrate prior to contacting the sample. In other embodiments the first antibody, or antigen-binding fragment thereof, may not be affixed, or attached, to anything at all prior to contacting the sample.

The described GITR-specific antibodies and antigen-binding fragments may be detectably labeled. In some embodiments labeled antibodies and antigen-binding fragments may facilitate the detection of GITR via the methods described herein. Many such labels are readily known to those skilled in the art. For example, suitable labels include, but should not be considered limited to, radiolabels, fluorescent labels, epitope tags, biotin, chromophore labels, ECL labels, or enzymes. More specifically, the described labels include ruthenium, $^{111}$In-DOTA, $^{111}$In-diethylenetriamine-pentaacetic acid (DTPA), horseradish peroxidase, alkaline phosphatase and beta-galactosidase, poly-histidine (HIS tag), acridine dyes, cyanine dyes, fluorone dyes, oxazin dyes, phenanthridine dyes, rhodamine dyes, Alexafluor® dyes, and the like.

The described GITR-specific antibodies and antigen-binding fragments may be used in a variety of assays to detect GITR in a biological sample. Some suitable assays include, but should not be considered limited to, western blot analysis, radioimmunoassay, surface plasmon resonance, immunofluorimetry, immunoprecipitation, equilibrium dialysis, immunodiffusion, electrochemiluminescence (ECL) immunoassay, immunohistochemistry, fluorescence-activated cell sorting (FACS) or ELISA assay.

Kits for Detecting GITR

Provided herein are kits for detecting GITR in a biological sample. These kits include one or more of the GITR-specific antibodies described herein, or an antigen-binding fragment thereof, and instructions for use of the kit.

The provided GITR-specific antibody, or antigen-binding fragment, may be in solution; lyophilized; affixed to a substrate, carrier, or plate; or detectably labeled. The described kits may also include additional components useful for performing the methods described herein. By way of example, the kits may comprise means for obtaining a sample from a subject, a control or reference sample, e.g., a sample from a subject having slowly progressing cancer and/or a subject not having cancer, one or more sample compartments, and/or instructional material which describes performance of a method of the invention and tissue specific controls or standards.

The means for determining the level of GITR can further include, for example, buffers or other reagents for use in an assay for determining the level of GITR. The instructions can be, for example, printed instructions for performing the assay and/or instructions for evaluating the level of expression of GITR.

The described kits may also include means for isolating a sample from a subject. These means can comprise one or more items of equipment or reagents that can be used to obtain a fluid or tissue from a subject. The means for obtaining a sample from a subject may also comprise means

EXEMPLARY EMBODIMENTS OF THE DESCRIBED SUBJECT MATTER

To better and more fully describe the subject matter herein, this section provides enumerated exemplary embodiments of the subject matter presented.

Enumerated Embodiments

Embodiments

1. An isolated antibody, or an antigen-binding fragment thereof, that specifically binds to human GITR comprising:

a. a heavy chain CDR1 having the amino acid sequence of SEQ ID NO: 1, a heavy chain CDR2 having the amino acid sequence of SEQ ID NO: 5, and a heavy chain CDR3 having the amino acid sequence of SEQ ID NO: 12, a light chain CDR1 having the amino acid sequence of SEQ ID NO: 28, a light chain CDR2 having the amino acid sequence of SEQ ID NO: 32, and a light chain CDR3 having the amino acid sequence of SEQ ID NO: 35;

b. a heavy chain CDR1 having the amino acid sequence of SEQ ID NO: 2, a heavy chain CDR2 having the amino acid sequence of SEQ ID NO: 5, and a heavy chain CDR3 having the amino acid sequence of SEQ ID NO: 13, a light chain CDR1 having the amino acid sequence of SEQ ID NO: 29, a light chain CDR2 having the amino acid sequence of SEQ ID NO: 32, and a light chain CDR3 having the amino acid sequence of SEQ ID NO: 36;

c. a heavy chain CDR1 having the amino acid sequence of SEQ ID NO: 1, a heavy chain CDR2 having the amino acid sequence of SEQ ID NO: 6, and a heavy chain CDR3 having the amino acid sequence of SEQ ID NO: 14, a light chain CDR1 having the amino acid sequence of SEQ ID NO: 30, a light chain CDR2 having the amino acid sequence of SEQ ID NO: 33, and a light chain CDR3 having the amino acid sequence of SEQ ID NO: 37;

d. a heavy chain CDR1 having the amino acid sequence of SEQ ID NO: 3, a heavy chain CDR2 having the amino acid sequence of SEQ ID NO: 7, and a heavy chain CDR3 having the amino acid sequence of SEQ ID NO: 15, a light chain CDR1 having the amino acid sequence of SEQ ID NO: 28, a light chain CDR2 having the amino acid sequence of SEQ ID NO: 32, and a light chain CDR3 having the amino acid sequence of SEQ ID NO: 35;

e. a heavy chain CDR1 having the amino acid sequence of SEQ ID NO: 3, a heavy chain CDR2 having the amino acid sequence of SEQ ID NO: 7, and a heavy chain CDR3 having the amino acid sequence of SEQ ID NO: 16, a light chain CDR1 having the amino acid sequence of SEQ ID NO: 28, a light chain CDR2 having the amino acid sequence of SEQ ID NO: 32, and a light chain CDR3 having the amino acid sequence of SEQ ID NO: 35;

f. a heavy chain CDR1 having the amino acid sequence of SEQ ID NO: 4, a heavy chain CDR2 having the amino acid sequence of SEQ ID NO: 8, and a heavy chain CDR3 having the amino acid sequence of SEQ ID NO: 17, a light chain CDR1 having the amino acid sequence of SEQ ID NO: 28, a light chain CDR2 having the amino acid sequence of SEQ ID NO: 32, and a light chain CDR3 having the amino acid sequence of SEQ ID NO: 35;

g. a heavy chain CDR1 having the amino acid sequence of SEQ ID NO: 4, a heavy chain CDR2 having the amino acid sequence of SEQ ID NO: 9, and a heavy chain CDR3 having the amino acid sequence of SEQ ID NO: 18, a light chain CDR1 having the amino acid sequence of SEQ ID NO: 28, a light chain CDR2 having the amino acid sequence of SEQ ID NO: 32, and a light chain CDR3 having the amino acid sequence of SEQ ID NO: 35;

h. a heavy chain CDR1 having the amino acid sequence of SEQ ID NO: 4, a heavy chain CDR2 having the amino acid sequence of SEQ ID NO: 10, and a heavy chain CDR3 having the amino acid sequence of SEQ ID NO: 19, a light chain CDR1 having the amino acid sequence of SEQ ID NO: 28, a light chain CDR2 having the amino acid sequence of SEQ ID NO: 32, and a light chain CDR3 having the amino acid sequence of SEQ ID NO: 35;

i. a heavy chain CDR1 having the amino acid sequence of SEQ ID NO: 3, a heavy chain CDR2 having the amino acid sequence of SEQ ID NO: 7, and a heavy chain CDR3 having the amino acid sequence of SEQ ID NO: 20, a light chain CDR1 having the amino acid sequence of SEQ ID NO: 31, a light chain CDR2 having the amino acid sequence of SEQ ID NO: 34, and a light chain CDR3 having the amino acid sequence of SEQ ID NO: 38;

j. a heavy chain CDR1 having the amino acid sequence of SEQ ID NO: 3, a heavy chain CDR2 having the amino acid sequence of SEQ ID NO: 11, and a heavy chain CDR3 having the amino acid sequence of SEQ ID NO: 21, a light chain CDR1 having the amino acid sequence of SEQ ID NO: 31, a light chain CDR2 having the amino acid sequence of SEQ ID NO: 34, and a light chain CDR3 having the amino acid sequence of SEQ ID NO: 38;

k. a heavy chain CDR1 having the amino acid sequence of SEQ ID NO: 3, a heavy chain CDR2 having the amino acid sequence of SEQ ID NO: 7, and a heavy chain CDR3 having the amino acid sequence of SEQ ID NO: 22, a light chain CDR1 having the amino acid sequence of SEQ ID NO: 28, a light chain CDR2 having the amino acid sequence of SEQ ID NO: 32, and a light chain CDR3 having the amino acid sequence of SEQ ID NO: 35;

l. a heavy chain CDR1 having the amino acid sequence of SEQ ID NO: 3, a heavy chain CDR2 having the amino acid sequence of SEQ ID NO: 7, and a heavy chain CDR3 having the amino acid sequence of SEQ ID NO: 23, a light chain CDR1 having the amino acid sequence of SEQ ID NO: 28, a light chain CDR2 having the amino acid sequence of SEQ ID NO: 32, and a light chain CDR3 having the amino acid sequence of SEQ ID NO: 35;

m. a heavy chain CDR1 having the amino acid sequence of SEQ ID NO: 3, a heavy chain CDR2 having the amino acid sequence of SEQ ID NO: 7, and a heavy chain CDR3 having the amino acid sequence of SEQ ID NO: 24, a light chain CDR1 having the amino acid sequence of SEQ ID NO: 28, a light chain CDR2 having the amino acid sequence of SEQ ID NO: 32, and a light chain CDR3 having the amino acid sequence of SEQ ID NO: 35;

n. a heavy chain CDR1 having the amino acid sequence of SEQ ID NO: 3, a heavy chain CDR2 having the amino acid sequence of SEQ ID NO: 7, and a heavy chain CDR3 having the amino acid sequence of SEQ ID NO: 25, a light chain CDR1 having the amino acid sequence of SEQ ID NO: 28, a light chain CDR2 having the amino acid sequence of SEQ ID NO: 32, and a light chain CDR3 having the amino acid sequence of SEQ ID NO: 35;

o. a heavy chain CDR1 having the amino acid sequence of SEQ ID NO: 27, a heavy chain CDR2 having the amino acid sequence of SEQ ID NO: 5, and a heavy chain CDR3 having the amino acid sequence of SEQ ID NO: 26, a light chain CDR1 having the amino acid sequence of SEQ ID NO:

28, a light chain CDR2 having the amino acid sequence of SEQ ID NO: 32, and a light chain CDR3 having the amino acid sequence of SEQ ID NO: 35; or p. a heavy chain CDR1 having the amino acid sequence of SEQ ID NO: 3, a heavy chain CDR2 having the amino acid sequence of SEQ ID NO: 11, and a heavy chain CDR3 having the amino acid sequence of SEQ ID NO: 21, a light chain CDR1 having the amino acid sequence of SEQ ID NO: 28, a light chain CDR2 having the amino acid sequence of SEQ ID NO: 32, and a light chain CDR3 having the amino acid sequence of SEQ ID NO: 35.

2. An isolated antibody, or an antigen-binding fragment thereof, that specifically binds to human GITR comprising a heavy chain region selected from the group consisting of SEQ ID NOs: 39-54, 63 and 64.

3. The antibody of embodiment 2, wherein the antibody or antigen binding fragment thereof comprises a light chain region selected from the group consisting of SEQ ID NOs: 55-58.

4. The antibody of embodiment 2, wherein the antibody or antigen binding fragment thereof comprises a heavy chain region selected from the group consisting of SEQ ID NOs: 39-54, 63 and 64 and a light chain region selected from the group consisting of SEQ ID NOs: 55-58.

5. The antibody of embodiment 4, wherein
   a. the heavy chain region comprises SEQ ID NO: 39 paired with a light chain region comprising SEQ ID NO: 55;
   b. the heavy chain region comprises SEQ ID NO: 40 paired with a light chain region comprising SEQ ID NO: 56;
   c. the heavy chain region comprises SEQ ID NO: 41 paired with a light chain region comprising SEQ ID NO: 57;
   d. the heavy chain region comprises SEQ ID NO: 42 paired with a light chain region comprising SEQ ID NO: 55;
   e. the heavy chain region comprises SEQ ID NO: 43 paired with a light chain region comprising SEQ ID NO: 55;
   f. the heavy chain region comprises SEQ ID NO: 44 paired with a light chain region comprising SEQ ID NO: 55;
   g. the heavy chain region comprises SEQ ID NO: 45 paired with a light chain region comprising SEQ ID NO: 55;
   h. the heavy chain region comprises SEQ ID NO: 46 paired with a light chain region comprising SEQ ID NO: 55;
   i. the heavy chain region comprises SEQ ID NO: 47 paired with a light chain region comprising SEQ ID NO: 58;
   j. the heavy chain region comprises SEQ ID NO: 48 paired with a light chain region comprising SEQ ID NO: 58;
   k. the heavy chain region comprises SEQ ID NO: 49 paired with a light chain region comprising SEQ ID NO: 55;
   l. the heavy chain region comprises SEQ ID NO: 50 paired with a light chain region comprising SEQ ID NO: 55;
   m. the heavy chain region comprises SEQ ID NO: 51 paired with a light chain region comprising SEQ ID NO: 55;
   n. the heavy chain region comprises SEQ ID NO: 52 paired with a light chain region comprising SEQ ID NO: 55;
   o. the heavy chain region comprises SEQ ID NO: 53 paired with a light chain region comprising SEQ ID NO: 55;
   p. the heavy chain region comprises SEQ ID NO: 54 paired with a light chain region comprising SEQ ID NO: 55;
   q. the heavy chain region comprises SEQ ID NO: 63 paired with a light chain region comprising SEQ ID NO: 55; or
   r. the heavy chain region comprises SEQ ID NO: 64 paired with a light chain region comprising SEQ ID NO: 55.

6. The antibody or antigen-binding fragment of embodiment 5, wherein the antibody specifically binds to human GITR by interacting with GITR (SEQ ID NO: 62 amino acid residues:
   a. 40-45; and
   b. 75-79.

7. The antibody or antigen-binding fragment of embodiment 1 wherein the antibody or antigen-binding fragment thereof binds to a polypeptide having the amino acid sequence of SEQ ID NO: 59.

8. The antibody or antigen-binding fragment of embodiment 1 wherein the antibody or antigen-binding fragment thereof specifically binds human GITR with a binding affinity of at least 30 nM as measured by surface plasmon resonance using experimental design described in Example 9.

9. The antibody or antigen-binding fragment of embodiment 1 wherein the antibody or antigen-binding fragment induces an increase in luciferase expression in NF-κB luciferase gene assay.

10. The antibody or antigen-binding fragment of embodiment 1 wherein the antibody or antigen-binding fragment induces ADCC in vitro with an $EC_{50}$ of less than about 67 ng/mL.

11. The antibody or antigen-binding fragment of embodiment 1 wherein the antibody or antigen-binding fragment is a human antibody or antigen-binding fragment.

12. The antigen-binding fragment of embodiment 1 wherein the antigen binding fragment is a Fab fragment, a Fab2 fragment, or a single chain antibody.

13. The antibody or antigen-binding fragment of embodiment 1 wherein the antibody or antigen-binding fragment is recombinant.

14. The antibody or antigen-binding fragment of embodiment 1 wherein the antibody or antigen-binding fragment thereof are of IgG1, IgG2, IgG3, or IgG4 isotype.

15. The antibody or antigen-binding fragment of embodiment 1 is IgG1 isotype.

16. The antibody or antigen-binding fragment of any one of embodiments 1 wherein the antibody or antigen-binding fragment thereof specifically binds human GITR and cynomolgus monkey GITR.

17. A polynucleotide encoding the antibody or antigen binding fragment of any one of embodiment 1.

18. A vector comprising the polynucleotide of embodiment 17.

19. A host cell comprising the vector of embodiment 18.

20. A process for the production of an antibody or antigen-binding fragment, comprising:
   culturing the host cell as defined in embodiment 19 under the conditions allowing the expression of the antibody or antigen-binding fragment, and recovering the antibody or antigen-binding molecule from the culture.

21. A method of alleviating a symptom of a cancer or other neoplastic condition, the method comprising administering the antibody, or antigen binding fragment thereof, of embodiment 1 to a subject in need thereof in an amount sufficient to alleviate the symptom of the cancer or other neoplastic condition in the subject.

22. The method of embodiment 21, wherein the subject is a human.

23. The method of embodiment 21 further comprising one or more of the following:
   a. administering chemotherapy
   b. administering radiation therapy; or
   c. administering one or more additional therapeutic agents.

24. The method of embodiment 23 wherein the additional therapeutic agent is an immunostimulatory agent.

25. The method of embodiment 24, wherein the immunostimulatory agent is selected from the group consisting of PD-1 antibody, CTLA-4 antibody, CD122 antibody, CD40 antibody, OX40 antibody, and a CD8 Ag-specific OVA peptide vaccine.

26. A pharmaceutical composition comprising the antibody, or antigen binding fragment thereof, of embodiment 1 and a pharmaceutically acceptable carrier.

27. A kit comprising the antibody, or antigen binding fragment thereof, of embodiment 1 and packaging for the same.

EXAMPLES

The following examples are provided to supplement the prior disclosure and to provide a better understanding of the subject matter described herein. These examples should not be considered to limit the described subject matter. It is understood that the examples and embodiments described herein are for illustrative purposes only and that various modifications or changes in light thereof will be apparent to persons skilled in the art and are to be included within, and can be made without departing from, the true scope of the invention.

Example 1: Materials

GITR ECD Molecules:

Recombinant human (h) GITR-Fc fusion protein (R&D Systems catalog number 689-GR) corresponding to amino acid 26 to 161 of hGITR (SEQ ID NO:59). The protein was biotinylated for phage panning studies. This protein was also used for binding and affinity measurements.

GITR Cell Lines

GITR was expressed in HEK293F cells by transfection or lentiviral transduction for anti-GITR antibody reactivity confirmation, to test phage and Next Generation Sequencing panels, and to check cross-reactivity of GITR mAb hits against cyno-GITR.

The transfected cells presented the following GITR sequences:

```
Human GITR
                                             (SEQ ID NO: 60)
QRPTGGPGCGPGRLLLGTGTDARCCRVHTTRCCRDYPGEECCSEWDCMCV

QPEFHCGDPCCTTCRHHPCPPGQGVQSQGKFSFGFQCIDCASGTFSGGHE

GHCKPWTDCTQFGFLTVFPGNKTHNAVCVPGSPPAEPLGWLTVVLLAVAA

CVLLLTSAQLGLHIWQLRSQCMWPRETQLLLEVPPSTEDARSCQFPEEER

GERSAEEKGRLGDLWV

Cyno GITR
                                             (SEQ ID NO: 61)
QRPTGGPGCGPGRLLLGTGKDARCCRVHPTRCCRDYQSEECCSEWDCVCV

QPEFHCGNPCCTTCQHHPCPSGQGVQPQGKFSFGFRCVDCALGTFSRGHD

GHCKPWTDCTQFGFLTVFPGNKTHNAVCVPGSPPAEPPGWLTIVLLAVAA

CVLLLTSAQLGLHIWQLGSQPTGPRETQLLLEVPPSTEDASSCQFPEEER

GERLAEEKGRLGDLWV
```

The lentivirally-transduced cells presented the following GITR sequences:

```
Human GITR
                                             (SEQ ID NO: 62)
MAQHGAMGAFRALCGLALLCALSLGQRPTGGPGCGPGRLLLGTGTDARCC

RVHTTRCCRDYPGEECCSEWDCMCVQPEFHCGDPCCTTCRHHPCPPGQGV

QSQGKFSFGFQCIDCASGTFSGGHEGHCKPWTDCTQFGFLTVFPGNKTHN

AVCVPGSPPAEPLGWLTVVLLAVAACVLLLTSAQLGLHIWQLRSQCMWPR

ETQLLLEVPPSTEDARSCQFPEEERGERSAEEKGRLGDLWV

Cyno GITR
                                             (SEQ ID NO: 61)
QRPTGGPGCGPGRLLLGTGKDARCCRVHPTRCCRDYQSEECCSEWDCVCV

QPEFHCGNPCCTTCQHHPCPSGQGVQPQGKFSFGFRCVDCALGTFSRGHD

GHCKPWTDCTQFGFLTVFPGNKTHNAVCVPGSPPAEPPGWLTIVLLAVAA

CVLLLTSAQLGLHIWQLGSQPTGPRETQLLLEVPPSTEDASSCQFPEEER

GERLAEEKGRLGDLWV
```

Transient expression of HEK 293F cells was performed by placing cells in Freestyle™ 293 media (Gibco #12338) at a density of 1e$^6$ cells/ml to a volume of 30 mls in a 125 ml vented cap shake flask with shaking at 130 RPM, 24 hours prior to transfection. Transfection was carried out using Freestyle max reagent (Invitrogen #16447). For a single 30 ml transfection, in one tube 37.5 µl of freestyle max reagent was diluted in 1 ml of OptiMEM media (Gibco #31985). In a separate tube, 37.5 µg of DNA (300 nanograms target and 37.2 µg of an unrelated carrier plasmid) was mixed into 1 ml OptiMEM. The two tubes were then mixed together, incubated in the biosafety cabinet for 1 minute and then the mixture added directly to the flask of HEK293F cells. After 48 hours of growth, the cells were ready for use in the indicated assays.

Lentiviral particles presenting full-length GITR generated by Genecopoeia (Genecopoeia catalog #LPP-U0202-LV105-200-S for human GITR and Genecopoeia catalog #LPP-U0202-LV105-200-S for cyno GITR) were transduced in cells using the manufacturer's protocol. Transduced cells were selected for stable plasmid integration and then single cell sorted using the BD Biosciences FACS Jazz cell sorter. The GITR surface expression was quantified by flow cytometry staining with R&D Systems FAB689P anti-huGITR antibody and analyzed on the BD Biosciences Accuri C6.

Example 2: Discovery of GITR Antibodies Using Phage Display Technology

The de novo pIX Fab libraries (Shi, L., et al J Mol Biol, 2010. 397(2):p. 385-396. WO 2009/085462), consisting of VH1-69, 3-23 and 5-51 heavy chain libraries paired with Vκ VLK3-20, VLK4-1, VLK3-11, and VLK1-39 light chain libraries, were panned against biotinylated human GITR-ECD Fc fusion at a concentration of 100 nM (rounds 1-3) or 10 nM (round 4) in a selection process similar to that described in Rothe et al, J Mol Biol 376:1182-1200, 2008 and Steidl et al, Mol Immunol. 46: 135-144, 2008.

The pIX gene was excised from phagemid DNA following the fourth round of panning to generate soluble his-tagged Fab coding regions. Fabs were expressed in E. coli and screened for binding to GITR in an ELISA. Briefly, 96-well Nunc Maxisorp plates (Nunc #437111) were coated with either streptavidin (Promega) or sheep anti-human Fd (The Binding Site #PC075) in PBS at 5 µg/mL overnight at 4° C. Bacterial cultures containing the Fab expression vector were grown in 1 mL of 2×YT (Carbenecillin) in deep-well culture plates until turbid (OD600 Z 0.6). Fab expression was then induced by the addition of IPTG to a concentration of 1 mM. Cultures were grown overnight at 30° C. and then clarified by centrifugation the next day. Streptavidin-coated plates were washed thrice with TBS, 0.5% Tween-20 (Sigma #79039-10PAK), loaded with biotinylated GITR-Fc at 5 μg/mL, and held at room temperature for 30 minutes. Using the Biomek Liquid Handling Robot (Beckman Coulter) both anti-Fd coated Maxisorp plates and streptavidin-coated plates were washed three times with TBS, 0.5% Tween-20 (Sigma #79039-10PAK) and blocked with 200 μL PBS-Tween (0.5%)+nonfat dried milk (3%) per well for one hr at room temperature. At this step and all subsequent steps plates were washed three times with TBS, 0.5% Tween-20 (Sigma #79039-10PAK). Each well received 50 μL of Fab supernatant followed by one hr incubation at room temperature. After washing, 50 μL of goat anti-human kappa-HRP (Southern Biotech) was added at a 1:5000 dilution in TBST with 0.3% milk and plates were incubated for one hour at room temperature. Plates were washed and 50 uL chemiluminescent substrate, PoD (Roche #121-5829500001), was added according to manufacturer's instructions. Plates were then read for luminescence on an EnVision (Perkin Elmer) plate reader. Clones that were positive in both the fab expression ELISA and the GITR binding ELISA were selected for DNA sequencing. A total of 50 unique Fab sequences were discovered via this phage panning process. The unique heavy chain V-regions were cloned into human IgG1_G1m(17,1) expression vectors, the unique light chains were cloned into human kappa expression vectors, and the resultant antibodies were tested again for binding activity in an ELISA.

Example 3: Initial Characterization of GITR Antibodies Obtained Through Phage Display Technology Human GITR Binding Assay
Binding of GITR antibodies to engineered cells was assessed using FACS. The object of the screening assay was to identify antibodies that bound to cells expressing hGITR.

Briefly, 300,000 cells per well were plated into a 96-well plate (Greiner bio one cat #651261) and the cells were pelleted. The cells were washed with 100 μL of FACS staining buffer (BD Pharmingen Stain Buffer (BSA) cat #554657), incubated at 4° C. for 30 minutes with a mixture of 50 μL FACS staining buffer and 20 μL per well of the unpurified antibody supernatants, and washed once with 200 μL of FACS staining buffer. For detection, the cells were subjected to a 30 minute incubation at 4° C. with 50 μL per well of Alexa Fluor 488 goat anti-human IgG (H+L) (Molecular Probes, cat #A11013) at 2 μg per mL in FACS staining buffer. The cells were washed once with 200 μL per well of FACS staining buffer, resuspended in 150 μL per well of FACS staining buffer, and then transferred to FACS tubes that contained 200 μL per well of FACS staining buffer. FACS analysis was then carried out. The assay was repeated for data consistency and top binders were selected for further development.

NF-κB-Luciferase Gene Assay
To assess agonist activity of the GITR antibodies, the panel was screened using an NF-κB-luciferase gene assay. Briefly, HEK293 cells were transiently transfected with a reporter plasmid encoding the luciferase gene under control of the NF-κB promoter together with human GITR expression plasmid. The cells were allowed to recover from the transfection and to express human GITR for four hours at 37° C., at which point the assay could be performed. To confirm that the assay worked as intended, recombinant human GITR ligand (R&D Systems 6987-GL/CF) was added to positive control wells at a final concentration of 2.5 micrograms per mL. Anti-GITR antibodies undergoing testing were added to experimental wells at a final concentration of 5 micrograms per mL. The plates were then incubated at 37° C. for four hours. Successful GITR signaling was expected to activate the NF-kB pathway, followed by luciferase expression, which could be detected by adding Steady Glo, as indicated by the manufacturer (Promega cat #E2550), and measuring the resultant luminescence in an Envision plate reader (Perkin Elmer).

Figure 1A:
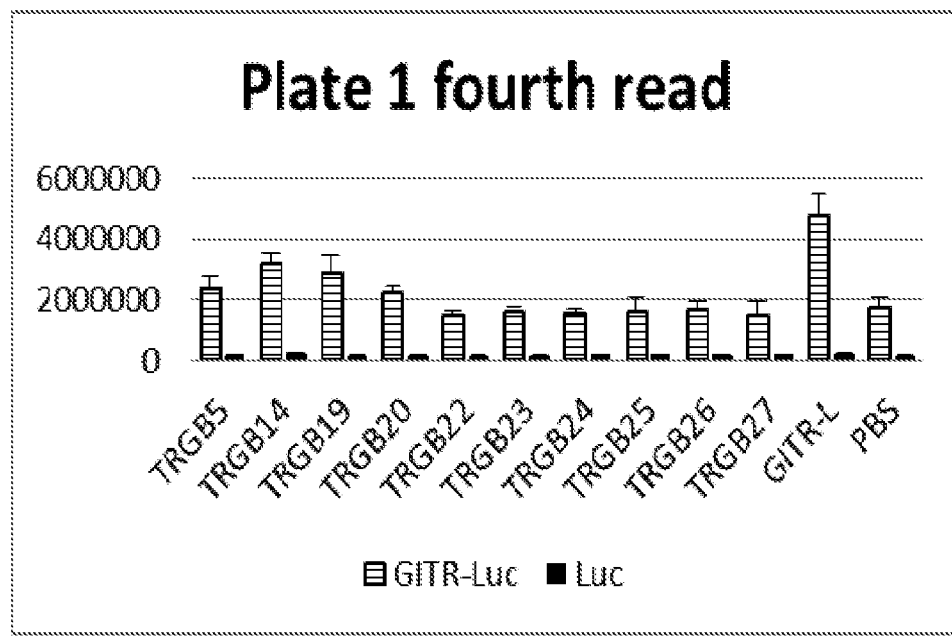
FIG. 1A-1C. Agonist activity exhibited by the anti-GITR mAbs from the traditional screen panel. Data shown are the Cell-Titer Glo signal from cells that were treated with the indicated reagent after being transfected with either the NF-kB luciferase reporter gene only (Luc) or with both the GITR expression vector and the NF-kB luciferase reporter gene (GITR-Luc). Antibodies that produced a signal greater than that found with PBS treatment were preliminarily categorized as agonists.
Figure 1B:
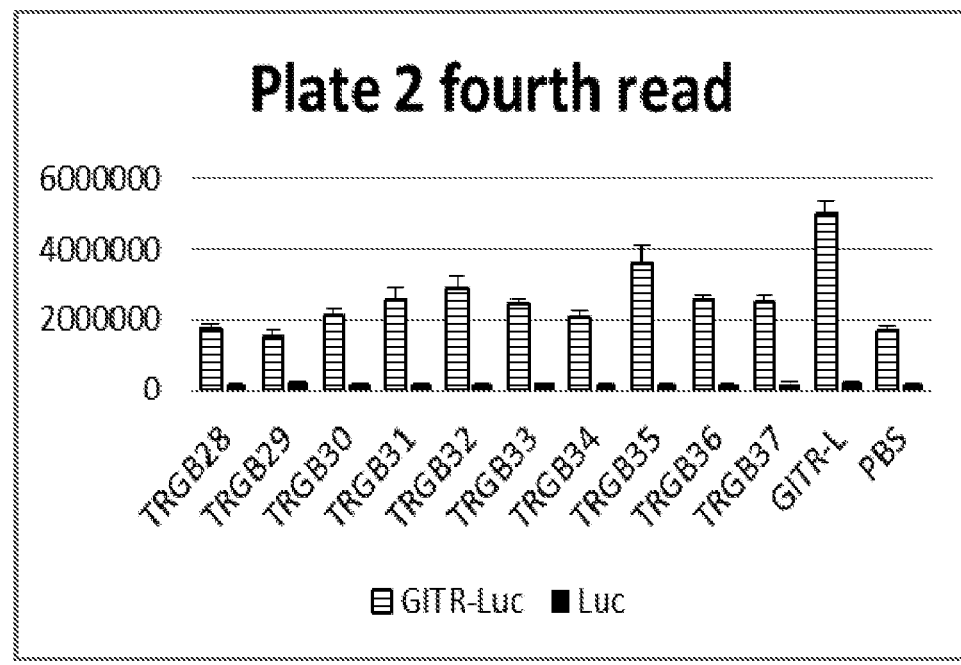
Figure 1C:
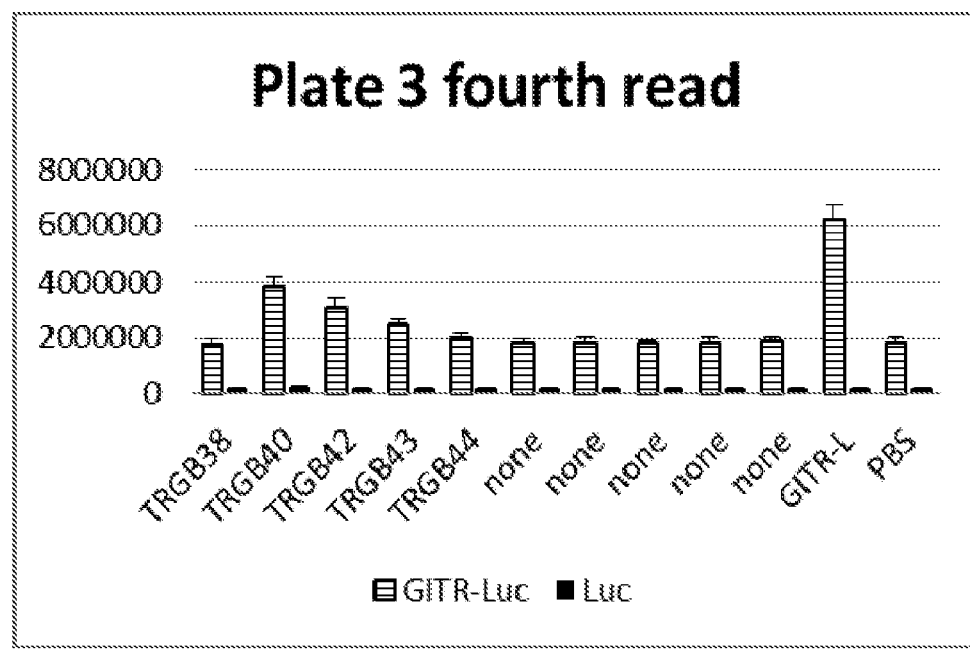
Figure 2A:
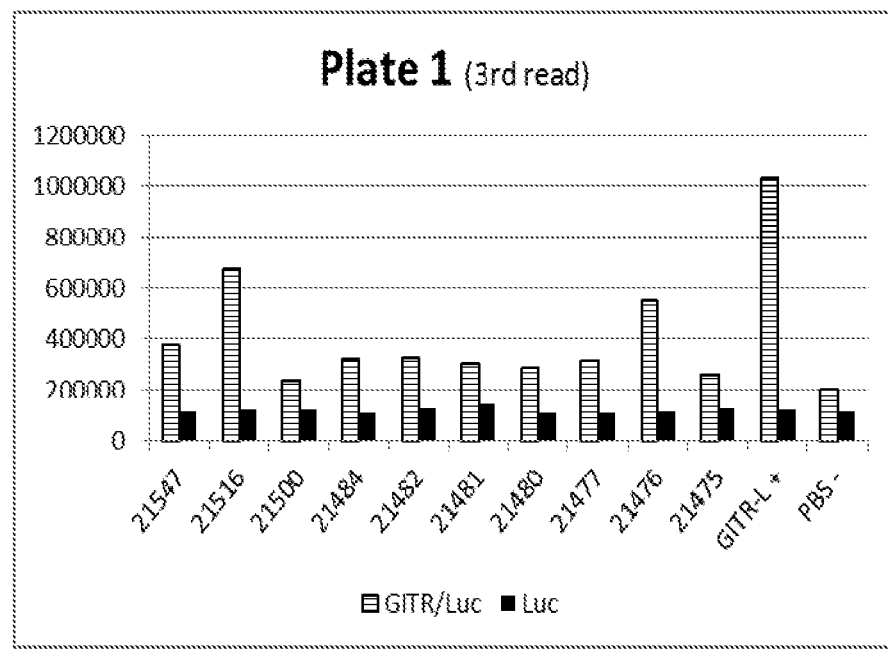
FIG. 2A shows signals from Plate 2.
Figure 2B:
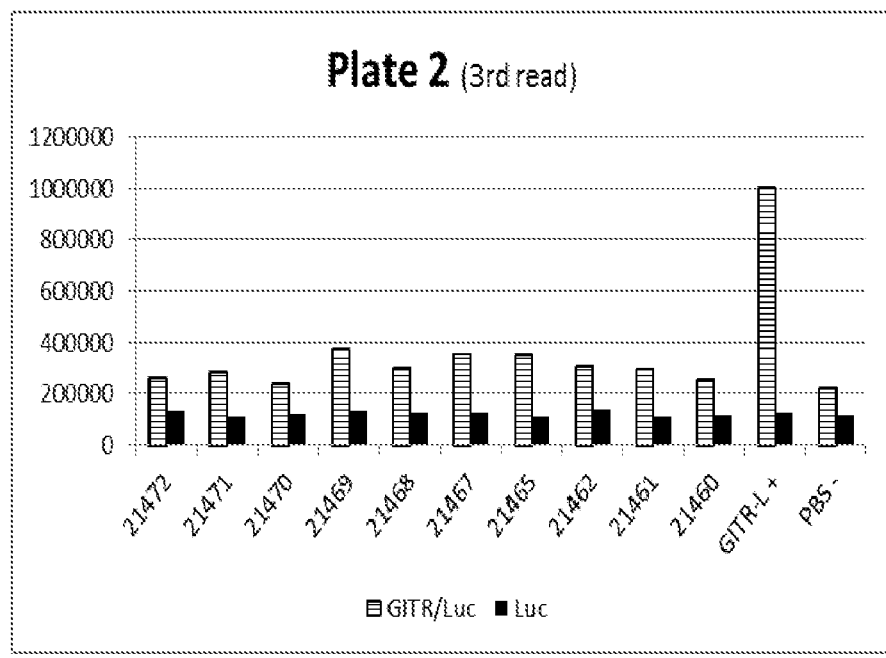
FIG. 2B shows signals from Plate 2.
Figure 2C:
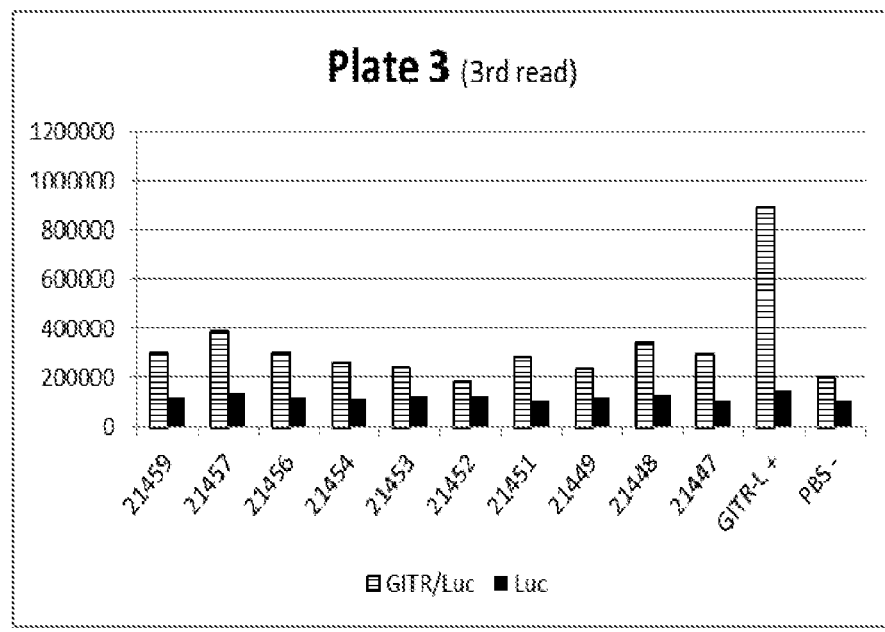
FIG. 2C shows signals from Plate 3.
Figure 2D:
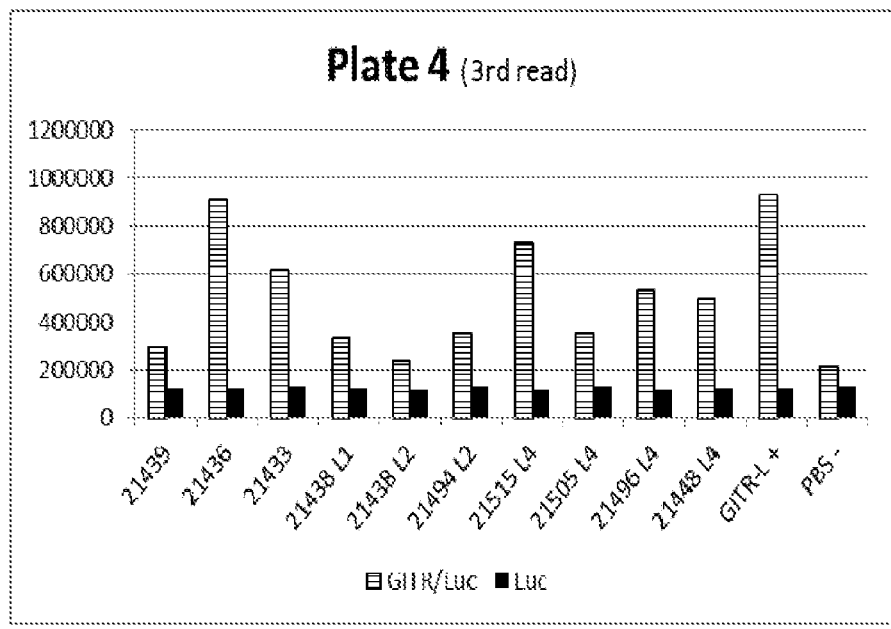
FIG. 2D shows signals from Plate 4.
Figures 2E, 2F:
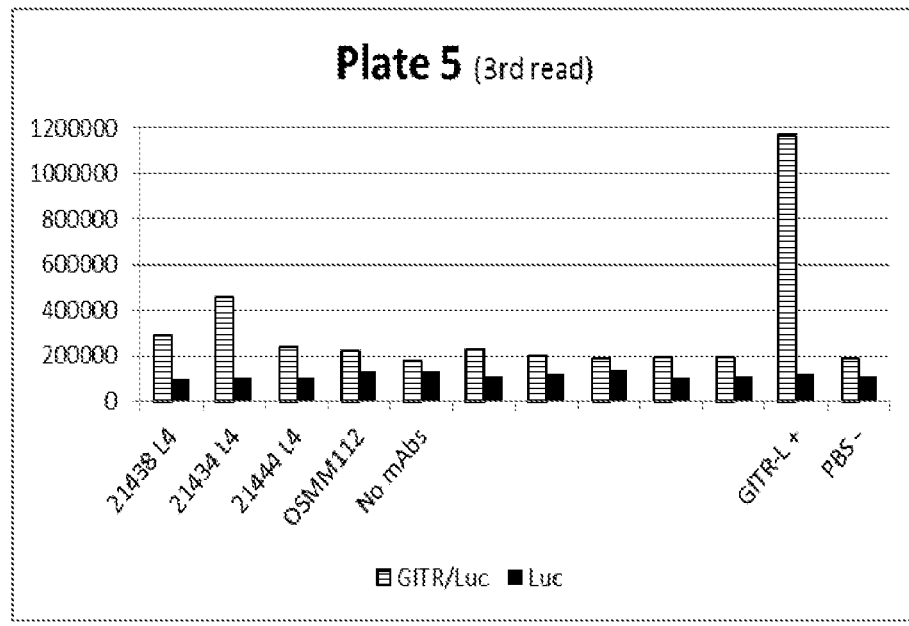
FIG. 2E shows signals from Plate 5.
FIG. 2F shows the X-axis legend for all of the Plates.
Figure 3A:
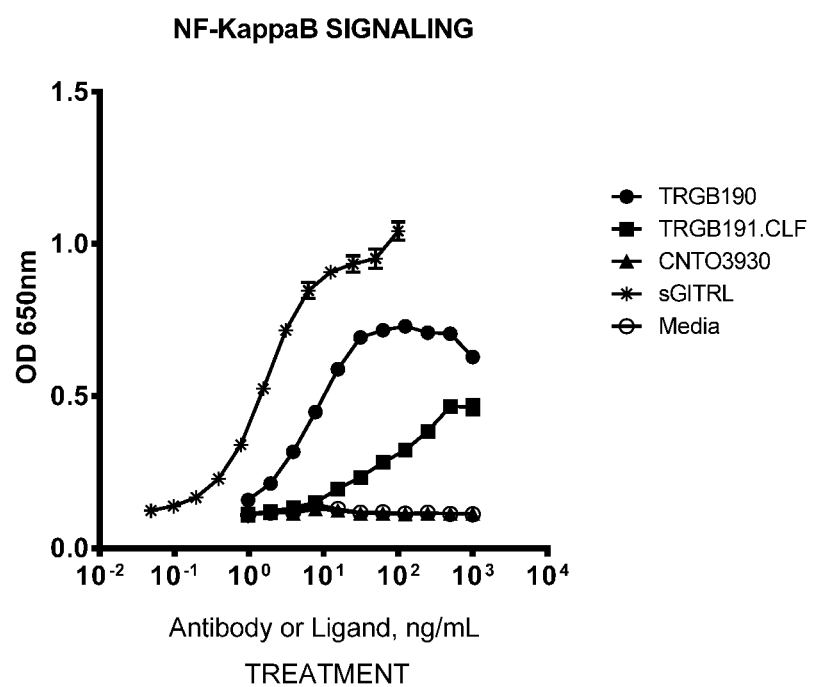
FIG. 3A-3D. The effect of anti-GITR antibody ligation on NF-κB activity. Results shown are representative of SEAP activity as a measure of NF-κB activation in HEK-Blue NF-κB cells stably transfected with GITR. Cells were treated with varying concentrations of anti-GITR antibody in the absence (FIG. 3A, FIG. 3B) or presence (FIG. 3C, FIG. 3D) of 25 ng/mL of soluble GITR ligand. Media and CNTO3930 were used as no antibody and isotype antibody controls.
Figure 3B:
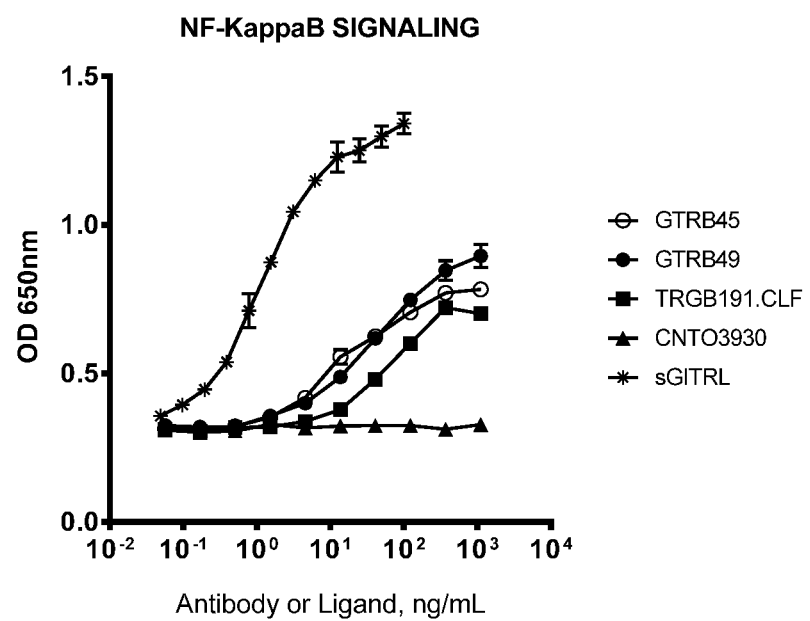
Figure 3C:
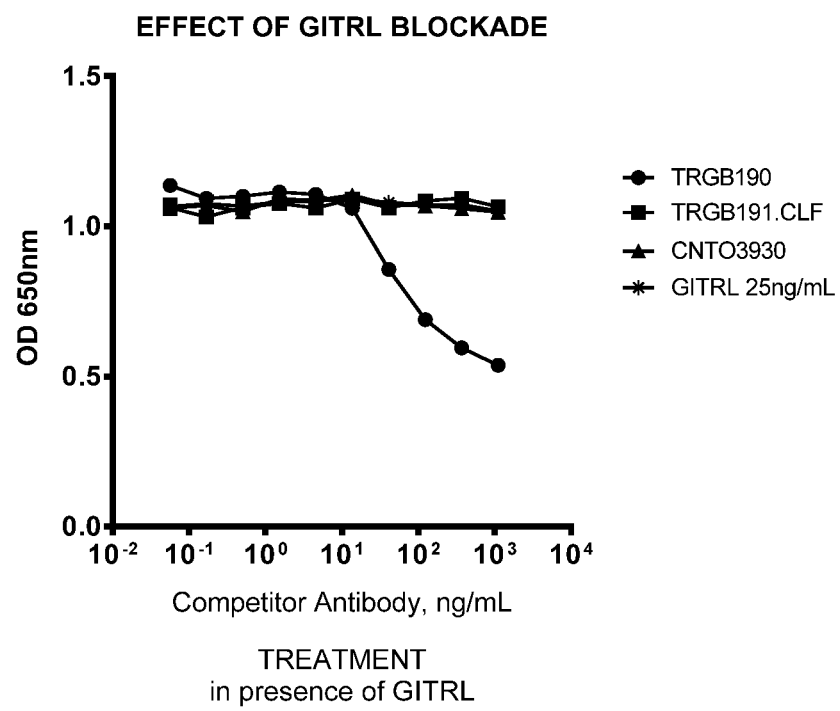
Figure 3D:
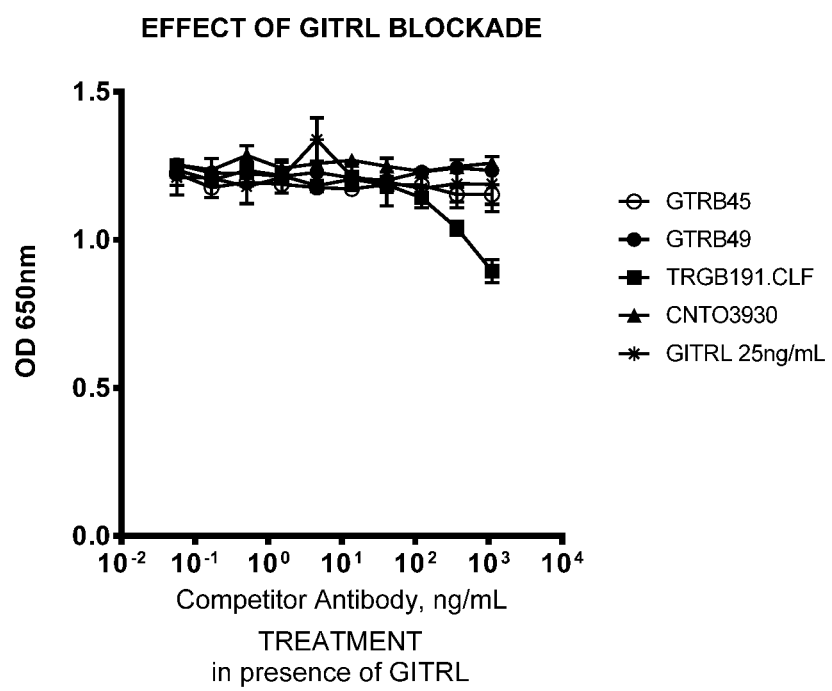

Fifteen antibodies induced an increase in luciferase expression compared to treatment with PBS only (FIG. 1). Antibodies that produced an increase in luciferase expression compared to treatment with PBS only were preliminarily categorized as agonists, while the remaining antibodies could be antagonists or might simply bind to GITR without influencing signaling.

Example 4: Discovery of GITR Antibodies Through Next-Generation Sequencing

Subsequent to the discovery of the first set of anti-GITR antibodies, DNA samples from the output of the final round of the phage selection were provided to Beckman Coulter Genomics for next generation sequencing of the heavy chain V-regions using the Roche 454 sequencing platform. Raw data from Beckman Coulter Genomics was subjected to an initial analysis at IMGT and then more closely examined internally using the proprietary Janssen software program 3DX. The idea of using next-generation sequencing to examine phage selection outputs more extensively has recently been developed as a method to increase the number and quality of antibodies discovered (Ravn et al, Methods 60 (2013) pg 99-110).

The sequences provided by IMGT were filtered for samples that were poor quality or that contained stop codons, and then the remaining sequences were sorted by heavy chain CDR3. This approach was chosen because CDR3 is expected to drive the majority of the binding energy for the antigen, and the majority of the diversity in the phage libraries is located in heavy chain CDR3. Eighty-seven V-regions were chosen for DNA synthesis and cloning into a human IgG1_G1m(17) vector based on both frequency of occurrence and lack of cysteines, methionines, or highly hydrophobic sequences.

After synthesis, the putative anti-GITR heavy chains were tested for binding to GITR as previously described. Because the next-generation sequencing dataset contained no information about the appropriate light chain partners for these heavy chain V-regions, the heavy chains were co-transfected with each of the 4 light chain germline genes found in the phage libraries: Vk3-20, Vk4-1, Vk3-11, and Vk1-39. Unpurified antibody supernatants from these four standard transfections were tested in an ELISA for the ability to bind to recombinant human GITR ECD-Fc fusion protein. The top binders from this assay were selected for further development.

Example 5: Initial Characterization of GITR Antibodies Obtained Through Next Generation Sequencing After the anti-GITR mAbs from the next-generation sequencing dataset were shown to bind to a GITR ECD-Fc fusion protein in an ELISA, a subset was tested for binding to cell-surface GITR as described in EXAMPLE 3. Positive binders were tested for agonist activity using an NF-κB-luciferase gene assay as described in EXAMPLE 3. At 40 micrograms per mL, antibodies that induced an increase in luciferase expression equal to at least 20% of the increase over background observed upon treatment with the natural ligand were considered to have agonistic activity (FIG. 2).

Example 6: Cyno Cross Reactivity

The purified antibodies from both phage display and next generation sequencing were tested for binding to the cynomolgus monkey GITR using flow cytomentry. Transiently transfected cells were incubated at 2-8° C. for 30 minutes with 0.1 mg/mL of test antibodies, washed, and incubated at 2-8° C. for 30 minutes with PE-labeled goat anti-human IgG. The cells were then washed and analyzed on a MAC-SQuant flow cytometer. Antibodies identified as positive binders exhibited a 1.5 to 2 log shift in the mean fluorescent intensity of cells transfected with human or cyno GITR compared to the mean fluorescent intensity of cells transfected with the empty vector. The binding results are compiled in Table 2.

TABLE 2

Binding of anti-GITR antibodies to HEK293f cells transiently transfected with human or cynomolgus monkey GITR. Note that only antibodies that showed binding to cyno GITR cells are represented in this table - antibodies tested but not shown demonstrated no binding to cyno GITR. Antibodies were assigned a ++ for a strongly shifted binding curve and a + for a moderate shift in binding.

|   | Human GITR binding | Cyno GITR binding |
|---|---|---|
| TRGB5 | ++ | ++ |
| TRGB14 | ++ | + |

TABLE 2-continued

Binding of anti-GITR antibodies to HEK293f cells transiently transfected with human or cynomolgus monkey GITR. Note that only antibodies that showed binding to cyno GITR cells are represented in this table - antibodies tested but not shown demonstrated no binding to cyno GITR. Antibodies were assigned a ++ for a strongly shifted binding curve and a + for a moderate shift in binding.

|   | Human GITR binding | Cyno GITR binding |
|---|---|---|
| TRGB20 | ++ | ++ |
| TRGB23 | ++ | ++ |
| TRGB25 | ++ | + |
| TRGB31 | ++ | + |
| TRGB34 | ++ | + |
| TRGB35 | ++ | + |
| TRGB120 | ++ | + |
| TRGB127 | ++ | + |
| TRGB134 | ++ | ++ |
| TRGB144 | ++ | + |
| TRGB153 | ++ | ++ |
| TRGB159 | ++ | ++ |
| TRGB160 | ++ | ++ |
| TRGB162 | ++ | ++ |

Thus, in total a panel of 16 GITR antibodies—all depicted in Table 3—were found to bind to human and cyno GITR.

TABLE 3

CDR sequences of the 16 GITR mAb candidates that showed binding against human and cyno GITR
(SEQ ID NO:)

| ID | HC-CDR1 | HC-CDR2 | HC-CDR3 | LC-CDR1 | LC-CDR2 | LC-CDR3 |
|---|---|---|---|---|---|---|
| TRGB5 | GFTFSGYW (1) | ISGSGGST (5) | AKDFYWDAFDY (12) | QSVSSY (28) | DAS (32) | QQRSNWPLT (35) |
| TRGB14 | GFTFSSYA (2) | ISGSGGST (5) | AKPIRGLDY (13) | QSVNNF (29) | DAS (32) | QQGFNAPLT (36) |
| TRGB20 | GFTFSGYW (1) | ISSDGGSK (6) | AKEVVYDHYAALDY (14) | QSVNSF (30) | YAS (33) | QQYIRWPLT (37) |
| TRGB23 | GGTFSSYA (3) | IIPIFGTA (7) | ARHGNWLITFNLDY (15) | QSVSSY (28) | DAS (32) | QQRSNWPLT (35) |
| TRGB25 | GGTFSSYA (3) | IIPIFGTA (7) | ARHRRFWLDY (16) | QSVSSY (28) | DAS (32) | QQRSNWPLT (35) |
| TRGB31 | GYSFTSYW (4) | IDPSDSDT (8) | ARVFPYYGLVLDY (17) | QSVSSY (28) | DAS (32) | QQRSNWPLT (35) |
| TRGB34 | GYSFTSYW (4) | IYPGDSDT (9) | ARDYGWHDFDY (18) | QSVSSY (28) | DAS (32) | QQRSNWPLT (35) |
| TRGB35 | GYSFTSYW (4) | IDPGDSDT (10) | ARHRWSTSLLLDY (19) | QSVSSY (28) | DAS (32) | QQRSNWPLT (35) |
| TRGB120 | GGTFSSYA (3) | IIPIFGTA (7) | ARPRRNTNELDY (20) | QSISSY (31) | AAS (34) | QQSYSTPLT (38) |
| TRGB127 | GGTFSSYA (3) | IIPIFGNA (11) | ARHVYKRGVLNY (21) | QSISSY (31) | AAS (34) | QQSYSTPLT (38) |

TABLE 3-continued

CDR sequences of the 16 GITR mAb candidates that showed binding against human and cyno GITR
(SEQ ID NO:)

| ID | HC-CDR1 | HC-CDR2 | HC-CDR3 | LC-CDR1 | LC-CDR2 | LC-CDR3 |
|---|---|---|---|---|---|---|
| TRGB134 | GGTFSSYA (3) | IIPIFGTA (7) | ARHRWGSGNLDY (22) | QSVSSY (28) | DAS (32) | QQRSNWPLT (35) |
| TRGB144 | GGTFSSYA (3) | IIPIFGTA (7) | ARHGFQRGYLDY (23) | QSVSSY (28) | DAS (32) | QQRSNWPLT (35) |
| TRGB153 | GGTFSSYA (3) | IIPIFGTA (7) | ARHAWLGHLDY (24) | QSVSSY (28) | DAS (32) | QQRSNWPLT (35) |
| TRGB159 | GGTFSSYA (3) | IIPIFGTA (7) | ARHGRNSGRLDY (25) | QSVSSY (28) | DAS (32) | QQRSNWPLT (35) |
| TRGB160 | GFTFSNYW (27) | ISGSGGST (5) | AKDFYWDSFDY (26) | QSVSSY (28) | DAS (32) | QQRSNWPLT (35) |
| TRGB162 | GGTFSSYA (3) | IIPIFGNA (11) | ARHVYKRGVLNY (21) | QSVSSY (28) | DAS (32) | QQRSNWPLT (35) |

VH and VL of the 16 GITR mAbs are shown below in Table 4.

TABLE 4

Heavy chain and light chain sequences of the 16 GITR mAb candidates that showed binding against human and cyno GITR.

| mAb ID | Heavy Chain Amino Acid Sequence | SEQ ID NO: | Light Chain Amino Acid Sequence | SEQ ID NO: |
|---|---|---|---|---|
| TRGB5 | EVQLLESGGGLVQPGGSLRLSCAASGFTFSGYWMSWVRQAPGKGLEWVSAISGSGGSTYYADSVKGRFTISRDNSKNTLYLQMNSLRAEDTAVYYCAKDFYWDAFDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK | 39 | EIVLTQSPATLSLSPGERATLSCRASQSVSSYLAWYQQKPGQAPRLLIYDASNRATGIPARFSGSGSGTDFTLTISSLEPEDFAVYYCQQRSNWPLTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 55 |
| TRGB14 | EVQLLESGGGLVQPGGSLRLSCAASGFTFSSYAMSWVRQAPGKGLEWVSAISGSGGSTYYADSVKGRFTISRDNSKNTLYLQMNSLRAEDTAVYYCAKPIRGLDYWGQGTLVTVSSASTKGPSVFPLAPSSKSTSGGTAALGCLVKDYFPEPVTVSWNSGALTSGVHTFPAVLQSSGLYSLSS | 40 | EIVLTQSPATLSLSPGERATLSCRASQSVNNFLAWYQQKPGQAPRLLIYDASNRATGIPARFSGSGSGTDFTLTISSLEPEDFAVYYCQQGFNAPLTFGQGTKVEIKRTVAAPSVFIFPPSDEQLKSGTASVVCLLNNFYPREAKVQWKVDNALQSGNSQESVTEQDSKDSTYSLSS | 56 |

TABLE 4-continued

Heavy chain and light chain sequences of the 16 GITR mAb candidates that showed binding against human and cyno GITR.

| mAb ID | Heavy Chain Amino Acid Sequence | SEQ ID NO: | Light Chain Amino Acid Sequence | SEQ ID NO: |
|---|---|---|---|---|
| | SSGLYSLSSVVTVPSSS LGTQTYICNVNHKPSN TKVDKKVEPKSCDKT HTCPPCPAPELLGGPS VFLFPPKPKDTLMISRT PEVTCVVVDVSHEDPE VKFNWYVDGVEVHN AKTKPREEQYNSTYRV VSVLTVLHQDWLNGK EYKCKVSNKALPAPIE KTISKAKGQPREPQVY TLPPSRDELTKNQVSL TCLVKGFYPSDIAVEW ESNGQPENNYKTTPPV LDSDGSFFLYSKLTVD KSRWQQGNVFSCSVM HEALHNHYTQKSLSLS PGK | | TLTLSKADYEKHKVY ACEVTHQGLSSPVTKS FNRGEC | |
| TRGB20 | EVQLLESGGGLVQPGG SLRLSCAASGFTFSGY WMNWVRQAPGKGLE WVSGISSDGGSKYYAD SVKGRFTISRDNSKNT LYLQMNSLRAEDTAV YYCAKEVVYDHYAAL DYWGQGTLVTVSSAS TKGPSVFPLAPSSKSTS GGTAALGCLVKDYFPE PVTVSWNSGALTSGV HTFPAVLQSSGLYSLSS VVTVPSSSLGTQTYICN VNHKPSNTKVDKKVE PKSCDKTHTCPPCPAP ELLGGPSVFLFPPKPKD TLMISRTPEVTCVVVD VSHEDPEVKFNWYVD GVEVHNAKTKPREEQ YNSTYRVVSVLTVLHQ DWLNGKEYKCKVSNK ALPAPIEKTISKAKGQP REPQVYTLPPSRDELT KNQVSLTCLVKGFYPS DIAVEWESNGQPENNY KTTPPVLDSDGSFFLYS KLTVDKSRWQQGNVF SCSVMHEALHNHYTQ KSLSLSPGK | 41 | EIVLTQSPATLSLSPGE RATLSCRASQSVNSFL AWYQQKPGQAPRLLI YYASNRATGIPARFSG SGSGTDFTLTISSLEPE DFAVYYCQQYIRWPLT FGQGTKVEIKRTVAAP SVFIFPPSDEQLKSGTA SVVCLLNNFYPREAKV QWKVDNALQSGNSQE SVTEQDSKDSTYSLSST LTLSKADYEKHKVYA CEVTHQGLSSPVTKSF NRGEC | 57 |
| TRGB23 | QVQLVQSGAEVKKPG SSVKVSCKASGGTFSS YAISWVRQAPGQGLE WMGGIIPIFGTANYAQ KFQGRVTITADESTST AYMELSSLRSEDTAVY YCARHGNWLHFNLDY WGQGTLVTVSSASTK GPSVFPLAPSSKSTSGG TAALGCLVKDYFPEPV TVSWNSGALTSGVHTF PAVLQSSGLYSLSSVV TVPSSSLGTQTYICNVN HKPSNTKVDKKVEPKS CDKTHTCPPCPAPELL GGPSVFLFPPKPKDTL MISRTPEVTCVVVDVS HEDPEVKFNWYVDGV EVHNAKTKPREEQYNS TYRVVSVLTVLHQDW LNGKEYKCKVSNKAL PAPIEKTISKAKGQPRE PQVYTLPPSRDELTKN QVSLTCLVKGFYPSDI AVEWESNGQPENNYK | 42 | EIVLTQSPATLSLSPGE RATLSCRASQSVSSYL AWYQQKPGQAPRLLI YDASNRATGIPARFSG SGSGTDFTLTISSLEPE DFAVYYCQQRSNWPL TFGQGTKVEIKRTVAA PSVFIFPPSDEQLKSGT ASVVCLLNNFYPREAK VQWKVDNALQSGNSQ ESVTEQDSKDSTYSLSS TLTLSKADYEKHKVY ACEVTHQGLSSPVTKS FNRGEC | 55 |

TABLE 4-continued

Heavy chain and light chain sequences of the 16 GITR mAb candidates that showed binding against human and cyno GITR.

| mAb ID | Heavy Chain Amino Acid Sequence | SEQ ID NO: | Light Chain Amino Acid Sequence | SEQ ID NO: |
|---|---|---|---|---|
| | TTPPVLDSDGSFFLYSK LTVDKSRWQQGNVFS CSVMHEALHNHYTQK SLSLSPGK | | | |
| TRGB25 | QVQLVQSGAEVKKPG SSVKVSCKASGGTFSS YAISWVRQAPGQGLE WMGGIIPIFGTANYAQ KFQGRVTITADESTST AYMELSSLRSEDTAVY YCARHRRFWLDYWG QGTLVTVSSASTKGPS VFPLAPSSKSTSGGTA ALGCLVKDYFPEPVTV SWNSGALTSGVHTFPA VLQSSGLYSLSSVVTV PSSSLGTQTYICNVNH KPSNTKVDKKVEPKSC DKTHTCPPCPAPELLG GPSVFLFPPKPKDTLMI SRTPEVTCVVVDVSHE DPEVKFNWYVDGVEV HNAKTKPREEQYNSTY RVVSVLTVLHQDWLN GKEYKCKVSNKALPA PIEKTISKAKGQPREPQ VYTLPPSRDELTKNQV SLTCLVKGFYPSDIAVE WESNGQPENNYKTTPP VLDSDGSFFLYSKLTV DKSRWQQGNVFSCSV MHEALHNHYTQKSLS LSPGK | 43 | EIVLTQSPATLSLSPGE RATLSCRASQSVSSYL AWYQQKPGQAPRLLI YDASNRATGIPARFSG SGSGTDFTLTISSLEPE DFAVYYCQQRSNWPL TFGQGTKVEIKRTVAA PSVFIFPPSDEQLKSGT ASVVCLLNNFYPREAK VQWKVDNALQSGNSQ ESVTEQDSKDSTYSLSS TLTLSKADYEKHKVY ACEVTHQGLSSPVTKS FNRGEC | 55 |
| TRGB31 | EVQLVQSGAEVKKPG ESLKISCKGSGYSFTSY WIGWVRQMPGKGLE WMGIIDPSDSDTRYSPS FQGQVTISADKSISTAY LQWSSLKASDTAMYY CARVFPYYGLVLDYW GQGTLVTVSSASTKGP SVFPLAPSSKSTSGGTA ALGCLVKDYFPEPVTV SWNSGALTSGVHTFPA VLQSSGLYSLSSVVTV PSSSLGTQTYICNVNH KPSNTKVDKKVEPKSC DKTHTCPPCPAPELLG GPSVFLFPPKPKDTLMI SRTPEVTCVVVDVSHE DPEVKFNWYVDGVEV HNAKTKPREEQYNSTY RVVSVLTVLHQDWLN GKEYKCKVSNKALPA PIEKTISKAKGQPREPQ VYTLPPSRDELTKNQV SLTCLVKGFYPSDIAVE WESNGQPENNYKTTPP VLDSDGSFFLYSKLTV DKSRWQQGNVFSCSV MHEALHNHYTQKSLS LSPGK | 44 | EIVLTQSPATLSLSPGE RATLSCRASQSVSSYL AWYQQKPGQAPRLLI YDASNRATGIPARFSG SGSGTDFTLTISSLEPE DFAVYYCQQRSNWPL TFGQGTKVEIKRTVAA PSVFIFPPSDEQLKSGT ASVVCLLNNFYPREAK VQWKVDNALQSGNSQ ESVTEQDSKDSTYSLSS TLTLSKADYEKHKVY ACEVTHQGLSSPVTKS FNRGEC | 55 |
| TRGB34 | EVQLVQSGAEVKKPG ESLKISCKGSGYSFTSY WIGWVRQMPGKGLE WMGIIYPGDSDTRYSP SFQGQVTISADKSISTA YLQWSSLKASDTAMY YCARDYGWHDFDYW GQGTLVTVSSASTKGP SVFPLAPSSKSTSGGTA | 45 | EIVLTQSPATLSLSPGE RATLSCRASQSVSSYL AWYQQKPGQAPRLLI YDASNRATGIPARFSG SGSGTDFTLTISSLEPE DFAVYYCQQRSNWPL TFGQGTKVEIKRTVAA PSVFIFPPSDEQLKSGT ASVVCLLNNFYPREAK | 55 |

TABLE 4-continued

Heavy chain and light chain sequences of the 16 GITR mAb candidates that showed binding against human and cyno GITR.

| mAb ID | Heavy Chain Amino Acid Sequence | SEQ ID NO: | Light Chain Amino Acid Sequence | SEQ ID NO: |
|---|---|---|---|---|
| | ALGCLVKDYFPEPVTV SWNSGALTSGVHTFPA VLQSSGLYSLSSVVTV PSSSLGTQTYICNVNH KPSNTKVDKKVEPKSC DKTHTCPPCPAPELLG GPSVFLFPPKPKDTLMI SRTPEVTCVVVDVSHE DPEVKFNWYVDGVEV HNAKTKPREEQYNSTY RVVSVLTVLHQDWLN GKEYKCKVSNKALPA PIEKTISKAKGQPREPQ VYTLPPSRDELTKNQV SLTCLVKGFYPSDIAVE WESNGQPENNYKTTPP VLDSDGSFFLYSKLTV DKSRWQQGNVFSCSV MHEALHNHYTQKSLS LSPGK | | VQWKVDNALQSGNSQ ESVTEQDSKDSTYSLSS TLTLSKADYEKHKVY ACEVTHQGLSSPVTKS FNRGEC | |
| TRGB35 | EVQLVQSGAEVKKPG ESLKISCKGSGYSFTSY WISWVRQMPGKGLEW MGIIDPGDSDTRYSPSF QGQVTISADKSISTAYL QWSSLKASDTAMYYC ARHRWSTSLLLDYWG QGTLVTVSSASTKGPS VFPLAPSSKSTSGGTA ALGCLVKDYFPEPVTV SWNSGALTSGVHTFPA VLQSSGLYSLSSVVTV PSSSLGTQTYICNVNH KPSNTKVDKKVEPKSC DKTHTCPPCPAPELLG GPSVFLFPPKPKDTLMI SRTPEVTCVVVDVSHE DPEVKFNWYVDGVEV HNAKTKPREEQYNSTY RVVSVLTVLHQDWLN GKEYKCKVSNKALPA PIEKTISKAKGQPREPQ VYTLPPSRDELTKNQV SLTCLVKGFYPSDIAVE WESNGQPENNYKTTPP VLDSDGSFFLYSKLTV DKSRWQQGNVFSCSV MHEALHNHYTQKSLS LSPGK | 46 | EIVLTQSPATLSLSPGE RATLSCRASQSVSSYL AWYQQKPGQAPRLLI YDASNRATGIPARFSG SGSGTDFTLTISSLEPE DFAVYYCQQRSNWPL TFGQGTKVEIKRTVAA PSVFIFPPSDEQLKSGT ASVVCLLNNFYPREAK VQWKVDNALQSGNSQ ESVTEQDSKDSTYSLSS TLTLSKADYEKHKVY ACEVTHQGLSSPVTKS FNRGEC | 55 |
| TRGB120 | QVQLVQSGAEVKKPG SSVKVSCKASGGTFSS YAISWVRQAPGQGLE WMGGIIPIFGTANYAQ KFQGRVTITADESTST AYMELSSLRSEDTAVY YCARPRRNTNELDYW GQGTLVTVSSASTKGP SVFPLAPSSKSTSGGTA ALGCLVKDYFPEPVTV SWNSGALTSGVHTFPA VLQSSGLYSLSSVVTV PSSSLGTQTYICNVNH KPSNTKVDKKVEPKSC DKTHTCPPCPAPELLG GPSVFLFPPKPKDTLMI SRTPEVTCVVVDVSHE DPEVKFNWYVDGVEV HNAKTKPREEQYNSTY RVVSVLTVLHQDWLN GKEYKCKVSNKALPA PIEKTISKAKGQPREPQ VYTLPPSREEMTKNQV | 47 | DIQMTQSPSSLSASVG DRVTITCRASQSISSYL NWYQQKPGKAPKLLI YAASSLQSGVPSRFSG SGSGTDFTLTISSLQPE DFATYYCQQSYSTPLT FGQGTKVEIKRTVAAP SVFIFPPSDEQLKSGTA SVVCLLNNFYPREAKV QWKVDNALQSGNSQE SVTEQDSKDSTYSLSST LTLSKADYEKHKVYA CEVTHQGLSSPVTKSF NRGEC | 58 |

TABLE 4-continued

Heavy chain and light chain sequences of the 16 GITR mAb candidates that showed binding against human and cyno GITR.

| mAb ID | Heavy Chain Amino Acid Sequence | SEQ ID NO: | Light Chain Amino Acid Sequence | SEQ ID NO: |
|---|---|---|---|---|
| | SLTCLVKGFYPSDIAVE WESNGQPENNYKTTPP VLDSDGSFFLYSKLTV DKSRWQQGNVFSCSV MHEALHNHYTQKSLS LSPGK | | | |
| TRGB127 | QVQLVQSGAEVKKPG SSVKVSCKASGGTFSS YAISWVRQAPGQGLE WMGGIIPIFGNANYAQ KFQGRVTITADESTST AYMELSSLRSEDTAVY YCARHVYKRGVLNY WGQGTLVTVSSASTK GPSVFPLAPSSKSTSGG TAALGCLVKDYFPEPV TVSWNSGALTSGVHTF PAVLQSSGLYSLSSVV TVPSSSLGTQTYICNVN HKPSNTKVDKKVEPKS CDKTHTCPPCPAPELL GGPSVFLFPPKPKDTL MISRTPEVTCVVVDVS HEDPEVKFNWYVDGV EVHNAKTKPREEQYNS TYRVVSVLTVLHQDW LNGKEYKCKVSNKAL PAPIEKTISKAKGQPRE PQVYTLPPSREEMTKN QVSLTCLVKGFYPSDI AVEWESNGQPENNYK TTPPVLDSDGSFFLYSK LTVDKSRWQQGNVFS CSVMHEALHNHYTQK SLSLSPGK | 48 | DIQMTQSPSSLSASVG DRVTITCRASQSISSYL NWYQQKPGKAPKLLI YAASSLQSGVPSRFSG SGSGTDFTLTISSLQPE DFATYYCQQSYSTPLT FGQGTKVEIKRTVAAP SVFIFPPSDEQLKSGTA SVVCLLNNFYPREAKV QWKVDNALQSGNSQE SVTEQDSKDSTYSLSST LTLSKADYEKHKVYA CEVTHQGLSSPVTKSF NRGEC | 58 |
| TRGB134 | QVQLVQSGAEVKKPG SSVKVSCKASGGTFSS YAISWVRQAPGQGLE WMGGIIPIFGTANYAQ KFQGRVTITADESTST AYMELSSLRSEDTAVY YCARHRWGSGNLDY WGQGTLVTVSSASTK GPSVFPLAPSSKSTSGG TAALGCLVKDYFPEPV TVSWNSGALTSGVHTF PAVLQSSGLYSLSSVV TVPSSSLGTQTYICNVN HKPSNTKVDKKVEPKS CDKTHTCPPCPAPELL GGPSVFLFPPKPKDTL MISRTPEVTCVVVDVS HEDPEVKFNWYVDGV EVHNAKTKPREEQYNS TYRVVSVLTVLHQDW LNGKEYKCKVSNKAL PAPIEKTISKAKGQPRE PQVYTLPPSREEMTKN QVSLTCLVKGFYPSDI AVEWESNGQPENNYK TTPPVLDSDGSFFLYSK LTVDKSRWQQGNVFS CSVMHEALHNHYTQK SLSLSPGK | 49 | EIVLTQSPATLSLSPGE RATLSCRASQSVSSYL AWYQQKPGQAPRLLI YDASNRATGIPARFSG SGSGTDFTLTISSLEPE DFAVYYCQQRSNWPL TFGQGTKVEIKRTVAA PSVFIFPPSDEQLKSGT ASVVCLLNNFYPREAK VQWKVDNALQSGNSQ ESVTEQDSKDSTYSLSS TLTLSKADYEKHKVY ACEVTHQGLSSPVTKS FNRGEC | 55 |
| TRGB144 | QVQLVQSGAEVKKPG SSVKVSCKASGGTFSS YAISWVRQAPGQGLE WMGGIIPIFGTANYAQ KFQGRVTITADESTST AYMELSSLRSEDTAVY YCARHGFQRGYLDYW | 50 | EIVLTQSPATLSLSPGE RATLSCRASQSVSSYL AWYQQKPGQAPRLLI YDASNRATGIPARFSG SGSGTDFTLTISSLEPE DFAVYYCQQRSNWPL TFGQGTKVEIKRTVAA | 55 |

TABLE 4-continued

Heavy chain and light chain sequences of the 16 GITR mAb candidates that showed binding against human and cyno GITR.

| mAb ID | Heavy Chain Amino Acid Sequence | SEQ ID NO: | Light Chain Amino Acid Sequence | SEQ ID NO: |
|---|---|---|---|---|
| | GQGTLVTVSSASTKGP SVFPLAPSSKSTSGGTA ALGCLVKDYFPEPVTV SWNSGALTSGVHTFPA VLQSSGLYSLSSVVTV PSSSLGTQTYICNVNH KPSNTKVDKKVEPKSC DKTHTCPPCPAPELLG GPSVFLFPPKPKDTLMI SRTPEVTCVVVDVSHE DPEVKFNWYVDGVEV HNAKTKPREEQYNSTY RVVSVLTVLHQDWLN GKEYKCKVSNKALPA PIEKTISKAKGQPREPQ VYTLPPSREEMTKNQV SLTCLVKGFYPSDIAVE WESNGQPENNYKTTPP VLDSDGSFFLYSKLTV DKSRWQQGNVFSCSV MHEALHNHYTQKSLS LSPGK | | PSVFIFPPSDEQLKSGT ASVVCLLNNFYPREAK VQWKVDNALQSGNSQ ESVTEQDSKDSTYSLSS TLTLSKADYEKHKVY ACEVTHQGLSSPVTKS FNRGEC | |
| TRGB153 | QVQLVQSGAEVKKPG SSVKVSCKASGGTFSS YAISWVRQAPGQGLE WMGGIIPIFGTANYAQ KFQGRVTITADESTST AYMELSSLRSEDTAVY YCARHAWLGHLDYW GQGTLVTVSSASTKGP SVFPLAPSSKSTSGGTA ALGCLVKDYFPEPVTV SWNSGALTSGVHTFPA VLQSSGLYSLSSVVTV PSSSLGTQTYICNVNH KPSNTKVDKKVEPKSC DKTHTCPPCPAPELLG GPSVFLFPPKPKDTLMI SRTPEVTCVVVDVSHE DPEVKFNWYVDGVEV HNAKTKPREEQYNSTY RVVSVLTVLHQDWLN GKEYKCKVSNKALPA PIEKTISKAKGQPREPQ VYTLPPSREEMTKNQV SLTCLVKGFYPSDIAVE WESNGQPENNYKTTPP VLDSDGSFFLYSKLTV DKSRWQQGNVFSCSV MHEALHNHYTQKSLS LSPGK | 51 | EIVLTQSPATLSLSPGE RATLSCRASQSVSSYL AWYQQKPGQAPRLLI YDASNRATGIPARFSG SGSGTDFTLTISSLEPE DFAVYYCQQRSNWPL TFGQGTKVEIKRTVAA PSVFIFPPSDEQLKSGT ASVVCLLNNFYPREAK VQWKVDNALQSGNSQ ESVTEQDSKDSTYSLSS TLTLSKADYEKHKVY ACEVTHQGLSSPVTKS FNRGEC | 55 |
| TRGB159 | QVQLVQSGAEVKKPG SSVKVSCKASGGTFSS YAISWVRQAPGQGLE WMGGIIPIFGTANYAQ KFQGRVTITADESTST AYMELSSLRSEDTAVY YCARHGRNSGRLDYW GQGTLVTVSSASTKGP SVFPLAPSSKSTSGGTA ALGCLVKDYFPEPVTV SWNSGALTSGVHTFPA VLQSSGLYSLSSVVTV PSSSLGTQTYICNVNH KPSNTKVDKKVEPKSC DKTHTCPPCPAPELLG GPSVFLFPPKPKDTLMI SRTPEVTCVVVDVSHE DPEVKFNWYVDGVEV HNAKTKPREEQYNSTY RVVSVLTVLHQDWLN GKEYKCKVSNKALPA | 52 | EIVLTQSPATLSLSPGE RATLSCRASQSVSSYL AWYQQKPGQAPRLLI YDASNRATGIPARFSG SGSGTDFTLTISSLEPE DFAVYYCQQRSNWPL TFGQGTKVEIKRTVAA PSVFIFPPSDEQLKSGT ASVVCLLNNFYPREAK VQWKVDNALQSGNSQ ESVTEQDSKDSTYSLSS TLTLSKADYEKHKVY ACEVTHQGLSSPVTKS FNRGEC | 55 |

TABLE 4-continued

Heavy chain and light chain sequences of the 16 GITR mAb candidates that showed binding against human and cyno GITR.

| mAb ID | Heavy Chain Amino Acid Sequence | SEQ ID NO: | Light Chain Amino Acid Sequence | SEQ ID NO: |
|---|---|---|---|---|
| | PIEKTISKAKGQPREPQ VYTLPPSREEMTKNQV SLTCLVKGFYPSDIAVE WESNGQPENNYKTTPP VLDSDGSFFLYSKLTV DKSRWQQGNVFSCSV MHEALHNHYTQKSLS LSPGK | | | |
| TRGB160 | QVQLLESGGGLVQPG GSLRLSCAASGFTFSN YWMSWVRQAPGKGL EWVSAISGSGGSTYYA DSVKGRFTISRDNSKN TLYLQMNSLRAEDTA VYYCAKDFYWDSFDY WGQGTLVTVSSASTK GPSVFPLAPSSKSTSGG TAALGCLVKDYFPEPV TVSWNSGALTSGVHTF PAVLQSSGLYSLSSVV TVPSSSLGTQTYICNVN HKPSNTKVDKKVEPKS CDKTHTCPPCPAPELL GGPSVFLFPPKPKDTL MISRTPEVTCVVVDVS HEDPEVKFNWYVDGV EVHNAKTKPREEQYNS TYRVVSVLTVLHQDW LNGKEYKCKVSNKAL PAPIEKTISKAKGQPRE PQVYTLPPSREEMTKN QVSLTCLVKGFYPSDI AVEWESNGQPENNYK TTPPVLDSDGSFFLYSK LTVDKSRWQQGNVFS CSVMHEALHNHYTQK SLSLSPGK | 53 | EIVLTQSPATLSLSPGE RATLSCRASQSVSSYL AWYQQKPGQAPRLLI YDASNRATGIPARFSG SGSGTDFTLTISSLEPE DFAVYYCQQRSNWPL TFGQGTKVEIKRTVAA PSVFIFPPSDEQLKSGT ASVVCLLNNFYPREAK VQWKVDNALQSGNSQ ESVTEQDSKDSTYSLSS TLTLSKADYEKHKVY ACEVTHQGLSSPVTKS FNRGEC | 55 |
| TRGB162 | QVQLVQSGAEV KKPGSSVKVSCKASGG TFSSYAISWVRQAPGQ GLEWMGGIIPIFGNAN YAQKFQGRVTITADES TSTAYMELSSLRSEDT AVYYCARHVYKRGVL NYWGQGTLVTVSSAS TKGPSVFPLAPSSKSTS GGTAALGCLVKDYFPE PVTVSWNSGALTSGV HTFPAVLQSSGLYSLSS VVTVPSSSLGTQTYICN VNHKPSNTKVDKKVE PKSCDKTHTCPPCPAP ELLGGPSVFLFPPKPKD TLMISRTPEVTCVVVD VSHEDPEVKFNWYVD GVEVHNAKTKPREEQ YNSTYRVVSVLTVLHQ | 54 | EIVLTQSPATLSLSPGE RATLSCRASQSVSSYL AWYQQKPGQAPRLLI YDASNRATGIPARFSG SGSGTDFTLTISSLEPE DFAVYYCQQRSNWPL TFGQGTKVEIKRTVAA PSVFIFPPSDEQLKSGT ASVVCLLNNFYPREAK VQWKVDNALQSGNSQ ESVTEQDSKDSTYSLSS TLTLSKADYEKHKVY ACEVTHQGLSSPVTKS FNRGEC | 55 |

TABLE 4-continued

Heavy chain and light chain sequences of the 16 GITR mAb candidates that showed binding against human and cyno GITR.

| mAb ID | Heavy Chain Amino Acid Sequence | SEQ ID NO: | Light Chain Amino Acid Sequence | SEQ ID NO: |
|---|---|---|---|---|
| | DWLNGKEYKCKVSNK ALPAPIEKTISKAKGQP REPQVYTLPPSREEMT KNQVSLTCLVKGFYPS DIAVEWESNGQPENNY KTTPPVLDSDGSFFLYS KLTVDKSRWQQGNVF SCSVMHEALHNHYTQ KSLSLSPGK | | | |

Example 7: Evaluation of GITR Antibodies in Functional Cell Killing Assay

Antibodies that bound to both human and cyno GITR were tested for activity in ADCC and CDC assays. The huIgG1 isotype control antibody was included in these assays for comparison. ADCC assays were used to look at cell killing carried out by NK-92 cells genetically modified to express the high affinity FcγRIIIa 176V/V polymorphism. Three types of target cells were used: HuT102 cells, which endogenously express human GITR, pooled HT1080-hu-GITR stable transfectants, and HEK293 cells that were transiently transfected with either human GITR or cyno GITR. To carry out the ADCC assays, the target cells were labelled with calcein AM, washed, resuspended in assay medium, and seeded at 50,000 cells/50 microliters/well in V bottom 96 well plates. Anti-hGITR or control antibodies were added to the wells at various concentrations (100 microliters/well). NK-92 176V effector cells were washed, resuspended in assay medium, and seeded at 50,000 cells/50 microliters/well or 100,000 cells/50 microliters/well along with target cells and antibodies. Medium alone (background signal), target cells alone (spontaneous lysis signal), cells that would eventually be treated with Triton X-100 (Max lysis signal) and isotype control antibody at a final concentration of 1 microgram/mL were included as controls. After 1 hour incubation at 37° C., complete cell lysis was induced in the Max signal wells through the addition of 20 microliters of 2% Triton X-100 and the plates were centrifuged. 100 microliters of supernatants were removed and added to clear bottom black plates. Fluorescence intensity (FI) units were measured using a Molecular Devices SpectraMax5. Percent specific lysis was calculated after subtracting the average FI observed with medium alone from all wells. The formula to determine percent specific lysis was (Sample−Spontaneous lysis)/(Max lysis−Spontaneous lysis)*100. Analysis of the half maximal effective concentration (EC50) was carried out for each antibody in Prism.

Table 5 depicts the activity of the GITR antibodies in the different cell lines tested.

TABLE 5

Activity of GITR antibodies in ADCC assays

| | TRGB23^ $EC_{50}$ (ng/mL) | TRGB25^ $EC_{50}$ (ng/mL) | TRGB31 $EC_{50}$ (ng/mL) | TRGB34 $EC_{50}$ (ng/mL) | TRGB153 $EC_{50}$ (ng/mL) | TRGB159 $EC_{50}$ (ng/mL) | TRGB160 $EC_{50}$ (ng/mL) |
|---|---|---|---|---|---|---|---|
| HuT102 | 1.6 to 1.9 | 6.8 to 9.4 | 2.9 to 3.7 | 1.3 to 1.7 | 0.6 to 1.8 | 32.7 to 61.1 | 11.2 to 21.3 |
| HT1080-hGITR | 0.9 to 4.5 | 15.0 to 67.4 | 2.0 to 4.2 | 2.4 to 9.8 | 0.01 to 1.2 | 6.7 | 4.2 to 26.6 |
| HEK293-hGITR | 4.4 | 52.0 | 7.6 | 5.8 | 1.9 | 2.9 | 30.2 |
| HEK293-cyno GITR | 10.2 | 465.9 | No activity | No activity | 2.5 | 25.8 | 56.7 |

^TRGB23 is TRGB25, TRGB25 is TRGB19

Example 8. Double Gene Construction and Production of Low-Fucose Molecules

In preparation for cell line development, double gene construction was initiated for TRGB25, TRGB153, TRGB159, and TRGB160. During this process it was discovered that heavy chain of TRGB25 was in the human allotype IgG1_G1m(17,1) rather than the preferred human allotype IgG1_G1m(17). The heavy chain V-region from TRGB25 was switched into a human IgG1_G1m(17) allotype framework during double gene construction, thereby creating the new protein TRGB190. At this point it was also noted that TRGB160 had a framework mutation at the amino terminus of the heavy chain. During the construction of the double gene, the amino terminal residue of the TRGB160 heavy chain was switched from Q to E, thereby creating the new protein TRGB191. In addition, it was decided to produce a low-fucose version of TRGB191, ie TRGB191.CLF. Table 6 outlines the sequences of this modified anti-GITR antibodies.

TABLE 6

V_H and V_L sequences of the 2 GITR mAb candidates that were modified in the framework region. The CDRs remained identical to the parent.

| mAb ID | VH Amino Acid Sequence | SEQ ID NO: | VL Amino Acid Sequence | SEQ ID NO: |
|---|---|---|---|---|
| TRGB190 | QVQLVQSGAEVKKPGSSVKVSCKASGGTFSSYAISWVRQAPGQGLEWMGGIIPIFGTANYAQKFQGRVTITADESTSTAYMELSSLRSEDTAVYYCARHRRFWLDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK | 63 | EIVLTQSPATLSLSPGERATLSCRASQSVSSYLAWYQQKPGQAPRLLIYDASNRATGIPARFSGSGSGTDFTLTISSLEPEDFAVYYCQQRSNWPLTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 55 |
| TRGB191.CLF | EVQLLESGGGLVQPGGSLRLSCAASGFTFSNYWMSWVRQAPGKGLEWVSAISGSGGSTYYADSVKGRFTISRDNSKNTLYLQMNSLRAEDTAVYYCAKDFYWDSFDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK | 64 | EIVLTQSPATLSLSPGERATLSCRASQSVSSYLAWYQQKPGQAPRLLIYDASNRATGIPARFSGSGSGTDFTLTISSLEPEDFAVYYCQQRSNWPLTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 55 |

Example 9: Affinity Measurements by SPR

The affinities of the GITR antibodies to recombinant human GITR ECD were measured by Surface Plasmon Resonance (SPR) using a ProteOn XPR36 protein interaction array system (BioRad).

The rates of GITR ECD association and dissociation were measured for each variant. The biosensor surface was prepared by covalently coupling Goat anti-Human IgG (Fc) to the surface of a GLC chip (BioRad) using the manufacturer instructions for amine-coupling chemistry. Approximately 8800 RU (response units) of Goat anti-Human IgG (Fc) antibody (Jackson ImmunoResearch laboratories Prod #109-005-098) were immobilized. The RU immobilized also included a goat anti-mouse Fc antibody that was added to capture other antibodies not included in the ones reported here. Since the mixture was 1:1 about 50% of these RU immobilized are expected to be goat anti-human Fc. The binding kinetics experiments were performed at 25° C. in running buffer (PBS pH 7.4, 0.005% P20, 3 mM EDTA). Four-fold (1:3) serial dilutions of human GITR ECD or cyno GITR ECD starting at 100 nM were prepared in running buffer. An average of 300 RU of mAb (174-600) were captured on each channel of the sensor chip. The reference spots (Goat anti-Human IgG (Fc)-modified surface) containing no candidate captured were used as a reference surface. Capture of mAb was followed by 3 min injection (association phase) of antigen at 40 µL/min, followed by 10 min of buffer flow (dissociation phase). The chip surface was regenerated by injection of 0.85% phosphoric acid at 100 µL/min. Data were processed on the instrument software. Double reference subtraction of the data was performed by subtracting the curves generated by buffer injection from the reference-subtracted curves for analyte injections. Kinetic analysis of the data was performed using 1:1 Langmuir binding model with group fit. The result for each mAb was reported in the format of kon or on-rate, koff or off-rate, and $K_D$ (Equilibrium dissociation constant) (Table 7).

TABLE 7

SPR affinity results for anti-GITR mAbs binding to human and cyno GITR ECD protein

| mAb | GITR | AVG. $k_{on}$ (1/Ms) | AVG. $k_{off}$ (1/s) | $K_D$ (pM) |
|---|---|---|---|---|
| TRGB25 | Human | 7.93E+05 | 4.31E−05 | 54.3 |
| | Cyno | 2.37E+05 | 9.31E−04 | 3936 |
| TRGB160 | Human | 1.40E+05 | 1.50E−04 | 1077 |
| | Cyno | 8.80E+04 | 4.19E−05 | 476 |
| TRGB153 | Human | 9.96E+05 | 2.02E−05 | 20.2 |
| | Cyno | 2.99E+05 | 2.57E−03 | 8597 |
| TRGB159 | Human | 5.32E+05 | 1.62E−03 | 3045 |
| | Cyno | 1.85E+05 | 1.97E−03 | 10629 |
| negative control | Human/ Cyno | | No binding under tested conditions | |

The results indicated that few of the antibodies met the objective of binding to the cyno GITR ECD with affinity within five-fold of binding to the human GITR ECD. This outcome seemed to conflict with the cell killing data discussed in EXAMPLE 7, in which most of the antibodies killed cells that expressed cyno GITR with a potency only slightly less than that shown against cells that expressed the human GITR protein. It is possible that the truncated GITR extracellular domains that had been overexpressed in insect cells may not have been properly folded, which resulted in the disagreement between the cell killing and affinity analysis experiments. It is further possible that full-length GITR expressed in human cells was more likely to fold properly, and that measurements of binding affinity to GITR-expressing cells would be more likely to align with the observed cell killing activity. To test these possibilities the affinities of these antibodies for cells that express either human or cyno GITR should be evaluated.

Example 10: Affinity Measurements by MSD

Cell-based affinity experiments were performed to assess the binding of anti-GITR antibodies with human and cyno GITR transfected HEK293 cell lines using MSD-Cell Affinity Technology (MSD-CAT). The MSD-CAT was developed in-house as a label-free method to determine affinity using intact cells in a high throughput format. The parental HEK293 cell line without any GITR expressed was used as a negative control.

In order to measure the affinity of an interaction by this technique, a series of solutions with a fixed concentration of anti-GITR antibody (300, 60, 12, 2.4 pM) and varying concentrations of human or cyno GITR expressing cells (2.0×10⁷-1.0×10³ cells/mL) were prepared and allowed to reach equilibrium by rotating the plates for 18 hr at 4° C. These samples were prepared in DMEM Glutamax medium (Invitrogen, Prod #10569-044) with 0.05% Azide, 1% BSA, 3 mM EDTA. After equilibration the plates were centrifuged for 5 min at 2000 rpm and free anti-GITR mAbs are detected in the supernatant. The free anti-GITR mAbs in the mixture were detected by electrochemiluminescence (ECL) using MSD reader instrument. For detection, MSD-Streptavidin plates (MesoScale Discovery, Prod #L11SA-1) were coated with 0.1 µg/mL of biotinylated human-GITR antigen in assay buffer at 50 µL/well and equilibrated overnight (~16 hr at 4° C.). After equilibration, the plates were blocked by adding 150 µL/well of assay buffer without removing coating antigen, incubated for ~1 hr at ambient temperature and washed 3 times with wash buffer. The supernatants from the centrifuged plates were transferred to antigen-coated plates (50 µL/well), incubated for 60 min, and then washed three times with wash buffer. After this, 50 µL/well of 0.7 µg/mL ruthenium-conjugated F(ab')2 donkey anti-human IgG (H+L) (Jackson ImmunoResearch; Prod #709-006-149) was added and incubated for 1 hr. After 1 hr, the plates were washed three times with wash buffer and 150 µL of MSD Read Buffer (MesoScale Discovery Cat #R92TC-1; prepared by diluting 1:3 of stock into d. H2O) were added per well. The plates were read immediately on the MSD Sector Imager 6000 Reader for luminescence levels. ECL signal detected by MSD was expressed in term of % free antibody in the mixture and the data was analyzed to determine affinity using a user defined equation (derived from the law of mass action) introduced in Prism software. The free mAb concentration as a function of receptor concentration is subject to non-linear least squares analysis with a 1:1 binding model to determine binding affinities. Table 8 summarizes the cell binding affinities for all the tested molecules.

TABLE 8

MSD-CAT based affinity assessment of anti-GITR mAbs with human and cyno GITR expressing HEK293 cell lines.

| Sample | Study | Human-GITR ($K_D$, pM) | Cyno-GITR ($K_D$, pM) | $K_D$ Fold Difference (Cy/Hu) |
|---|---|---|---|---|
| TRGB190 | 2 | 41 ± 22 | 63 ± 40* (91 ± 97) | 1.5 |
| | 3 | 17 ± 4 | 27 ± 8 | 1.6 |
| TRGB25 | 1 | 29.2 | 194 | 6.6 |
| | 2 | 26 ± 11 | 47 ± ND | 1.8 |
| | 3 | 19 ± 4 | 45 ± 29 | 2.4 |
| | 4 | 23 ± 1 | 29 ± 7 | 1.3 |
| TRGB191.CLF | 2 | 287 ± 182 | 424 ± 155 | 1.5 |
| | 3 | 83 ± 18 | 262 ± 159 | 3.2 |
| | 4 | 158 ± 86 | 321 ± 63 | 2.0 |
| TRGB160 | 1 | 112 | 711 | 6.3 |
| | 2 | 273 ± 192 | 464 ± 244* (598 ± 481) | 1.7 |
| | 3 | 83 ± 43 | 210 ± 78 | 2.5 |
| TRGB153 | 1 | ~10** | 115 | 11.4 |

The affinities for cell-surface expressed GITR were measured by MSD-CAT for TRGB25, TRGB190, TRGB160, TRGB191.CLF and TRGB153. Four studies were performed where the first study was considered preliminary data and consisted of only one replicate. Further studies with larger number of repeats were performed (Studies 2 and 3). Studies 2 and 3 indicate that for TRGB190, the mAb affinity for cyno GITR is 1.5-1.6-fold weaker than for human GITR. Studies 2 and 3 also indicate that for TRGB191.CLF, the mAb affinity for cyno GITR is 1.5-3.2-fold weaker than for human GITR. Study 4 was carried out at a later date to confirm the TRGB191.CLF data from the earlier studies. The data in Study 4 indicates that for TRGB191.CLF, the mAb affinity for cyno GITR is 2.0-fold weaker than for human GITR.

Example 11: GITR Signals Through NF-kB and Effect of GITRL Blockade on Signaling Antigen primed T lymphocytes need to expand and persist to promote adaptive immunity. The growth and survival signals required are contributed in large part by the NF-κB pathway in activated T cells. Interferon gamma (IFNγ), a well-known target gene of the NF-kB transcription factor, is a critical cytokine for immunity against foreign pathogens, and is produced by Th1 CD4 and CD8 cytotoxic T lymphocyte (CTL) effector T cells once antigen-specific immunity develops (Schoenborn J R, Wilson C B. Adv Immunol. 2007; 96:41-101).

The tumor necrosis factor receptor (TNFR) superfamily members, of which GITR is a member, can provide a co-stimulatory signal to the T cells. This is initiated by binding to their respective ligand and via recruitment of adaptor proteins known as TRAFs (TNF receptor associated factor) which can signal through the NF-κB pathway. In addition, the strength of the co-stimulatory signaling is dependent on receptor oligomerization, which can be achieved with trimeric or hexameric soluble ligands, or via antibody-mediated cross-linking.

To detect the effect of anti-GITR antibody ligation on NF-κB activity, a modified version of the HEK-Blue NF-κB system (Invivogen) were utilized. These cells express the SEAP (Secreted Embroyonic Alkaline Phosphatase) reporter gene under the control of a minimal promoter fused to five NF-κB and AP-1 binding sites. They were stably transfected to express human GITR. GITR receptor crosslinking in this system drives NF-κB activity which can be detected by SEAP secretion in the supernatant. A trimeric soluble GITR ligand chimeric protein (R&D Systems) was used as a positive control.

For "agonist" testing 25,000 HEK-Blue-NF-κB-GITR cells were treated with serial 1:2 dilutions of soluble GITRL (starting at 100 ng/mL) or anti-GITR antibody (starting at 1 ug/mL) in the presence of 5× excess crosslinker antibody (anti-HA or anti-Fc, respectively) for 16-20 hours. Supernatant (40 uLs) was removed and mixed with 160 uLs of Quanti-Blue™ reagent. The colorimetric reaction was allowed to incubate at 37° C. for up to 1 hr before being read in a spectrophotometer at $OD_{650\ nm}$.

To test the antibodies in "antagonist" mode, cells were treated with serial 1:2 dilutions of anti-GITR antibody (starting at 2 ug/mL) in the presence of 25 ng/mL constant concentration of soluble GITRL. Antagonists were defined as antibodies that blocked binding and NF-κB activity of soluble GITRL by more than 50%. Representative graphs are provided below and serve to illustrate experiment variability.

In agonist mode, anti-GITR antibodies are capable of cross-linking GITR on the HEK-Blue-NF-κB-GITR cells, causing a dose-dependent increase in NF-κB activity, compared to an isotype control antibody, CNTO3930 (FIG. 3). In the presence of sGITRL, some anti-GITR antibodies are observed to reduce the level of sGITRL-dependent NF-κB activation, whereas other antibodies do not, even when used at 400× the concentration. TRGB191.CLF, GTRB45 and GTRB49 do not appear to block GITRL:GITR interaction by greater than 30%, which may be attributed to assay variability. GTRB45 and GTRB49 are uncharacterized antibodies that also bind to GITR.

Example 12. GITR Antibodies can Enhance Memory T Cell Response to CMV and TT Antigen A hallmark of immunity is the generation of memory T cells against foreign antigens such that an immune response can be mounted more rapidly upon subsequent exposure.

Cytomegalovirus (CMV) is a herpesvirus and is a common infection that is usually asymptomatic in healthy adults and children. It is estimated that 50-80% of adults are infected with CMV by the time they reach 40 years old. Tetanus toxin (TT) is produced bacteria called *Clostridium tetani*. Most adults in the US are vaccinated for tetanus 5 times before the age of 6, and receive boosters every 10 years thereafter.

By exposing sero-positive individuals to their respective antigens, memory T cells can be reactivated to mount a recall response. GITR expression has been shown to be upregulated on T cells and GITRL on the antigen presenting cells. An agonist GITR antibody could strengthen the T cell activation by signaling through GITR and further enhancing the antigen specific immune response.

Interferon gamma (IFNγ) is a critical cytokine for immunity against foreign pathogens, and is produced by Th1 CD4 and CD8 cytotoxic T lymphocyte (CTL) effector T cells once antigen-specific immunity develops (Schoenborn J R, Wilson C B. Adv Immunol. 2007; 96:41-101).

Here, we have developed a CMV and TT recall assay to characterize our anti-GITR antibodies for their ability to enhance T cell activation, as measured by IFNγ secretion. Briefly, 150,000 PBMCs obtained from sero-positive donors for CMV and TT were incubated in the presence of 0.1 ug/mL of CMV antigen or TT antigen (CMV whole antigen, Astarte #1004; TT antigen, Astarte #1002) in wells pre-coated with a 1:2 dilution series of test antibodies starting at 5 ug/mL to 156 ng/mL (left to right on x-axis). Supernatant was harvested 4-6 days afterwards and IFNγ levels were quantified by MSD. Antigen only controls were used to assess reactivity of the donor and CNTO3930 was an antibody isotype control. Each antibody concentration was run in replicates (n=6).

Figure 4A:
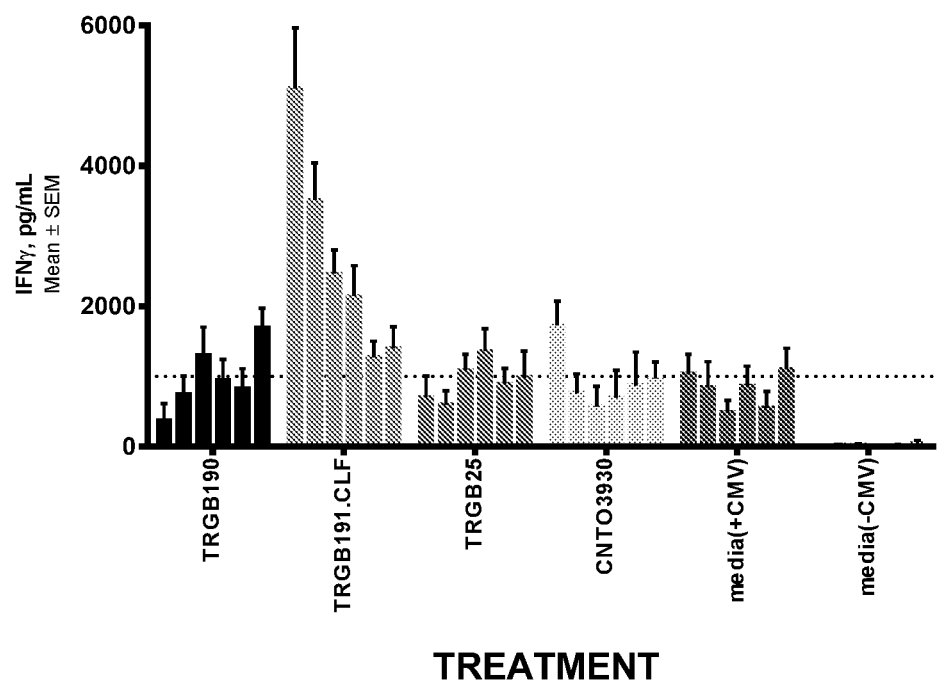
FIGS. 4A and 4B. The effect of anti-GITR antibodies on memory T cell responses to CMV (FIG. 4A) and TT (FIG. 4B). Sero-reactive PBMCs were pulsed with CMV and TT antigen in the absence or presence of anti-GITR antibodies, CNTO3930 isotype control antibody or no antibody. Supernatant was collected and measured for the presence of IFNγ.
Figure 4B:
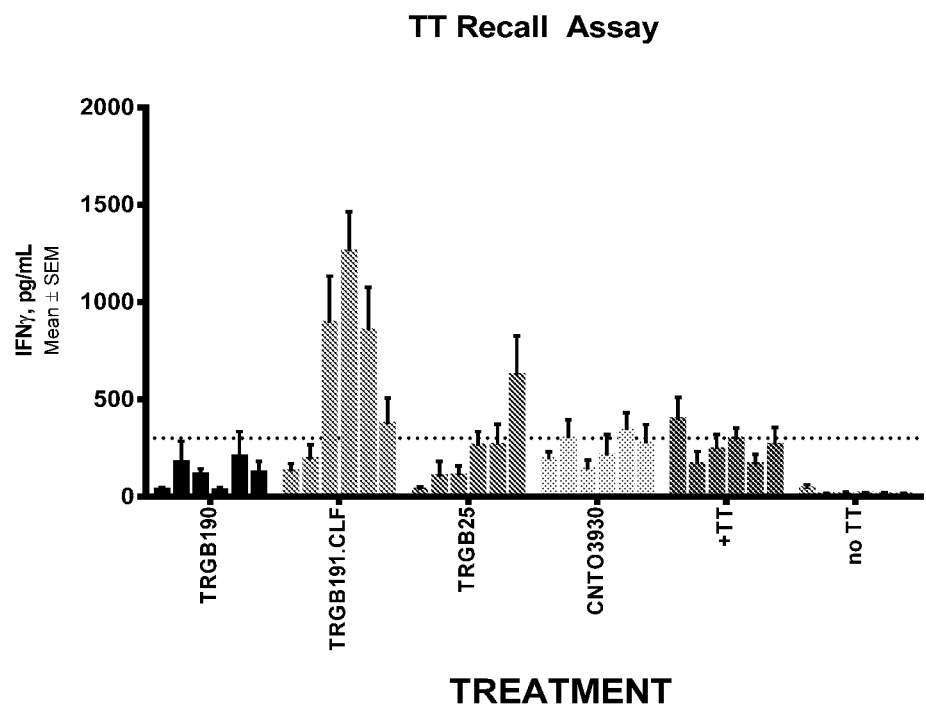

TRGB191.CLF augments CMV-dependent memory T cell activation in a dose dependent manner, as measured by IFNγ secretion, peaking at [Ab]=5 ug/mL (FIG. 4A). In the TT-recall assay, peak T cell co-activation was observed at [Ab]=625 ng/mL (FIG. 4B).

Example 13. Anti-GITR Single Agent Immunotherapy Induces Robust Anti-Tumor Immunity The efficacy of anti-GITR on anti-tumor immunity can only be studied in tumor models where the host has an intact immune system. For this reason, the GITR mouse surrogate antibody, DTA-1, was studied in the established syngeneic colon carcinoma models, CT26 and MC38, in Balb/C or C57/BL6 mice, respectively Mice were implanted subcutaneously (sc) with $5\times10^5$ CT26 or MC38 tumor cells on the right flank. On day 7 post-tumor cell implantation, mice were randomized into experimental groups with an average tumor size of approximately 85 mm³ or 120 mm³, respectively.

Mice were administered DTA-1 (BioXcell #BE0063) or rat IgG2b isotype control (clone LTF-2, BioXcell #BE0090) intraperitoneally at 200 μg/animal q3d-q4d for a total of 3 doses on days 7, 11 and 14 (n=10/group). Tumor caliper measurements were taken twice weekly until the end of the study. Tumor volume was calculated using the formula: Tumor Volume (mm3)=(1×w2/2); where '1' represents the length, and 'w' the width of the tumor as determined by caliper measurements, and monitored twice weekly throughout the study. Percent tumor growth inhibition (% TGI) was defined as the difference between mean tumor volumes of the treated vs. control group, calculated as % TGI=[(TVc−TVt)/TVc)*100] where TVc is the mean tumor volume of a given control group and TVt is the mean tumor volume of the treatment group. As defined by NCI criteria, ≥60% TGI is considered biologically significant.

In the MC38 model, statistically significant tumor growth inhibition was achieved with DTA-1 treatment (80% TGI on day 21 vs. isotype control, p<0.0001) with tumor regressions observed as early as day 14 after DTA-1 treatment, and complete responses (CR) in 5/10 animals achieved by day 28. The CRs appear durable, with no re-growth observed up to 35 days post last treatment dose.

Figure 5A:
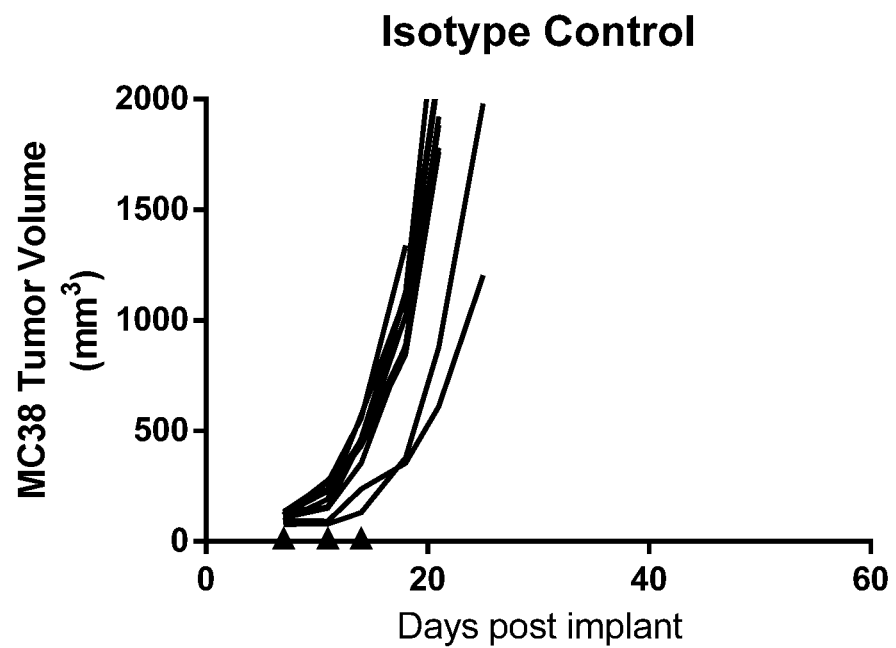
FIGS. 5A and 5B. Single agent anti-tumor activity of a surrogate anti-GITR antibody (DTA-1) in the syngeneic MC38 colon carcinoma model. DTA-1 (FIG. 5B) or an isotype rat IgG2b (FIG. 5A) was administered at 200 ug/mouse to animals on days indicated by black arrowheads (n=10 per group) starting when tumor volumes reached 100 mm$^3$. DTA-1 treatment resulted in complete tumor regression in 5/10 animals.
Figure 5B:
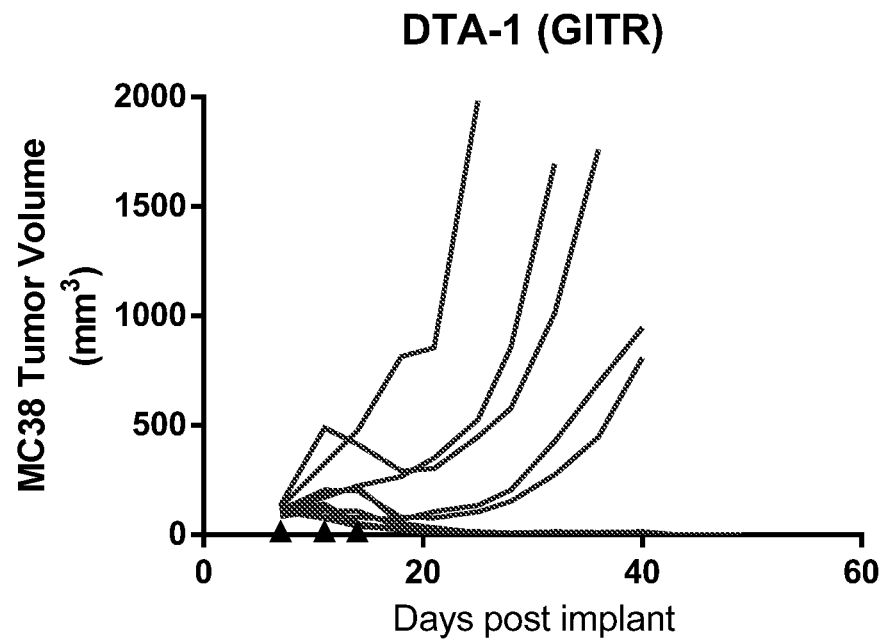

In the CT26 model, statistically significant tumor growth inhibition was achieved with DTA-1 treatment as compared to isotype treated control animals (>65% TGI on day 27, p<0.0001), with tumor regressions observed in half the group (5/10 animals) as early as day 14, and with complete responses (CRs) observed by day 31 (FIG. 5). The CRs appear durable, with no re-growth observed up to 42 days post last treatment dose.

Example 14. Anti-Gitr Combination Therapy with Immune Checkpoint Antibodies and T Cell Agonist Antibody Augments Anti-Tumor Immunity The MC38 syngeneic colon carcinoma model was used to evaluate combination anti-GITR therapy in combination with anti-PD-1, anti-CTLA-4 checkpoint blockade or anti OX-40 antibody.

Mice were implanted subcutaneously (sc) with 5×10$^5$ MC38 tumor cells on the right flank. On day 14-21 post-tumor cell implantation, mice were randomized into experimental groups with an average tumor size of approximately 200 mm$^3$. Mice were administered with surrogate anti-GITR (DTA-1, BioXcell #BE0063), anti-PD-1 (RMP1-14, BioXcell #BE0146), anti-CTLA-4 (9D9, BioXcell #BP0164), anti-OX40 (OX-86, BioXcell #BE0031) or rat IgG2b isotype control (LTF-2, BioXcell #BE0090) intraperitoneally at 100 μg/animal q4d for a total of 3 doses on days 1, 5 and 9 post randomization (n=10/group). Tumor caliper measurements were taken twice weekly until the end of the study. Tumor volume was calculated using the formula: Tumor Volume (mm3)=(1×w2/2); where '1' represents the length, and 'w' the width of the tumor as determined by caliper measurements, and monitored twice weekly throughout the study. Percent tumor growth inhibition (% TGI) was defined as the difference between mean tumor volumes of the treated vs. control group, calculated as % TGI=[(TVc−TVt)/TVc) *100] where TVc is the mean tumor volume of a given control group and TVt is the mean tumor volume of the treatment group. As defined by NCI criteria, ≥60% TGI is considered biologically significant.

Figure 6A:
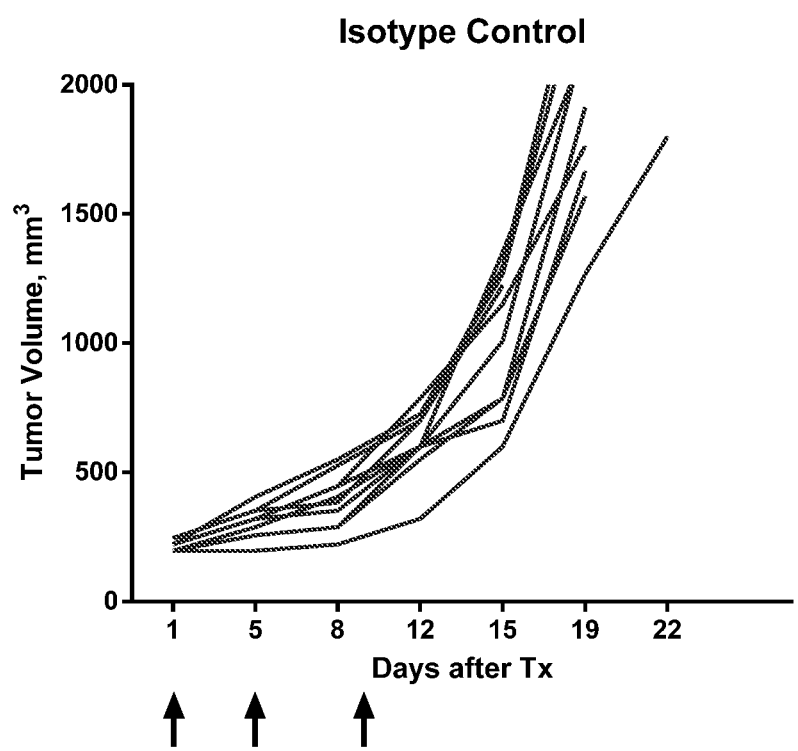
FIG. 6A-6C. Combination of surrogate anti-GITR antibody (DTA-1) and anti-PD-1 antibody (RMP1-14) leads to synergistic anti-tumor activity in the syngeneic MC38 colon carcinoma model. Isotype rat IgG2b (FIG. 6A), DTA-1 (FIG. 6B) or DTA-1+RMP1-14 (FIG. 6C) was administered at 100 ug/antibody/mouse to animals on days indicated by black arrowheads (n=10 per group) starting when tumor volumes reached 200 mm$^3$. Combination treatment resulted in tumor regressions in 5/10 animals.
Figure 6B:
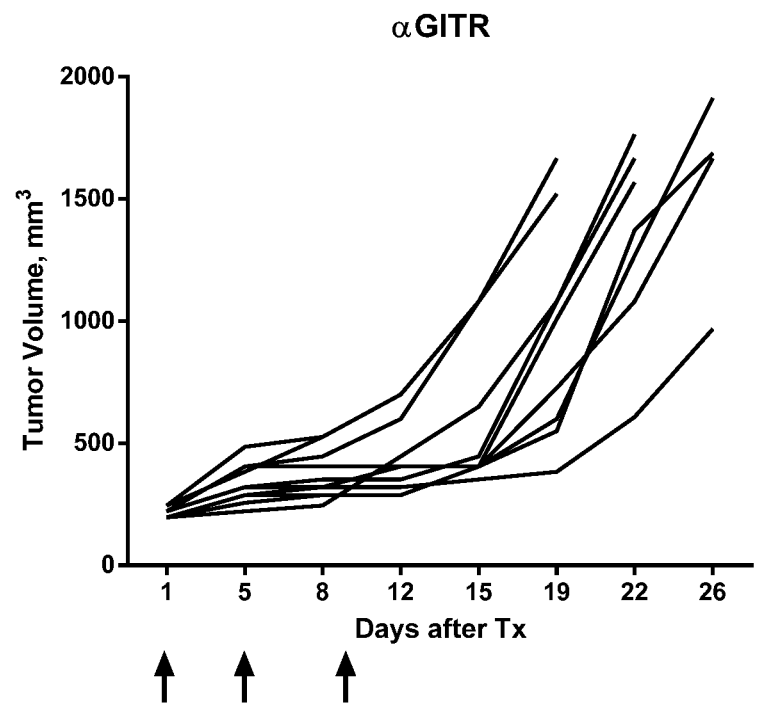
Figure 6C:
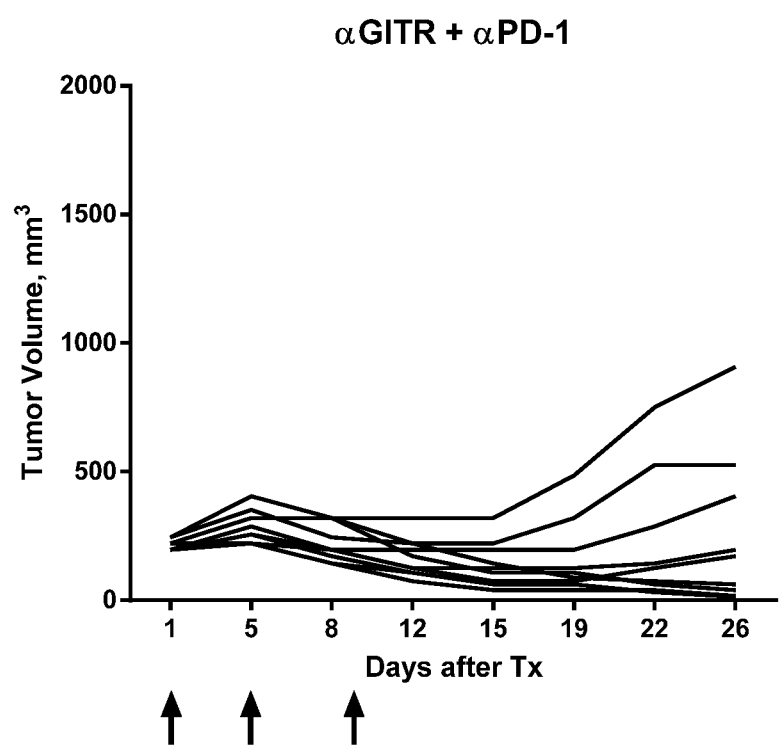
Figure 7A:
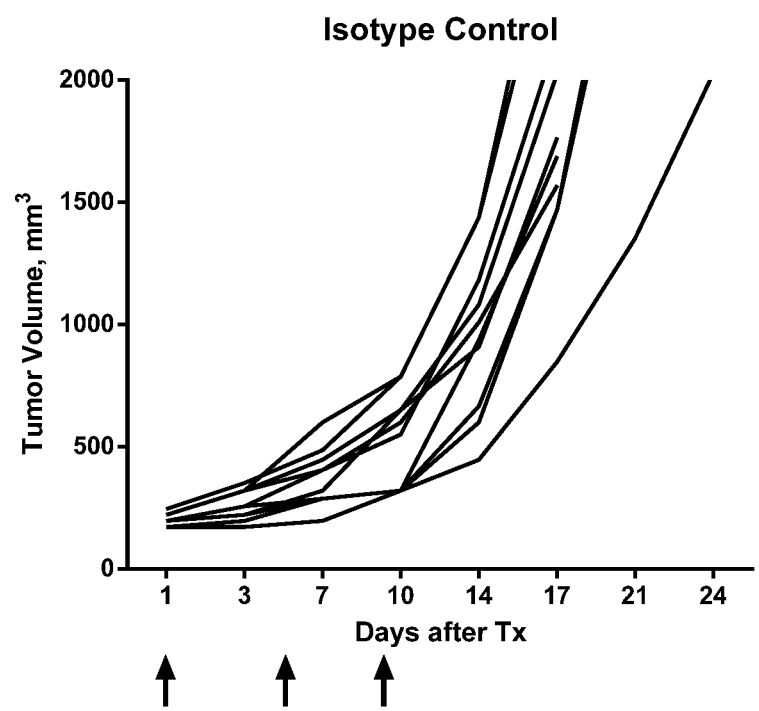
FIG. 7A-7C. Combination of surrogate anti-GITR antibody (DTA-1) and anti-CTLA-4 antibody (9D9) leads to synergistic anti-tumor activity in the syngeneic MC38 colon carcinoma model. Isotype rat IgG2b (FIG. 7A), DTA-1 (FIG. 7B) or DTA-1+9D9 (FIG. 7C) was administered at 100 ug/antibody/mouse to animals on days indicated by black arrowheads (n=10 per group) starting when tumor volumes reached 200 mm3. Combination treatment resulted in tumor regressions in 3/10 animals.
Figure 7B:
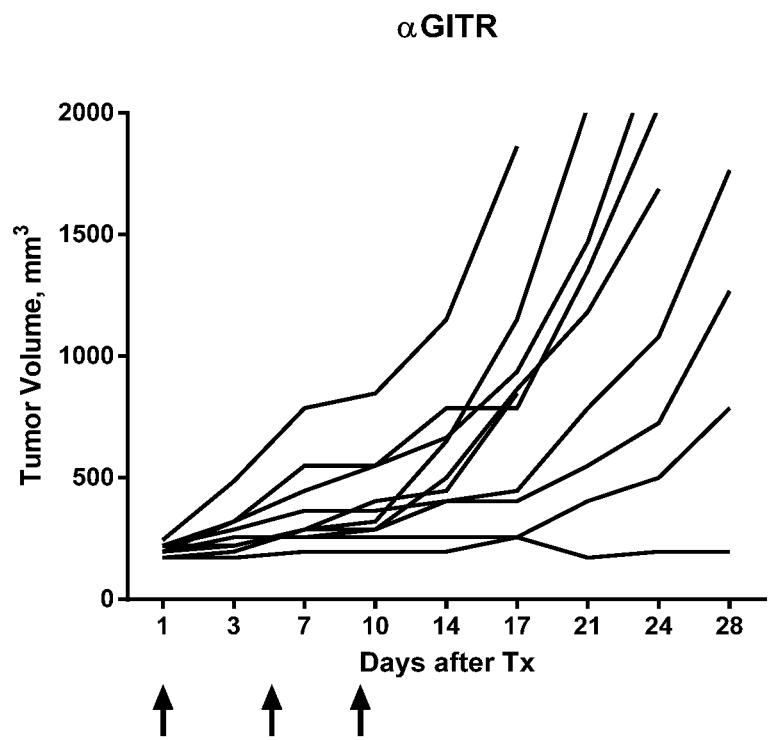
Figure 7C:
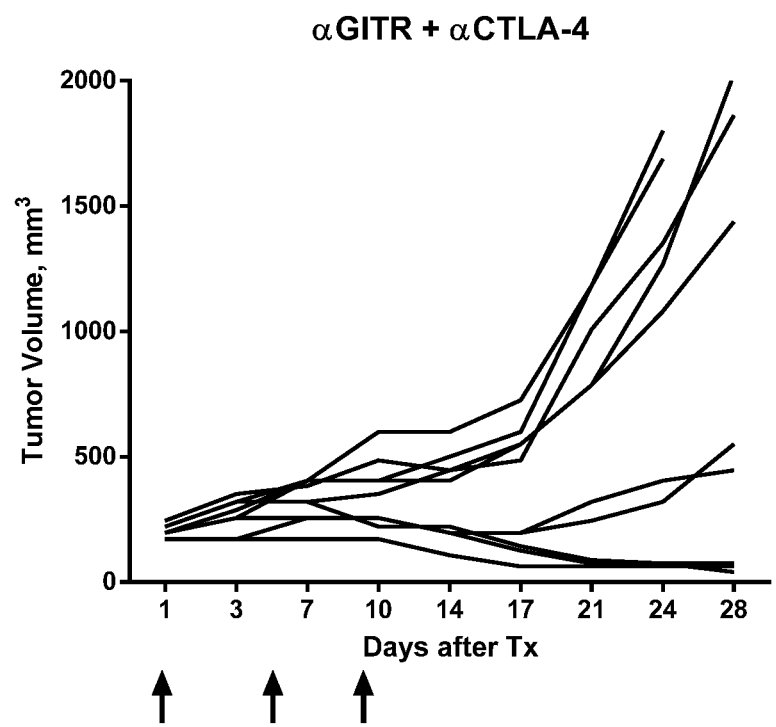

Statistically significant tumor growth inhibition was achieved with anti-GITR treatment compared to the isotype control cohort, even though treatment was initiated when tumors were larger, and the dosage was reduced from 200 μg/mouse to 100 ug/mouse. In the anti-GITR+anti-PD-1 combination group, tumor regressions in 5/10 animals were observed by day 26 after randomization (FIG. 6). In the anti-GITR+anti-CTLA-4 combination group, tumor regressions were observed in 3/10 animals and delayed tumor progression was observed in 2/10 animals (FIG. 7). Lastly, combination of anti-GITR (d1)+anti-OX40 (d5, d9) was better than anti-GITR therapy alone (d1, d5, d9) and anti-OX40 alone (d5, d9) (FIG. 8).

Figure 9A:
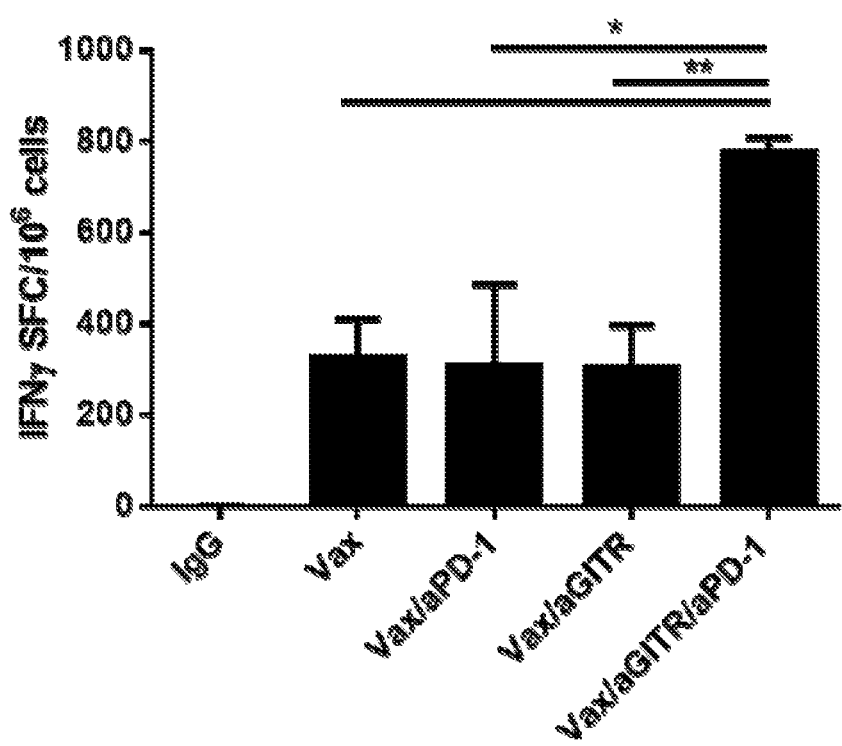
FIG. 9A-9F. Combination anti-GITR/anti-PD-1 therapy with vaccination boosts the expansion, function and differentiation of Ag-specific CD8$^+$ T cells. Naïve B6 non-tumor bearing mice (n=5/group) were immunized once with an OVA$_{257-264}$ peptide (day 0), along with mono- or combination therapy: 200 μg anti-GITR or control rat IgG on days 0, 3 and 6, and 200 μg of anti-PD-1 on days 3, 6, 9 and 12. Desired immune responses were monitored at day 7 (d7) and day 14 (d14) in the blood and/or spleen.
Figure 9B:
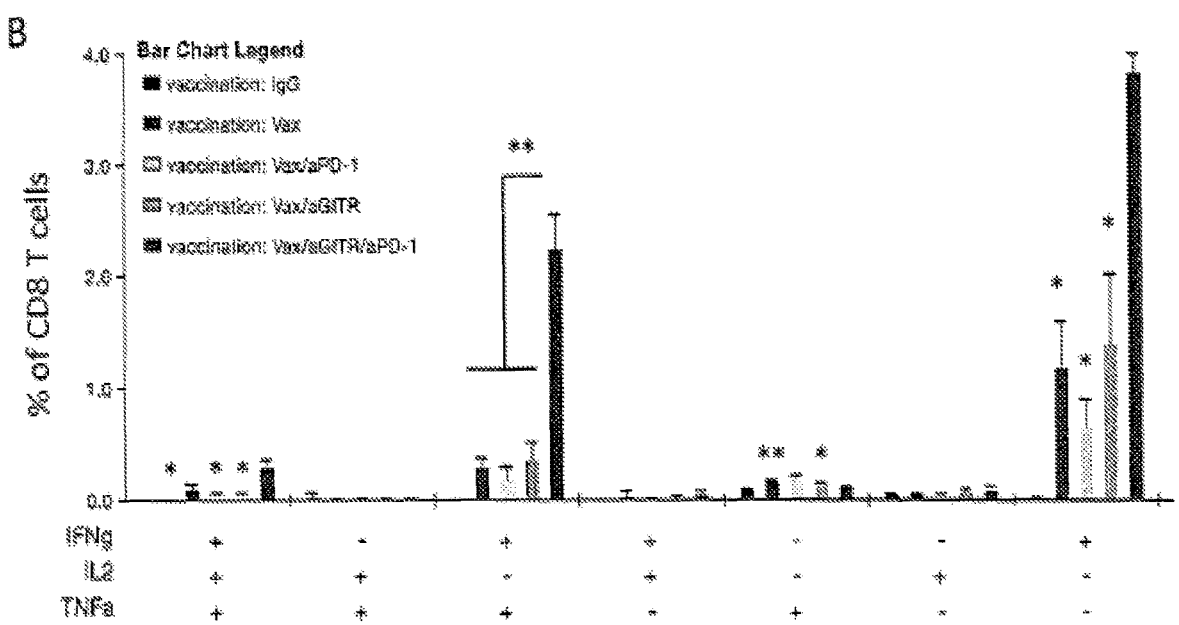
Figure 9C:
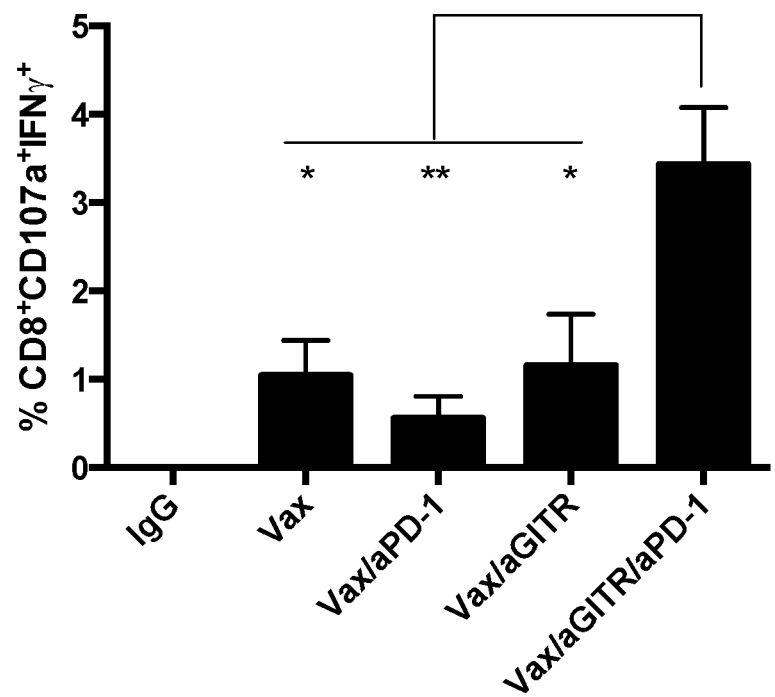
Figure 9D:
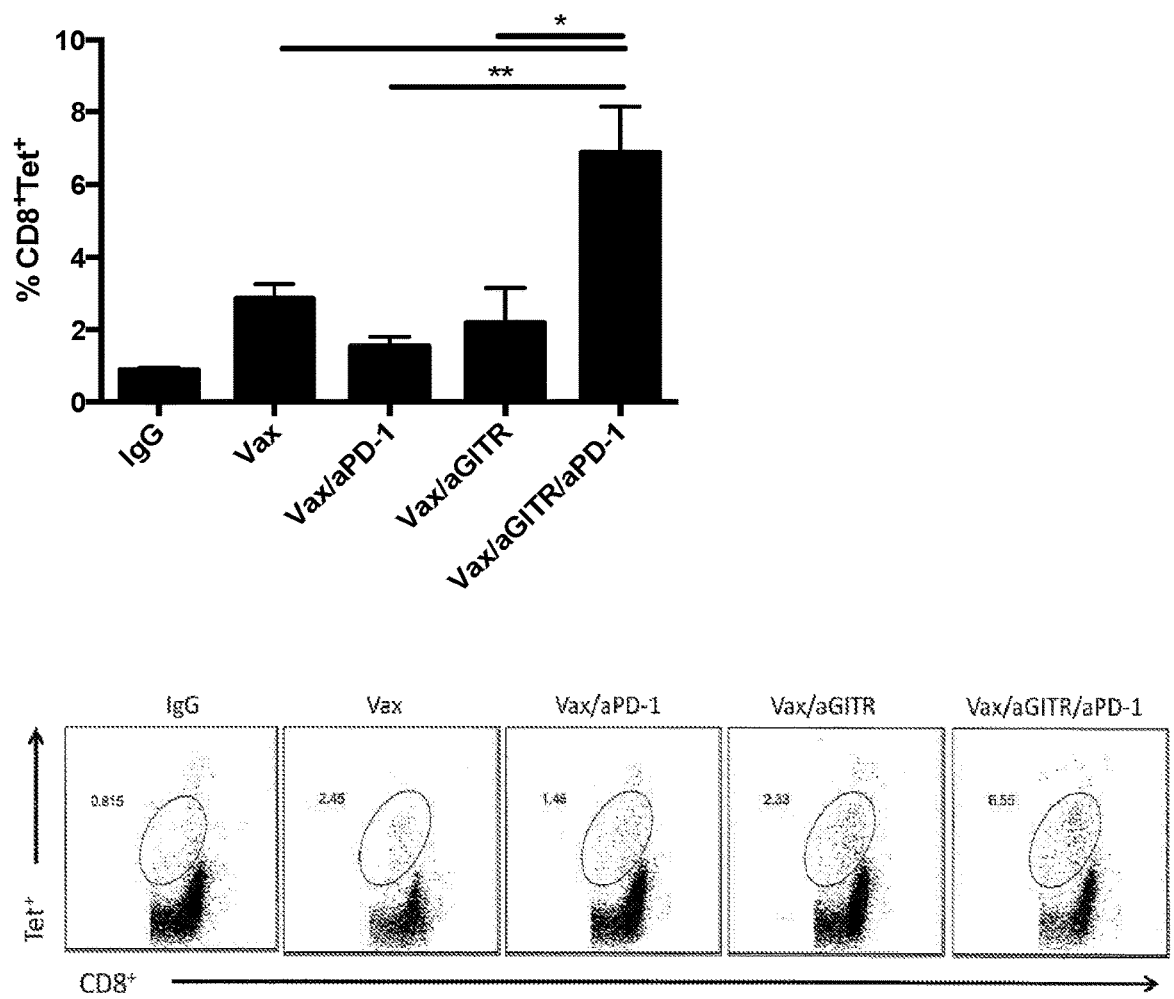

Example 15. Combined Anti-GITR and Anti-PD1 Therapy with Vaccination Induces Robust Antigen-Specific CD8$^+$ T Cell Expansion, Function and Differentiation in Non-Tumor Bearing Mice The mechanisms by which combination therapy targeting GITR with PD-1 blockade augments Ag-specific CD8$^+$ T cell responses in a vaccine setting were assessed. To address this, non-tumor bearing mice were immunized once with the OVA immunodominant CTL epitope OVA$_{257-264}$ peptide vaccine (hereafter referred to as Vax) and treated with 200 μg anti-GITR on days 0, 3, and 6 and 200 μg and anti-PD-1 on days 3, 6, 9, and 12. Combination Vax/anti-GITR/anti-PD-1 therapy augmented CD8$^+$ effector function over controls, as evidenced by increased levels of splenic Ag-specific IFNγ ELISpot responses, polyfunctional CD8 T cell responses, and increased levels of CD107a/IFNγ CD8$^+$ T cells demonstrating cytolytic activity (FIGS. 9A, B, and C, respectively). The triple therapy elicited significantly higher frequencies of polyfunctional effector CD8$^+$ T cells expressing single IFNγ, dual IFNγ/TNFα, and triple IFNγ/TNFα/IL-2, as compared with the other treatments and control groups (FIG. 9B). By direct staining with OVA$_{267-264}$ H-2K$^b$-SIINFEKL tetramer, Vax/anti-GITR/antiPD-1 amplified significantly the frequency of OVA tetramer-specific CD8$^+$ T cell responses in the peripheral blood at day 7 and 14 (FIGS. 9D and 9E), suggesting the trafficking of target-specific CD8$^+$ T cells. The high frequencies of effector cells secreting Th1 inflammatory cytokines are indicative that in vivo combination of anti-GITR/anti-PD-1 can enhance vaccine-induced Ag-specific CD8$^+$ T cell responses.

Figure 9E:
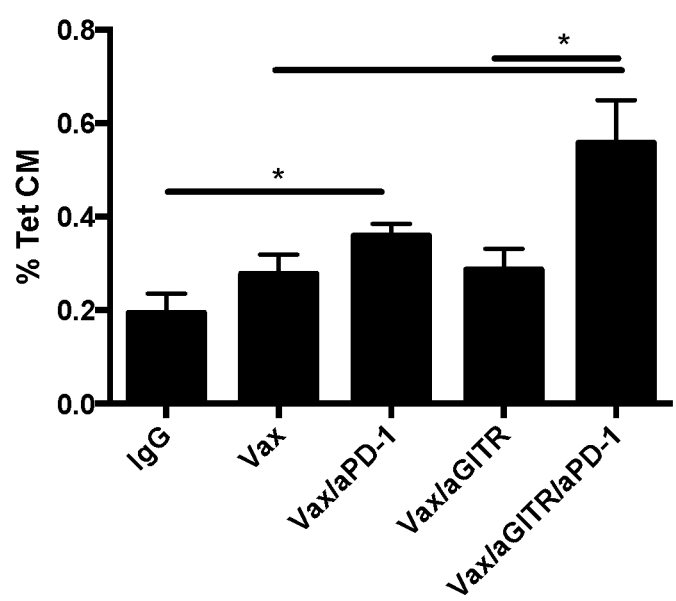
Figure 9F:
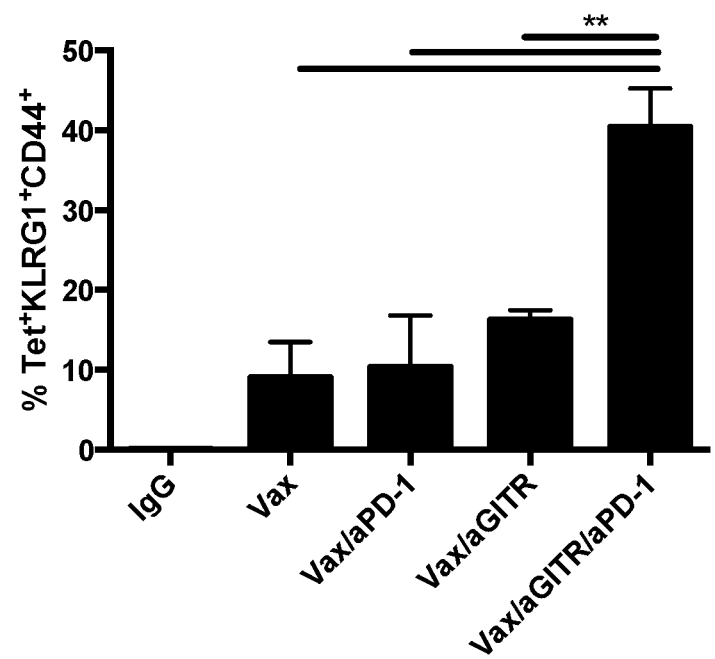

The extent to which combination therapy skewed Ag-specific CD8$^+$ T cell differentiation toward an effector versus memory phenotype, by surface expression of CD44 and CD62L, 14 days after vaccine priming, was determined. The phenotypic profile for central memory (CM) is typically CD44$^+$ and CD62L$^+$, and effector memory (EM) cells are CD44$^+$ and CD62L$^-$. A significant increase was observed in the tetramer OVA-specific EM and CM CD8$^+$ T cell population in mice given triple combination therapy, compared to other groups (FIG. 9E). Furthermore, it has been highlighted that a predominant population of KLRG1$^+$CD8$^+$ T cells are an optimal effector subset for protective immunity (25-27), and likely a vital subset that correlates with the efficacy of cancer immunotherapies (23,28-29). Therefore, the phenotype of the Ag-specific CD8$^+$ T cell population to express the cell surface expression of killer cell lectin-like receptor subfamily G, member 1 (KLRG1) was characterized as a correlate. As shown in FIG. 9F, the percentages of tetramer-specific KLRG1$^+$ effector memory CD8$^+$ T cells were significantly higher in the triple combination group compared with control groups. Together, these results demonstrate that anti-GITR/anti-PD-1 combination with vaccination can enhance the expansion and function of potent Ag-specific memory CD8$^+$ T cells in vivo.

Figure 10A:
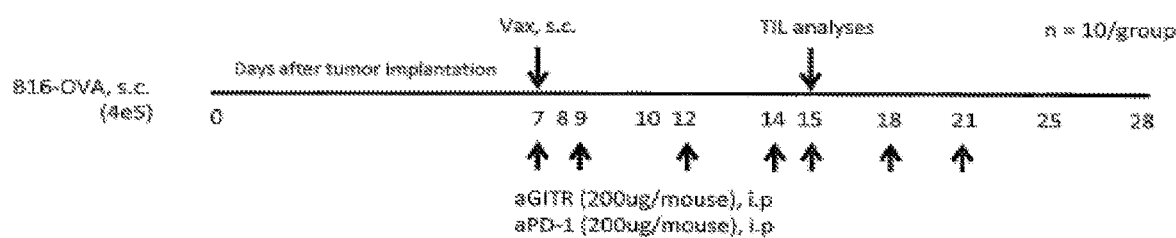
FIG. 10A-10D. In vivo combination therapy with vaccination promotes B16-OVA tumor rejection in mice.
Figure 10B:
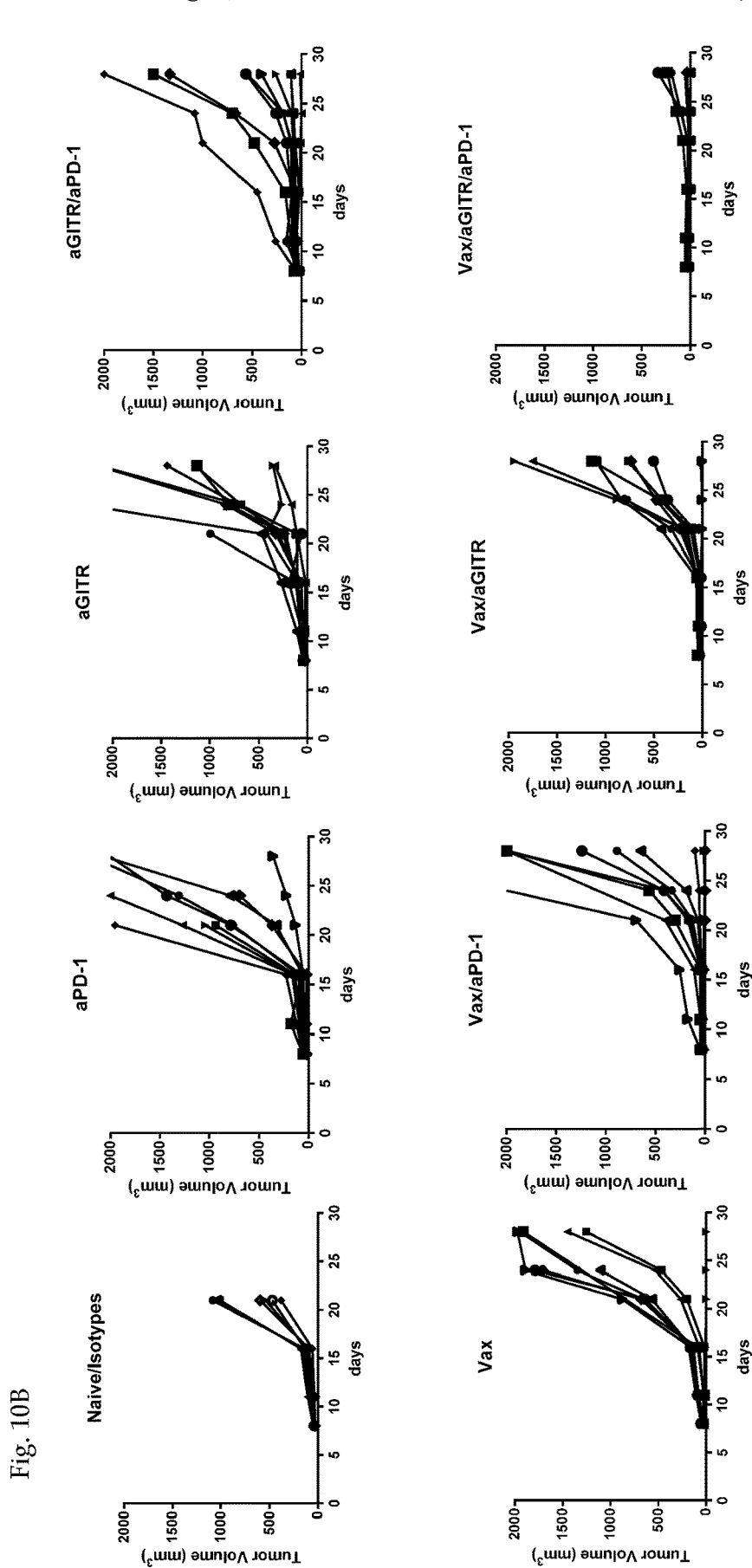
Figure 10C:
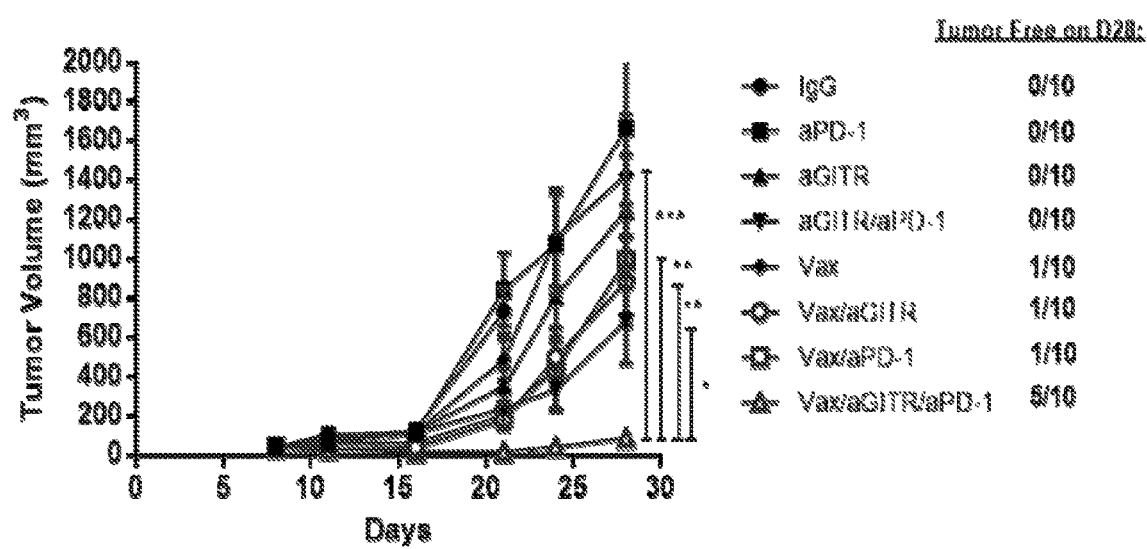
Figure 10D:
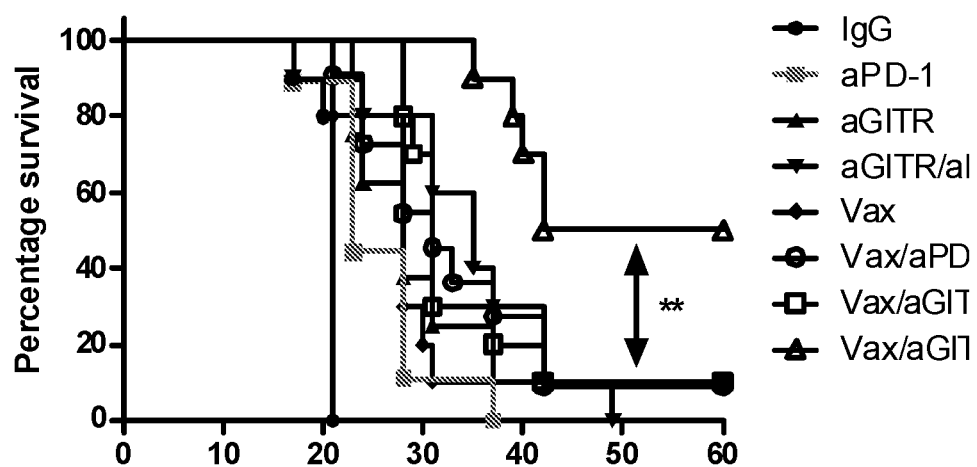

Example 16. Combination Therapy with Vaccination Induced Tumor Regression and Enhanced Survival in Tumor-Bearing Mice Given the increase of Ag-specific effector CD8$^+$ T cell responses induced by the triple combination therapy in the non-tumor bearing setting, the next question was whether the combination could induce an antitumor response using the poorly immunogenic B16-OVA melanoma model. B16-OVA tumor cells were implanted into cohorts of naïve recipient B6 mice (n=10/group). Seven days after implantation when tumors reached an average size of ~30-40 mm$^3$, mice were randomized, and treated with the therapies as outlined in FIG. 10A. The antibody regimens without a vaccine slowed tumors modestly, but did not lead to tumor clearance, likely due to weak induction of Ag-specific T cells. Similarly, neither Vax alone or in combination with anti GITR or anti PD-1 mAb resulted in greater than 10-20% survival. However, tumors in mice treated with Vax/anti-GITR/anti-PD-1 grew significantly slower than all other groups (FIGS. 10B-10C). Interestingly, the combination Vax/anti-GITR/anti-PD-1 therapy significantly enhanced tumor regression and survival in approximately 50% of mice over other combination therapies or vaccine alone (FIGS. 10C-10D). Taken together, the data shows that anti-GITR targeting and anti-PD-1 blockade combination can synergize with a vaccine to enhance overall survival.

Figure 11A:
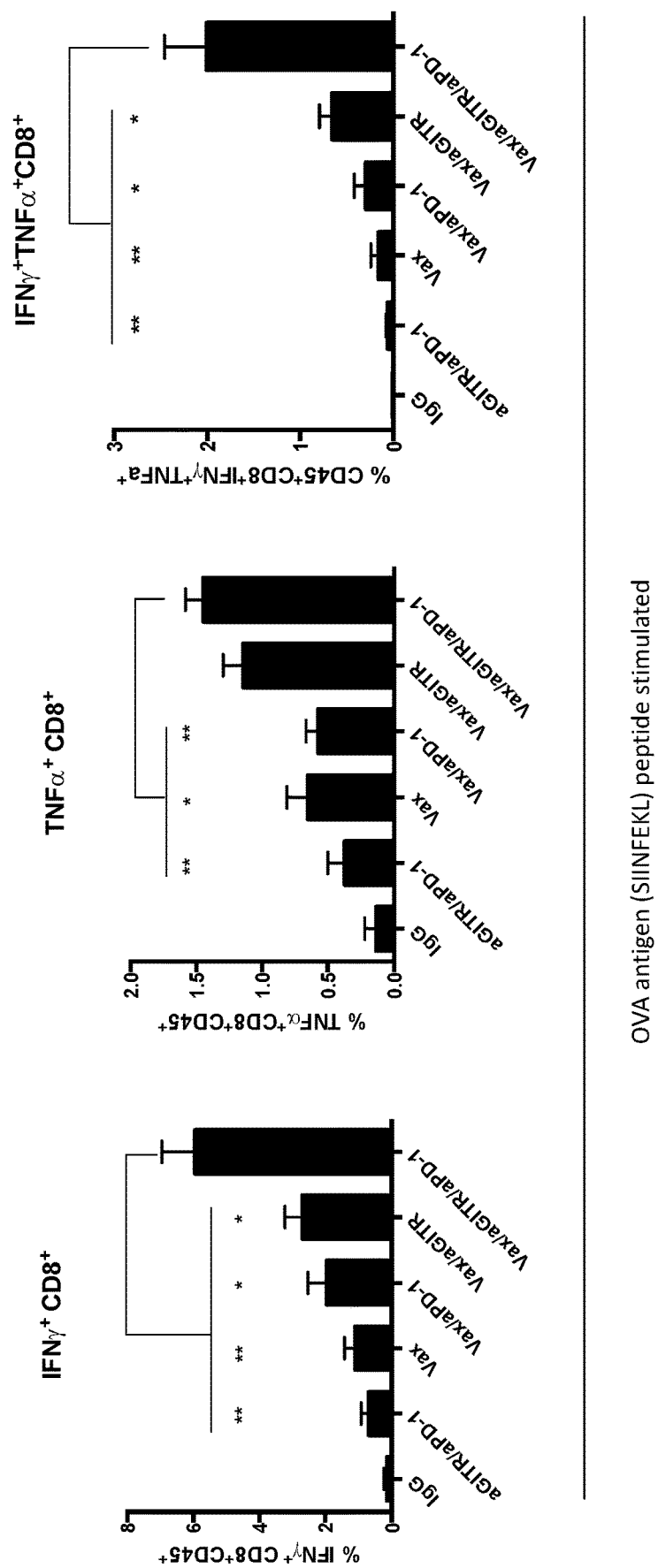
Figure 11B:
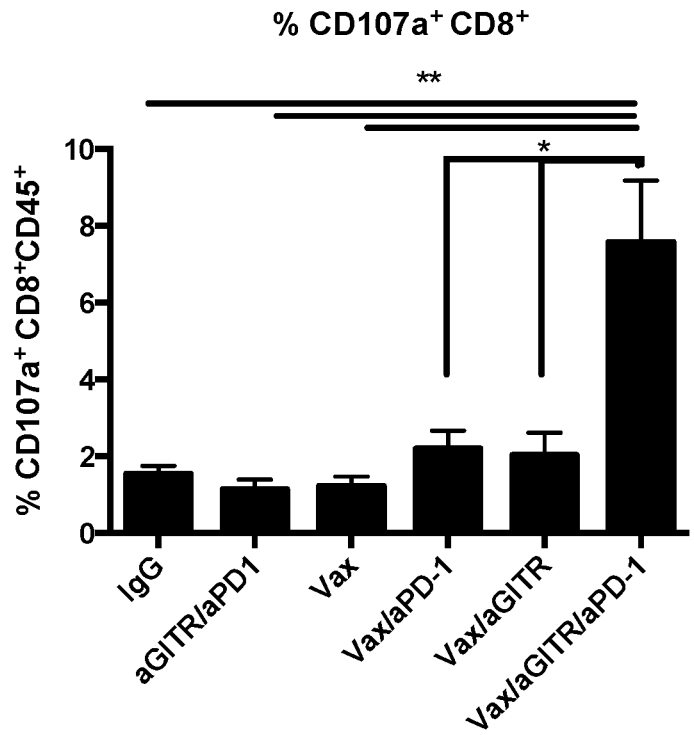
Figure 11C:
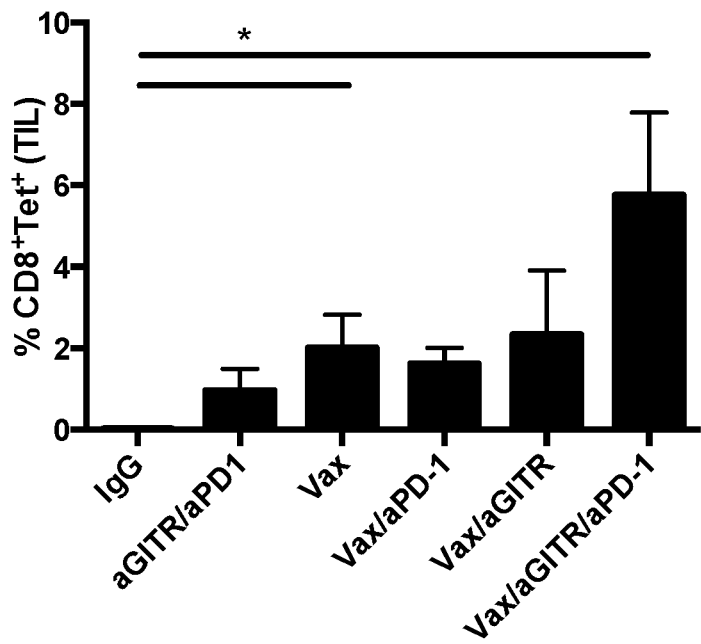

Example 17. Combined Vax/Anti-GITR/Anti-PD-1 Immunotherapy Induces Ag-Specific Polyfunctional CD8$^+$ T Cells and Reduces Treg Population in Tumors To understand the mechanism of action of the combination therapy, the Ag-specific phenotype and functional response of CD8$^+$ effector and CD4$^+$ Tregs isolated from tumors following the various immunotherapies was characterized. Given the importance of multifunctional effector CD8$^+$ T cell immunity in anti-tumor immunity (Villarreal D O, et al. *Cancer Res* 2014; 74:1789-800; Slaney C Y, et al. *Cancer Res* 2014; 74:7168-7174), the Ag-specific CD8$^+$ T cell population and its expression of IFNγ and TNFα, in response to ex vivo OVA$_{257-264}$ SIINFEKL peptide stimulation, was measured 15 days after tumor implantation (FIG. 11A). The Vax/anti-GITR/anti-PD-1 combination therapy significantly increased IFNγ and T NFα production from effector CD8$^+$ T cells in tumors compared to all other groups (FIG. 11A). Moreover, the Vax/anti-GITR/anti-PD-1 therapy showed a synergistic effect, as illustrated by the higher frequency of OVA-specific IFNγ/TNFα dual-positive CD8$^+$ T cells within the tumor (FIG. 11A). Given that cytolytic CD8$^+$ CTLs are critical components in protection against tumors (Villarreal D O, et al. *Cancer Res* 2014; 74:1789-800; Slaney C Y, et al. *Cancer Res* 2014; 74:7168-7174), the cytolytic potential of the cells to undergo degranulation was determined by the expression marker CD107a. The results show that CD8$^+$ tumor infiltrating lymphocytes (TILs) isolated from tumor-bearing mice treated with Vax/anti-GITR/anti-PD-1 had a significantly higher frequency of CD8$^+$ T cells with lytic activity against OVA$_{257-264}$ compared to controls, suggesting these T cells have greater potential to target tumor cells (FIG. 11B). The triple combination also induced higher frequency of tetramer OVA-specific CD8$^+$ T cells trafficking into the tumors (FIG. 11C). Furthermore, a similar trend was seen with the frequency of CD8$^+$ T cells secreting IFNγ, TNFα and/or expressing CD107a when stimulated with PMA/ION, indicating that the combination Vax/anti-GITR/anti-PD-1 induced more functional CD8$^+$ T cell responses overall (FIG. 11D). The Vax/anti-GITR/anti-PD-1 treated TILs stimulated with PMA/ION had higher frequencies of cytolytic CD8$^+$ T cells coexpressing CD107a$^+$IFNγ$^+$. This correlates the substantial increase in cytolytic activity with its significant control and/or regression of established tumors in the mice.

Figure 12A:
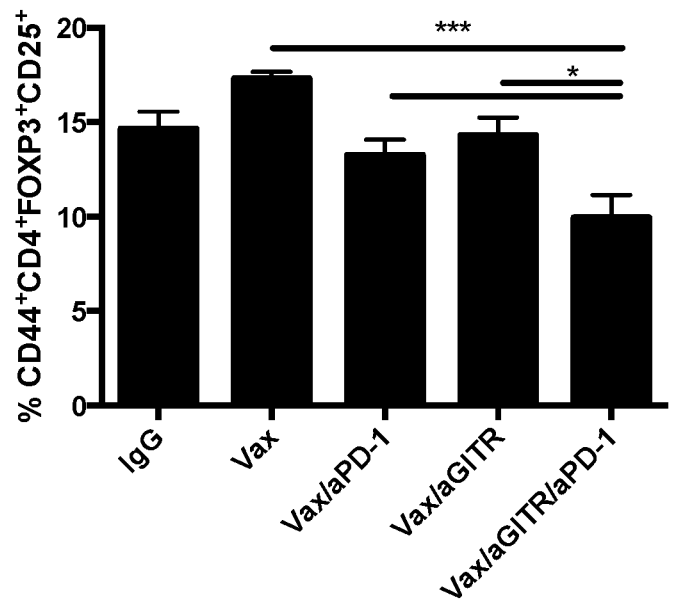
FIG. 12A-12D. Combination therapy enhances $CD8^+$ T cell infiltration and reduces frequency of Tregs in B16-OVA tumors.
Figure 12B:
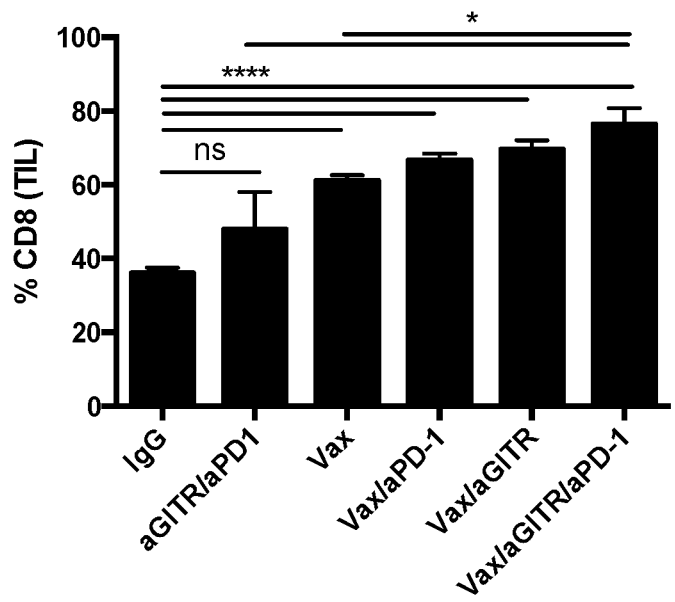
Figure 12C:
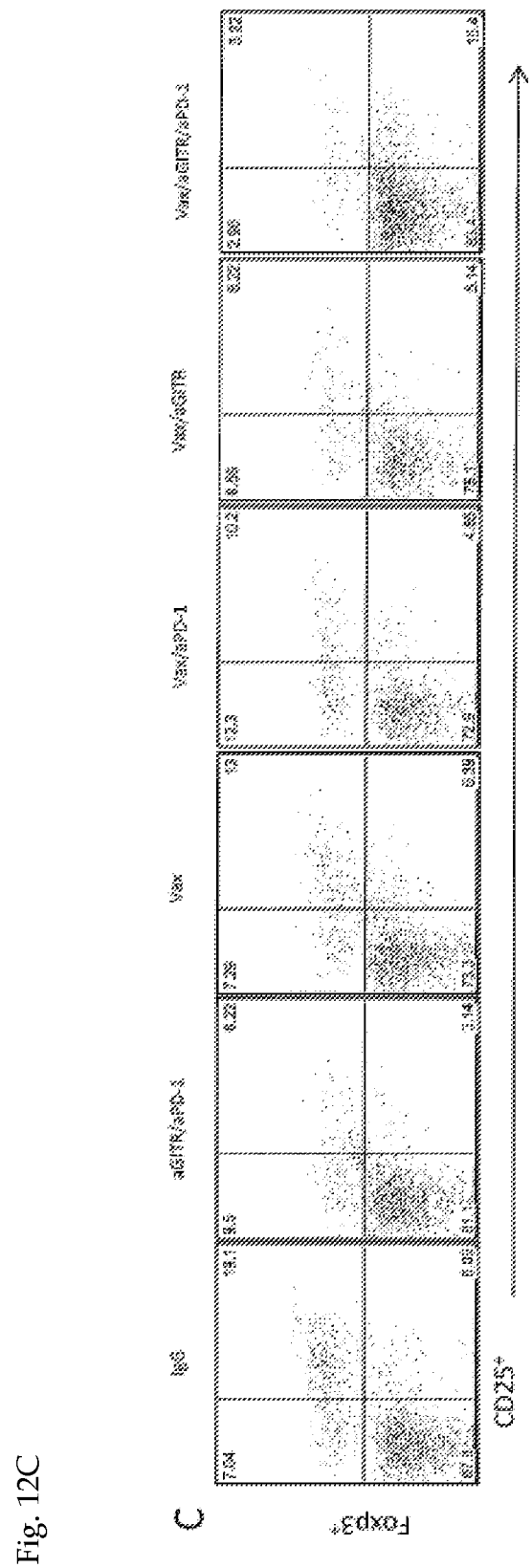
Figure 12D:
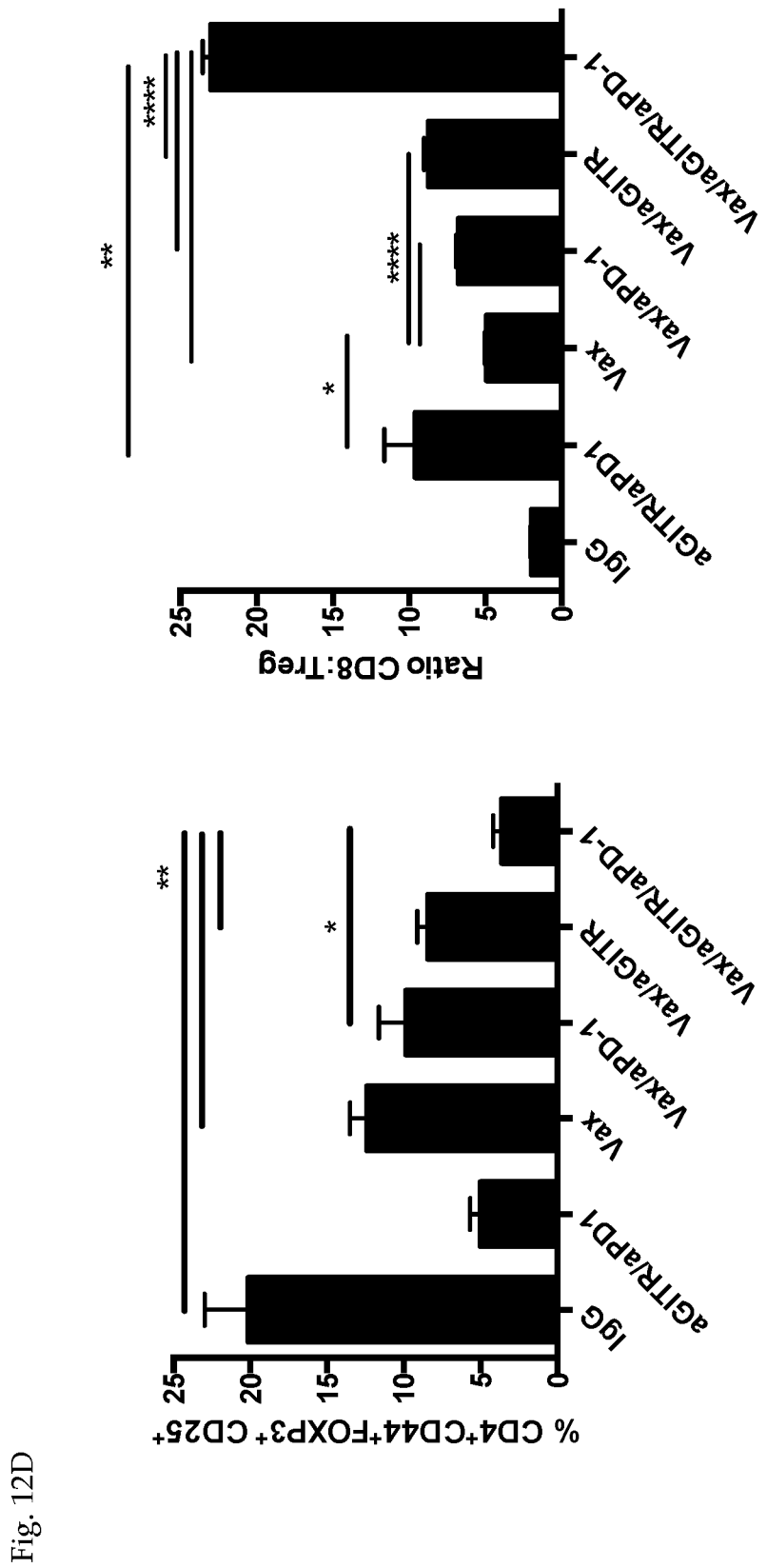

Given that one mechanism of the anti-GITR mAb is to reduce CD4$^+$ Tregs in the tumors (Cohen A D, et al. *PloS one* 2010; 5:e10436; Schaer D A, et al. *Curr Opin Immunol* 2012; 24:217-224; Schaer D A, et al. *Immunother Cancer* 2014:15:2-7), the effects of combined Vax/anti-GITR/anti-PD-1 immunotherapy on these cells in the tumors was evaluated. However, prior to assessing the Treg population in the tumors, the splenic Treg population at day 14 in non-tumor bearing mice was monitored, using the scheme in FIG. 10 but in naive bearing mice. A significant decrease of Tregs in the Vax/anti-GITR/anti-PD-1 treated group compared to the other immunotherapeutic groups was observed (FIG. 12A). Therefore, based on these results, it was anticipated that the triple combination therapy would lead to a decrease of Tregs in the tumors. When the Treg population at day 15 post-tumor implantation was monitored, both anti-GITR/anti-PD-1 and Vax/anti-GITR/anti-PD-1 immunotherapies similarly and drastically reduced the infiltrating Tregs in the tumors (FIGS. 12C-12D), indicating that combination anti-GITR in both settings may reduce tumor infiltrating Tregs. The triple combination overall showed better reduction of Tregs in the tumors compared to all treated groups. The overall reduction of the Treg population in the majority of the vaccinated groups was potentially due to a favorable Th1 response in the TME, shifting the TME from suppressive to inflammatory (Tatsumi T, et al. *J Exp Med* 2002; 196:619-628; Fridman W H, et al. *Nat Rev Cancer* 2012; 12:298-306). All immunotherapies, except anti-GITR/anti-PD1, strongly increased CD8$^+$ T cell infiltration into the tumors (FIG. 12B), likely due to the induction of Ag-specific CTL responses induced by the peptide vaccine as demonstrated in FIG. 9 and FIG. 11A. As a result, the CD8/Treg ratios within the tumor increased markedly, with the triple combination therapy being statistically superior to any other Ab combination therapy (FIG. 12D), a response which has been described as a correlate for therapeutic efficacy in the melanoma model (Quezada S A, et al. *J Clin Invest* 2006; 116:1935-1945). Collectively, the synergistic effects of the combination Vax/anti-GITR/anti-PD-1 to enhance tumor-reactive CTL responses, reduce Tregs, and drive higher ratios of effector T cells to Tregs in the tumors, may represent a more Ag-specific inflammatory microenvironment that is more capable of mediating tumor clearance.

Figure 13A:
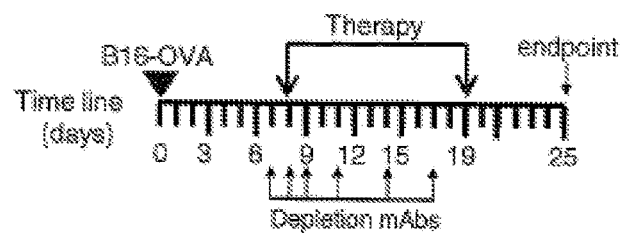
FIG. 13A-13D. Vax/anti-GITR/anti-PD-1 efficacy depends on $CD8^+$ T cells and treatment induces long-term memory.
Figure 13B:
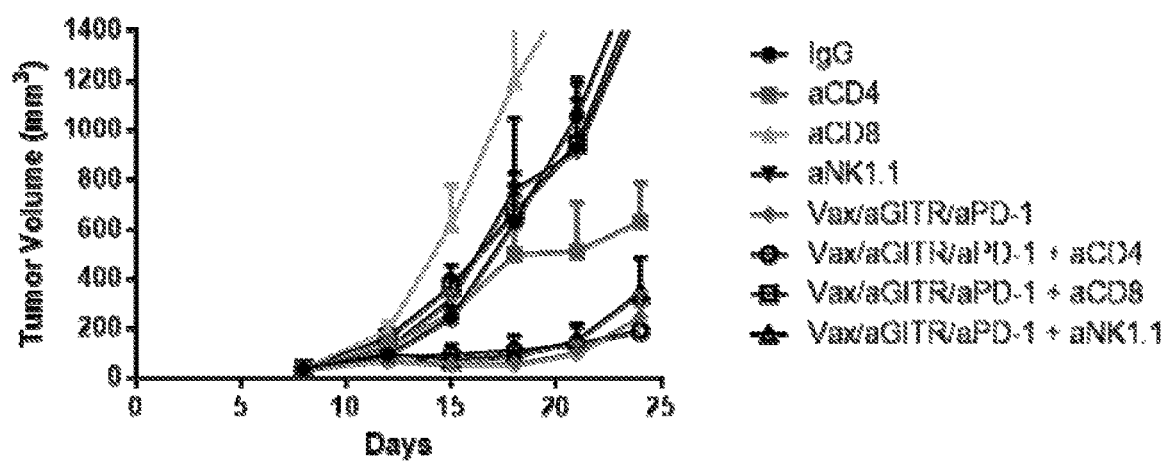
Figure 16:
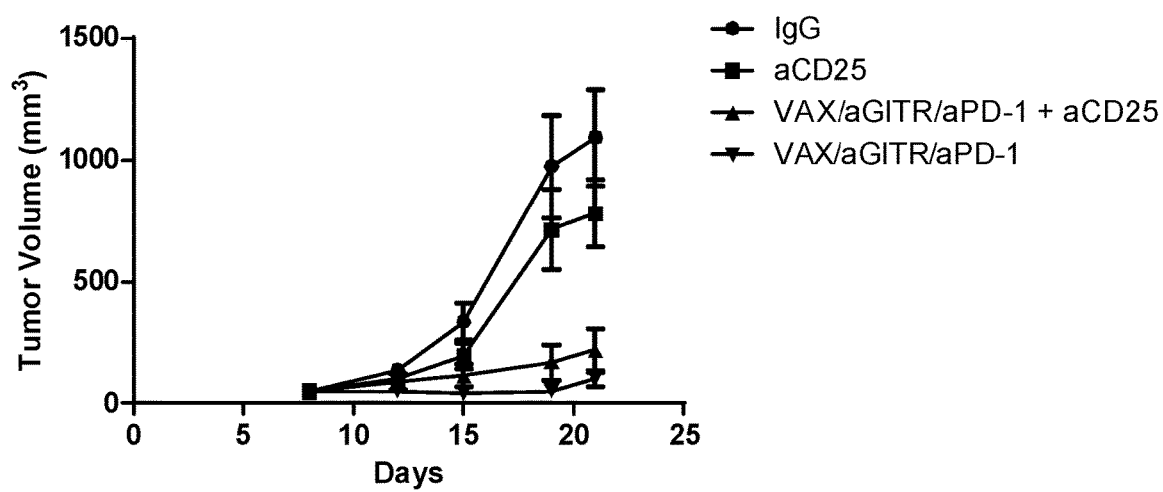
FIG. 16. Depletion of $CD25^+$ cells with combination Vax/anti-GITR/anti-PD-1 therapy does not abrogate or enhance tumor efficacy. Combination treatment and dosing of 200 μg of anti-CD25 were delivered as illustrated in FIG. 5A. Tumor volume was monitored twice a week (mean+/−SEM are plotted). Results are representative of two independent experiments with 10 mice per group.

Example 18. Combination Vax/Anti-GITR/Anti-PD-1 Therapy Induced B16-Ova Tumor Rejection Mediated by CD8$^+$ T Cells and Elicited Long-Term Memory Tumor-infiltrating CD8$^+$ T cells showed a synergistic enhancement against an immunizing peptide in the Vax/anti-GITR/anti-PD-1 combination therapy, indicating that the superior induction of potent CTL responses was most likely critical for the efficacy of the combination therapy. Therefore, the relevance of the effector populations on tumor rejection induced by the combination therapy was investigated. In a therapeutic setting, CD8$^+$ T cells, CD4$^+$ T cells, and NK cells were depleted in tumor-bearing mice as illustrated in FIG. 13A. The results show that CD8 depletion completely abrogated the beneficial effects provided by Vax/anti-GITR/anti-PD-1, as no mice survived past 22 days post-implantation (FIG. 13B). In contrast, the depletion of CD4 and NK cells did not affect antitumor activity of Vax/anti-GITR/anti-PD-1 therapy (FIG. 13B), indicating these cells played no role in the efficacy observed. Overall, there was no statistical difference in tumors from control mice or those treated with anti-CD8 alone and anti-NK1.1 alone. In accordance with a previous study (Fujiwara S, et al. *J Invest Dermatol* 2014; 134:1884-92), we observed a delay in tumor growth and a significant difference in the observed survival (p=0.0037; CD4-depleted vs. Isotype) with the group treated with anti-CD4 alone (FIG. 13B). However, there was no added benefit of administering aCD4 (FIG. 13B) or aCD25 (FIG. 16) with the combination Vax/anti-GITR/anti-PD-1 therapy, suggesting that the combination can act independently of helper T cells or depletion of regulatory $CD4^+$ T cells. Overall, the results demonstrate that $CD8^+$ T cells are the main effector population responsible for prolonging survival and eliciting tumor rejection.

Figure 13C:
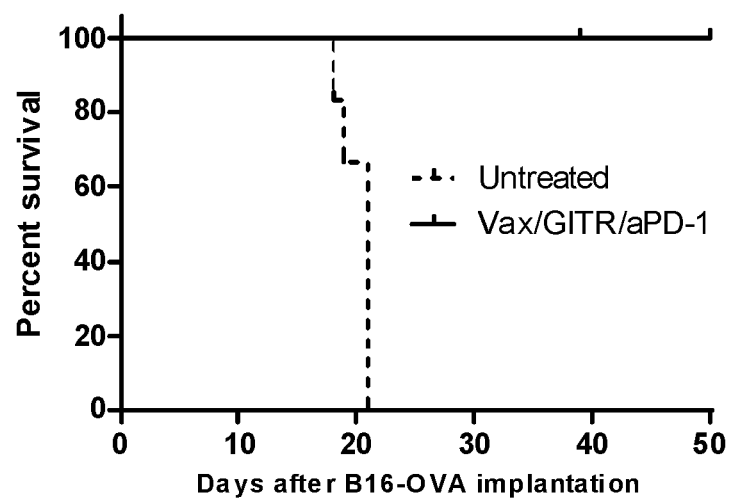
Figure 13D:
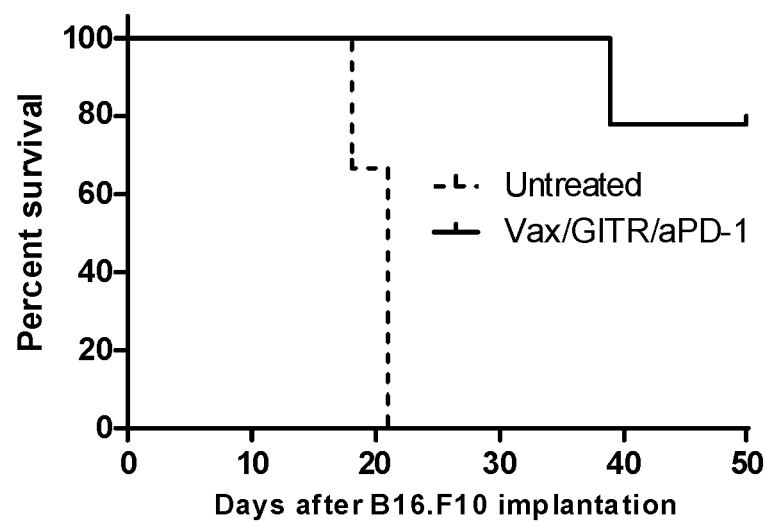

The ultimate goal of both vaccination and active immunotherapy against cancer is the generation of long-lasting memory T cells, which can rapidly respond to subsequent Ag exposure. To assess memory responses, re-challenge experiments were carried out in tumor-free surviving animals, 6 months after completing treatment. All the mice that survived the first tumor challenge with Vax/anti-GITR/anti-PD-1 treatment survived a second tumor challenge against the same tumor 6 months later (FIG. 13C), indicating durable antitumor immunity and induction of long-term memory responses. In addition, when mice cured after treatment with Vax/anti-GITR/anti-PD-1 were rechallenged with the parental B16.F10 tumor strain, which does not express OVA, ~80% of the mice remained tumor free, rejecting the tumor on re-challenge (FIG. 13D). Overall, these data suggest that the combination Vax/anti-GITR/anti-PD-1 therapy can induce long-term memory responses, as well as epitope spreading against other antigens expressed by tumor cells.

Figure 14A:
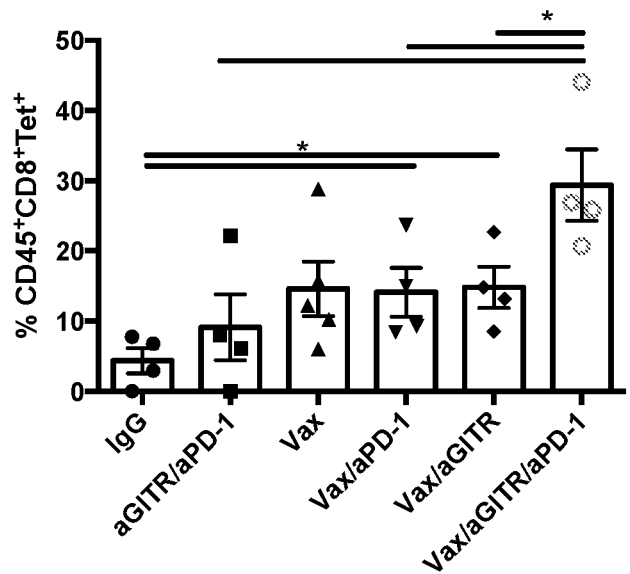
FIG. 14A-14D. Combination Vax/anti-GITR/anti-PD-1 therapy expands tumor-specific $CD8^+$ TILs and induces tumor clearance mediated by $KLRG1^+$ effector-memory $CD8^+$ T cells.
Figure 14B:
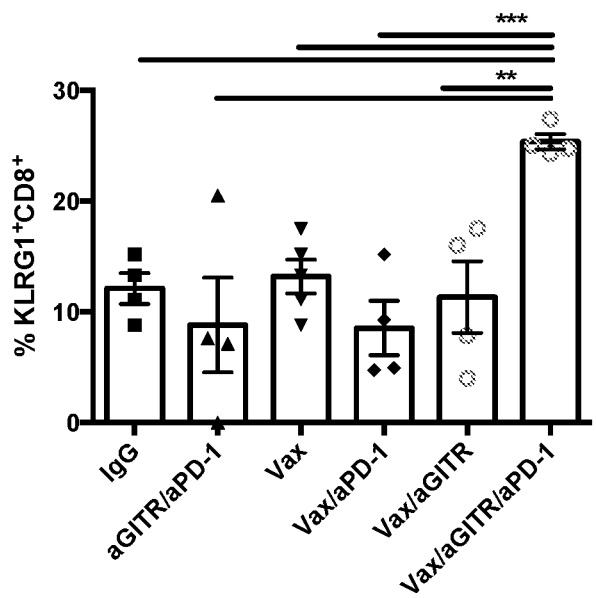
Figure 14C:
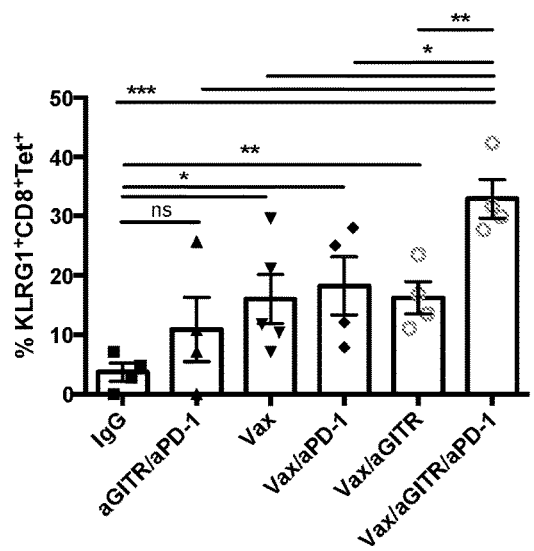

Example 19. Combination Vax/Anti-GITR/Anti-PD-1 Elicits Potent Ag-Specific Tumor Infiltrating $KLRG1^+$ Effector $CD8^+$ T Cells Critical for Tumor Control and Clearance Extensive research in the field has demonstrated that CTLs play a major role in tumor rejection, and the numbers of tumor-infiltrating effector CD8+ T cells are often correlated with a good prognosis (Blohm, U., et al. *Eur. J. Immunol.* 2006; 36: 468-477; Boissonnas, A. et al. *J. Exp. Med.* 2007; 204:345-356: Steer, H. J., et al. *Oncogene* 2010; 29:6301-6313). More recently, several studies have begun to support the hypothesis that the subset of $KLRG1^+$ effector memory $CD8^+$ T cells may predict therapeutic efficacy against pathogens and tumors (Villarreal D O, et al. *Molecular Therapy* 2015; 10:1653-1662; Olson J A, et al. *Immunity* 2013; 38:1250-60; Cush S S, Flano E. *J Immunol* 2011; 186:4051-8; Ye F, et al. *J Immunol* 2012; 189:5206-11; van Duikeren S, et al. *J Immunol* 2012; 189:3397-403; Villarreal D O, et al. *Cancer Res* 2014; 74:1789-800; Slaney C Y, et al. *Cancer Res* 2014; 74:7168-7174; Brunner S M, et al. *Hepatology* 2015; 61:1957-67). The increase of $KLRG1^+$ $CD8^+$ T cells in the peripheral blood of non-tumor bearing mice in FIG. 9F suggested these cells may be an immune correlate for the complete tumor regression elicited by the triple combination therapy (FIG. 10). Thus, it was examined whether tumor regression is associated with its ability to drive robust tumor infiltrating $KLRG1^+$ effector memory Ag-specific $CD8^+$ T cell responses. Twelve days after tumor implantation (5 days after the start of therapy; FIG. 10A), it was noted that the combination Vax/anti-GITR/anti-PD-1 therapy had the highest increase of tetramer-specific $CD8^+$ T cell responses in the tumors (FIG. 14A). Then, the effector memory $CD8^+$ T cell subset based on the expression marker KLRG1 was evaluated. Interestingly, the Vax/anti-GITR/anti-PD-1 therapy resulted in a ~2-fold increase in the frequency of tumor-infiltrating $KLRG1^+CD8^+$ effector cells and $KLRG1^+CD8^+Tet^+$ cells, compared to all other groups (FIGS. 14B-14C), inferring that Ag-specific $KLRG1^+CD8^+$ effector cells can traffic to the tumor site to elicit rapid effector function. Overall, we demonstrated that generating higher $KLRG1^+CD8^+$ effector T cells correlated with the regression of established tumors seen in the combination Vax/anti-GITR/anti-PD-1 therapy.

Figure 14D:
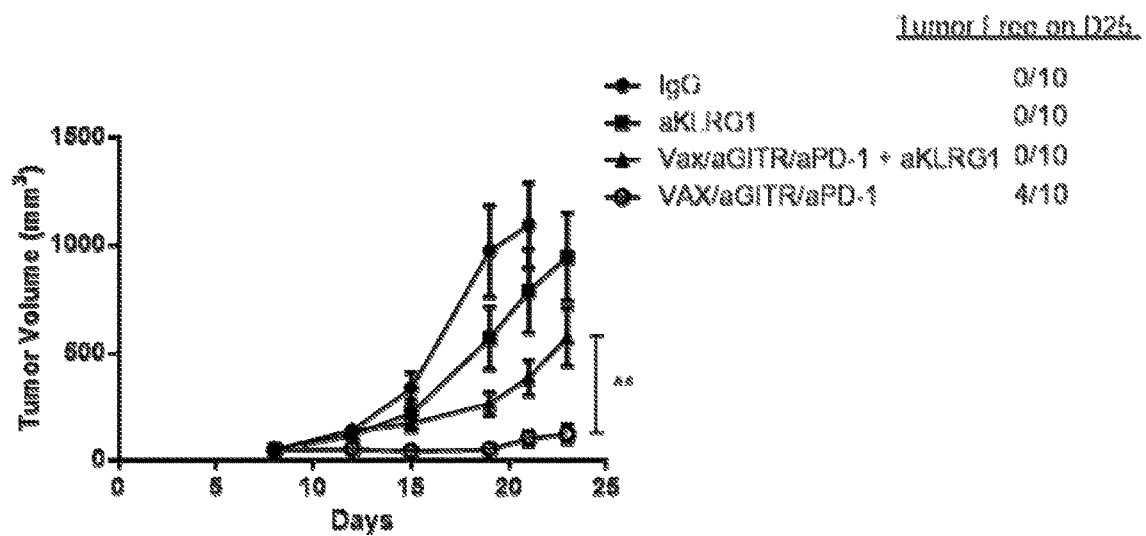
Figure 17A:
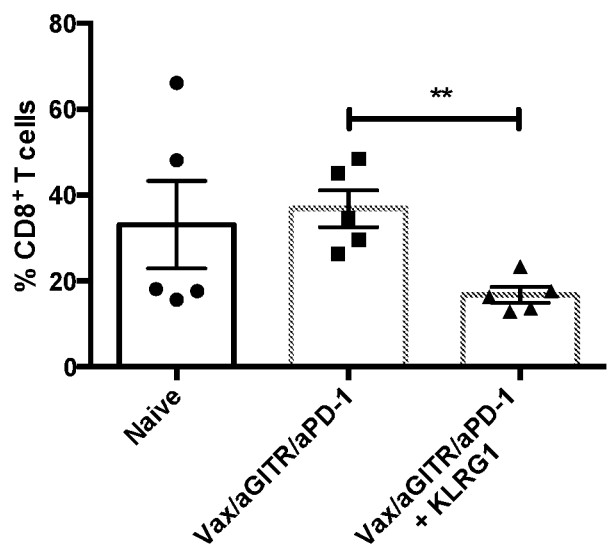
FIG. 17A-17C. Anti-KLRG1 antibody depletes $KLRG1^+$ $CD8^+$ target population. A-B, Naïve tumor-free mice were dosed with Vax/anti-GITR/anti-PD-1 combination and isotype as in FIG. 9. The anti-KLRG1-treated mice were administered 100 μg of anti-KLRG1 mAb on 2, 4, and 6 days post vaccination. Mice were sacrificed on day 7 post vaccination and lymphocytes from both the blood and spleens were collected to assess expression of CD8, KLRG1, and CD44.
Figure 17B:
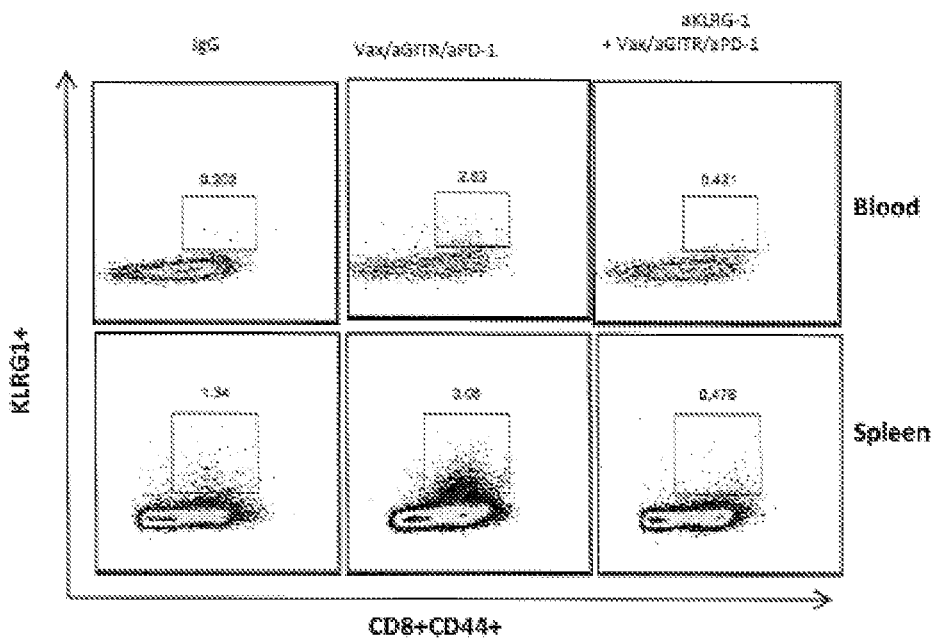
Figure 17C:
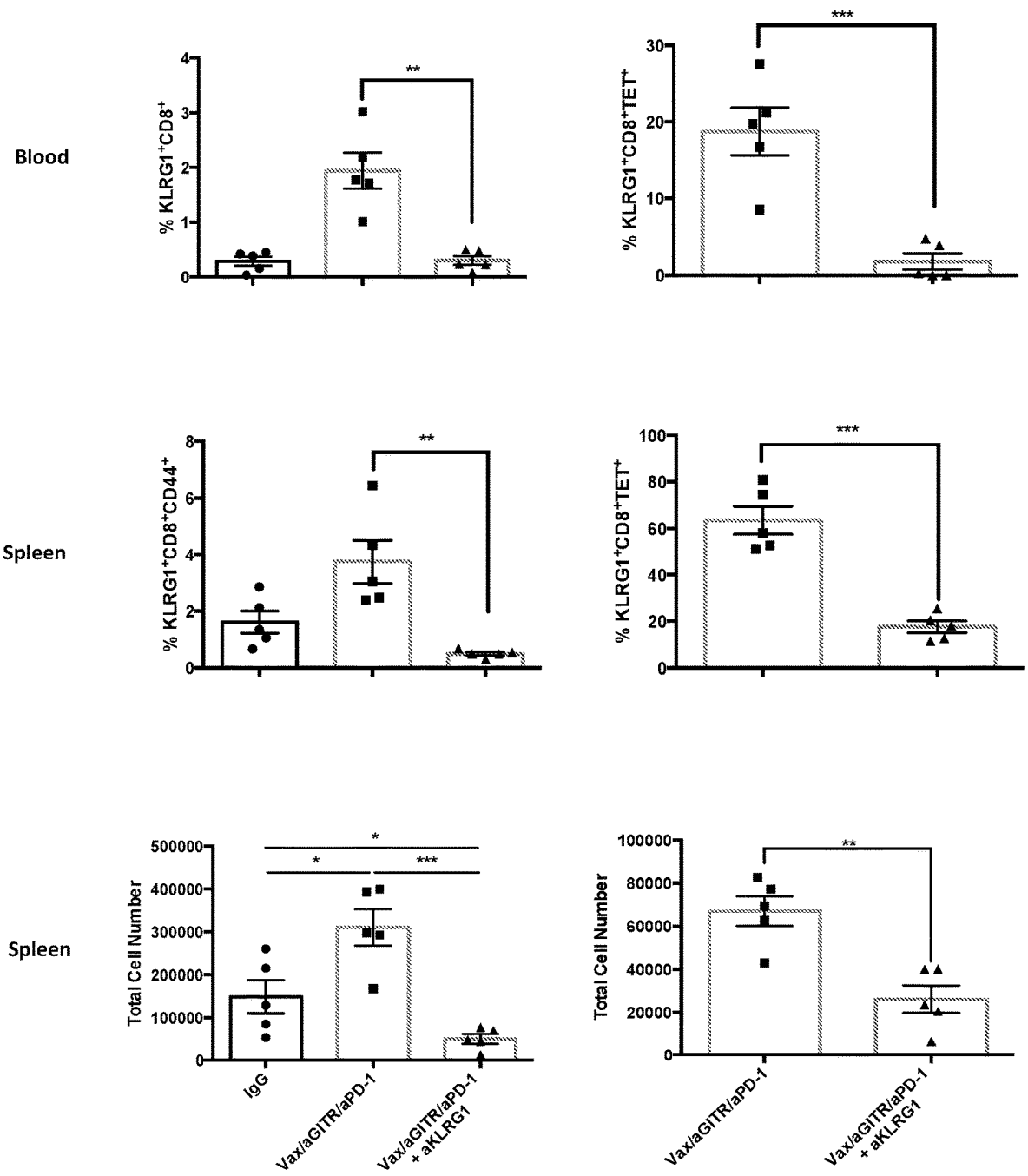

If the expansion of the $KLRG1^+CD8^+$ subset population is one mechanism that helped establish better tumor growth control/regression in the combination Vax/anti-GITR/anti-PD-1 therapy, it was important to determine whether depletion of the $KLRG1^+CD8^+CD44^+$ effector T cell subpopulation would lead to a loss of tumor growth control. First, the ability of anti-KLRG1 (aKLRG1) antibody to deplete the target population was determined. To examine this, two groups of non-tumor bearing mice were vaccinated with the combination Vax/anti-GITR/anti-PD-1 therapy and one group was treated with 200 µg of anti-KLRG1 mAb (200 µg) at day 0, 2, 4, and 6 post-vaccination, and at day 7 after therapy initiation the expression of KLRG1 was monitored on $CD8^+$ T cells from the blood and spleen (FIG. 17). It was observed that the anti-KLRG1 mAb reduced the percentage of $CD8^+$ T cells (FIG. 17A) and depleted the target $KLRG1^+$ $CD8^+CD44$ population (FIGS. 17B-17C). The Vax/anti-GITR/anti-PD-1 treated anti-KLRG1 mice resulted in a significant decrease in the frequency and/or absolute total number of $KLRG1^+CD8^+CD44^+$ and $KLRG1^+CD8^+Tet^+$ populations in the blood and spleen, compared with the non-treated KLRG1 control group (FIG. 17B-17C). Next, the contribution of the $KLRG1^+CD8^+CD44^+$ population at facilitating tumor rejection induced by the triple combination therapy was assessed by depleting $KLRG1^+CD8^+$ $CD44^+$ cells in tumor-bearing mice. The results reveal that KLRG1 depletion significantly reduced protection as mice depleted with KLRG1 Ab showed faster tumor growth than combination treated without KLRG1 depletion (FIG. 14D). More strikingly, the combination therapy with αKLRG1 depletion no longer established tumor regression and long-term survival over combination therapy without aKLRG1 treatment (0% vs 40% tumor rejection). Taken together, these results suggest that the increase of Ag-specific $KLRG1^+$ effector $CD8^+$ T cells induced by the triple combination was a mechanism by which it facilitated tumor growth control, regression, and long-term survival in this melanoma therapeutic model. Thus, the expansion of such an effector $CD8^+$ T cell subpopulation could be a major benefit for future cancer immunotherapeutic strategies.

Figure 15A:
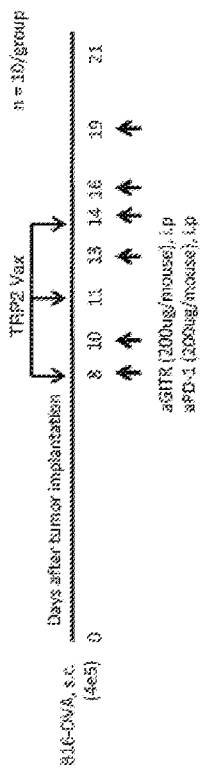
FIGS. 15A and 15B. Dual anti-GITR/anti-PD-1 combination synergizes with a TRP2-based peptide vaccine to induce regression of established B16-OVA tumors. B6 mice (10 per group) were injected s.c. with $4 \times 10^5$ B16-OVA tumor cells; when tumors reached ~50 $mm^3$ treatment was initiated.
Figure 15B:
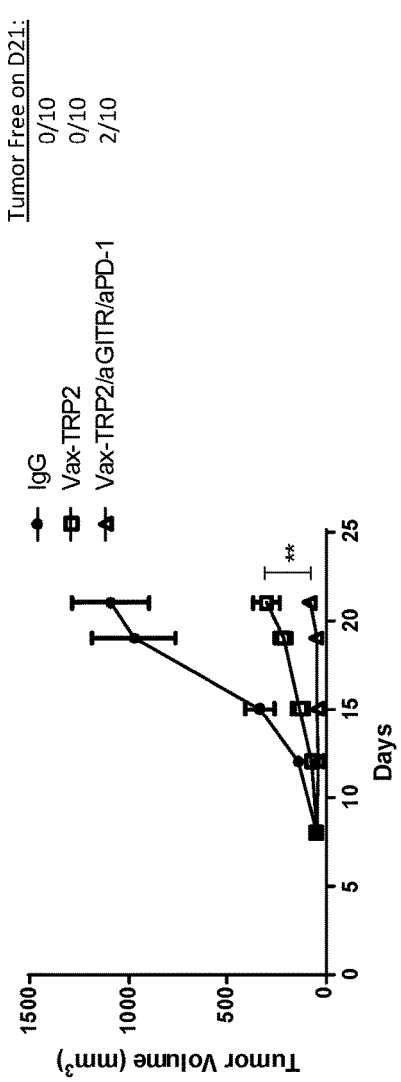

Example 20. Combination Anti-GITR/Anti-PD-1 Therapy Synergizes with a Self-Antigen Tumor Associated Antigen Vaccine to Enhance Anti-Tumor Efficacy A major challenge for developing effective cancer immunotherapies is driving potent antitumor responses against poorly immunogenic tumor associated antigens (TAAs), such as self-antigens. The results in FIG. 13D suggested that the combination Vax/anti-GITR/anti-PD-1 treatment likely induced epitope spreading to other melanoma TAAs beyond OVA. Thus, this prompted the question about whether combination anti-GITR/anti-PD-1 therapy could enhance the efficacy of a vaccine encoding a self-tumor associated antigen. The melanoma tumor antigen tyrosinase-related protein-2 (TRP-2) was chosen because it is one of the most well studied weakly immunogenic melanoma tumor antigens. It has been shown that single-agent TRP2 vaccination has potent antitumor effects in a prophylactic setting in the B16 melanoma mouse model (Avogadri F, et al. *Cancer Immuno Res* 2014; 2:448-458; Pedersen S R, et al. *J Immunol* 2013; 191:3955-3967). However, this activity is significantly reduced and limited in controlling tumors in a therapeutic setting. Likewise, anti-GITR/anti-PD-1 antibody therapy alone has limited efficacy (FIG. 10). Therefore, a stringent therapeutic intervention was applied on 8-day tumors (with average tumor diameter ~50 mm$^3$) using the combinatorial therapy of anti-GITR/anti-PD-1 and concomitantly immunizing the mice three times with the TRP2 peptide vaccine as demonstrated in FIG. 15A. The combination treatment of established tumors showed significant suppression of tumor growth compared to the control groups (FIG. 15B), suggesting the treatment is capable of breaking tolerance to a self-antigen. More importantly, the 3× TRP2/anti-GITR6/anti-PD-1 combination therapy led to complete and durable regressions in ~20% of mice, while the monotherapy elicited no complete regression (FIG. 15B). This observation reconfirms that anti-GITR/anti-PD-1 can synergize with peptide vaccines to augment antitumor immunity. Overall, these studies support the concept that anti-GITR/anti-PD-1 combination can be a useful immunotherapy to augment both vaccine-induced responses against self- and non-self-tumor antigens.

Figure 18A:
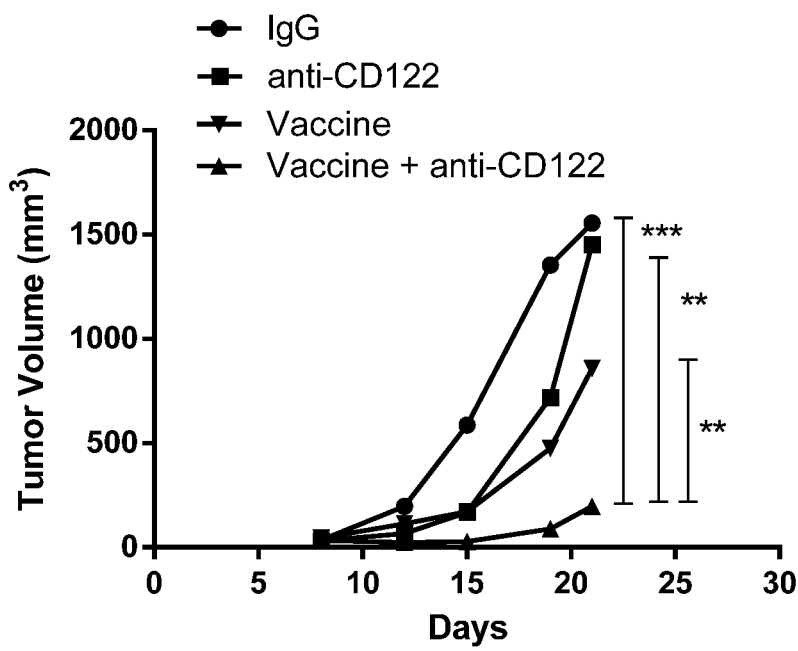
FIGS. 18A and 18B illustrates tumor growth (FIG. 18A) and survival (FIG. 18B) of mice (n=10 per group) implanted with B16-OVA cells (400,000), followed by a treatment with either anti-CD122 mAb 5H4 (administered 5 times at 2-3 day intervals), or with peptide vaccine complex (1 dose), or the combination, as indicated, on the 7$^{th}$ day post implantation.
Figure 18B:
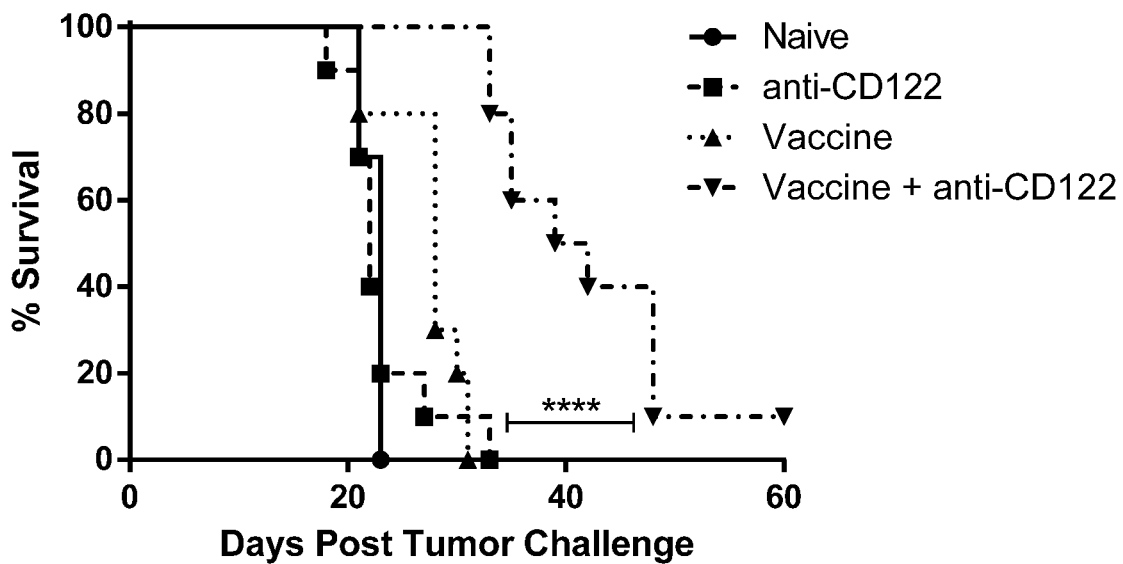
Figure 19A:
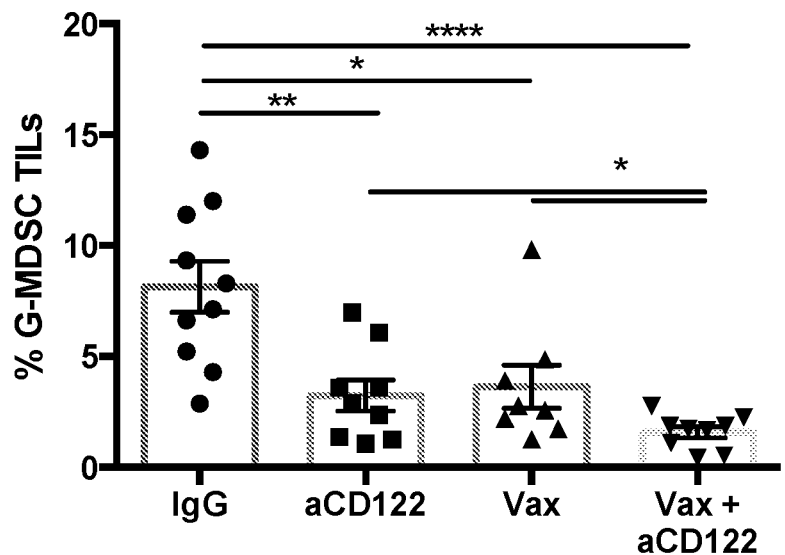
Figure 19B:
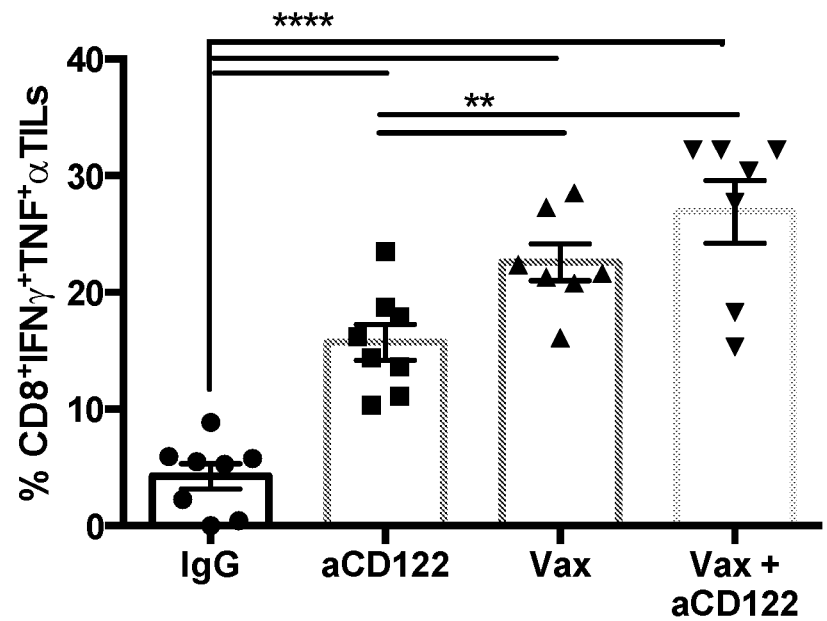
Figure 19C:
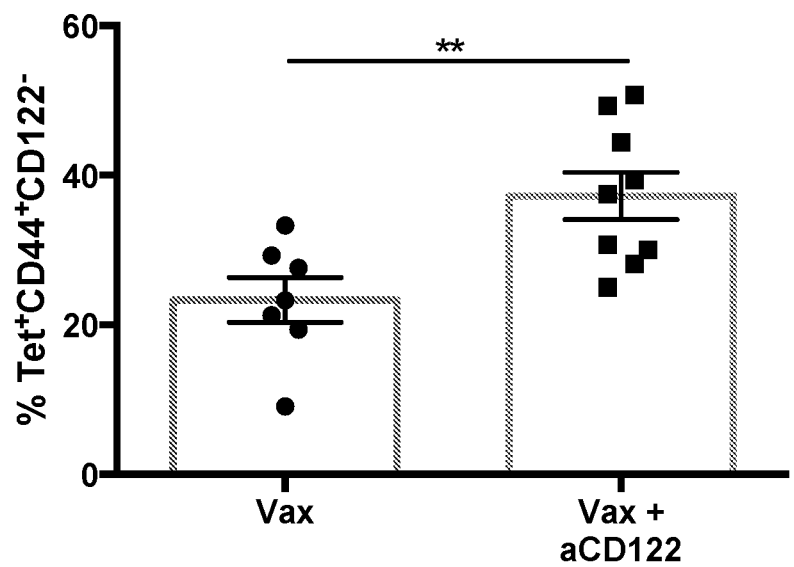
Figure 19D:
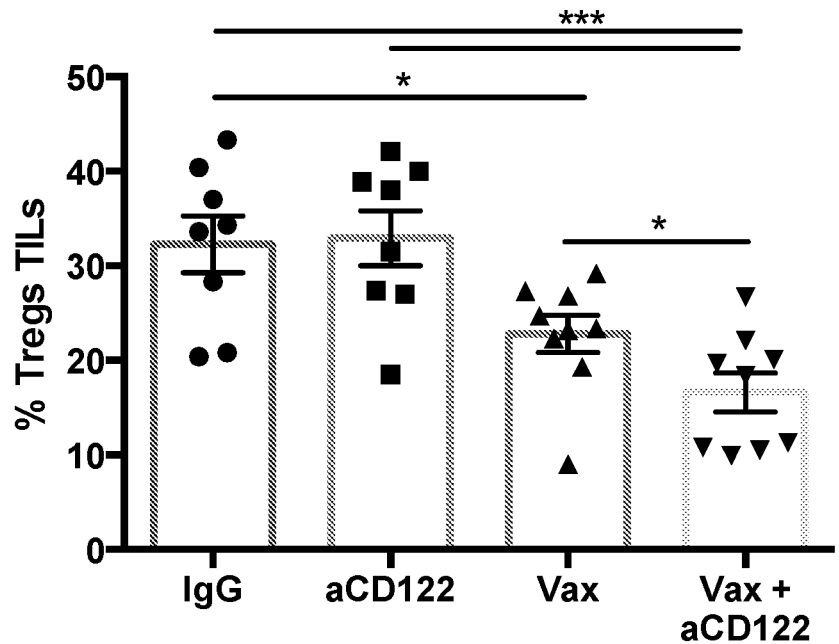

Example 21. Anti-CD122 Treatment Synergizes with a Tumor Vaccine and an Anti-GITR mAb to Achieve Optimal Therapeutic Efficacy Although anti-CD122 as a monotherapy delayed tumor progression, it was not curative in a more stringent therapeutic intervention on 7-day tumors (with average tumor diameter ~30 mm$^3$) under the conditions tested (FIGS. 18A-B). Therefore, in an attempt to enhance the magnitude of the tumor-specific immune response, a peptide-based cancer vaccine targeting OVA (SIINFEKL) as the neo-tumor antigen was used in combination with anti-CD122 therapy. Therapeutic intervention of 7-day established tumors using anti-CD122 and a single dose of peptide vaccine showed significant suppression of tumor growth, leading to ~10% long-term survival, whereas either monotherapy had little to no effect (FIGS. 18A-B). Analysis of TILs showed that when anti-CD122 was combined with the vaccine, there was a significant reduction in the frequency of G-MDSCs relative to each agent alone (FIGS. 19A-D). In addition, combination therapy also significantly increased the dual IFNγ/TNFα production from effector CD8$^+$ TILs and synergistically enhanced the OVA-tetramer-specific CD44$^+$CD8$^+$ memory T cells in the tumors (FIG. 19A-D). The increase of OVA-tetramer-specific CD8$^+$ T cells was also noted in the periphery of non-tumor bearing mice treated with combination vaccine and anti-CD122 therapy (FIGS. 20A-C). The combination therapy markedly reduced the proportion of CD4$^+$ Tregs relative to each agent alone (FIG. 19D), suggesting the overall improved protection observed in the combination group was associated with (1) increased Ag-specific CD8$^+$ T cell responses, (2) decreased G-MDSCs and (3) reduction of CD4$^+$ Treg populations in the tumor. These changes could result in a more supportive environment for tumor rejection.

A prime-boost vaccination strategy was applied on day 7, 10, and 14 for treating 7-day established tumors, and showed greater long-term survival (30%) than a single vaccine dose in this therapeutic setting (FIG. 21A). Given that CD8+ CD122+ T cells have been described to have memory CD8+ T cells properties (Li S et al., Cell Mol Immunol 2014; 11:326-31; Liu J et al., Front Immunol 2015; 6:494), we examined if targeting such a population can likely affect the generation of long-lasting memory T cells. A second tumor challenge of the prime-boost survivors at day 80 post-treatment showed no tumor growth, indicating that levels of T-cell memory was developed and maintained during the combination therapy (FIG. 21B).

Finally, given the improved efficacy by the additive benefit of reducing Tregs in the Vax/anti-CD122 combination and anti-CD4/anti-CD122 combination studies, we determined if anti-CD122 alone can synergize with anti-GITR mAb, an immunotherapy capable of reducing the number of CD4+ Tregs in the tumor (Schaer D A et al., Curr Opin Immunol 2012; 24:217-224). Therapeutic intervention on 4-day tumors using combinatorial therapy of anti-CD122 and anti-GITR targeting mAb demonstrated synergy, showing significant suppression of tumor growth that yielded ~40% long-term survival, compared to anti-CD122 monotherapy (FIGS. 22A-22B). These studies further set the stage for designing GITR-targeted approaches in combination with additional cancer immunotherapies.

Example 22. Mapping of TRGB191 Binding Epitope

To identify the binding epitopes for TRGB191 on human GITR extracellular domain, solution hydrogen/deuterium exchange-mass spectrometry (HDX-MS) was performed.

Pepsin/Protease XIII Digestion and LC-MS

For pepsin/protease XIII digestion, 3.2 μg of human GITR in 133 μL control buffer (50 mM phosphate, 100 mM sodium chloride at pH 7.4) was denatured by adding 135 μL of 4 M guanidine hydrochloride, 0.85 M TCEP buffer (final pH is 2.5) and incubating the mixture for 3 min at 25° C. Then, the mixture was subjected to online pepsin/protease XIII digestion and the resultant peptides was analyzed using an UPLC-MS system comprised of a Waters Acquity UPLC coupled to a Q Exactive™ Hybrid Quadrupole-Orbitrap Mass Spectrometer (Thermo). The peptides were separated on a 50 mm×1 mm C8 column with a 19 min gradient from 2-28% solvent B (0.2% formic acid in acetonitrile) for samples containing human GITR. Solvent A is 0.2% formic acid in water. The injection valve and pepsin/protease XIII column and their related connecting tubings are inside a cooling box maintained at 11° C. And the second switching valve, C8 column and their related connecting stainless steel tubings are inside another chilled circulating box maintained at 0° C. Peptide identification is done through searching MS/MS data against the human GITR sequence with Mascot. The mass tolerance for the precursor and product ions is 10 ppm and 0.05 Da, respectively.

Glycan Mass Identification

10 μg human GITR was deglycosylated by incubation with 1 μL of PNGase F at 37°C for overnight. The sample was then dried down and glycan was reconstituted and incubated with 5 μL 400 mM procainamide (prepared in 3:7 ratio of acetic acid:DMSO (v/v) and 1M sodium cyanoborohydride) at 65°C for 3 h. To remove the excess labeling reagents, the sample was reconstituted in 90% ACN to a total of 500 μL solution. After conditioning the HILIC-SPE plate with 200 μL water and 200 μL 90% ACN, the sample was loaded to the HILIC-SPE plates, washed with 200 µL 90% ACN and eluted with 50 µL 20% ACN. The 75 µL ACN was added prior to further analysis. Glycan masses were measured using a UPLC-MS comprised of Waters ACQUITY UPLC and Bruker MicroTOF QII.

HDX

8 µL human GITR (3.2 µg) or 8 µL human GITR & mAb mixture (3.2 µg: 24 µg) was incubated with 125 µL deuterium oxide labeling buffer (50 mM sodium phosphate, 100 mM sodium chloride at pD 7.4) for 0 sec, 60 sec, 300 sec, 1800 sec, 7200 sec, and 14400 sec at 25□C. Hydrogen/deuterium exchange was quenched by adding 135 µL of 4 M guanidine hydrochloride, 0.85 M TCEP buffer (final pH is 2.5). Subsequently, the quenched samples were subjected to on column pepsin/protease XIII digestion and LC-MS analysis as described above. The mass spectra were recorded in MS only mode.

Raw MS data was processed using HDX WorkBench, software for the analysis of H/D exchange MS data (*J. Am. Soc. Mass Spectrom.* 2012, 23 (9), 1512-1521). The deuterium levels were calculated using the average mass difference between the deuteriated peptide and its native form (to).

Results

The deuterium levels at the identified peptides were monitored from the mass shift on LC-MS. Native human GITR-ECD show significant reduction in deuterium uptakes upon binding to mAb TRGB191.CLF at residues 28-50 and 70-79 of SEQ ID NO: 62. These regions with significant reduction in deuterium uptakes upon binding to mAb are thus assigned as the epitope peptides, which are highlighted in dark or light Grey in FIG. 23.

Modeling the Epitope to the GITR Structure

HDX-MS measurements of mAb TRGB191 binding to human GITR ECD indicate that the binding epitope is discontinuous and located within two peptide regions of GITR:

region 1 (residues 28-50 of SEQ ID NO: 62)
region 2 (residues 70-79 of SEQ ID NO: 62):

The binding epitope of mAb TRGB191 was further refined by mapping the HDX data on the 3D model of GITR obtained from the crystal structure of GITR ECD in complex with TRGB159 Fab. According to the structure, the large portion of the two peptides is inaccessible for solvent. The exposed portions of the peptides are proximal in space and include residues 40-45 and 75-79 of SEQ ID NO:62 (highlighted in FIG. 24).

The structure was determined as follows. The GITR: TRGB159 complex was prepared by mixing Fab with the 25% molar excess of GITR ECD in 20 mM Tris, pH 8.5, 250 mM NaCl, and incubated at 4° C. overnight. Formation of the complex was monitored on a Superdex 200 column. Crystallization of the complex was carried out by the vapor-diffusion method in sitting drops at 20° C. The crystals suitable for X-ray analysis were obtained from 14% PEG 3350 and 0.2 M Na formate in 0.1 M HEPES buffer, pH 7.5. For X-ray data collection, one crystal was soaked for a few seconds in a cryo-protectant solution containing mother liquor supplemented with 24% glycerol and flash-cooled in liquid nitrogen. X-ray diffraction data were collected at the Advanced Photon Source (Argonne, Ill.) using a Mar225 detector. Diffraction intensities were detected to 2.8 Angstrom resolution and processed with the program XDS (Kabsch, W. (2010). XDS. Acta Cryst. D66, 125-132). The structure was solved by molecular replacement with the program Phaser (McCoy, A. J., Grosse-Kunstleve, R. W., Adams, P. D., Winn, M. D., Storoni, L. C. & Read, R. J. (2007). J. Appl. Cryst. 40, 658-674) using structure 5116 from the Protein Data Bank as a search model. When the Fab was positioned in the unit cell, the GITR molecule was manually built in the electron density using program Coot (Emsley, P., Lohkamp, B., Scott, W. G. & Cowtan, K. (2010). Acta Cryst. D66, 486-501).

Example 23. ADCC Activity of TRGB191.CLF on Primary Activated T Cells and the JJN-3 Cell Line A polymorphism in the FcγRIIIA gene (rs396991) results in an amino acid substitution change from a valine to phenylalanine at position 158 (V158F), with the 158V allotype displaying a higher affinity for human IgG1 and increased ADCC; this polymorphism is occasionally denoted in the literature as V176F (Wu J, Edberg J C, Redecha P B, Bansal V, Guyre P M, Coleman K, Salmon J E, Kimberly R P. J Clin Invest; 1997; 100(5):1059-70) Cartron et al. confirmed the homozygous FcγRIIIA-158V genotype to be the single parameter associated with a positive clinical response to rituximab, an antibody whose mechanisms of action include ADCC of tumor cells (Cartron G, Dacheux L, Salles G, Solal-Celigny P, Bardos P, Colombat P, Watier H. Blood; 2002; 99(3):754-8).

TRGB191.CLF is manufactured as a low fucose antibody and subsequently has a roughly 10-fold enhanced affinity to the FcγRIIIA, the Fc receptor present on NK cells, compared to a "regular" fucosylated version (RFV) of the same mAb ($K_D$ was ~37 nM versus ~370 nM to the high affinity FcγRIIIA-158V variant, and ~180 nM versus 1,750 nM to the low affinity FcγRIIIA-158F variant, respectively).

Antibodies with enhanced affinity for FcγRIIIA have been demonstrated to possess increased ADCC activity (Strohl W, Strohl L. Therapeutic Antibody Engineering—Current and Future Advances Driving the Strongest Growth Area in the Pharmaceutical Industry. 1st ed. Sawston: Woodhead Publishing; 2012). The ADCC activity of TRGB191.CLF was evaluated against several target cells or cell lines expressing varying levels of hGITR. For example, resting peripheral T cells express minimal levels of GITR, but GITR expression is upregulated on these cells when activated in vitro. The JJN-3 cell line is a human plasma cell leukemia line that expresses endogenous hGITR at more physiological levels compared to the HuT102 cells, and more similar to those seen on activated T cells and on in vitro differentiated Tregs.

The ADCC activity of TRGB191.CLF was characterized across a wide range of E:T cell ratios on primary resting or activated T cells (see FIG. 25) and JJN-3 cells (see FIG. 26), using NK-92 158V/V effector cells.

TRGB191.CLF had minimal ADCC activity on resting, unactivated CD4$^+$ T cells (see FIG. 25A, left panel) and unactivated CD8$^+$ T cells (see FIG. 25B, left panel). On activated primary T cells expressing GITR, JNJ-64164711 elicited potent ADCC activity with $EC_{50}$ values ranging from 11 ng/mL to 32 ng/mL at the highest E:T ratio of 5:1; values varied depending on the E:T ratios (see Table 9). The $B_{max}$ value also was dependent on the E:T cell ratio and increased as more effector cells were present in the system. An isotype control antibody (CNTO3930) did not induce ADCC.

The JJN-3 cells were previously characterized to express lower levels of GITR than HuT102 cells, and within a range that was more comparable to activated primary T cells and in vitro generated $T_{regs}$, although levels were several-fold higher. When JJN-3 cells were tested using the NK-92 158V high affinity effector cells across a wide range of E:T ratios (see FIG. 26), TRGB191.CLF induced ADCC activity ranging from 50 ng/mL to 130 ng/mL, with very similar $B_{max}$ values to those obtained in ADCC assays with activated primary T cells (see Table 9). The isotype control (CNTO3930) had no effect.

TABLE 9

Summary of JNJ-64164711-dependent NK-92-mediated ADCC activity as a function of E:T ratio.

| | Primary activated CD4+ T cells | | Primary activated CD8+ T cells | | JJN-3 | |
|---|---|---|---|---|---|---|
| | $EC_{50}$ (ng/mL) | $B_{max}$ | $EC_{50}$ (ng/mL) | $B_{max}$ | $EC_{50}$ (ng/mL) | $B_{max}$ |
| E:T (5:1) | 11.32 | 95.48 | 32.18 | 93.84 | 53.78 | 97.26 |
| E:T (2:1) | No data | No data | No data | No data | 78.92 | 87.5 |
| E:T (1:1) | 20.31 | 78.02 | 49.02 | 62.71 | 83.35 | 76.05 |
| E:T (1:2) | No data | No data | No data | No data | 105 | 58.7 |
| E:T (1:5) | 29.61 | 51.11 | 47.5 | 37.97 | 126.8 | 42.84 |

No data, conditions not tested. CNTO3930 isotype control and non-activated primary target cell data are not shown as the software was unable to generate a reliable curve fit. E: NK-92 158VN effector cells; T: target cells (CD4+ T cells, CD8+ T cells, or JJN-3 cells.

Example 24. ADCC Activity of TRGB191.CLF on In Vitro Differentiated Tregs

Recently published and internal data have demonstrated that GITR is expressed on tumor-infiltrating lymphocytes present within the tumor microenvironment in both mice and humans, with the highest level of expression being observed on CD4+ $T_{regs}$ in solid tumors.

Peripheral CD4+ T cells were differentiated and expanded to become functionally suppressive $T_{regs}$ that are defined as CD4+CD25+FOXP3+. These $T_{regs}$ express similar levels of GITR compared to activated primary CD4+ and CD8+ T cells. TRGB191.CLF induced antibody-dependent $T_{reg}$ cell killing comparable to the potency observed with JJN-3 cells (see FIG. 27). The isotype control (CNTO3930) had no effect.

Example 25. ADCC Activity of TRGB191.CLF Using Effector Cells with High and Los Affinity FcγRIIA Polymorphisms TRGB191.CLF has a roughly 10-fold enhanced affinity to both FcγRIIIA-158V/V and FcγRIIIA-158F/F compared to an RFV of the same mAb; its $K_D$ value to the low affinity FcγRIIIA-158F/F variant was equal to ~180 nM, which is about 2-fold of the affinity of the RFV to the high affinity variant receptor (370 nM).

The ADCC activity of TRGB191.CLF to JJN-3 cells was comparable when using NK-92 effector cells expressing either the high affinity FcγRIIIA-158V/V or low affinity FcγRIIIA-158F/F variant, with the $EC_{50}$ value varying ~2-fold (40.01 ng/mL and 87.44 ng/mL, respectively) (see FIG. 28).

Example 26. Combination Anti-GITR with Anti-CD40, Anti-OX40 or Anti-PD1-1 Leads to Better Tumor Growth Delay Animals treated with isotype control antibodies with smaller starting tumor volumes (~100 mm³) reached median time-to-endpoint (MTE) of roughly 19 days. DTA-1 dosed at a single of 10 mg/kg on day 1 led to 2 durable complete regressions (CR) and a delay of MTE to 29.3 days. FGK4.5, anti-CD40 dosed at 2 mg/kg on days 1, 5 and 9 resulted in 6 CRs and a measurable delay in MTE of 60 days. The combination of a single injection of 10 mg/kg of DTA-1 on day 1 along with FGK4.5 (q4dx3), resulted in 8 CRs up to day 40 at which point there appears to be 1 progression (FIG. 29).

Animals treated with isotype control antibodies with larger starting tumor volumes (~230 mm³) reached median time-to-endpoint (MTE) of roughly 10.5 days. FGK4.5 dosed at 10 mg/kg on days 1, 5 and 9 resulted in 1 complete response (CR), and a measurable delay in MTE of 33 days. The combination of a single injection of 10 mg/kg of DTA-1 on day 1 along with FGK4.5 (q4dx3), resulted in 4 durable CRs (FIG. 30).

Concurrent combination of DTA-1 (10 mg/kg, q1, day 1) and OX86 (anti-OX40, 10 mg/kg, q4dx3 starting on day 1) antibodies also resulted in better anti-tumor growth responses with an increase from 2 CRs with DTA-1 to 5 CRs with DTA-1 plus OX86 combination. OX86 did not inhibit tumor progression as a single agent (FIG. 31).

Concurrent combination of DTA-1 (10 mg/kg, q1, day 1) and RMP1-14 (anti-PD-1, 10 mg/kg, q4dx3) was also more efficacious than delaying one of the therapies by giving it two days after the first agent. Anti-PD-1 single agent led to 3 CRs, anti-GITR single agent led to 2 CRs and combination anti-GITR and anti-PD-1 therapies given concurrently resulted in 8 CRs. This efficacy was reduced to 4 or 5 CRs if anti-PD-1 or anti-GITR is dose sequenced first, respectively (FIG. 32).

Brief Description of the Sequence Listing

| SEQ ID NO: | Type | Species | Description | Sequence |
|---|---|---|---|---|
| 1 | PRT | human | TFGB5 and TRGB20-HCDR1 | GFTFSGYW |
| 2 | PRT | human | TFGB14-HCDR1 | GFTFSSYA |
| 3 | PRT | human | TFGB23, TFGB25, TFGB120, TFGB127, TFGB134, TFGB144, TFGB153, TFGB159, TRGB162, and TRGB190-HCDR1 | GGTFSSYA |
| 4 | PRT | human | TRGB31, TRGB34 and TRGB35-HCDR1 | GYSFTSYW |
| 5 | PRT | human | TRGB5, TRGB14, TRGB160, TRGB191, TRGB191.CLF-HCDR2 | ISGSGGST |
| 6 | PRT | human | TRGB20-HCDR2 | ISSDGGSK |

Brief Description of the Sequence Listing

| SEQ ID NO: | Type | Species Description | Sequence |
|---|---|---|---|
| 7 | PRT | humanTRGB23, TRGB25, TRGB120, TRGB134, TRGB144, TRGB153, TRGB159, and TRGB190-HCDR2 | IIPIFGTA |
| 8 | PRT | humanTRGB31-HCDR2 | IDPSDSDT |
| 9 | PRT | humanTRGB34-HCDR2 | IYPGDSDT |
| 10 | PRT | humanTRGB35-HCDR2 | IDPGDSDT |
| 11 | PRT | humanTRGB127. TRGB162-HCDR2 | IIPIFGNA |
| 12 | PRT | humanTRGB5-HCDR3 | AKDFYWDAFDY |
| 13 | PRT | humanTRGB14-HCDR3 | AKPIRGLDY |
| 14 | PRT | humanTRGB20-HCDR3 | AKEVVYDHYAALDY |
| 15 | PRT | humanTRGB23-HCDR3 | ARHGNWLHFNLDY |
| 16 | PRT | humanTRGB25-HCDR3 | ARHRRFWLDY |
| 17 | PRT | humanTRGB31-HCDR3 | ARVFPYYGLVLDY |
| 18 | PRT | humanTRGB34-HCDR3 | ARDYGWHDFDY |
| 19 | PRT | humanTRGB35-HCDR3 | ARHRWSTSLLLDY |
| 20 | PRT | humanTRGB120-HCDR3 | ARPRRNTNELDY |
| 21 | PRT | humanTRGB127, and TRGB162-HCDR3 | ARHVYKRGVLNY |
| 22 | PRT | humanTRGB134-HCDR3 | ARHRWGSGNLDY |
| 23 | PRT | humanTRGB144-HCDR3 | ARHGFQRGYLDY |
| 24 | PRT | humanTRGB153-HCDR3 | ARHAWLGHLDY |
| 25 | PRT | humanTRGB159-HCDR3 | ARHGRNSGRLDY |
| 26 | PRT | humanTRGB160, TRGB191, TRGB191.CLF-HCDR3 | AKDFYWDSFDY |
| 27 | PRT | humanTRGB160, TRGB191, and TRGB191.CLF-HCDR1 | GFTFSNYW |
| 28 | PRT | humanTRGB5, TRGB23, TRGB25, TRGB31, TRGB34, TRGB35, TRGB134, TRGB144, TRGB153, TRGB159, TRGB160, TRGB191, TRGB191.CLF, and TRGB162-LCDR1 | QSVSSY |
| 29 | PRT | humanTRGB14-LCDR1 | QSVNNF |
| 30 | PRT | humanTRGB20-LCDR1 | QSVNSF |
| 31 | PRT | humanTRGB120 and TRGB127-LCDR1 | QSISSY |
| 32 | PRT | humanTRGB5, TRGB14, TRGB23, TRGB25, TRGB31, TRGB34, TRGB35, TRGB134, TRGB144, TRGB153, TRGB159, TRGB160, TRGB191, TRGB191.CLF, and TRGB162-LCDR2 | DAS |
| 33 | PRT | humanTRGB20-LCDR2 | YAS |
| 34 | PRT | humanTRGB120 and TRGB127-LCDR2 | AAS |
| 35 | PRT | humanTRGB5, TRGB23, TRGB25, TRGB31, TRGB34, TRGB35, TRGB134, TRGB144, TRGB153, TRGB159, TRGB160, | QQRSNWPLT |

Brief Description of the Sequence Listing

| SEQ ID NO: | Type | Species Description | Sequence |
|---|---|---|---|
| | | TRGB191, TRGB191.CLF, and TRGB162-LCDR3 | |
| 36 | PRT | humanTRGB14-LCDR3 | QQGFNAPLT |
| 37 | PRT | humanTRGB20-LCDR3 | QQYIRWPLT |
| 38 | PRT | humanTRGB120 and TRGB127-LCDR3 | QQSYSTPLT |
| 39 | PRT | humanTRGB5-Heavy Chain | EVQLLESGGGLVQPGGSLRLSCAASGFTFSGYWMSWVRQAPGKGLEWVSAISGSGGSTYYADSVKGRFTISRDNSKNTLYLQMNSLRAEDTAVYYCAKDFYWDAFDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 40 | PRT | humanTRGB14-Heavy Chain | EVQLLESGGGLVQPGGSLRLSCAASGFTFSSYAMSWVRQAPGKGLEWVSAISGSGGSTYYADSVKGRFTISRDNSKNTLYLQMNSLRAEDTAVYYCAKPIRGLDYFWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 41 | PRT | humanTRGB20-Heavy Chain | EVQLLESGGGLVQPGGSLRLSCAASGFTFSGYWMNWVRQAPGKGLEWVSGISSDGGSKYYADSVKGRFTISRDNSKNTLYLQMNSLRAEDTAVYYCAKEVVYDHYAALDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 42 | PRT | humanTRGB23-Heavy Chain | QVQLVQSGAEVKKPGSSVKVSCKASGGTFSSYAISWVRQAPGQGLEWMGGIIPIFGTANYAQKFQGRVTITADESTSTAYMELSSLRSEDTAVYYCARHGNWLHFNLDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 43 | PRT | humanTRGB25-Heavy Chain | QVQLVQSGAEVKKPGSSVKVSCKASGGTFSSYAISWVRQAPGQGLEWMGGIIPIFGTANYAQKFQGRVTITADESTSTAYMELSSLRSEDTAVYYCARHRRFWLDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 44 | PRT | humanTRGB31-Heavy Chain | EVQLVQSGAEVKKPGESLKISCKGSGYSFTSYWIGWVRQMPGKGLEWMGIIDPSDSDTRYSPSFQGQVTISADKSISTAYLQWSSLKASDTAMYYCARVPPYYGLVLDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 45 | PRT | humanTRGB34-Heavy Chain | EVQLVQSGAEVKKPGESLKISCKGSGYSFTSYWIGWVRQMPGKGLEWMGIIYPGDSDTRYSPSFQGQVTISADKSISTAYLQWSSLKASDTAMYYCARDYGWHDFDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWE |

Brief Description of the Sequence Listing

| SEQ ID NO: | Type | Species Description | Sequence |
|---|---|---|---|
| | | | SNGQPENNYKTTPPVLDSDGSFFLYS KLTVDKSRWQQGNVFSCSVMHEAL HNHYTQKSLSLSPGK |
| 46 | PRT | humanTRGB35-Heavy Chain | EVQLVQSGAEVKKPGESLKISCKGSG YSFTSYWISWVRQMPGKGLEWMGII DPGDSDTRYSPSFQGQVTISADKSIST AYLQWSSLKASDTAMYYCARHRWS TSLLLDYWGQGTLVTVSSASTKGPS VFPLAPSSKSTSGGTAALGCLVKDYF PEPVTVSWNSGALTSGVHTFPAVLQS SGLYSLSSVVTVPSSSLGTQTYICNVN HKPSNTKVDKKVEPKSCDKTHTCPP CPAPELLGGPSVFLFPPKPKDTLMISR TPEVTCVVVDVSHEDPEVKFNWYVD GVEVHNAKTKPREEQYNSTYRVVSV LTVLHQDWLNGKEYKCKVSNKALP APIEKTISKAKGQPREPQVYTLPPSRD ELTKNQVSLTCLVKGFYPSDIAVEWE SNGQPENNYKTTPPVLDSDGSFFLYS KLTVDKSRWQQGNVFSCSVMHEAL HNHYTQKSLSLSPGK |
| 47 | PRT | humanTRGB120-Heavy Chain | QVQLVQSGAEVKKPGSSVKVSCKAS GGTFSSYAISWVRQAPGQGLEWMGG IIPIFGTANYAQKFQGRVTITADESTS TAYMELSSLRSEDTAVYYCARPRRN TNELDYWGQGTLVTVSSASTKGPSV FPLAPSSKSTSGGTAALGCLVKDYFP EPVTVSWNSGALTSGVHTFPAVLQSS GLYSLSSVVTVPSSSLGTQTYICNVN HKPSNTKVDKKVEPKSCDKTHTCPP CPAPELLGGPSVFLFPPKPKDTLMISR TPEVTCVVVDVSHEDPEVKFNWYVD GVEVHNAKTKPREEQYNSTYRVVSV LTVLHQDWLNGKEYKCKVSNKALP APIEKTISKAKGQPREPQVYTLPPSRE EMTKNQVSLTCLVKGFYPSDIAVEW ESNGQPENNYKTTPPVLDSDGSFFLY SKLTVDKSRWQQGNVFSCSVMHEAL HNHYTQKSLSLSPGK |
| 48 | PRT | humanTRGB127-Heavy Chain | QVQLVQSGAEVKKPGSSVKVSCKAS GGTFSSYAISWVRQAPGQGLEWMGG IIPIFGNANYAQKFQGRVTITADESTS TAYMELSSLRSEDTAVYYCARHVYK RGVLNYWGQGTLVTVSSASTKGPSV FPLAPSSKSTSGGTAALGCLVKDYFP EPVTVSWNSGALTSGVHTFPAVLQSS GLYSLSSVVTVPSSSLGTQTYICNVN HKPSNTKVDKKVEPKSCDKTHTCPP CPAPELLGGPSVFLFPPKPKDTLMISR TPEVTCVVVDVSHEDPEVKFNWYVD GVEVHNAKTKPREEQYNSTYRVVSV LTVLHQDWLNGKEYKCKVSNKALP APIEKTISKAKGQPREPQVYTLPPSRE EMTKNQVSLTCLVKGFYPSDIAVEW ESNGQPENNYKTTPPVLDSDGSFFLY SKLTVDKSRWQQGNVFSCSVMHEAL HNHYTQKSLSLSPGK |
| 49 | PRT | humanTRGB134-Heavy Chain | QVQLVQSGAEVKKPGSSVKVSCKAS GGTFSSYAISWVRQAPGQGLEWMGG IIPIFGTANYAQKFQGRVTITADESTS TAYMELSSLRSEDTAVYYCARHRWG SGNLDYWGQGTLVTVSSASTKGPSV FPLAPSSKSTSGGTAALGCLVKDYFP EPVTVSWNSGALTSGVHTFPAVLQSS GLYSLSSVVTVPSSSLGTQTYICNVN HKPSNTKVDKKVEPKSCDKTHTCPP CPAPELLGGPSVFLFPPKPKDTLMISR TPEVTCVVVDVSHEDPEVKFNWYVD GVEVHNAKTKPREEQYNSTYRVVSV LTVLHQDWLNGKEYKCKVSNKALP APIEKTISKAKGQPREPQVYTLPPSRE EMTKNQVSLTCLVKGFYPSDIAVEW ESNGQPENNYKTTPPVLDSDGSFFLY SKLTVDKSRWQQGNVFSCSVMHEAL HNHYTQKSLSLSPGK |
| 50 | PRT | humanTRGB144-Heavy Chain | QVQLVQSGAEVKKPGSSVKVSCKAS GGTFSSYAISWVRQAPGQGLEWMGG IIPIFGTANYAQKFQGRVTITADESTS TAYMELSSLRSEDTAVYYCARHGFQ RGYLDYWGQGTLVTVSSASTKGPSV FPLAPSSKSTSGGTAALGCLVKDYFP EPVTVSWNSGALTSGVHTFPAVLQSS GLYSLSSVVTVPSSSLGTQTYICNVN HKPSNTKVDKKVEPKSCDKTHTCPP CPAPELLGGPSVFLFPPKPKDTLMISR TPEVTCVVVDVSHEDPEVKFNWYVD GVEVHNAKTKPREEQYNSTYRVVSV LTVLHQDWLNGKEYKCKVSNKALP APIEKTISKAKGQPREPQVYTLPPSRE EMTKNQVSLTCLVKGFYPSDIAVEW ESNGQPENNYKTTPPVLDSDGSFFLY SKLTVDKSRWQQGNVFSCSVMHEAL HNHYTQKSLSLSPGK |
| 51 | PRT | humanTRGB153-Heavy Chain | QVQLVQSGAEVKKPGSSVKVSCKAS GGTFSSYAISWVRQAPGQGLEWMGG IIPIFGTANYAQKFQGRVTITADESTS TAYMELSSLRSEDTAVYYCARHAWL GHLDYWGQGTLVTVSSASTKGPSVF PLAPSSKSTSGGTAALGCLVKDYFPE PVTVSWNSGALTSGVHTFPAVLQSS GLYSLSSVVTVPSSSLGTQTYICNVN HKPSNTKVDKKVEPKSCDKTHTCPP CPAPELLGGPSVFLFPPKPKDTLMISR TPEVTCVVVDVSHEDPEVKFNWYVD GVEVHNAKTKPREEQYNSTYRVVSV LTVLHQDWLNGKEYKCKVSNKALP APIEKTISKAKGQPREPQVYTLPPSRE EMTKNQVSLTCLVKGFYPSDIAVEW ESNGQPENNYKTTPPVLDSDGSFFLY SKLTVDKSRWQQGNVFSCSVMHEAL HNHYTQKSLSLSPGK |
| 52 | PRT | humanTRGB159-Heavy Chain | QVQLVQSGAEVKKPGSSVKVSCKAS GGTFSSYAISWVRQAPGQGLEWMGG IIPIFGTANYAQKFQGRVTITADESTS TAYMELSSLRSEDTAVYYCARHGRN SGRLDYWGQGTLVTVSSASTKGPSV FPLAPSSKSTSGGTAALGCLVKDYFP EPVTVSWNSGALTSGVHTFPAVLQSS GLYSLSSVVTVPSSSLGTQTYICNVN HKPSNTKVDKKVEPKSCDKTHTCPP CPAPELLGGPSVFLFPPKPKDTLMISR TPEVTCVVVDVSHEDPEVKFNWYVD GVEVHNAKTKPREEQYNSTYRVVSV LTVLHQDWLNGKEYKCKVSNKALP APIEKTISKAKGQPREPQVYTLPPSRE EMTKNQVSLTCLVKGFYPSDIAVEW ESNGQPENNYKTTPPVLDSDGSFFLY SKLTVDKSRWQQGNVFSCSVMHEAL HNHYTQKSLSLSPGK |
| 53 | PRT | humanTRGB160-Heavy Chain | QVQLLESGGGLVQPGGSLRLSCAAS GFTFSNYWMSWVRQAPGKGLEWVS AISGSGGSTYYADSVKGRFTISRDNS KNTLYLQMNSLRAEDTAVYYCAKD FYWDSFDYWGQGTLVTVSSASTKGP SVFPPLAPSSKSTSGGTAALGCLVKDY FPEPVTVSWNSGALTSGVHTFPAVLQ SSGLYSLSSVVTVPSSSLGTQTYICNV NHKPSNTKVDKKVEPKSCDKTHTCP |

Brief Description of the Sequence Listing

| SEQ ID NO: | Type | Species Description | Sequence |
|---|---|---|---|
| | | | PCPAPELLGGPSVFLFPPKPKDTLMIS RTPEVTCVVVDVSHEDPEVKFNWYV DGVEVHNAKTKPREEQYNSTYRVVS VLTVLHQDWLNGKEYKCKVSNKAL PAPIEKTISKAKGQPREPQVYTLPPSR EEMTKNQVSLTCLVKGFYPSDIAVE WESNGQPENNYKTTPPVLDSDGSFFL YSKLTVDKSRWQQGNVFSCSVMHE ALHNHYTQKSLSLSPGK |
| 54 | PRT | humanTRGB162-Heavy Chain | QVQLVQSGAEVKKPGSSVKV SCKASGGTFSSYAISWVRQAPGQGLE WMGGIIPIFGNANYAQKFQGRVTITA DESTSTAYMELSSLRSEDTAVYYCAR HVYKRGVLNYWGQGTLVTVSSAST KGPSVFPLAPSSKSTSGGTAALGCLV KDYFPEPVTVSWNSGALTSGVHTFP AVLQSSGLYSLSSVVTVPSSSLGTQT YICNVNHKPSNTKVDKKVEPKSCDK THTCPPCPAPELLGGPSVFLFPPKPKD TLMISRTPEVTCVVVDVSHEDPEVKF NWYVDGVEVHNAKTKPREEQYNST YRVVSVLTVLHQDWLNGKEYKCKV SNKALPAPIEKTISKAKGQPREPQVY TLPPSREEMTKNQVSLTCLVKGFYPS DIAVEWESNGQPENNYKTTPPVLDS DGSFFLYSKLTVDKSRWQQGNVFSC SVMHEALHNHYTQKSLSLSPGK |
| 55 | PRT | humanTRGB5, TRGB23, TRGB25, TRGB31, TRGB34, TRGB35, TRGB134, TRGB144, TRGB153, TRGB159, TRGB160, TRGB162, TRGB190, TRGB191 and TRGB191. CLF-Light Chain | EIVLTQSPATLSLSPGERATLSCRASQ SVSSYLAWYQQKPGQAPRLLIYDAS NRATGIPARFSGSGSGTDFTLTISSLEP EDFAVYYCQQRSNWPLTFGQGTKVE IKRTVAAPSVFIFPPSDEQLKSGTASV VCLLNNFYPREAKVQWKVDNALQS GNSQESVTEQDSKDSTYSLSSTLTLS KADYEKHKVYACEVTHQGLSSPVTK SFNRGEC |
| 56 | PRT | humanTRGB14-Light Chain | EIVLTQSPATLSLSPGERATLSCRASQ SVNNFLAWYQQKPGQAPRLLIYDAS NRATGIPARFSGSGSGTDFTLTISSLEP EDFAVYYCQQGFNAPLTFGQGTKVE IKRTVAAPSVFIFPPSDEQLKSGTASV VCLLNNFYPREAKVQWKVDNALQS GNSQESVTEQDSKDSTYSLSSTLTLS KADYEKHKVYACEVTHQGLSSPVTK SFNRGEC |
| 57 | PRT | humanTRGB20-Light Chain | EIVLTQSPATLSLSPGERATLSCRASQ SVNSFLAWYQQKPGQAPRLLIYYAS NRATGIPARFSGSGSGTDFTLTISSLEP EDFAVYYCQQYIRWPLTFGQGTKVEI KRTVAAPSVFIFPPSDEQLKSGTASV VCLLNNFYPREAKVQWKVDNALQS GNSQESVTEQDSKDSTYSLSSTLTLS KADYEKHKVYACEVTHQGLSSPVTK SFNRGEC |
| 58 | PRT | humanTRGB120 and TRGB127-Light Chain | DIQMTQSPSSLSASVGDRVTITCRAS QSISSYLNWYQQKPGKAPKLLIYAAS SLQSGVPSRFSGSGSGTDFTLTISSLQ PEDFATYYCQQSYSTPLTFGQGTKVE IKRTVAAPSVFIFPPSDEQLKSGTASV VCLLNNFYPREAKVQWKVDNALQS GNSQESVTEQDSKDSTYSLSSTLTLS KADYEKHKVYACEVTHQGLSSPVTK SFNRGEC |
| 59 | PRT | humanGITR 26-161 | QRPTGGPGCGPGRLLLGTGTDARCC RVHTTRCCRDYPGEECCSEWDCMCV QPEFHCGDPCCTTCRHHPCPPGQGV QSQGKFSFGFQCIDCASGTFSGGHEG HCKPWTDCTQFGFLTVFPGNKTHNA VCVPGSPPAE |
| 60 | PRT | humanGITR 26-241 | QRPTGGPGCGPGRLLLGTGTDARCC RVHTTRCCRDYPGEECCSEWDCMCV QPEFHCGDPCCTTCRHHPCPPGQGV QSQGKFSFGFQCIDCASGTFSGGHEG HCKPWTDCTQFGFLTVFPGNKTHNA VCVPGSPPAEPLGWLTVVLLAVAAC VLLLTSAQLGLHIWQLRSQCMWPRE TQLLLEVPPSTEDARSCQFPEEERGER SAEEKGRLGDLWV |
| 61 | PRT | cyno GITR | QRPTGGPGCGPGRLLLGTGKDARCC RVHPTRCCRDYQSEECCSEWDCVCV QPEFHCGNPCCTTCQHHPCPSGQGV QPQGKFSFGFRCVDCALGTFSRGHD GHCKPWTDCTQFGFLTVFPGNKTHN AVCVPGSPPAEPPGWLTIVLLAVAAC VLLLTSAQLGLHIWQLGSQPTGPRET QLLLEVPPSTEDASSCQFPEEERGERL AEEKGRLGDLWV |
| 62 | PRT | humanFull-length GITR | MAQHGAMGAFRALCGLALLCALSL GQRPTGGPGCGPGRLLLGTGTDARC CRVHTTRCCRDYPGEECCSEWDCMC VQPEFHCGDPCCTTCRHHPCPPGQG VQSQGKFSFGFQCIDCASGTFSGGHE GHCKPWTDCTQFGFLTVFPGNKTHN AVCVPGSPPAEPLGWLTVVLLAVAA CVLLLTSAQLGLHIWQLRSQCMWPR ETQLLLEVPPSTEDARSCQFPEEERGE RSAEEKGRLGDLWV |
| 63 | PRT | humanTRGB190-VH | QVQLVQSGAEVKKPGSSVKVSCKAS GGTFSSYAISWVRQAPGQGLEWMGG IIPIFGTANYAQKFQGRVTITADESTS TAYMELSSLRSEDTAVYYCARHRRF WLDYWGQGTLVTVSSASTKGPSVFP LAPSSKSTSGGTAALGCLVKDYFPEP VTVSWNSGALTSGVHTFPAVLQSSG LYSLSSVVTVPSSSLGTQTYICNVNH KPSNTKVDKKVEPKSCDKTHTCPPCP APELLGGPSVFLFPPKPKDTLMISRTP EVTCVVVDVSHEDPEVKFNWYVDG VEVHNAKTKPREEQYNSTYRVVSVL TVLHQDWLNGKEYKCKVSNKALPA PIEKTISKAKGQPREPQVYTLPPSREE MTKNQVSLTCLVKGFYPSDIAVEWE SNGQPENNYKTTPPVLDSDGSFFLYS KLTVDKSRWQQGNVFSCSVMHEAL HNHYTQKSLSLSPGK |
| 64 | PRT | humanTRGB191 and TRGB191. CLF-VH | EVQLLESGGGLVQPGGSLRLSCAASG FTFSNYWMSWVRQAPGKGLEWVSA ISGSGGSTYYADSVKGRFTISRDNSK NTLYLQMNSLRAEDTAVYYCAKDF YWDSFDYWGQGTLVTVSSASTKGPS VFPLAPSSKSTSGGTAALGCLVKDYF PEPVTVSWNSGALTSGVHTFPAVLQS SGLYSLSSVVTVPSSSLGTQTYICNVN HKPSNTKVDKKVEPKSCDKTHTCPP CPAPELLGGPSVFLFPPKPKDTLMISR TPEVTCVVVDVSHEDPEVKFNWYVD |

Brief Description of the Sequence Listing

| SEQ ID NO: | Type | Species | Description | Sequence |
|---|---|---|---|---|
| | | | | GVEVHNAKTKPREEQYNSTYRVVSV LTVLHQDWLNGKEYKCKVSNKALP APIEKTISKAKGQPREPQVYTLPPSRE EMTKNQVSLTCLVKGFYPSDIAVEW ESNGQPENNYKTTPPVLDSDGSFFLY SKLTVDKSRWQQGNVFSCSVMHEAL HNHYTQKSLSLSPGK |
| 65 | PRT | | humanGITR-L | MTLHPSPITCEFLFSTALISPKMCLSH LENMPLSHSRTQGAQRSSWKLWLFC SIVMLLFLCSFSWLIFIFLQLETAKEPC MAKFGPLPSKWQMASSEPPCVNKVS DWKLEILQNGLYLIYGQVAPNANYN DVAPFEVRLYKNKDMIQTLTNKSKIQ NVGGTYELHVGDTIDLIFNSEHQV LKNNTYWGIILLANPQFIS |

We claim:

1. An isolated antibody, or an antigen-binding fragment thereof, that specifically binds to human GITR comprising a heavy chain CDR1 having the amino acid sequence of SEQ ID NO: 27, a heavy chain CDR2 having the amino acid sequence of SEQ ID NO: 5, and a heavy chain CDR3 having the amino acid sequence of SEQ ID NO: 26, a light chain CDR1 having the amino acid sequence of SEQ ID NO: 28, a light chain CDR2 having the amino acid sequence of SEQ ID NO: 32, and a light chain CDR3 having the amino acid sequence of SEQ ID NO: 35.

2. The antibody or an antigen-binding fragment of claim 1, wherein the antibody or antigen-binding fragment thereof comprises SEQ ID NO: 64.

3. The antibody or an antigen-binding fragment of claim 2, wherein the antibody or antigen binding fragment thereof comprises a light chain region comprising SEQ ID NO: 55.

4. The antibody or antigen-binding fragment of claim 1 wherein the antibody or antigen-binding fragment thereof specifically binds human GITR with a binding affinity of at least 30 nM as measured by surface plasmon resonance.

5. The antibody or antigen-binding fragment of claim 1 wherein the antibody or antigen-binding fragment induces ADCC in vitro with an $EC_{50}$ of less than about 67 ng/mL.

6. The antibody or antigen-binding fragment of claim 1 wherein the antibody or antigen-binding fragment is a human antibody or antigen-binding fragment.

7. The antigen-binding fragment of claim 1 wherein the antigen binding fragment is a Fab fragment, a Fab2 fragment, or a single chain antibody.

8. The antibody or antigen-binding fragment of claim 1 wherein the antibody or antigen-binding fragment is recombinant.

9. The antibody or antigen-binding fragment of claim 1 wherein the antibody or antigen-binding fragment thereof are of IgG1, IgG2, IgG3, or IgG4 isotype.

10. The antibody or antigen-binding fragment of claim 1 is IgG1 isotype.

11. A pharmaceutical composition comprising the antibody, or antigen binding fragment thereof, of claim 1 and a pharmaceutically acceptable carrier.

12. A kit comprising the antibody, or antigen binding fragment thereof, of claim 1.

* * * * *

SEQUENCE LISTING

```
<160> NUMBER OF SEQ ID NOS: 66

<210> SEQ ID NO 1
<211> LENGTH: 8
<212> TYPE: PRT
<213> ORGANISM: Homo sapiens

<400> SEQUENCE: 1

Gly Phe Thr Phe Ser Gly Tyr Trp
1               5

<210> SEQ ID NO 2
<211> LENGTH: 8
<212> TYPE: PRT
<213> ORGANISM: Homo sapiens

<400> SEQUENCE: 2

Gly Phe Thr Phe Ser Ser Tyr Ala
1               5

<210> SEQ ID NO 3
<211> LENGTH: 8
<212> TYPE: PRT
<213> ORGANISM: Homo sapiens

<400> SEQUENCE: 3

Gly Gly Thr Phe Ser Ser Tyr Ala
1               5

<210> SEQ ID NO 4
<211> LENGTH: 8
<212> TYPE: PRT
<213> ORGANISM: Homo sapiens

<400> SEQUENCE: 4

Gly Tyr Ser Phe Thr Ser Tyr Trp
1               5

<210> SEQ ID NO 5
<211> LENGTH: 8
<212> TYPE: PRT
<213> ORGANISM: Homo sapiens

<400> SEQUENCE: 5

Ile Ser Gly Ser Gly Gly Ser Thr
1               5

<210> SEQ ID NO 6
```

```
<211> LENGTH: 8
<212> TYPE: PRT
<213> ORGANISM: Homo sapiens

<400> SEQUENCE: 6

Ile Ser Ser Asp Gly Gly Ser Lys
1               5

<210> SEQ ID NO 7
<211> LENGTH: 8
<212> TYPE: PRT
<213> ORGANISM: Homo sapiens

<400> SEQUENCE: 7

Ile Ile Pro Ile Phe Gly Thr Ala
1               5

<210> SEQ ID NO 8
<211> LENGTH: 8
<212> TYPE: PRT
<213> ORGANISM: Homo sapiens

<400> SEQUENCE: 8

Ile Asp Pro Ser Asp Ser Asp Thr
1               5

<210> SEQ ID NO 9
<211> LENGTH: 8
<212> TYPE: PRT
<213> ORGANISM: Homo sapiens

<400> SEQUENCE: 9

Ile Tyr Pro Gly Asp Ser Asp Thr
1               5

<210> SEQ ID NO 10
<211> LENGTH: 8
<212> TYPE: PRT
<213> ORGANISM: Homo sapiens

<400> SEQUENCE: 10

Ile Asp Pro Gly Asp Ser Asp Thr
1               5

<210> SEQ ID NO 11
<211> LENGTH: 8
<212> TYPE: PRT
<213> ORGANISM: Homo sapiens

<400> SEQUENCE: 11

Ile Ile Pro Ile Phe Gly Asn Ala
1               5

<210> SEQ ID NO 12
<211> LENGTH: 11
<212> TYPE: PRT
<213> ORGANISM: Homo sapiens

<400> SEQUENCE: 12

Ala Lys Asp Phe Tyr Trp Asp Ala Phe Asp Tyr
1               5                   10

<210> SEQ ID NO 13
<211> LENGTH: 9
<212> TYPE: PRT
```

```
<213> ORGANISM: Homo sapiens

<400> SEQUENCE: 13

Ala Lys Pro Ile Arg Gly Leu Asp Tyr
1               5

<210> SEQ ID NO 14
<211> LENGTH: 14
<212> TYPE: PRT
<213> ORGANISM: Homo sapiens

<400> SEQUENCE: 14

Ala Lys Glu Val Val Tyr Asp His Tyr Ala Ala Leu Asp Tyr
1               5                   10

<210> SEQ ID NO 15
<211> LENGTH: 13
<212> TYPE: PRT
<213> ORGANISM: Homo sapiens

<400> SEQUENCE: 15

Ala Arg His Gly Asn Trp Leu His Phe Asn Leu Asp Tyr
1               5                   10

<210> SEQ ID NO 16
<211> LENGTH: 10
<212> TYPE: PRT
<213> ORGANISM: Homo sapiens

<400> SEQUENCE: 16

Ala Arg His Arg Arg Phe Trp Leu Asp Tyr
1               5                   10

<210> SEQ ID NO 17
<211> LENGTH: 13
<212> TYPE: PRT
<213> ORGANISM: Homo sapiens

<400> SEQUENCE: 17

Ala Arg Val Phe Pro Tyr Tyr Gly Leu Val Leu Asp Tyr
1               5                   10

<210> SEQ ID NO 18
<211> LENGTH: 11
<212> TYPE: PRT
<213> ORGANISM: Homo sapiens

<400> SEQUENCE: 18

Ala Arg Asp Tyr Gly Trp His Asp Phe Asp Tyr
1               5                   10

<210> SEQ ID NO 19
<211> LENGTH: 13
<212> TYPE: PRT
<213> ORGANISM: Homo sapiens

<400> SEQUENCE: 19

Ala Arg His Arg Trp Ser Thr Ser Leu Leu Leu Asp Tyr
1               5                   10

<210> SEQ ID NO 20
<211> LENGTH: 12
<212> TYPE: PRT
<213> ORGANISM: Homo sapiens
```

```
<400> SEQUENCE: 20

Ala Arg Pro Arg Arg Asn Thr Asn Glu Leu Asp Tyr
1               5                   10

<210> SEQ ID NO 21
<211> LENGTH: 12
<212> TYPE: PRT
<213> ORGANISM: Homo sapiens

<400> SEQUENCE: 21

Ala Arg His Val Tyr Lys Arg Gly Val Leu Asn Tyr
1               5                   10

<210> SEQ ID NO 22
<211> LENGTH: 12
<212> TYPE: PRT
<213> ORGANISM: Homo sapiens

<400> SEQUENCE: 22

Ala Arg His Arg Trp Gly Ser Gly Asn Leu Asp Tyr
1               5                   10

<210> SEQ ID NO 23
<211> LENGTH: 12
<212> TYPE: PRT
<213> ORGANISM: Homo sapiens

<400> SEQUENCE: 23

Ala Arg His Gly Phe Gln Arg Gly Tyr Leu Asp Tyr
1               5                   10

<210> SEQ ID NO 24
<211> LENGTH: 11
<212> TYPE: PRT
<213> ORGANISM: Homo sapiens

<400> SEQUENCE: 24

Ala Arg His Ala Trp Leu Gly His Leu Asp Tyr
1               5                   10

<210> SEQ ID NO 25
<211> LENGTH: 12
<212> TYPE: PRT
<213> ORGANISM: Homo sapiens

<400> SEQUENCE: 25

Ala Arg His Gly Arg Asn Ser Gly Arg Leu Asp Tyr
1               5                   10

<210> SEQ ID NO 26
<211> LENGTH: 11
<212> TYPE: PRT
<213> ORGANISM: Homo sapiens

<400> SEQUENCE: 26

Ala Lys Asp Phe Tyr Trp Asp Ser Phe Asp Tyr
1               5                   10

<210> SEQ ID NO 27
<211> LENGTH: 8
<212> TYPE: PRT
<213> ORGANISM: Homo sapiens

<400> SEQUENCE: 27
```

Gly Phe Thr Phe Ser Asn Tyr Trp
1               5

<210> SEQ ID NO 28
<211> LENGTH: 6
<212> TYPE: PRT
<213> ORGANISM: Homo sapiens

<400> SEQUENCE: 28

Gln Ser Val Ser Ser Tyr
1               5

<210> SEQ ID NO 29
<211> LENGTH: 6
<212> TYPE: PRT
<213> ORGANISM: Homo sapiens

<400> SEQUENCE: 29

Gln Ser Val Asn Asn Phe
1               5

<210> SEQ ID NO 30
<211> LENGTH: 6
<212> TYPE: PRT
<213> ORGANISM: Homo sapiens

<400> SEQUENCE: 30

Gln Ser Val Asn Ser Phe
1               5

<210> SEQ ID NO 31
<211> LENGTH: 6
<212> TYPE: PRT
<213> ORGANISM: Homo sapiens

<400> SEQUENCE: 31

Gln Ser Ile Ser Ser Tyr
1               5

<210> SEQ ID NO 32
<211> LENGTH: 3
<212> TYPE: PRT
<213> ORGANISM: Homo sapiens

<400> SEQUENCE: 32

Asp Ala Ser
1

<210> SEQ ID NO 33
<211> LENGTH: 3
<212> TYPE: PRT
<213> ORGANISM: Homo sapiens

<400> SEQUENCE: 33

Tyr Ala Ser
1

<210> SEQ ID NO 34
<211> LENGTH: 3
<212> TYPE: PRT
<213> ORGANISM: Homo sapiens

<400> SEQUENCE: 34

Ala Ala Ser
1

<210> SEQ ID NO 35
<211> LENGTH: 9
<212> TYPE: PRT
<213> ORGANISM: Homo sapiens

<400> SEQUENCE: 35

Gln Gln Arg Ser Asn Trp Pro Leu Thr
1               5

<210> SEQ ID NO 36
<211> LENGTH: 9
<212> TYPE: PRT
<213> ORGANISM: Homo sapiens

<400> SEQUENCE: 36

Gln Gln Gly Phe Asn Ala Pro Leu Thr
1               5

<210> SEQ ID NO 37
<211> LENGTH: 9
<212> TYPE: PRT
<213> ORGANISM: Homo sapiens

<400> SEQUENCE: 37

Gln Gln Tyr Ile Arg Trp Pro Leu Thr
1               5

<210> SEQ ID NO 38
<211> LENGTH: 9
<212> TYPE: PRT
<213> ORGANISM: Homo sapiens

<400> SEQUENCE: 38

Gln Gln Ser Tyr Ser Thr Pro Leu Thr
1               5

<210> SEQ ID NO 39
<211> LENGTH: 448
<212> TYPE: PRT
<213> ORGANISM: Homo sapiens

<400> SEQUENCE: 39

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gly Tyr
            20                  25                  30

Trp Met Ser Trp Val Arg Gln Ala Pro Gly Lys Gly Leu Glu Trp Val
        35                  40                  45

Ser Ala Ile Ser Gly Ser Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Phe Tyr Trp Asp Ala Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
        210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
            355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445

<210> SEQ ID NO 40
<211> LENGTH: 446
<212> TYPE: PRT
<213> ORGANISM: Homo sapiens

<400> SEQUENCE: 40

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
50                  55                  60

Lys Gly Arg Phe Thr Ile Ser Arg Asp Asn Ser Lys Asn Thr Leu Tyr

```
                65                  70                  75                  80
Leu Gln Met Asn Ser Leu Arg Ala Glu Asp Thr Ala Val Tyr Tyr Cys
                    85                  90                  95
Ala Lys Pro Ile Arg Gly Leu Asp Tyr Trp Gly Gln Gly Thr Leu Val
                    100                 105                 110
Thr Val Ser Ser Ala Ser Thr Lys Gly Pro Ser Val Phe Pro Leu Ala
                    115                 120                 125
Pro Ser Ser Lys Ser Thr Ser Gly Gly Thr Ala Ala Leu Gly Cys Leu
                    130                 135                 140
Val Lys Asp Tyr Phe Pro Glu Pro Val Thr Val Ser Trp Asn Ser Gly
145                 150                 155                 160
Ala Leu Thr Ser Gly Val His Thr Phe Pro Ala Val Leu Gln Ser Ser
                    165                 170                 175
Gly Leu Tyr Ser Leu Ser Ser Val Val Thr Val Pro Ser Ser Ser Leu
                    180                 185                 190
Gly Thr Gln Thr Tyr Ile Cys Asn Val Asn His Lys Pro Ser Asn Thr
                    195                 200                 205
Lys Val Asp Lys Lys Val Glu Pro Lys Ser Cys Asp Lys Thr His Thr
                    210                 215                 220
Cys Pro Pro Cys Pro Ala Pro Glu Leu Leu Gly Gly Pro Ser Val Phe
225                 230                 235                 240
Leu Phe Pro Pro Lys Pro Lys Asp Thr Leu Met Ile Ser Arg Thr Pro
                    245                 250                 255
Glu Val Thr Cys Val Val Val Asp Val Ser His Glu Asp Pro Glu Val
                    260                 265                 270
Lys Phe Asn Trp Tyr Val Asp Gly Val Glu Val His Asn Ala Lys Thr
                    275                 280                 285
Lys Pro Arg Glu Glu Gln Tyr Asn Ser Thr Tyr Arg Val Val Ser Val
                    290                 295                 300
Leu Thr Val Leu His Gln Asp Trp Leu Asn Gly Lys Glu Tyr Lys Cys
305                 310                 315                 320
Lys Val Ser Asn Lys Ala Leu Pro Ala Pro Ile Glu Lys Thr Ile Ser
                    325                 330                 335
Lys Ala Lys Gly Gln Pro Arg Glu Pro Gln Val Tyr Thr Leu Pro Pro
                    340                 345                 350
Ser Arg Asp Glu Leu Thr Lys Asn Gln Val Ser Leu Thr Cys Leu Val
                    355                 360                 365
Lys Gly Phe Tyr Pro Ser Asp Ile Ala Val Glu Trp Glu Ser Asn Gly
                    370                 375                 380
Gln Pro Glu Asn Asn Tyr Lys Thr Thr Pro Pro Val Leu Asp Ser Asp
385                 390                 395                 400
Gly Ser Phe Phe Leu Tyr Ser Lys Leu Thr Val Asp Lys Ser Arg Trp
                    405                 410                 415
Gln Gln Gly Asn Val Phe Ser Cys Ser Val Met His Glu Ala Leu His
                    420                 425                 430
Asn His Tyr Thr Gln Lys Ser Leu Ser Leu Ser Pro Gly Lys
                    435                 440                 445

<210> SEQ ID NO 41
<211> LENGTH: 451
<212> TYPE: PRT
<213> ORGANISM: Homo sapiens

<400> SEQUENCE: 41
```

-continued

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gly Tyr
            20                  25                  30

Trp Met Asn Trp Val Arg Gln Ala Pro Gly Lys Gly Leu Glu Trp Val
        35                  40                  45

Ser Gly Ile Ser Ser Asp Gly Ser Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Glu Val Val Tyr Asp His Tyr Ala Ala Leu Asp Tyr Trp Gly
            100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
            130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
            245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
            290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
            355                 360                 365

Leu Thr Cys Leu Val Lys Gly Phe Tyr Pro Ser Asp Ile Ala Val Glu
            370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met

His Glu Ala Leu His Asn His Tyr Thr Gln Lys Ser Leu Ser Leu Ser
              420                 425                 430

Pro Gly Lys
    435                 440                 445

450

<210> SEQ ID NO 42
<211> LENGTH: 450
<212> TYPE: PRT
<213> ORGANISM: Homo sapiens

<400> SEQUENCE: 42

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg His Gly Asn Trp Leu His Phe Asn Leu Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

```
Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 43
<211> LENGTH: 447
<212> TYPE: PRT
<213> ORGANISM: Homo sapiens

<400> SEQUENCE: 43

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg His Arg Arg Phe Trp Leu Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255
```

```
Pro Glu Val Thr Cys Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 44
<211> LENGTH: 450
<212> TYPE: PRT
<213> ORGANISM: Homo sapiens

<400> SEQUENCE: 44

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Asp Pro Ser Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Val Phe Pro Tyr Tyr Gly Leu Val Leu Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
```

```
            180                 185                 190
Ser Ser Ser Leu Gly Thr Gln Thr Tyr Ile Cys Asn Val Asn His Lys
        195                 200                 205
Pro Ser Asn Thr Lys Val Asp Lys Lys Val Glu Pro Lys Ser Cys Asp
    210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
            260                 265                 270
Asp Pro Glu Val Lys Phe Asn Trp Tyr Val Asp Gly Val Glu Val His
        275                 280                 285
Asn Ala Lys Thr Lys Pro Arg Glu Glu Gln Tyr Asn Ser Thr Tyr Arg
    290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Asp Glu Leu Thr Lys Asn Gln Val Ser Leu
        355                 360                 365
Thr Cys Leu Val Lys Gly Phe Tyr Pro Ser Asp Ile Ala Val Glu Trp
    370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
        435                 440                 445
Gly Lys
    450

<210> SEQ ID NO 45
<211> LENGTH: 448
<212> TYPE: PRT
<213> ORGANISM: Homo sapiens

<400> SEQUENCE: 45

Glu Val Gln Leu Val Gln Ser Gly Ala Glu Val Lys Lys Pro Gly Glu
1               5                   10                  15
Ser Leu Lys Ile Ser Cys Lys Gly Ser Gly Tyr Ser Phe Thr Ser Tyr
            20                  25                  30
Trp Ile Gly Trp Val Arg Gln Met Pro Gly Lys Gly Leu Glu Trp Met
        35                  40                  45
Gly Ile Ile Tyr Pro Gly Asp Ser Asp Thr Arg Tyr Ser Pro Ser Phe
    50                  55                  60
Gln Gly Gln Val Thr Ile Ser Ala Asp Lys Ser Ile Ser Thr Ala Tyr
65                  70                  75                  80
Leu Gln Trp Ser Ser Leu Lys Ala Ser Asp Thr Ala Met Tyr Tyr Cys
                85                  90                  95
```

Ala Arg Asp Tyr Gly Trp His Asp Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 46
<211> LENGTH: 450
<212> TYPE: PRT
<213> ORGANISM: Homo sapiens

<400> SEQUENCE: 46

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

```
Trp Ile Ser Trp Val Arg Gln Met Pro Gly Lys Gly Leu Glu Trp Met
            35                  40                  45
Gly Ile Ile Asp Pro Gly Asp Ser Asp Thr Arg Tyr Ser Pro Ser Phe
 50                      55                  60
Gln Gly Gln Val Thr Ile Ser Ala Asp Lys Ser Ile Ser Thr Ala Tyr
 65                  70                  75                  80
Leu Gln Trp Ser Ser Leu Lys Ala Ser Asp Thr Ala Met Tyr Tyr Cys
                 85                  90                  95
Ala Arg His Arg Trp Ser Thr Ser Leu Leu Asp Tyr Trp Gly Gln
                 100                 105                 110
Gly Thr Leu Val Thr Val Ser Ser Ala Ser Thr Lys Gly Pro Ser Val
            115                 120                 125
Phe Pro Leu Ala Pro Ser Ser Lys Ser Thr Ser Gly Gly Thr Ala Ala
            130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                 165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
            195                 200                 205
Pro Ser Asn Thr Lys Val Asp Lys Lys Val Glu Pro Lys Ser Cys Asp
210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                 245                 250                 255
Ser Arg Thr Pro Glu Val Thr Cys Val Val Val Asp Val Ser His Glu
                 260                 265                 270
Asp Pro Glu Val Lys Phe Asn Trp Tyr Val Asp Gly Val Glu Val His
            275                 280                 285
Asn Ala Lys Thr Lys Pro Arg Glu Glu Gln Tyr Asn Ser Thr Tyr Arg
 290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                 325                 330                 335
Lys Thr Ile Ser Lys Ala Lys Gly Gln Pro Arg Glu Pro Gln Val Tyr
            340                 345                 350
Thr Leu Pro Pro Ser Arg Asp Glu Leu Thr Lys Asn Gln Val Ser Leu
            355                 360                 365
Thr Cys Leu Val Lys Gly Phe Tyr Pro Ser Asp Ile Ala Val Glu Trp
370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                 405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
            435                 440                 445
```

```
Gly Lys
    450

<210> SEQ ID NO 47
<211> LENGTH: 449
<212> TYPE: PRT
<213> ORGANISM: Homo sapiens

<400> SEQUENCE: 47

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Pro Arg Arg Asn Thr Asn Glu Leu Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365
```

```
Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 48
<211> LENGTH: 449
<212> TYPE: PRT
<213> ORGANISM: Homo sapiens

<400> SEQUENCE: 48

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Asn Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg His Val Tyr Lys Arg Gly Val Leu Asn Tyr Trp Gly Gln Gly
                100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285
```

-continued

```
Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 49
<211> LENGTH: 449
<212> TYPE: PRT
<213> ORGANISM: Homo sapiens

<400> SEQUENCE: 49

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg His Arg Trp Gly Ser Gly Asn Leu Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205
```

```
Ser Asn Thr Lys Val Asp Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 50
<211> LENGTH: 449
<212> TYPE: PRT
<213> ORGANISM: Homo sapiens

<400> SEQUENCE: 50

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg His Gly Phe Gln Arg Gly Tyr Leu Asp Tyr Trp Gly Gln Gly
            100                 105                 110

Thr Leu Val Thr Val Ser Ser Ala Ser Thr Lys Gly Pro Ser Val Phe
        115                 120                 125
```

```
Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 51
<211> LENGTH: 448
<212> TYPE: PRT
<213> ORGANISM: Homo sapiens

<400> SEQUENCE: 51

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45
```

Gly Gly Ile Ile Pro Ile Phe Gly Thr Ala Asn Tyr Ala Gln Lys Phe
50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg His Ala Trp Leu Gly His Leu Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 52
<211> LENGTH: 449

<212> TYPE: PRT
<213> ORGANISM: Homo sapiens

<400> SEQUENCE: 52

Gln Val Gln Leu Val Gln Ser Gly Ala Glu Val Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg His Gly Arg Asn Ser Gly Arg Leu Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 53
<211> LENGTH: 448
<212> TYPE: PRT
<213> ORGANISM: Homo sapiens

<400> SEQUENCE: 53

Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Phe Tyr Trp Asp Ser Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

```
Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 54
<211> LENGTH: 449
<212> TYPE: PRT
<213> ORGANISM: Homo sapiens

<400> SEQUENCE: 54

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Asn Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg His Val Tyr Lys Arg Gly Val Leu Asn Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
```

-continued

```
                245                 250                 255
Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 55
<211> LENGTH: 214
<212> TYPE: PRT
<213> ORGANISM: Homo sapiens

<400> SEQUENCE: 55

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
```

```
                165                 170                 175
Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 56
<211> LENGTH: 214
<212> TYPE: PRT
<213> ORGANISM: Homo sapiens

<400> SEQUENCE: 56

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Asn Asn Phe
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Gly Phe Asn Ala Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 57
<211> LENGTH: 214
<212> TYPE: PRT
<213> ORGANISM: Homo sapiens

<400> SEQUENCE: 57

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Asn Ser Phe
            20                  25                  30

Leu Ala Trp Tyr Gln Gln Lys Pro Gly Gln Ala Pro Arg Leu Leu Ile
        35                  40                  45

Tyr Tyr Ala Ser Asn Arg Ala Thr Gly Ile Pro Ala Arg Phe Ser Gly
```

```
            50                  55                  60
Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Tyr Ile Arg Trp Pro Leu
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 58
<211> LENGTH: 214
<212> TYPE: PRT
<213> ORGANISM: Homo sapiens

<400> SEQUENCE: 58

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Ser Ile Ser Ser Tyr
             20                  25                  30

Leu Asn Trp Tyr Gln Gln Lys Pro Gly Lys Ala Pro Lys Leu Leu Ile
         35                  40                  45

Tyr Ala Ala Ser Ser Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Leu
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205
```

Phe Asn Arg Gly Glu Cys
    210

<210> SEQ ID NO 59
<211> LENGTH: 136
<212> TYPE: PRT
<213> ORGANISM: Homo sapiens

<400> SEQUENCE: 59

Gln Arg Pro Thr Gly Gly Pro Gly Cys Gly Pro Gly Arg Leu Leu Leu
1               5                   10                  15

Gly Thr Gly Thr Asp Ala Arg Cys Cys Arg Val His Thr Thr Arg Cys
                20                  25                  30

Cys Arg Asp Tyr Pro Gly Glu Glu Cys Cys Ser Glu Trp Asp Cys Met
            35                  40                  45

Cys Val Gln Pro Glu Phe His Cys Gly Asp Pro Cys Cys Thr Thr Cys
        50                  55                  60

Arg His His Pro Cys Pro Pro Gly Gln Gly Val Gln Ser Gln Gly Lys
65                  70                  75                  80

Phe Ser Phe Gly Phe Gln Cys Ile Asp Cys Ala Ser Gly Thr Phe Ser
                85                  90                  95

Gly Gly His Glu Gly His Cys Lys Pro Trp Thr Asp Cys Thr Gln Phe
                100                 105                 110

Gly Phe Leu Thr Val Phe Pro Gly Asn Lys Thr His Asn Ala Val Cys
            115                 120                 125

Val Pro Gly Ser Pro Ala Glu
        130                 135

<210> SEQ ID NO 60
<211> LENGTH: 216
<212> TYPE: PRT
<213> ORGANISM: Homo sapiens

<400> SEQUENCE: 60

Gln Arg Pro Thr Gly Gly Pro Gly Cys Gly Pro Gly Arg Leu Leu Leu
1               5                   10                  15

Gly Thr Gly Thr Asp Ala Arg Cys Cys Arg Val His Thr Thr Arg Cys
                20                  25                  30

Cys Arg Asp Tyr Pro Gly Glu Glu Cys Cys Ser Glu Trp Asp Cys Met
            35                  40                  45

Cys Val Gln Pro Glu Phe His Cys Gly Asp Pro Cys Cys Thr Thr Cys
        50                  55                  60

Arg His His Pro Cys Pro Pro Gly Gln Gly Val Gln Ser Gln Gly Lys
65                  70                  75                  80

Phe Ser Phe Gly Phe Gln Cys Ile Asp Cys Ala Ser Gly Thr Phe Ser
                85                  90                  95

Gly Gly His Glu Gly His Cys Lys Pro Trp Thr Asp Cys Thr Gln Phe
                100                 105                 110

Gly Phe Leu Thr Val Phe Pro Gly Asn Lys Thr His Asn Ala Val Cys
            115                 120                 125

Val Pro Gly Ser Pro Ala Glu Pro Leu Gly Trp Leu Thr Val Val
        130                 135                 140

Leu Leu Ala Val Ala Ala Cys Val Leu Leu Leu Thr Ser Ala Gln Leu
145                 150                 155                 160

Gly Leu His Ile Trp Gln Leu Arg Ser Gln Cys Met Trp Pro Arg Glu
                165                 170                 175

Thr Gln Leu Leu Leu Glu Val Pro Pro Ser Thr Glu Asp Ala Arg Ser
            180                 185                 190

Cys Gln Phe Pro Glu Glu Glu Arg Gly Glu Arg Ser Ala Glu Glu Lys
        195                 200                 205

Gly Arg Leu Gly Asp Leu Trp Val
        210                 215

<210> SEQ ID NO 61
<211> LENGTH: 216
<212> TYPE: PRT
<213> ORGANISM: Macaca fascicularis

<400> SEQUENCE: 61

Gln Arg Pro Thr Gly Gly Pro Gly Cys Gly Pro Gly Arg Leu Leu Leu
1               5                   10                  15

Gly Thr Gly Lys Asp Ala Arg Cys Cys Arg Val His Pro Thr Arg Cys
            20                  25                  30

Cys Arg Asp Tyr Gln Ser Glu Glu Cys Cys Ser Glu Trp Asp Cys Val
        35                  40                  45

Cys Val Gln Pro Glu Phe His Cys Gly Asn Pro Cys Cys Thr Thr Cys
    50                  55                  60

Gln His His Pro Cys Pro Ser Gly Gln Gly Val Gln Pro Gln Gly Lys
65                  70                  75                  80

Phe Ser Phe Gly Phe Arg Cys Val Asp Cys Ala Leu Gly Thr Phe Ser
                85                  90                  95

Arg Gly His Asp Gly His Cys Lys Pro Trp Thr Asp Cys Thr Gln Phe
            100                 105                 110

Gly Phe Leu Thr Val Phe Pro Gly Asn Lys Thr His Asn Ala Val Cys
        115                 120                 125

Val Pro Gly Ser Pro Pro Ala Glu Pro Pro Gly Trp Leu Thr Ile Val
    130                 135                 140

Leu Leu Ala Val Ala Ala Cys Val Leu Leu Thr Ser Ala Gln Leu
145                 150                 155                 160

Gly Leu His Ile Trp Gln Leu Gly Ser Gln Pro Thr Gly Pro Arg Glu
                165                 170                 175

Thr Gln Leu Leu Leu Glu Val Pro Pro Ser Thr Glu Asp Ala Ser Ser
            180                 185                 190

Cys Gln Phe Pro Glu Glu Glu Arg Gly Glu Arg Leu Ala Glu Glu Lys
        195                 200                 205

Gly Arg Leu Gly Asp Leu Trp Val
        210                 215

<210> SEQ ID NO 62
<211> LENGTH: 241
<212> TYPE: PRT
<213> ORGANISM: Homo sapiens

<400> SEQUENCE: 62

Met Ala Gln His Gly Ala Met Gly Ala Phe Arg Ala Leu Cys Gly Leu
1               5                   10                  15

Ala Leu Leu Cys Ala Leu Ser Leu Gly Gln Arg Pro Thr Gly Gly Pro
            20                  25                  30

Gly Cys Gly Pro Gly Arg Leu Leu Leu Gly Thr Gly Thr Asp Ala Arg
        35                  40                  45

Cys Cys Arg Val His Thr Thr Arg Cys Cys Arg Asp Tyr Pro Gly Glu
    50                  55                  60

-continued

```
Glu Cys Cys Ser Glu Trp Asp Cys Met Cys Val Gln Pro Glu Phe His
 65                  70                  75                  80

Cys Gly Asp Pro Cys Cys Thr Thr Cys Arg His His Pro Cys Pro Pro
                 85                  90                  95

Gly Gln Gly Val Gln Ser Gln Gly Lys Phe Ser Phe Gly Phe Gln Cys
            100                 105                 110

Ile Asp Cys Ala Ser Gly Thr Phe Ser Gly Gly His Glu Gly His Cys
        115                 120                 125

Lys Pro Trp Thr Asp Cys Thr Gln Phe Gly Phe Leu Thr Val Phe Pro
    130                 135                 140

Gly Asn Lys Thr His Asn Ala Val Cys Val Pro Gly Ser Pro Pro Ala
145                 150                 155                 160

Glu Pro Leu Gly Trp Leu Thr Val Val Leu Leu Ala Val Ala Ala Cys
                165                 170                 175

Val Leu Leu Leu Thr Ser Ala Gln Leu Gly Leu His Ile Trp Gln Leu
            180                 185                 190

Arg Ser Gln Cys Met Trp Pro Arg Glu Thr Gln Leu Leu Leu Glu Val
        195                 200                 205

Pro Pro Ser Thr Glu Asp Ala Arg Ser Cys Gln Phe Pro Glu Glu Glu
    210                 215                 220

Arg Gly Glu Arg Ser Ala Glu Glu Lys Gly Arg Leu Gly Asp Leu Trp
225                 230                 235                 240

Val
```

<210> SEQ ID NO 63
<211> LENGTH: 447
<212> TYPE: PRT
<213> ORGANISM: Homo sapiens
<400> SEQUENCE: 63

```
Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Ser Tyr
             20                  25                  30

Ala Ile Ser Trp Val Arg Gln Ala Pro Gly Gln Gly Leu Glu Trp Met
         35                  40                  45

Gly Gly Ile Ile Pro Ile Phe Gly Thr Ala Asn Tyr Ala Gln Lys Phe
     50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg His Arg Arg Phe Trp Leu Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190
```

-continued

```
Leu Gly Thr Gln Thr Tyr Ile Cys Asn Val Asn His Lys Pro Ser Asn
            195                 200                 205
Thr Lys Val Asp Lys Lys Val Glu Pro Lys Ser Cys Asp Lys Thr His
        210                 215                 220
Thr Cys Pro Pro Cys Pro Ala Pro Glu Leu Leu Gly Gly Pro Ser Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Val Asp Val Ser His Glu Asp Pro Glu
            260                 265                 270
Val Lys Phe Asn Trp Tyr Val Asp Gly Val Glu Val His Asn Ala Lys
        275                 280                 285
Thr Lys Pro Arg Glu Glu Gln Tyr Asn Ser Thr Tyr Arg Val Val Ser
    290                 295                 300
Val Leu Thr Val Leu His Gln Asp Trp Leu Asn Gly Lys Glu Tyr Lys
305                 310                 315                 320
Cys Lys Val Ser Asn Lys Ala Leu Pro Ala Pro Ile Glu Lys Thr Ile
                325                 330                 335
Ser Lys Ala Lys Gly Gln Pro Arg Glu Pro Gln Val Tyr Thr Leu Pro
            340                 345                 350
Pro Ser Arg Glu Glu Met Thr Lys Asn Gln Val Ser Leu Thr Cys Leu
        355                 360                 365
Val Lys Gly Phe Tyr Pro Ser Asp Ile Ala Val Glu Trp Glu Ser Asn
    370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Lys Leu Thr Val Asp Lys Ser Arg
                405                 410                 415
Trp Gln Gln Gly Asn Val Phe Ser Cys Ser Val Met His Glu Ala Leu
            420                 425                 430
His Asn His Tyr Thr Gln Lys Ser Leu Ser Leu Ser Pro Gly Lys
        435                 440                 445

<210> SEQ ID NO 64
<211> LENGTH: 448
<212> TYPE: PRT
<213> ORGANISM: Homo sapiens

<400> SEQUENCE: 64

Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Ser Asn Tyr
            20                  25                  30
Trp Met Ser Trp Val Arg Gln Ala Pro Gly Lys Gly Leu Glu Trp Val
        35                  40                  45
Ser Ala Ile Ser Gly Ser Gly Gly Ser Thr Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Lys Asp Phe Tyr Trp Asp Ser Phe Asp Tyr Trp Gly Gln Gly Thr
            100                 105                 110
Leu Val Thr Val Ser Ser Ala Ser Thr Lys Gly Pro Ser Val Phe Pro
        115                 120                 125
```

```
Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
                180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 65
<211> LENGTH: 199
<212> TYPE: PRT
<213> ORGANISM: Homo sapiens

<400> SEQUENCE: 65

Met Thr Leu His Pro Ser Pro Ile Thr Cys Glu Phe Leu Phe Ser Thr
1               5                   10                  15

Ala Leu Ile Ser Pro Lys Met Cys Leu Ser His Leu Glu Asn Met Pro
                20                  25                  30

Leu Ser His Ser Arg Thr Gln Gly Ala Gln Arg Ser Ser Trp Lys Leu
            35                  40                  45

Trp Leu Phe Cys Ser Ile Val Met Leu Leu Phe Leu Cys Ser Phe Ser
```

```
                    50                   55                   60
Trp Leu Ile Phe Ile Phe Leu Gln Leu Glu Thr Ala Lys Glu Pro Cys
 65                   70                   75                   80

Met Ala Lys Phe Gly Pro Leu Pro Ser Lys Trp Gln Met Ala Ser Ser
                 85                   90                   95

Glu Pro Pro Cys Val Asn Lys Val Ser Asp Trp Lys Leu Glu Ile Leu
                100                  105                  110

Gln Asn Gly Leu Tyr Leu Ile Tyr Gly Gln Val Ala Pro Asn Ala Asn
            115                  120                  125

Tyr Asn Asp Val Ala Pro Phe Glu Val Arg Leu Tyr Lys Asn Lys Asp
        130                  135                  140

Met Ile Gln Thr Leu Thr Asn Lys Ser Lys Ile Gln Asn Val Gly Gly
145                  150                  155                  160

Thr Tyr Glu Leu His Val Gly Asp Thr Ile Asp Leu Ile Phe Asn Ser
                165                  170                  175

Glu His Gln Val Leu Lys Asn Asn Thr Tyr Trp Gly Ile Ile Leu Leu
                180                  185                  190

Ala Asn Pro Gln Phe Ile Ser
            195

<210> SEQ ID NO 66
<211> LENGTH: 8
<212> TYPE: PRT
<213> ORGANISM: Gallus gallus

<400> SEQUENCE: 66

Ser Ile Ile Asn Phe Glu Lys Leu
 1               5
```